United States Patent [19]

Reitz

[11] Patent Number: 5,098,920

[45] Date of Patent: Mar. 24, 1992

[54] 1H-SUBSTITUTED-1,2,4-TRIAZOLE COMPOUNDS AND METHODS OF USE THEREOF FOR TREATMENT OF CARDIOVASCULAR DISORDERS

[75] Inventor: David B. Reitz, Chesterfield, Mo.

[73] Assignee: G. D. Searle & Co., Chicago, Ill.

[21] Appl. No.: 519,380

[22] Filed: May 4, 1990

[51] Int. Cl.$^5$ .................... C07D 403/06; A61K 31/41
[52] U.S. Cl. .................... 514/381; 548/254; 548/250; 548/262.24 D
[58] Field of Search .................... 548/262, 254; 514/381

[56] References Cited

U.S. PATENT DOCUMENTS

| | | | |
|---|---|---|---|
| 4,118,487 | 10/1978 | Regel et al. | 424/232 |
| 4,381,306 | 4/1983 | Regel et al. | 424/269 |
| 4,480,114 | 10/1984 | Regel | 549/563 |
| 4,816,463 | 3/1989 | Blankley | 514/293 |
| 4,880,804 | 11/1989 | Carini et al. | 514/381 |

FOREIGN PATENT DOCUMENTS

| | | |
|---|---|---|
| 253310 | 1/1988 | European Pat. Off. . |
| 323841 | 7/1989 | European Pat. Off. . |

OTHER PUBLICATIONS

P. C. Wong et al, *J. Pharmacol. Exp. Ther.*, 247(1), 1–7.
A. T. Chiu et al, *European J. Pharmacol.*, 157, 3121 (1988).
A. T. Chiu et al, *J. Pharmacol. Exp. Ther.*, 250(3), 867–8 (1989).

*Primary Examiner*—David B. Springer
*Attorney, Agent, or Firm*—J. Timothy Keane; Paul D. Matukaitis

[57] ABSTRACT

A class of 1H-substituted-1,2,4-triazole compounds is described for use in treatment of cardiovascular disorders. Compounds of particular interest are angiotensin II antagonists of the formula

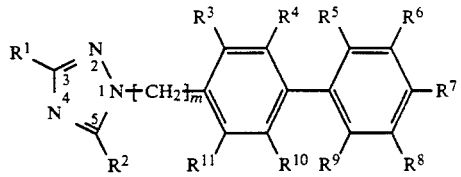

wherein $R^1$ is selected from hydroxy, methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxy-butyl, 1,1-dimethoxypentyl, hydroxyalkyl, halo, difluoro-methyl, 1,1-difluoroethyl, 1,1-difluoropropyl, 1,1-di-fluorobotyl and 1,1-difluoropentyl; wherein $R^2$ is selected from ethyl, n-propyl, isopropyl, n-butyl, sec-butyl, isobutyl, 4-methylbutyl, tert-butyl, n-pentyl and neo-pentyl; wherein each of $R^3$ through $R^{11}$ is hydrido with the provision that at least one of $R^5$ and $R^9$ must be selected from COOH, SH, $PO_3H_2$, $SO_3H$, $CONHNH_2$, $CONHNHSO_2CF_3$, OH,

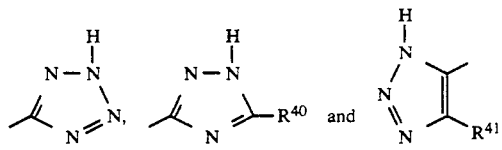

wherein each of $R^{40}$ and $R^{41}$ is independently selected from chloro, cyano, nitro, trifluoromethyl, methoxycarbonyl and trifluoromethylsulfonyl. These compounds are particularly useful in treatment or control of hypertension and congestive heart failure.

18 Claims, No Drawings

1H-SUBSTITUTED-1,2,4-TRIAZOLE COMPOUNDS AND METHODS OF USE THEREOF FOR TREATMENT OF CARDIOVASCULAR DISORDERS

FIELD OF THE INVENTION

Non-peptidic 1H-substituted-1,2,4-triazole compounds are described for use in treatment of cardiovascular disorders such as hypertension and congestive heart failure. Of particular interest are angiotensin II antagonist compounds provided by 1,2,4-triazoles having a biphenylmethyl moiety attached to the nitrogen atom at the one-position of the 1,2,4-triazole.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247(1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 3121 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenyl-methyl substituted imidazoles, as antagonists to the angiotensin II receptor. EP No. 323,841 published 12 July 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of 1,2,4-triazole compounds having substituents attached to the nitrogen atom at the one-position of the 1H-triazole. For example, U.S. Pat. No. 4,118,487 to Regel et al describes a family azol-1-ylmethane compounds for use as antimycotic and antibacterial agents including, specifically, the compound (1-biphenyl-4-yl-1-phenyl)methyl-1H-1,2,4-triazole. U.S. Pat. No. 4,381,306 to Regel et al describes a family of hydroxpropyl-triazole compounds for use as antimycotic agents including, specifically, the compound (1,2,4-triazol-1-yl)methyl-4-chlorobenzyl-biphenyl-4-ylcarbinol. U.S. Pat. No. 4,480,114 to Regel describes a family of 2-(4-biphenyl)-2-(halophenyl)-oxirane compounds having antimycotic activity including, specifically, the compound (1,2,4-triazol-1-yl)methyl-4-chlorophenyl-4-chlorobiphenyl-4-yl carbinol.

DESCRIPTION OF THE INVENTION

A class of 1H-substituted-1,2,4-triazole compounds useful in treating circulatory and cardiovascular disorders is defined by Formula I:

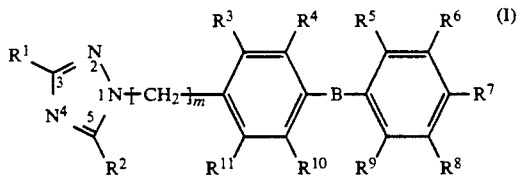

wherein m is a number selected from one to four, inclusive;

wherein each of $R^1$ through $R^{11}$ is independently selected from hydrido, hydroxy, alkyl, hydroxyalkyl, halo, difluoroalkyl, cycloalkyl, cycloalkylalkyl, formyl, alkoxy, aralkyl, aryl, aroyl, aryloxy, aralkoxy, alkoxyalkyl, alkylcarbonyl, alkylcarbonylalkyl, alkoxycarbonyl, alkenyl, cycloalkenyl, alkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

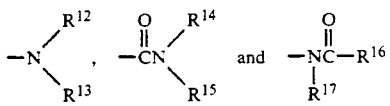

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together, $R^{14}$ and $R^{15}$ taken together and $R^{16}$ and $R^{17}$ taken together may form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together and each of $R^{14}$ and $R^{15}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydrido and haloalkyl, and from acidic moieties of the formula $-Y_n A$ wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

wherein B is a single bond connecting the phenyl rings to form a biphenyl moiety or B is a group selected from

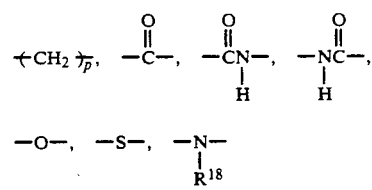

and $-CH=CH-$, wherein p is a number selected from one through three, inclusive; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl; and wherein any of the foregoing $R^1$ through $R^{18}$, Y, A and B groups having a substitutable position may be substituted by one or more groups selected from hydroxy, alkyl, alkenyl, alkynyl, aralkyl, hydroxyalkyl, trifluoromethyl, oxo, difluoroalkyl, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, carboxyl, mercapto, mercaptocarbonyl, alkylthio, arylthio, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

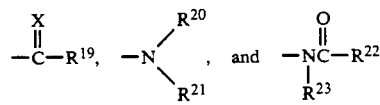

wherein X is selected from oxygen atom and sulfur atom;

wherein $R^{19}$ is selected from hydrido, alkyl, cycloalkyl, cycloalkylalkyl, aralkyl, aryl, $DR^{24}$ and

wherein D is selected from oxygen atom and sulfur atom and $R^{24}$ is selected from hydrido, alkyl, cycloalkyl, cycloalkylalkyl, aralkyl and aryl; wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{20}$, $R^{21}$, $R^{22}$, $R^{23}$ $R^{25}$ and $R^{26}$ is further independently selected from amino and amido radicals of the formula

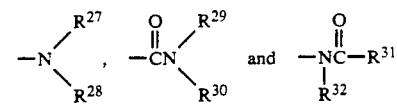

wherein each of $R^{27}$, $R^{28}$, $R^{29}$, $R^{30}$ $R^{31}$ and $R^{32}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl, and wherein $R^{20}$ and $R^{21}$ taken together and each of $R^{22}$ and $R^{23}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{20}$ and $R^{21}$ taken together and each of $R^{25}$ and $R^{26}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

Compounds of Formula I would be useful in treating a variety of circulatory disorders including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

Preferred compounds of Formula I are all characterized in having a substituent, other than hydrido, at each of the three- and five-positions of the triazole ring. Such substituents are selected from the aforementioned $R^1$ and $R^2$ groups. Compounds having alkyl groups, especially lower alkyl groups, at both of the $R^1$ and $R^2$ positions are particularly useful as angiotensin II antagonists. Also especially useful are compounds having one of the $R^1$ and $R^2$ substituents selected from alkylcarbonyl, monoalkoxyalkyl, dialkoxyalkyl and difluoroalkyl groups. When the selected substituent for $R^1$ and $R^2$ is difluoroalkyl, then it is particularly useful for both of the fluoro atoms of the difluoroalkyl group to be substituted on the difluoroalkyl group carbon atom attached at the $R^1$ or $R^2$ positions of the triazole ring. Such difluoroalkyl group may be characterized as an "alpha-carbon difluoro-substituted difluoroalkyl group", or as an "alpha,alpha-difluoro-substituted alkyl group". When the selected substituent for $R^1$ or $R^2$ is monoalkoxyalkyl or dialkoxyalkyl, then it is particularly useful for the single alkoxy group or the two alkoxy groups, respectively, substituent which is attached at the $R^1$ or $R^2$ positions of the triazole ring. Such alkoxyalkyl groups may be characterized as "alpha-carbon monoalkoxy- or dialkoxy-substituted alkoxyalkyl groups", respectively, or "alpha-monoalkoxy-substituted or alpha,alpha-dialkoxy-substituted alkyl groups", respectively. When the selected substituent is alkylcarbonyl, then it is particularly useful for the carbonyl group to be attached at the $R^1$ or $R^2$ positions of the triazole ring. Such alkylcarbonyl group may be characterized as an "alpha-oxo-substituted alkyl group", and may be exemplified by the substituents 1-oxoethyl, 1-oxopropyl and 1-oxobutyl. Where compounds of Formula I contain any of these above-mentioned particularly-useful alpha-carbon substituted $R^1$ or $R^2$ groups at the triazole ring three- or five-position, it is preferred that such particularly-useful group be attached at the three-position, that is, as an $R^1$ substituent.

The phrase "acidic group selected to contain at least one acidic hydrogen atom", as used to define the $-Y_nA$ moiety, is intended to embrace chemical groups which, when attached to any of the $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $pK_a$ in a range from about one to about twelve. More typically, the Formula I compound would have a $pK_a$ in a range from about two to about seven. An example of an acidic group containing at least one acidic hydrogen atom is carboxyl group (—COOH). Where n is zero and A is —COOH, in the $-Y_nA$ moiety, such carboxyl group would be attached directly to one of the $R^3$ through $R^{11}$ positions. The Formula I compound may have one $-Y_nA$ moiety attached at one of the $R^3$ through $R^{11}$ positions, or may have a plurality of such $-Y_nA$ moieties attached at more than one of the $R^3$ through $R^{11}$ positions, up to a maximum of nine such $-Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the $-Y_nA$ moiety attached at one of positions $R^5$, $R^6$, $R^8$ and $R^9$ would be expected to have preferred properties, while attachment at $R^5$ or $R^9$ would be more preferred.

A preferred class of compounds consists of those compounds of Formula I wherein m is one; wherein each of $R^1$ through $R^{11}$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms and amino and amido radicals of the formula

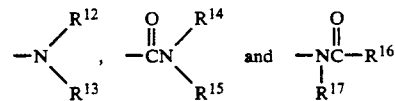

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydrido and haloalkyl, and from acidic moieties of the formula $-Y_nA$ wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

wherein B is a single bond or is a group selected from

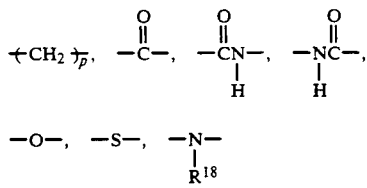

and —CH=CH—, wherein p is one or two; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl; and wherein any of the foregoing $R^1$ through $R^{18}$, Y, A and B groups having a substitutable position may be substituted by one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

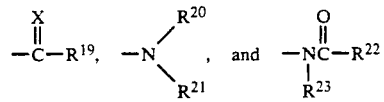

wherein X is selected from oxygen atom and sulfur atom; wherein $R^{19}$ is selected from hydrido, alkyl, cycloalkyl, cycloalkylalkyl, aralkyl, aryl, and $DR^{24}$ and

wherein D is selected from oxygen atom and sulfur atom, and $R^{24}$ is selected from hydrido, alkyl, cycloalkyl, cycloalkylalkyl, aralkyl and aryl; wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl, and wherein each of $R^{20}$, $R^{21}$, $R^{22}$, $R^{23}$, $R^{25}$, and $R^{26}$ is further independently selected from amino and amido radicals of the formula

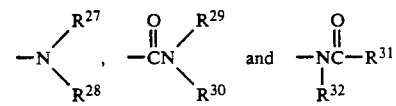

wherein each of $R^{27}$, $R^{28}$, $R^{29}$, $R^{30}$, $R^{31}$ and $R^{32}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl;

or a tautomer thereof or a pharmaceutically-acceptable salt thereof.

A more preferred class of compounds consists of those compounds of Formula I wherein m is one; wherein each of $R^1$ through $R^{11}$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, alkoxycarbonyloxy, alkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms; and amino and amido radicals of the formula

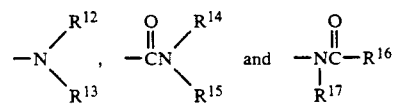

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be an acidic moiety further independently selected from hydrido and haloalkyl, and from acidic moieties of the formula

wherein n is a number selected from zero through three, inclusive;

wherein A is selected from carboxylic acid and bioisosteres of carboxylic acid selected from

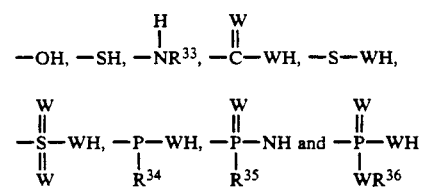

wherein each W is independently selected from oxygen atom, sulfur atom and $NR^{37}$; wherein each of $R^{33}$, $R^{34}$, $R^{35}$, $R^{36}$ and $R^{37}$ is independently selected from hydrido, alkyl, haloalkyl, haloalkylsulfonyl, haloalkylcarbonyl, cycloalkyl, cycloalkylalkyl, aryl and aralkyl; wherein each of $R^{33}$, $R^{34}$, $R^{35}$ and $R^{36}$ may be further independently selected from amino radical of the formula

wherein each of $R^{38}$ and $R^{39}$ is independently selected from hydrido, alkyl, cycloalkyl, hydroxyalkyl, haloalkyl, cycloalkylalkyl, alkoxyalkyl, aralkyl and aryl, and wherein $R^{38}$ and $R^{39}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{38}$ and $R^{39}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{34}$ and $R^{35}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein B is a single bond or is a group selected from

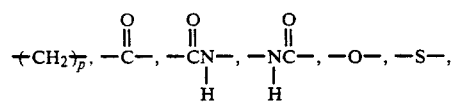

and —CH=CH—, wherein p is a number selected from one through three, inclusive; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl; and wherein any of the foregoing $R^1$ through $R^{18}$, Y, A and B groups having a substitutable position may be substituted by one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

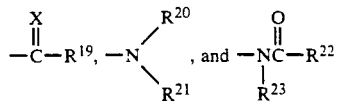

wherein X is selected from oxygen atom and sulfur atom; wherein $R^{19}$ is selected from hydrido, alkyl, cycloalkyl, cycloalkylalkyl, aralkyl, aryl and $DR^{24}$ and

wherein D is selected from oxygen atom and sulfur atom, wherein $R^{24}$ is selected from hydrido, alkyl, cycloalkyl, cycloalkylalkyl, aralkyl and aryl;

wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds consists of those compounds of Formula I wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, alkoxycarbonyloxy, alkylthio, arylthio, aralkylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

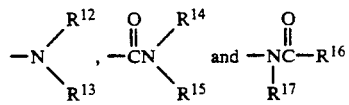

wherein each of $R^{12}$, $R^{13}$, $R^{14}$, $R^{15}$, $R^{16}$ and $R^{17}$ independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylthio, aralkylthio, mercapto, alkylsulfinyl, alkylsulfonyl, aralkylsulfinyl, aralkylsulfonyl, arylsulfinyl, arylsulfonyl and heteroaryl having one or more ring atoms selected from oxygen, sulfur and nitrogen atoms;

and wherein each of $R^3$ through $R^{11}$ may be an acidic moiety further independently selected from acidic moieties of the formula $$-Y_nA$$

wherein n is a number selected from zero through three, inclusive; wherein A is selected from carboxylic acid and bioisosteres of carboxylic acid selected from

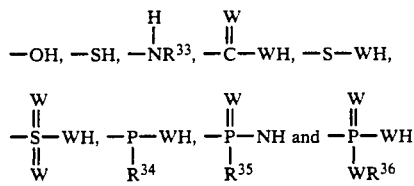

wherein each W is independently selected from oxygen atom, sulfur atom and $NR^{37}$; wherein each of $R^{33}$, $R^{36}$ and $R^{37}$ is independently selected from hydrido, alkyl, haloalkyl, haloalkylsulfonyl, haloalkylcarbonyl, cycloalkyl, cycloalkylalkyl, aryl and aralkyl; wherein each of $R^{33}$ and $R^{36}$ may be further independently selected from amino radical of the formula

wherein each of $R^{38}$ and $R^{39}$ is independently selected from hydrido, alkyl, cycloalkyl, hydroxyalkyl, haloalkyl, cycloalkylalkyl, alkoxyalkyl, aralkyl and aryl, and wherein $R^{38}$ and $R^{39}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{38}$ and $R^{39}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;
wherein B is a single bond or is a group selected from

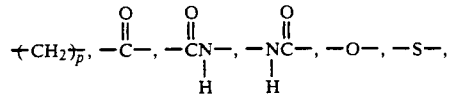

and —CH=CH—, is one or two; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl; wherein each of $R^1$ through $R^{11}$, Y, A and B independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds consists of those compounds wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, benzoyl, phenoxy, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, heteroaryl having one or more ring atoms selected from oxygen, sulfur and nitrogen atoms; and amino and amido radicals of the formula

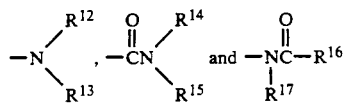

wherein each of $R^{12}$, $R^{13}$, $R^{14}$, $R^{15}$, $R^{16}$ and $R^{17}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio, mercapto and heteroaryl having one or more ring atoms selected from oxygen, sulfur and nitrogen atoms;

and wherein each of $R^3$ through $R^{11}$ may be an acidic moiety further independently selected from acidic moieties of the formula $$-Y_nA$$

wherein n is a number selected from zero through two, inclusive; wherein A is selected from carboxylic acid and bioisosteres of carboxylic acid selected from

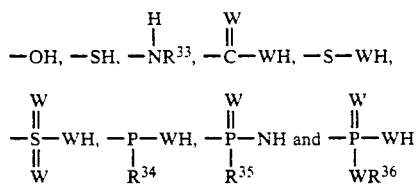

wherein each W is independently selected from oxygen atom, sulfur atom and $NR^{37}$; wherein each of $R^{33}$, $R^{36}$ and $R^{37}$ is independently selected from hydrido, alkyl, haloalkyl, haloalkylsulfonyl, haloalkylcarbonyl, cycloalkyl, phenyl and benzyl; wherein each of $R^{33}$ and $R^{36}$ may be further independently selected from amino radical of the formula

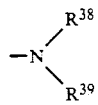

wherein each of $R^{38}$ and $R^{39}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein B is a single bond or is a group selected from

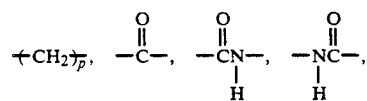

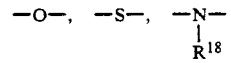

and $-CH=CH-$, wherein p is one; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl;

wherein each of $R^1$ through $R^{11}$, Y, A and B and independently may be substituted at any substitutable position with one or more groups selected from alkyl, cycloalkyl, cycloalkylalkyl, hydroxy, oxo, trifluoromethyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

An even more highly preferred class of compounds consists of those compounds of Formula I wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, benzoyl, phenoxy, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, and amino and amido radicals of the formula

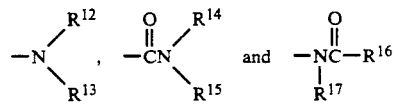

wherein each of $R^{12}$, $R^{13}$, $R^{14}$, $R^{15}$, $R^{16}$ and $R^{17}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, acetyl, alkoxycarbonyl, alkenyl, cyano, nitro, carboxyl, alkylthio and mercapto;

and wherein each of $R^3$ through $R^{11}$ may be an acidic moiety further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$ and heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups; wherein B is a single bond or is a group selected from

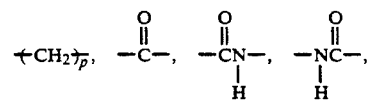

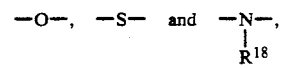

wherein p is one; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl;

or a tautomer thereof or a pharmaceutically-acceptable salt thereof.

A class of compounds of particular interest consists of those compounds of Formula I wherein m is one; wherein each of $R^1$ and $R^2$ is independently selected from hydroxy, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

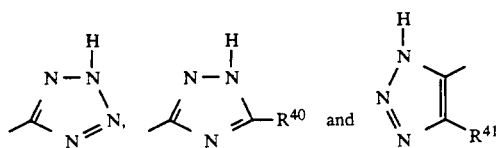

wherein each of $R^{40}$ and $R^{41}$ is independently selected from Cl, CN, $NO_2$, $CF_3$, $CO_2CH_3$ and $SO_2CF_3$; wherein B is a single bond or is a group selected from

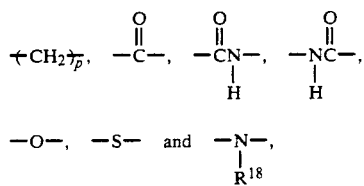

wherein p is one; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl;

or a tautomer thereof or a pharmaceutically-acceptable salt thereof.

A class of compounds of more particular interest consists of those compounds of Formula I wherein m is one; wherein $R^1$ is selected from hydroxy, methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein $R^2$ is selected from ethyl, n-propyl, isopropyl, n-butyl, sec-butyl, isobutyl, 4-methylbutyl, tert-butyl, n-pentyl and neopentyl; wherein at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

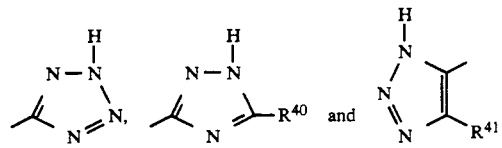

wherein each of $R^{40}$ and $R^{41}$ is independently selected from Cl, CN, $NO_2$, $CF_3$, $CO_2CH_3$ and $SO_2CF_3$; wherein B is a single bond or is a group selected from

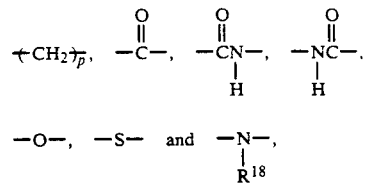

wherein p is one; wherein $R^{18}$ is selected from hydrido, alkyl, aryl, formyl, alkylcarbonyl, arylcarbonyl, carboxyl, alkoxycarbonyl, aryloxycarbonyl and aralkoxycarbonyl;

or a tautomer thereof or a pharmaceutically-acceptable salt thereof. Of even more particular interest are compounds wherein at least one of $R^5$ and $R^9$ is selected from the acidic groups specified for this class of compounds of more particular interest.

A sub-class of compounds within Formula I, consisting of biphenylmethyl 1H-substituted-1,2,4-triazole compounds useful in treating circulatory and cardiovascular disorders, is defined by Formula II:

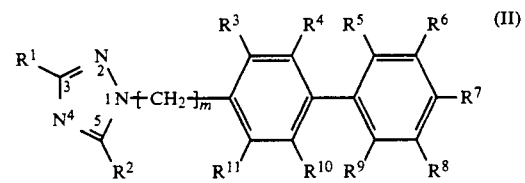

wherein m is a number selected from one to four, inclusive;

wherein each of $R^1$ through $R^{11}$ is independently selected from hydrido, hydroxy, alkyl, hydroxyalkyl, halo, difluoroalkyl, perfluoroalkyl, cycloalkyl, cycloalkylalkyl, formyl, alkoxy, aralkyl, aryl, aroyl, aryloxy, aralkoxy, alkoxyalkyl, alkylcarbonyl, alkylcarbonylalkyl, alkoxycarbonyl, alkenyl, cycloalkenyl, alkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiothiocarbonyl, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

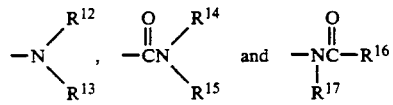

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together, $R^{14}$ and $R^{15}$ taken together and $R^{16}$ and $R^{17}$ taken together may form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together and each of $R^{14}$ and $R^{15}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydrido and haloalkyl, and from acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties;

wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{17}$, Y and A groups having a substitutable position may be substituted by one or more groups selected from hydroxy, alkyl, alkenyl, alkynyl, aralkyl, hydroxyalkyl, trifluoromethyl, difluoroalkyl, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, carboxyl, mercapto, mercaptocarbonyl, alkylthio, arylthio, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

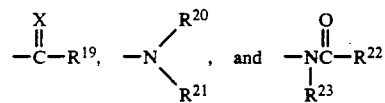

wherein X is selected from oxygen atom and sulfur atom; wherein $R^{19}$ is selected from hydrido, alkyl, cycloalkyl, cycloalkylalkyl, aralkyl, aryl, $DR^{24}$ and

wherein D is selected from oxygen atom and sulfur atom and $R^{24}$ is selected from hydrido, alkyl, cycloalkyl, cycloalkylalkyl, aralkyl and aryl; wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{20}$, $R^{21}$, $R^{22}$, $R^{23}$, $R^{25}$ and $R^{26}$ is further independently selected from amino and amido radicals of the formula

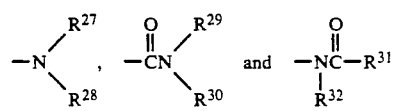

wherein each of $R^{27}$, $R^{28}$, $R^{29}$, $R^{30}$, $R^{31}$ and $R^{32}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl, and wherein each of $R^{20}$ and $R^{21}$ taken together and each of $R^{22}$ and $R^{23}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{20}$ and $R^{21}$ taken together and each of $R^{25}$ and $R^{26}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

Compounds of Formula II are all characterized in having a substituent, other than hydrido, at each of the three- and five-positions of the triazole ring. Such substituents are selected from the aforementioned $R^1$ and $R^2$ groups. Compounds having alkyl groups, especially lower alkyl groups, at both of the $R^1$ and $R^2$ positions are particularly useful as angiotensin II antagonists. Also especially useful are compounds having one of the $R^1$ and $R^2$ substituents selected from alkylcarbonyl, monoalkoxyalkyl, dialkoxyalkyl and difluoroalkyl groups. When the selected substituent for $R^1$ and $R^2$ is difluoroalkyl, then it is particularly useful for both of the fluoro atoms of the difluoroalkyl group to be substituted on the difluoroalkyl group carbon atom attached at the $R^1$ or $R^2$ positions of the triazole ring. Such difluoroalkyl group may be characterized as an "alpha-carbon difluoro-substituted difluoroalkyl group", or as an "alpha,alpha-difluoro-substituted alkyl group". When the selected substituent for $R^1$ or $R^2$ is monoalkoxyalkyl or dialkoxyalkyl, then it is particularly useful for the single alkoxy group or the two alkoxy groups, respectively, to be substituted on the carbon atom of the selected substituent which is attached at the $R^1$ or $R^2$ positions of the triazole ring. Such alkoxyalkyl groups may be characterized as "alpha-carbon monoalkoxy- or dialkoxy-substituted alkoxyalkyl groups", respectively, or "alpha-monoalkoxy-substituted or alpha,alpha-dialkoxy-substituted alkyl groups", respectively. When the selected substituent is alkylcarbonyl, then it is particularly useful for the carbonyl group to be attached at the $R^1$ or $R^2$ positions of the triazole ring. Such alkylcarbonyl group may be characterized as an "alpha-oxo-substituted alkyl group", and may be exemplified by the substituents 1-oxoethyl, 1-oxopropyl and 1-oxobutyl. Where compounds of Formula II contain any of these above-mentioned particularly-useful alpha-carbon substituted $R^1$ or $R^2$ groups at the triazole ring three- or five-position, it is preferred that such particularly-useful group be attached at the three-position, that is, as an $R^1$ substituent.

As described above for the Formula I compounds, the Formula II compounds may have one $-Y_nA$ moiety attached at one of the $R^3$ through $R^{11}$ positions of the biphenyl moiety, or may have a plurality of such $-Y_nA$ moieties attached at more than one of the $R^3$ through $R^{11}$ positions, up to a maximum of nine such $-Y_nA$ moieties. Compounds of Formula II having the $-Y_nA$ moiety attached at one of positions $R^5$, $R^6$, $R^8$ and $R^9$ of the biphenyl moiety of Formula II would be expected to have preferred properties, while attachment at $R^5$ or $R^9$ would be more preferred.

A preferred class of compounds within the sub-class defined by Formula II consists of those compounds wherein m is one; wherein each of $R^1$ through $R^{11}$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms and amino and amido radicals of the formula

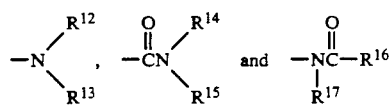

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
and wherein each of $R^3$ through $R^{11}$ may be further independently selected from hydrido and haloalkyl, and from acidic moieties of the formula $-Y_nA$ wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;
and wherein any of the foregoing $R^1$ through $R^{17}$, Y and A groups having a substitutable position may be substituted by one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

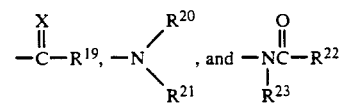

wherein X is selected from oxygen atom and sulfur atom; wherein $R^{19}$ is selected from hydrido, alkyl, cycloalkyl, cycloalkylalkyl, aralkyl, aryl, and $DR^{24}$ and

wherein D is selected from oxygen atom and sulfur atom, and $R^{24}$ is selected from hydrido, alkyl, cycloalkyl, cycloalkylalkyl, aralkyl and aryl; wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl, and wherein each of $R^{20}$, $R^{21}$, $R^{22}$, $R^{23}$, $R^{25}$, and $R^{26}$ is further independently selected from amino and amido radicals of the formula

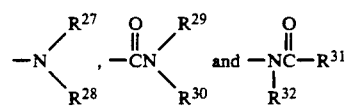

wherein each of $R^{27}$, $R^{28}$, $R^{29}$, $R^{30}$, $R^{31}$ and $R^{32}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl;
or a tautomer thereof or a pharmaceutically-acceptable salt thereof.

A more preferred class of compounds within the sub-class defined by Formula II consists of those compounds wherein m is one; wherein each of $R^1$ through $R^{11}$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, alkoxycarbonyloxy, alkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms; and amino and amido radicals of the formula

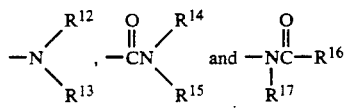

wherein each of $R^{12}$, $R^{13}$, $R^{14}$, $R^{15}$, $R^{16}$ and $R^{17}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be an acidic moiety further independently selected from hydrido and haloalkyl, and from acidic moieties of the formula $$-Y_nA$$

wherein n is a number selected from zero through three, inclusive;

wherein A is selected from carboxylic acid and bioisosteres of carboxylic acid selected from

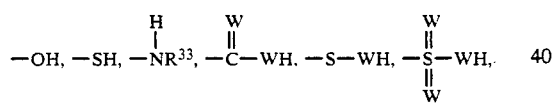

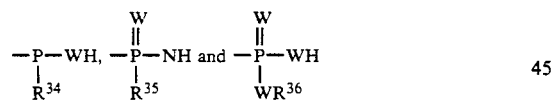

wherein each W is independently selected from oxygen atom, sulfur atom and $NR^{37}$; wherein each of $R^{33}$, $R^{34}$, $R^{35}$, $R^{36}$ and $R^{37}$ is independently selected from hydrido, alkyl, haloalkyl, haloalkylsulfonyl, haloalkylcarbonyl, cycloalkyl, cycloalkylalkyl, aryl and aralkyl; wherein each of $R^{33}$, $R^{34}$, $R^{35}$ and $R^{36}$ may be further independently selected from amino radical of the formula

wherein each of $R^{38}$ and $R^{39}$ is independently selected from hydrido, alkyl, cycloalkyl, hydroxyalkyl, haloalkyl, cycloalkylalkyl, alkoxyalkyl, aralkyl and aryl, and wherein $R^{38}$ and $R^{39}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{38}$ and $R^{39}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{34}$ and $R^{35}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula II; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^1$ through $R^{17}$, Y and A groups having a substitutable position may be substituted by one or more groups selected from alkyl, difluoroalkyl, alkenyl, aralkyl, hydroxyalkyl, trifluoromethyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

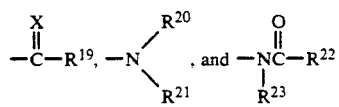

wherein X is selected from oxygen atom and sulfur atom; wherein $R^{19}$ is selected from hydrido, alkyl, cycloalkyl, cycloalkylalkyl, aralkyl, aryl and $DR^{24}$ and

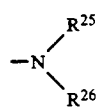

wherein D is selected from oxygen atom and sulfur atom, wherein $R^{24}$ is selected from hydrido, alkyl, cycloalkyl, cycloalkylalkyl, aralkyl and aryl;

wherein each of $R^{20}$, $R^{21}$, $R^{22}$, $R^{23}$, $R^{25}$ and $R^{26}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds within the sub-class defined by Formula II consists of those compounds wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, alkoxycarbonyloxy, alkylthio, arylthio, aralkylthio, mercapto, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

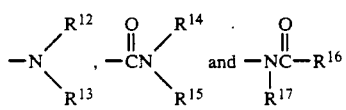

wherein each of $R^{12}$, $R^{13}$, $R^{14}$, $R^{15}$, $R^{16}$ and $R^{17}$ independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylthio, aralkylthio, mercapto, alkylsulfinyl, alkylsulfonyl, aralkylsulfinyl, aralkylsulfonyl, arylsulfinyl, arylsulfonyl and heteroaryl having one or more ring atoms selected from oxygen, sulfur and nitrogen atoms; and wherein each of $R^3$ through $R^{11}$ may be an acidic moiety further independently selected from acidic moieties of the formula $$-Y_n A$$

wherein n is a number selected from zero through three, inclusive; wherein A is selected from carboxylic acid and bioisosteres of carboxylic acid selected from $$-OH, -SH, -NR^{33}, -\overset{H}{\underset{|}{C}}-WH, -S-WH,$$

$$-\overset{W}{\underset{W}{\overset{\|}{S}}}-WH \text{ and } -\overset{W}{\underset{WR^{36}}{\overset{\|}{P}}}-WH$$

wherein each W is independently selected from oxygen atom, sulfur atom and $NR^{37}$; wherein each of $R^{33}$, $R^{36}$ and $R^{37}$ is independently selected from hydrido, alkyl, haloalkyl, haloalkylsulfonyl, haloalkylcarbonyl, cycloalkyl, cycloalkylalkyl, aryl and aralkyl; wherein each of $R^{33}$ and $R^{36}$ may be further independently selected from amino radical of the formula

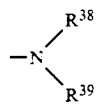

wherein each of $R^{38}$ and $R^{39}$ is independently selected from hydrido, alkyl, cycloalkyl, hydroxyalkyl, haloalkyl, cycloalkylalkyl, alkoxyalkyl, aralkyl and aryl, and wherein $R^{38}$ and $R^{39}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{38}$ and $R^{39}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^1$ through $R^{11}$, Y and A independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds within the sub-class defined by Formula II consists of those compounds wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, benzoyl, phenoxy, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, heteroaryl having one or more ring atoms selected from oxygen, sulfur and nitrogen atoms; and amino and amido radicals of the formula

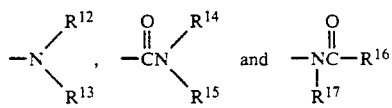

wherein each of $R^{12}$, $R^{13}$, $R^{14}$, $R^{15}$, $R^{16}$ and $R^{17}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio, mercapto and heteroaryl having one or more ring atoms selected from oxygen, sulfur and nitrogen atoms;

and wherein each of $R^3$ through $R^{11}$ may be an acidic moiety further independently selected from acidic moieties of the formula $-Y_nA$ wherein n is a number selected from zero through two, inclusive; wherein A is selected from carboxylic acid and bioisosteres of carboxylic acid selected from

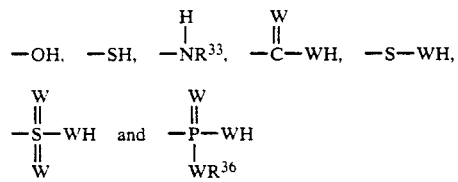

wherein each W is independently selected from oxygen atom, sulfur atom and $NR^{37}$; wherein each of $R^{33}$, $R^{36}$ and $R^{37}$ is independently selected from hydrido, alkyl, haloalkyl, haloalkylsulfonyl, haloalkylcarbonyl, cycloalkyl, phenyl and benzyl; wherein each of $R^{33}$ and $R^{36}$ may be further independently selected from amino radical of the formula

wherein each of $R^{38}$ and $R^{39}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula II; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein each of $R^1$ through $R^{11}$, Y and A and independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

An even more highly preferred class of compounds within the sub-class defined by Formula II consists of those compounds wherein m is one; wherein each of $R^1$ and $R^2$ is independently selected from hydroxy, alkyl, hydroxyalkyl, halo, difluoroalkyl, cycloalkyl, cycloalkylalkyl, alkoxy, aralkyl, aryl, benzoyl, phenoxy, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, and amino and amido radicals of the formula

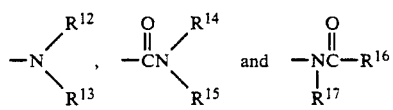

wherein each of $R^{12}$, $R^{13}$, $R^{14}$, $R^{15}$, $R^{16}$ and $R^{17}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, acetyl, alkoxycarbonyl, alkenyl, cyano, nitro, carboxyl, alkylthio and mercapto;

and wherein each of $R^3$ through $R^{11}$ may be an acidic moiety further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

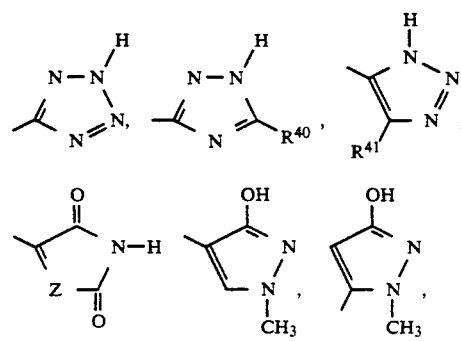

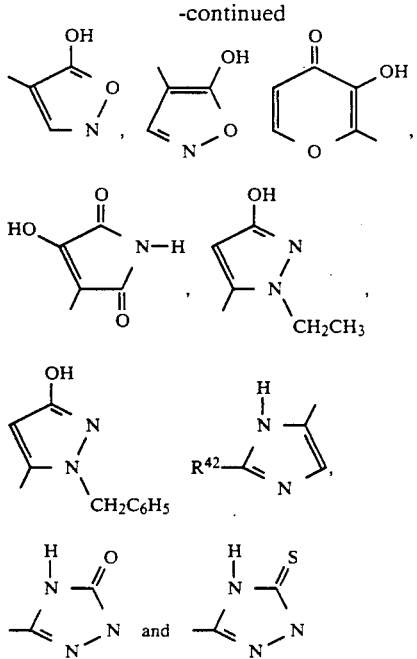

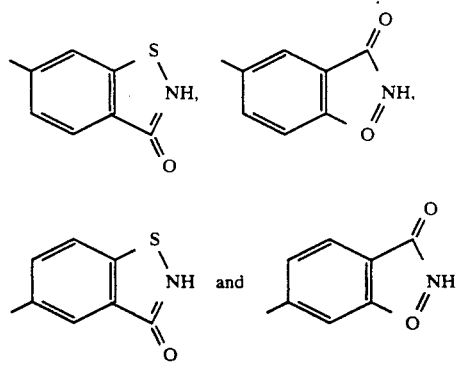

and the esters, amides and salts of said acidic moieties.

A class of compounds of particular interest within the sub-class defined by Formula II consists of those compounds wherein m is one; wherein each of $R^1$ and $R^2$ is independently selected from hydroxy, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

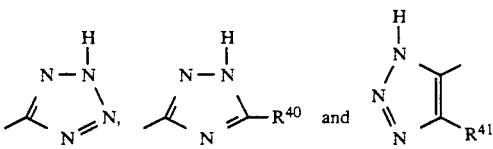

wherein each of $R^{40}$ and $R^{41}$ is independently selected from Cl, CN, $NO_2$, $CF_3$, $CO_2CH_3$ and $SO_2CF_3$.

A class of compounds of more particular interest within the sub-class defined by Formula II consists of those compounds wherein m is one; wherein $R^1$ is selected from hydroxy, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein $R^2$ is selected from ethyl, n-propyl, isopropyl, n-butyl, sec-butyl, isobutyl, 4-methylbutyl, tert-butyl, n-pentyl and neopentyl; wherein at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

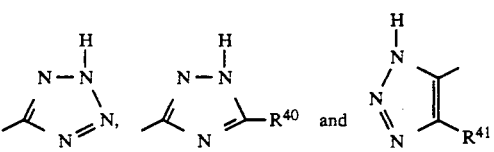

wherein each of $R^{40}$ and $R^{41}$ is independently selected from Cl, CN, $NO_2$, $CF_3$, $CO_2CH_3$ and $SO_2CF_3$. A class of compounds of even more particular interest within the sub-class defined by Formula II consists of those compounds wherein at least one of $R^5$ and $R^9$ is selected from the acidic groups selectable for the compounds of more particular interest.

The term "hydrido" denotes a single hydrogen atom (H) which may be attached, for example, to a carbon atom to form a hydrocarbyl group or attached to an oxygen atom to form an hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atomms. The term "cycloalkyl" embraces cyclic radicals having three to about ten ring carbon atoms, preferably three to about six carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. Preferably, when the difluoroalkyl group is attached at the triazole ring $R^1$ and $R^2$ positions of Formula I and II, the two fluoro atoms are substituted on the carbon atom which is attached directly to the triazole ring. Such preferred difluoroalkyl group may be characterized as an "alpha-carbon difluoro-substituted difluoroalkyl group". The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

Included within the family of compounds of Formula I are the tautomeric forms of the described compounds, diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxy butyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

A family of specific compounds of particular interest within Formula I, and more specifically within Formula II, consists of the following compounds:

4'-[(3,5-dibutyl-1H-1,2,4-triazol-1-yl)methyl][1,1'-biphenyl]-2-carboxylic acid, hydrazide;
4'-[(3,5-dibutyl-1H-1,2,4-triazol-1-yl)methyl][1,1'-biphenyl]-2-carboxylic acid, 2-[(trifluoromethyl)sulfonyl]hydrazide;
4'-[(5-butyl-3-chloro-1H-1,2,4-triazol-1-yl)methyl][1,1'-biphenyl]-2-carboxylic acid;
4'-[(3-butyl-5-chloro-1H-1,2,4-triazol-1-yl)methyl][1,1'-biphenyl]-2-carboxylic acid;
4'-[(5-butyl-3-ethyl-1H-1,2,4-triazol-1-yl)methyl][1,1'-biphenyl]-2-carboxylic acid;
4'-[(5-butyl-3-propyl-1H-1,2,4-triazol-1-yl)methyl][1,1'-biphenyl]-2-carboxylic acid;
4'-[(5-butyl-3-isopropyl-1H-1,2,4-triazol-1-yl)methyl][1,1'-biphenyl]-2-carboxylic acid; methyl 4'-[(3,5-dibutyl-1H-1,2,4-triazol-1-yl)methyl][1,1'-biphenyl]-2-carboxylate;
4'-[(3,5-dibutyl-1H-1,2,4-triazol-1-yl)methyl][1,1'-biphenyl]-2-carboxylic acid;
4'-[(5-butyl-3-secbutyl-1H-1,2,4-triazol-1-yl)methyl][1,1'-biphenyl]-2-carboxylic acid;
4'-[(5-butyl-3-isobutyl-1H-1,2,4-triazol-1-yl)methyl][1,1'-biphenyl]-2-carboxylic acid;
4'-[(5-butyl-3-tertbutyl-1H-1,2,4-triazol-1-yl)methyl][1,1'-biphenyl]-2-carboxylic acid;
4'-[(5-butyl-3-pentyl-1H-1,2,4-triazol-1-yl)methyl][1,1'-biphenyl]-2-carboxylic acid;
4'-[(5-butyl-3-isopentyl-1H-1,2,4-triazol-1-yl)methyl][1,1'-biphenyl]-2-carboxylic acid;
4'-[(5-butyl-3-mercapto-1H-1,2,4-triazol-1-yl)methyl][1,1'-biphenyl]-2-carboxylic acid;
4'-[(5-butyl-3-thiomethyl-1H-1,2,4-triazol-1-yl)methyl][1,1'-biphenyl]-2-carboxylic acid;
4'-[(5-butyl-3-thioethyl-1H-1,2,4-triazol-1-yl)methyl][1,1'-biphenyl]-2-carboxylic acid;
4'-[(5-butyl-3-thiopropyl-1H-1,2,4-triazol-1-yl)methyl][1,1'-biphenyl]-2-carboxylic acid;
4'-[(5-butyl-3-hydroxy-1H-1,2,4-triazol-1-yl)methyl][1,1'-biphenyl]-2-carboxylic acid;
4'-[(5-butyl-3-methoxy-1H-1,2,4-triazol-1-yl)methyl][1,1'-biphenyl]-2-carboxylic acid;
4'-[(5-butyl-3-ethoxy-1H-1,2,4-triazol-1-yl)methyl][1,1'-biphenyl]-2-carboxylic acid;
4'-[(5-butyl-3-propoxy-1H-1,2,4-triazol-1-yl)methyl][1,1'-biphenyl]-2-carboxylic acid;
4'-[(5-butyl-3-butoxy-1H-1,2,4-triazol-1-yl)methyl][1,1'-biphenyl]-2-carboxylic acid;
4'-[(5-butyl-3-cyclohexyl-1H-1,2,4-triazol-1-yl)methyl][1,1'-biphenyl]-2-carboxylic acid;
4'-[(5-butyl-3-cyclohexylmethyl-1H-1,2,4-triazol-1-yl)methyl][1,1'-biphenyl]-2-carboxylic acid;
4'-[[5-butyl-3-(2-cyclohexylethyl))-1H-1,2,4-triazol-1-yl]methyl][1,1'-biphenyl]-2-carboxylic acid;
4'-[(5-butyl-3-cyclohexanoyl-1,2,4,-triazol-1-yl)methyl][1,1'-biphenyl]-2-carboxylic acid;
4'-[[5-butyl-3-(1-oxo-2-cyclohexylethyl)-1H-1,2,4-triazol-1-yl]methyl][1,1'-biphenyl]-2-carboxylic acid;
4'-[(5-butyl-3-phenyl-1,2,4,-triazol-1-yl)methyl][1,1'-biphenyl]-2-carboxylic acid;
4'-[(5-butyl-3-phenylmethyl-1,2,4,-triazol-1-yl)methyl][1,1'-biphenyl]-2-carboxylic acid;
4'-[(5-butyl-1,2,4,-triazol-1-yl)methyl][1,1'-biphenyl]-2-carboxylic acid;
4'-[(3-butyl-1,2,4,-triazol-1-yl)methyl][1,1'-biphenyl]-2-carboxylic acid;
4'-[[5-butyl-3-(2-phenylethyl)-1H-1,2,4-triazol-1-yl]methyl][1,1'-biphenyl]-2-carboxylic acid;
4'-[(5-butyl-3-benzoyl-1,2,4,-triazol-1-yl)methyl][1,1'-biphenyl]-2-carboxylic acid;
4'-[[5-butyl-3-(1-oxo-2-phenylethyl)-1H-1,2,4-triazol-1-yl]methyl][1,1'-biphenyl]-2-carboxylic acid;
4'-[[5-butyl-3-(1,1-dimethoxypropyl)-1H-1,2,4-triazol-1-yl]methyl][1,1'-biphenyl]-2-carboxylic acid;
4'-[[5-butyl-3-(1,1-dimethoxybutyl)-1H-1,2,4-triazol-1-yl]methyl][1,1'-biphenyl]-2-carboxylic acid;
4'-[[5-butyl-3-(1,1-dimethoxypentyl)-1H-1,2,4-triazol-1-yl]methyl][1,1'-biphenyl]-2-carboxylic acid;
4'-[[5-butyl-3-(1-oxopropyl)-1H-1,2,4-triazol-1-yl]methyl][1,1'-biphenyl]-2-carboxylic acid;
4'-[[5-butyl-3-(1-oxobutyl)-1H-1,2,4-triazol-1-yl]methyl][1,1'-biphenyl]-2-carboxylic acid;
4'-[[5-butyl-3-(1-oxopentyl)-1H-1,2,4-triazol-1-yl]methyl][1,1'-biphenyl]-2-carboxylic acid;
4'-[[5-butyl-3-(1,1-difluoroethyl)-1H-1,2,4-triazol-1-yl]methyl][1,1'-biphenyl]-2-carboxylic acid;
4'-[[5-butyl-3-(1,1-difluoropropyl)-1H-1,2,4-triazol-1-yl]methyl][1,1'-biphenyl]-2-carboxylic acid;
4'-[[5-butyl-3-(1,1-difluorobutyl)-1H-1,2,4-triazol-1-yl]methyl][1,1'-biphenyl]-2-carboxylic acid;
4'-[[3-butyl-5-(1,1-difluorobutyl)-1H-1,2,4-triazol-1-yl]methyl][1,1'-biphenyl]-2-carboxylic acid;
4'-[[5-butyl-3-(1,1-difluoropentyl)-1H-1,2,4-triazol-1-yl]methyl][1,1'-biphenyl]-2-carboxylic acid;
4'-[(5-propyl-3-ethyl-1H-1,2,4-triazol-1-yl)methyl][1,1'-biphenyl]-2-carboxylic acid;
4'-[(3,5-dipropyl-1H-1,2,4-triazol-1-yl)methyl][1,1'-biphenyl]-2-carboxylic acid;
4'-[(3,5-isopropyl-1H-1,2,4-triazol-1-yl)methyl][1,1'-biphenyl]-2-carboxylic acid;
4'-[(5-propyl-3-isopropyl-1H-1,2,4-triazol-1-yl)methyl][1,1'-biphenyl]-2-carboxylic acid;
4'-[(5-propyl-3-butyl-1H-1,2,4-triazol-1-yl)methyl][1,1'-biphenyl]-2-carboxylic acid;
4'-[(5-propyl-3-secbutyl-1H-1,2,4-triazol-1-yl)methyl][1,1'-biphenyl]-2-carboxylic acid;
4'-[(5-propyl-3-isobutyl-1H-1,2,4-triazol-1-yl)methyl][1,1'-biphenyl]-2-carboxylic acid;
4'-[(5-propyl-3-tertbutyl-1H-1,2,4-triazol-1-yl)methyl][1,1'-biphenyl]-2-carboxylic acid;
4'-[(5-propyl-3-pentyl-1H-1,2,4-triazol-1-yl)methyl][1,1'-biphenyl]-2-carboxylic acid;
4'-[(5-propyl-3-isopentyl-1H-1,2,4-triazol-1-yl)methyl][1,1'-biphenyl]-2-carboxylic acid;
4'-[(5-propyl-3-mercapto-1H-1,2,4-triazol-1-yl)methyl][1,1'-biphenyl]-2-carboxylic acid;
4'-[(5-propyl-3-thiomethyl-1H-1,2,4-triazol-1-yl)methyl][1,1'-biphenyl]-2-carboxylic acid;
4'-[(5-propyl-3-thioethyl-1H-1,2,4-triazol-1-yl)methyl][1,1'-biphenyl]-2-carboxylic acid;
4'-[(5-propyl-3-thiopropyl-1H-1,2,4-triazol-1-yl)methyl][1,1'-biphenyl]-2-carboxylic acid;
4'-[(5-propyl-3-hydroxy-1H-1,2,4-triazol-1-yl)methyl][1,1'-biphenyl]-2-carboxylic acid;
4'-[(5-propyl-3-methoxy-1H-1,2,4-triazol-1-yl)methyl][1,1'-biphenyl]-2-carboxylic acid;
4'-[(5-propyl-3-ethoxy-1H-1,2,4-triazol-1-yl)methyl][1,1'-biphenyl]-2-carboxylic acid;
4'-[(5-propyl-3-propoxy-1H-1,2,4-triazol-1-yl)methyl][1,1'-biphenyl]-2-carboxylic acid;
4'-[(5-propyl-3-cyclohexyl-1H-1,2,4-triazol-1-yl)methyl][1,1'-biphenyl]-2-carboxylic acid;
4'-[(5-propyl-3-cyclohexylmethyl-1H-1,2,4-triazol-1-yl)methyl][1,1'-biphenyl]-2-carboxylic acid;

5-[4'-[[5-propyl-3-(2-cyclohexylethyl)-1H-1,2,4-triazol-1-yl]methyl][1,1'-biphenyl]-2-carboxylic acid;
4'-[(5-propyl-3-cyclohexanoyl-1H-1,2,4-triazol-1-yl)methyl][1,1'-biphenyl]-2-carboxylic acid;
5-[4'-[[5-propyl-3-(1-oxo-2-cyclohexylethyl)-1H-1,2,4-triazol-1-yl]methyl][1,1'-biphenyl]-2-carboxylic acid;
4'-[(5-propyl-3-phenyl-1H-1,2,4-triazol-1-yl)methyl][1,1'-biphenyl]-2-carboxylic acid;
4'-[(5-propyl-3-phenylmethyl-1H-1,2,4-triazol-1-yl)methyl][1,1'-biphenyl]-2-carboxylic acid;
4'-[[5-propyl-3-(2-phenylethyl)-1H-1,2,4-triazol-1-yl]methyl][1,1'-biphenyl]-2-carboxylic acid;
4'-[(5-propyl-3-benzoyl-1H-1,2,4-triazol-1-yl)methyl][1,1'-biphenyl]-2-carboxylic acid;
4'-[[5-propyl-3-(1-oxo-2-phenylethyl)-1H-1,2,4-triazol-1-yl]methyl][1,1'-biphenyl]-2-carboxylic acid;
4'-[[5-propyl-3-(1,1-dimethoxypropyl)-1H-1,2,4-triazol-1-yl]methyl][1,1'-biphenyl]-2-carboxylic acid;
4'-[[5-propyl-3-(1,1-dimethoxybutyl)-1H-1,2,4-triazol-1-yl]methyl][1,1'-biphenyl]-2-carboxylic acid;
4'-[[5-propyl-3-(1,1-dimethoxypentyl)-1H-1,2,4-triazol-1-yl]methyl][1,1'-biphenyl]-2-carboxylic acid;
4'-[[5-propyl-3-(1-oxopropyl)-1H-1,2,4-triazol-1-yl]methyl][1,1'-biphenyl]-2-carboxylic acid;
4'-[[5-propyl-3-(1-oxobutyl)-1H-1,2,4-triazol-1-yl]methyl][1,1'-biphenyl]-2-carboxylic acid;
4'-[[5-propyl-3-(1-oxopentyl)-1H-1,2,4-triazol-1-yl]methyl][1,1'-biphenyl]-2-carboxylic acid;
4'-[[5-propyl-3-(1,1-difluoroethyl)-1H-1,2,4-triazol-1-yl]methyl][1,1'-biphenyl]-2-carboxylic acid;
4'-[[3,5-bis(heptafluoropropyl)-1H-1,2,4-triazol-1-yl]methyl][1,1'-biphenyl]-2-carboxylic acid;
4'-[[5-propyl-3-(1,1-difluoropropyl)-1H-1,2,4-triazol-1-yl]methyl][1,1'-biphenyl]-2-carboxylic acid;
4'-[[5-propyl-3-(1,1-difluorobutyl)-1H-1,2,4-triazol-1-yl]methyl][1,1'-biphenyl]-2-carboxylic acid;
4'-[[5-propyl-3-(1,1-difluoropentyl)-1H-1,2,4-triazol-1-yl]methyl][1,1'-biphenyl]-2-carboxylic acid;
4'-[(3,5-diethyl-1H-1,2,4-triazol-1-yl)methyl][1,1'-biphenyl]-2-carboxylic acid;
4'-[(5-ethyl-3-propyl-1H-1,2,4-triazol-1-yl)methyl][1,1'-biphenyl]-2-carboxylic acid;
4'-[(5-ethyl-3-isopropyl-1H-1,2,4-triazol-1-yl)methyl][1,1'-biphenyl]-2-carboxylic acid;
4'-[(5-ethyl-3-butyl-1H-1,2,4-triazol-1-yl)methyl][1,1'-biphenyl]-2-carboxylic acid;
4'-[(5-ethyl-3-secbutyl-1H-1,2,4-triazol-1-yl)methyl][1,1'-biphenyl]-2-carboxylic acid;
4'-[(5-ethyl-3-isobutyl-1H-1,2,4-triazol-1-yl)methyl][1,1'-biphenyl]-2-carboxylic acid;
4'-[(5-ethyl-3-tertbutyl-1H-1,2,4-triazol-1-yl)methyl][1,1'-biphenyl]-2-carboxylic acid;
4'-[(5-ethyl-3-pentyl-1H-1,2,4-triazol-1-yl)methyl][1,1'-biphenyl]-2-carboxylic acid;
4'-[(5-ethyl-3-isopentyl-1H-1,2,4-triazol-1-yl)methyl][1,1'-biphenyl]-2-carboxylic acid;
4'-[(5-ethyl-3-mercapto-1H-1,2,4-triazol-1-yl)methyl][1,1'-biphenyl]-2-carboxylic acid;
4'-[(5-ethyl-3-thiomethyl-1H-1,2,4-triazol-1-yl)methyl][1,1'-biphenyl]-2-carboxylic acid;
4'-[(5-ethyl-3-thioethyl-1H-1,2,4-triazol-1-yl)methyl][1,1'-biphenyl]-2-carboxylic acid;
4'-[(5-ethyl-3-thiopropyl-1H-1,2,4-triazol-1-yl)methyl][1,1'-biphenyl]-2-carboxylic acid;
4'-[(5-ethyl-3-hydroxy-1H-1,2,4-triazol-1-yl)methyl][1,1'-biphenyl]-2-carboxylic acid;
4'-[(5-ethyl-3-methoxy-1H-1,2,4-triazol-1-yl)methyl][1,1'-biphenyl]-2-carboxylic acid;
4'-[(5-ethyl-3-ethoxy-1H-1,2,4-triazol-1-yl)methyl][1,1'-biphenyl]-2-carboxylic acid;
4'-[(5-ethyl-3-propoxy-1H-1,2,4-triazol-1-yl)methyl][1,1'-biphenyl]-2-carboxylic acid;
4'-[(5-ethyl-3-cyclohexyl-1H-1,2,4-triazol-1-yl)methyl][1,1'-biphenyl]-2-carboxylic acid;
4'-[(5-ethyl-3-cyclohexylmethyl-1H-1,2,4-triazol-1-yl)methyl][1,1'-biphenyl]-2-carboxylic acid;
4'-[[5-ethyl-3-(2-cyclohexylethyl)-1H-1,2,4-triazol-1-yl]methyl][1,1'-biphenyl]-2-carboxylic acid;
4'-[(5-ethyl-3-cyclohexanoyl-1H-1,2,4-triazol-1-yl)methyl][1,1'-biphenyl]-2-carboxylic acid;
4'-[[5-ethyl-3-(1-oxo-2-cyclohexylethyl)-1H-1,2,4-triazol-1-yl]methyl][1,1'-biphenyl]-2-carboxylic acid;
4'-[(5-ethyl-3-phenyl-1H-1,2,4-triazol-1-yl)methyl][1,1'-biphenyl]-2-carboxylic acid;
4'-[(5-ethyl-3-phenylmethyl-1H-1,2,4-triazol-1-yl)methyl][1,1'-biphenyl]-2-carboxylic acid;
4'-[[5-ethyl-3-(2-phenylethyl)-1H-1,2,4-triazol-1-yl]methyl][1,1'-biphenyl]-2-carboxylic acid;
4'-[(5-ethyl-3-benzoyl-1H-1,2,4-triazol-1-yl)methyl][1,1'-biphenyl]-2-carboxylic acid;
4'-[[5-ethyl-3-(1-oxo-2-phenylethyl)-1H-1,2,4-triazol-1-yl]methyl][1,1'-biphenyl]-2-carboxylic acid;
4'-[[5-ethyl-3-(1,1-dimethoxypropyl)-1H-1,2,4-triazol-1-yl]methyl][1,1'-biphenyl]-2-carboxylic acid;
4'-[[5-ethyl-3-(1,1-dimethoxybutyl)-1H-1,2,4-triazol-1-yl]methyl][1,1'-biphenyl]-2-carboxylic acid;
4'-[[5-ethyl-3-(1,1-dimethoxypentyl)-1H-1,2,4-triazol-1-yl]methyl][1,1'-biphenyl]-2-carboxylic acid;
4'-[[5-ethyl-3-(1-oxopropyl)-1H-1,2,4-triazol-1-yl]methyl][1,1'-biphenyl]-2-carboxylic acid;
4'-[[5-ethyl-3-(1-oxobutyl)-1H-1,2,4-triazol-1-yl]methyl][1,1'-biphenyl]-2-carboxylic acid;
4'-[[5-ethyl-3-(1-oxopentyl)-1H-1,2,4-triazol-1-yl]methyl][1,1'-biphenyl]-2-carboxylic acid;
4'-[[5-ethpyl-3-(1,1-difluoroethyl)-1H-1,2,4-triazol-1-yl]methyl][1,1'-biphenyl]-2-carboxylic acid;
4'-[[5-ethyl-3-(1,1-difluoropropyl)-1H-1,2,4-triazol-1-yl]methyl][1,1'-biphenyl]-2-carboxylic acid;
4'-[[5-ethyl-3-(1,1-difluorobutyl)-1H-1,2,4-triazol-1-yl]methyl][1,1'-biphenyl]-2-carboxylic acid;
4'-[[5-ethyl-3-(1,1-difluoropentyl)-1H-1,2,4-triazol-1-yl]methyl][1,1'-biphenyl]-2-carboxylic acid;
4'-[(5-secbutyl-3-ethyl-1H-1,2,4-triazol-1-yl)methyl][1,1'-biphenyl]-2-carboxylic acid;
4'-[(5-secbutyl-3-propyl-1H-1,2,4-triazol-1-yl)methyl][1,1'-biphenyl]-2-carboxylic acid;
4'-[(5-secbutyl-3-isopropyl-1H-1,2,4-triazol-1-yl)methyl][1,1'-biphenyl]-2-carboxylic acid;
4'-[(5-secbutyl-3-butyl-1H-1,2,4-triazol-1-yl)methyl][1,1'-biphenyl]-2-carboxylic acid;
4'-[(3,5-disecbutyl-1H-1,2,4-triazol-1-yl)methyl][1,1'-biphenyl]-2-carboxylic acid;
4'-[(5-secbutyl-3-isobutyl-1H-1,2,4-triazol-1-yl)methyl][1,1'-biphenyl]-2-carboxylic acid;
4'-[(5-secbutyl-3-tertbutyl-1H-1,2,4-triazol-1-yl)methyl][1,1'-biphenyl]-2-carboxylic acid;
4'-[(5-secbutyl-3-pentyl-1H-1,2,4-triazol-1-yl)methyl][1,1'-biphenyl]-2-carboxylic acid;
4'-[(5-secbutyl-3-isopentyl-1H-1,2,4-triazol-1-yl)methyl][1,1'-biphenyl]-2-carboxylic acid;
4'-[(5-secbutyl-3-mercapto-1H-1,2,4-triazol-1-yl)methyl][1,1'-biphenyl]-2-carboxylic acid;
4'-[(5-secbutyl-3-thiomethyl-1H-1,2,4-triazol-1-yl)methyl][1,1'-biphenyl]-2-carboxylic acid;
4'-[(5-secbutyl-3-thioethyl-1H-1,2,4-triazol-1-yl)methyl][1,1'-biphenyl]-2-carboxylic acid;

4'-[(5-secbutyl-3-thiopropyl-1H-1,2,4-triazol-1-yl)methyl][1,1'-biphenyl]-2-carboxylic acid;
4'-[(5-secbutyl-3-hydroxy-1H-1,2,4-triazol-1-yl)methyl][1,1'-biphenyl]-2-carboxylic acid;
4'-[(5-secbutyl-3-methoxy-1H-1,2,4-triazol-1-yl)methyl][1,1'-biphenyl]-2-carboxylic acid;
4'-[(5-secbutyl-3-ethoxy-1H-1,2,4-triazol-1-yl)methyl][1,1'-biphenyl]-2-carboxylic acid;
4'-[(5-secbutyl-3-propoxy-1H-1,2,4-triazol-1-yl)methyl][1,1'-biphenyl]-2-carboxylic acid;
4'-[(5-secbutyl-3-cyclohexyl-1H-1,2,4-triazol-1-yl)methyl][1,1'-biphenyl]-2-carboxylic acid;
4'-[(5-secbutyl-3-cyclohexylmethyl-1H-1,2,4-triazol-1-yl)methyl][1,1'-biphenyl]-2-carboxylic acid;
4'-[[5-secbutyl-3-(2-cyclohexylethyl)-1H-1,2,4-triazol-1-yl]methyl][1,1'-biphenyl]-2-carboxylic acid;
4'-[(5-secbutyl-3-cyclohexanoyl-1H-1,2,4-triazol-1-yl)methyl][1,1'-biphenyl]-2-carboxylic acid;
4'-[[5-secbutyl-3-(1-oxo-2-cyclohexylethyl)-1H-1,2,4-triazol-1-yl]methyl][1,1'-biphenyl]-2-carboxylic acid;
4'-[(5-secbutyl-3-phenyl-1H-1,2,4-triazol-1-yl)methyl][1,1'-biphenyl]-2-carboxylic acid;
4'-[(5-secbutyl-3-phenylmethyl-1H-1,2,4-triazol-1-yl)methyl][1,1'-biphenyl]-2-carboxylic acid;
4'-[[5-secbutyl-3-(2-phenylethyl)-1H-1,2,4-triazol-1-yl]methyl][1,1'-biphenyl]-2-carboxylic acid;
4'-[(5-secbutyl-3-benzoyl-1H-1,2,4-triazol-1-yl)methyl][1,1'-biphenyl]-2-carboxylic acid;
4'-[[5-secbutyl-3-(1-oxo-2-phenylethyl)-1H-1,2,4-triazol-1-yl]methyl][1,1'-biphenyl]-2-carboxylic acid;
4'-[[5-secbutyl-3-(1,1-dimethoxypropyl)-1H-1,2,4-triazol-1-yl]methyl][1,1'-biphenyl]-2-carboxylic acid;
4'-[[5-secbutyl-3-(1,1-dimethoxybutyl)-1H-1,2,4-triazol-1-yl]methyl][1,1'-biphenyl]-2-carboxylic acid;
4'-[[5-secbutyl-3-(1,1-dimethoxypentyl)-1H-1,2,4-triazol-1-yl]methyl][1,1'-biphenyl]-2-carboxylic acid;
4'-[[5-secbutyl-3-(1-oxopropyl)-1H-1,2,4-triazol-1-yl]methyl][1,1'-biphenyl]-2-carboxylic acid;
4'-[[5-secbutyl-3-(1-oxobutyl)-1H-1,2,4-triazol-1-yl]methyl][1,1'-biphenyl]-2-carboxylic acid;
4'-[[5-secbutyl-3-(1-oxopentyl)-1H-1,2,4-triazol-1-yl]methyl][1,1'-biphenyl]-2-carboxylic acid;
4'-[[5-secbutyl-3-(1,1-difluoroethyl)-1H-1,2,4-triazol-1-yl]methyl][1,1'-biphenyl]-2-carboxylic acid;
4'-[[5-secbutyl-3-(1,1-difluoropropyl)-1H-1,2,4-triazol-1-yl]methyl][1,1'-biphenyl]-2-carboxylic acid;
4'-[[5-secbutyl-3-(1,1-difluorobutyl)-1H-1,2,4-triazol-1-yl]methyl][1,1'-biphenyl]-2-carboxylic acid;
4'-[[5-secbutyl-3-(1,1-difluoropentyl)-1H-1,2,4-triazol-1-yl]methyl][1,1'-biphenyl]-2-carboxylic acid;
4'-[(5-isobutyl-3-ethyl-1H-1,2,4-triazol-1-yl)methyl][1,1'-biphenyl]-2-carboxylic acid;
4'-[(5-isobutyl-3-propyl-1H-1,2,4-triazol-1-yl)methyl][1,1'-biphenyl]-2-carboxylic acid;
4'-[(5-isobutyl-3-isopropyl-1H-1,2,4-triazol-1-yl)methyl][1,1'-biphenyl]-2-carboxylic acid;
4'-[(5-isobutyl-3-butyl-1H-1,2,4-triazol-1-yl)methyl][1,1'-biphenyl]-2-carboxylic acid;
4'-[(5-isobutyl-3-secbutyl-1H-1,2,4-triazol-1-yl)methyl][1,1'-biphenyl]-2-carboxylic acid;
4'-[(3,5-diisobutyl-1H-1,2,4-triazol-1-yl)methyl][1,1'-biphenyl]-2-carboxylic acid;
4'-[(5-isobutyl-3-tertbutyl-1H-1,2,4-triazol-1-yl)methyl][1,1'-biphenyl]-2-carboxylic acid;
4'-[(5-isobutyl-3-pentyl-1H-1,2,4-triazol-1-yl)methyl][1,1'-biphenyl]-2-carboxylic acid;
4'-[(5-isobutyl-3-isopentyl-1H-1,2,4-triazol-1-yl)methyl][1,1'-biphenyl]-2-carboxylic acid;
4'-[(5-isobutyl-3-mercapto-1H-1,2,4-triazol-1-yl)methyl][1,1'-biphenyl]-2-carboxylic acid;
4'-[(5-isobutyl-3-thiomethyl-1H-1,2,4-triazol-1-yl)methyl][1,1'-biphenyl]-2-carboxylic acid;
4'-[(5-isobutyl-3-thioethyl-1H-1,2,4-triazol-1-yl)methyl][1,1'-biphenyl]-2-carboxylic acid;
4'-[(5-isobutyl-3-thiopropyl-1H-1,2,4-triazol-1-yl)methyl][1,1'-biphenyl]-2-carboxylic acid;
4'-[(5-isobutyl-3-hydroxy-1H-1,2,4-triazol-1-yl)methyl][1,1'-biphenyl]-2-carboxylic acid;
4'-[(5-isobutyl-3-methoxy-1H-1,2,4-triazol-1-yl)methyl][1,1'-biphenyl]-2-carboxylic acid;
4'-[(5-isobutyl-3-ethoxy-1H-1,2,4-triazol-1-yl)methyl][1,1'-biphenyl]-2-carboxylic acid;
4'-[(5-isobutyl-3-propoxy-1H-1,2,4-triazol-1-yl)methyl][1,1'-biphenyl]-2-carboxylic acid;
4'-[(5-isobutyl-3-cyclohexyl-1H-1,2,4-triazol-1-yl)methyl][1,1'-biphenyl]-2-carboxylic acid;
4'-[(5-isobutyl-3-cyclohexylmethyl-1H-1,2,4-triazol-1-yl)methyl][1,1'-biphenyl]-2-carboxylic acid;
4'-[[5-isobutyl-3-(2-cyclohexylethyl)-1H-1,2,4-triazol-1-yl]methyl][1,1'-biphenyl]-2-carboxylic acid;
4'-[(5-isobutyl-3-cyclohexanoyl-1H-1,2,4-triazol-1-yl)methyl][1,1'-biphenyl]-2-carboxylic acid;
4'-[[5-isobutyl-3-(1-oxo-2-cyclohexylethyl)-1H-1,2,4-triazol-1-yl]methyl][1,1'-biphenyl]-2-carboxylic acid;
4'-[(5-isobutyl-3-phenyl-1H-1,2,4-triazol-1-yl)methyl][1,1'-biphenyl]-2-carboxylic acid;
4'-[(5-isobutyl-3-phenylmethyl-1H-1,2,4-triazol-1-yl)methyl][1,1'-biphenyl]-2-carboxylic acid;
4'-[[5-isobutyl-3-(2-phenylethyl)-1H-1,2,4-triazol-1-yl]methyl][1,1'-biphenyl]-2-carboxylic acid;
4'-[(5-isobutyl-3-benzoyl-1H-1,2,4-triazol-1-yl)methyl][1,1'-biphenyl]-2-carboxylic acid;
4'-[[5-isobutyl-3-(1-oxo-2-phenylethyl)-1H-1,2,4-triazol-1-yl]methyl][1,1'-biphenyl]-2-carboxylic acid;
4'-[[5-isobutyl-3-(1,1-dimethoxypropyl)-1H-1,2,4-triazol-1-yl]methyl][1,1'-biphenyl]-2-carboxylic acid;
4'-[[5-isobutyl-3-(1,1-dimethoxybutyl)-1H-1,2,4-triazol-1-yl]methyl][1,1'-biphenyl]-2-carboxylic acid;
4'-[[5-isobutyl-3-(1,1-dimethoxypentyl)-1H-1,2,4-triazol-1-yl]methyl][1,1'-biphenyl]-2-carboxylic acid;
4'-[[5-isobutyl-3-(1-oxopropyl)-1H-1,2,4-triazol-1-yl]methyl][1,1'-biphenyl]-2-carboxylic acid;
4'-[[5-isobutyl-3-(1-oxobutyl)-1H-1,2,4-triazol-1-yl]methyl][1,1'-biphenyl]-2-carboxylic acid;
4'-[[5-isobutyl-3-(1-oxopentyl)-1H-1,2,4-triazol-1-yl]methyl][1,1'-biphenyl]-2-carboxylic acid;
4'-[[5-isobutyl-3-(1,1-difluoroethyl)-1H-1,2,4-triazol-1-yl]methyl][1,1'-biphenyl]-2-carboxylic acid;
4'-[[5-isobutyl-3-(1,1-difluoropropyl)-1H-1,2,4-triazol-1-yl]methyl][1,1'-biphenyl]-2-carboxylic acid;
4'-[[5-isobutyl-3-(1,1-difluorobutyl)-1H-1,2,4-triazol-1-yl]methyl][1,1'-biphenyl]-2-carboxylic acid;
4'-[[5-isobutyl-3-(1,1-difluoropentyl)-1H-1,2,4-triazol-1-yl]methyl][1,1'-biphenyl]-2-carboxylic acid;
4'-[(5-tertbutyl-3-ethyl-1H-1,2,4-triazol-1-yl)methyl][1,1'-biphenyl]-2-carboxylic acid;
4'-[(5-tertbutyl-3-propyl-1H-1,2,4-triazol-1-yl)methyl][1,1'-biphenyl]-2-carboxylic acid;
4'-[(5-tertbutyl-3-isopropyl-1H-1,2,4-triazol-1-yl)methyl][1,1'-biphenyl]-2-carboxylic acid;
4'-[(5-tertbutyl-3-butyl-1H-1,2,4-triazol-1-yl)methyl][1,1'-biphenyl]-2-carboxylic acid;
4'-[(5-tertbutyl-3-secbutyl-1H-1,2,4-triazol-1-yl)methyl][1,1'-biphenyl]-2-carboxylic acid;
4'-[(5-tertbutyl-3-isobutyl-1H-1,2,4-triazol-1-yl)methyl][1,1'-biphenyl]-2-carboxylic acid;

4'-[(3,5-ditertbutyl-1H-1,2,4-triazol-1-yl)methyl][1,1'-biphenyl]-2-carboxylic acid;
4'-[(5-tertbutyl-3-pentyl-1H-1,2,4-triazol-1-yl)methyl][1,1'-biphenyl]-2-carboxylic acid;
4'-[(5-tertbutyl-3-isopentyl-1H-1,2,4-triazol-1-yl)methyl][1,1'-biphenyl]-2-carboxylic acid;
4'-[(5-tertbutyl-3-mercapto-1H-1,2,4-triazol-1-yl)methyl][1,1'-biphenyl]-2-carboxylic acid;
4'-[(5-tertbutyl-3-thiomethyl-1H-1,2,4-triazol-1-yl)methyl][1,1'-biphenyl]-2-carboxylic acid;
4'-[(5-tertbutyl-3-thioethyl-1H-1,2,4-triazol-1-yl)methyl][1,1'-biphenyl]-2-carboxylic acid;
4'-[(5-tertbutyl-3-thiopropyl-1H-1,2,4-triazol-1-yl)methyl][1,1'-biphenyl]-2-carboxylic acid;
4'-[(5-tertbutyl-3-hydroxy-1H-1,2,4-triazol-1-yl)methyl][1,1'-biphenyl]-2-carboxylic acid;
4'-[(5-tertbutyl-3-methoxy-1H-1,2,4-triazol-1-yl)methyl][1,1'-biphenyl]-2-carboxylic acid;
4'-[(5-tertbutyl-3-ethoxy-1H-1,2,4-triazol-1-yl)methyl][1,1'-biphenyl]-2-carboxylic acid;
4'-[(5-tertbutyl-3-propoxy-1H-1,2,4-triazol-1-yl)methyl][1,1'-biphenyl]-2-carboxylic acid;
4'-[(5-tertbutyl-3-cyclohexyl-1H-1,2,4-triazol-1-yl)methyl][1,1'-biphenyl]-2-carboxylic acid;
4'-[(5-tertbutyl-3-cyclohexylmethyl-1H-1,2,4-triazol-1-yl)methyl][1,1'-biphenyl]-2-carboxylic acid;
4'-[[5-tertbutyl-3-(2-cyclohexylethyl)-1H-1,2,4-triazol-1-yl]methyl][1,1'-biphenyl]-2-carboxylic acid;
4'-[(5-tertbutyl-3-cyclohexanoyl-1H-1,2,4-triazol-1-yl)methyl][1,1'-biphenyl]-2-carboxylic acid;
4'-[[5-tertbutyl-3-(1-oxo-2-cyclohexylethyl)-1H-1,2,4-triazol-1-yl]methyl][1,1'-biphenyl]-2-carboxylic acid;
4'-[(5-tertbutyl-3-phenyl-1H-1,2,4-triazol-1-yl)methyl][1,1'-biphenyl]-2-carboxylic acid;
4'-[(5-tertbutyl-3-phenylmethyl-1H-1,2,4-triazol-1-yl)methyl][1,1'-biphenyl]-2-carboxylic acid;
4'-[[5-tertbutyl-3-(2-phenylethyl)-1H-1,2,4-triazol-1-yl]methyl][1,1'-biphenyl]-2-carboxylic acid;
4'-[(5-tertbutyl-3-benzoyl-1H-1,2,4-triazol-1-yl)methyl][1,1'-biphenyl]-2-carboxylic acid;
4'-[[5-tertbutyl-3-(1-oxo-2-phenylethyl)-1H-1,2,4-triazol-1-yl]methyl][1,1'-biphenyl]-2-carboxylic acid;
4'-[[5-tertbutyl-3-(1,1-dimethoxypropyl)-1H-1,2,4-triazol-1-yl]methyl][1,1'-biphenyl]-2-carboxylic acid;
4'-[[5-tertbutyl-3-(1,1-dimethoxybutyl)-1H-1,2,4-triazol-1-yl]methyl][1,1'-biphenyl]-2-carboxylic acid;
4'-[[5-tertbutyl-3-(1,1-dimethoxypentyl)-1H-1,2,4-triazol-1-yl]methyl][1,1'-biphenyl]-2-carboxylic acid;
4'-[[5-tertbutyl-3-(1-oxopropyl)-1H-1,2,4-triazol-1-yl]methyl][1,1'-biphenyl]-2-carboxylic acid;
4'-[[5-tertbutyl-3-(1-oxobutyl)-1H-1,2,4-triazol-1-yl]methyl][1,1'-biphenyl]-2-carboxylic acid;
4'-[[5-tertbutyl-3-(1-oxopentyl)-1H-1,2,4-triazol-1-yl]methyl][1,1'-biphenyl]-2-carboxylic acid;
4'-[[5-tertbutyl-3-(1,1-difluoroethyl)-1H-1,2,4-triazol-1-yl]methyl][1,1'-biphenyl]-2-carboxylic acid;
4'-[[5-tertbutyl-3-(1,1-difluoropropyl)-1H-1,2,4-triazol-1-yl]methyl][1,1'-biphenyl]-2-carboxylic acid;
4'-[[5-tertbutyl-3-(1,1-difluorobutyl)-1H-1,2,4-triazol-1-yl]methyl][1,1'-biphenyl]-2-carboxylic acid;
4'-[[5-tertbutyl-3-(1,1-difluoropentyl)-1H-1,2,4-triazol-1-yl]methyl][1,1'-biphenyl]-2-carboxylic acid;
4'-[(5-pentyl-3-ethyl-1H-1,2,4-triazol-1-yl)methyl][1,1'-biphenyl]-2-carboxylic acid;
4'-[(5-pentyl-3-propyl-1H-1,2,4-triazol-1-yl)methyl][1,1'-biphenyl]-2-carboxylic acid;
4'-[(5-pentyl-3-isopropyl-1H-1,2,4-triazol-1-yl)methyl][1,1'-biphenyl]-2-carboxylic acid;
4'-[(5-pentyl-3-butyl-1H-1,2,4-triazol-1-yl)methyl][1,1'-biphenyl]-2-carboxylic acid;
4'-[(5-pentyl-3-secbutyl-1H-1,2,4-triazol-1-yl)methyl][1,1'-biphenyl]-2-carboxylic acid;
4'-[(5-pentyl-3-isobutyl-1H-1,2,4-triazol-1-yl)methyl][1,1'-biphenyl]-2-carboxylic acid;
4'-[(5-pentyl-3-tertbutyl-1H-1,2,4-triazol-1-yl)methyl][1,1'-biphenyl]-2-carboxylic acid;
4'-[(3,5-dipentyl-1H-1,2,4-triazol-1-yl)methyl][1,1'-biphenyl]-2-carboxylic acid;
4'-[(5-pentyl-3-isopentyl-1H-1,2,4-triazol-1-yl)methyl][1,1'-biphenyl]-2-carboxylic acid;
4'-[(5-pentyl-3-mercapto-1H-1,2,4-triazol-1-yl)methyl][1,1'-biphenyl]-2-carboxylic acid;
4'-[(5-pentyl-3-thiomethyl-1H-1,2,4-triazol-1-yl)methyl][1,1'-biphenyl]-2-carboxylic acid;
4'-[(5-pentyl-3-thioethyl-1H-1,2,4-triazol-1-yl)methyl][1,1'-biphenyl]-2-carboxylic acid;
4'-[(5-pentyl-3-thiopropyl-1H-1,2,4-triazol-1-yl)methyl][1,1'-biphenyl]-2-carboxylic acid;
4'-[(5-pentyl-3-hydroxy-1H-1,2,4-triazol-1-yl)methyl][1,1'-biphenyl]-2-carboxylic acid;
4'-[(5-pentyl-3-methoxy-1H-1,2,4-triazol-1-yl)methyl][1,1'-biphenyl]-2-carboxylic acid;
4'-[(5-pentyl-3-ethoxy-1H-1,2,4-triazol-1-yl)methyl][1,1'-biphenyl]-2-carboxylic acid;
4'-[(5-pentyl-3-propoxy-1H-1,2,4-triazol-1-yl)methyl][1,1'-biphenyl]-2-carboxylic acid;
4'-[(5-pentyl-3-cyclohexyl-1H-1,2,4-triazol-1-yl)methyl][1,1'-biphenyl]-2-carboxylic acid;
4'-[(5-pentyl-3-cyclohexylmethyl-1H-1,2,4-triazol-1-yl)methyl][1,1'-biphenyl]-2-carboxylic acid;
4'-[[5-pentyl-3-(2-cyclohexylethyl)-1H-1,2,4-triazol-1-yl]methyl][1,1'-biphenyl]-2-carboxylic acid;
4'-[(5-pentyl-3-cyclohexanoyl-1H-1,2,4-triazol-1-yl)methyl][1,1'-biphenyl]-2-carboxylic acid;
4'-[[5-pentyl-3-(1-oxo-2-cyclohexylethyl)-1H-1,2,4-triazol-1-yl]methyl][1,1'-biphenyl]-2-carboxylic acid;
4'-[(5-pentyl-3-phenyl-1H-1,2,4-triazol-1-yl)methyl][1,1'-biphenyl]-2-carboxylic acid;
4'-[(5-pentyl-3-phenylmethyl-1H-1,2,4-triazol-1-yl)methyl][1,1'-biphenyl]-2-carboxylic acid;
4'-[[5-pentyl-3-(2-phenylethyl)-1H-1,2,4-triazol-1-yl]methyl][1,1'-biphenyl]-2-carboxylic acid;
4'-[(5-pentyl-3-benzoyl-1H-1,2,4-triazol-1-yl)methyl][1,1'-biphenyl]-2-carboxylic acid;
4'-[[5-pentyl-3-(1-oxo-2-phenylethyl)-1H-1,2,4-triazol-1-yl]methyl][1,1'-biphenyl]-2-carboxylic acid;
4'-[[5-pentyl-3-(1,1-dimethoxypropyl)-1H-1,2,4-triazol-1-yl]methyl][1,1'-biphenyl]-2-carboxylic acid;
4'-[[5-pentyl-3-(1,1-dimethoxybutyl)-1H-1,2,4-triazol-1-yl]methyl][1,1'-biphenyl]-2-carboxylic acid;
4'-[[5-pentyl-3-(1,1-dimethoxypentyl)-1H-1,2,4-triazol-1-yl]methyl][1,1'-biphenyl]-2-carboxylic acid;
4'-[[5-pentyl-3-(1-oxopropyl)-1H-1,2,4-triazol-1-yl]methyl][1,1'-biphenyl]-2-carboxylic acid;
4'-[[5-pentyl-3-(1-oxobutyl)-1H-1,2,4-triazol-1-yl]methyl][1,1'-biphenyl]-2-carboxylic acid;
4'-[[5-pentyl-3-(1-oxopentyl)-1H-1,2,4-triazol-1-yl]methyl][1,1'-biphenyl]-2-carboxylic acid;
4'-[[5-pentyl-3-(1,1-difluoroethyl)-1H-1,2,4-triazol-1-yl]methyl][1,1'-biphenyl]-2-carboxylic acid;
4'-[[5-pentyl-3-(1,1-difluoropropyl)-1H-1,2,4-triazol-1-yl]methyl][1,1'-biphenyl]-2-carboxylic acid;
4'-[[5-pentyl-3-(1,1-difluorobutyl)-1H-1,2,4-triazol-1-yl]methyl][1,1'-biphenyl]-2-carboxylic acid;
4'-[[5-pentyl-3-(1,1-difluoropentyl)-1H-1,2,4-triazol-1-yl]methyl][1,1'-biphenyl]-2-carboxylic acid;

4'-[(5-isopentyl-3-ethyl-1H-1,2,4-triazol-1-yl)methyl][1,1'-biphenyl]-2-carboxylic acid;
4'-[(5-isopentyl-3-propyl-1H-1,2,4-triazol-1-yl)methyl][1,1'-biphenyl]-2-carboxylic acid;
4'-[(5-isopentyl-3-isopropyl-1H-1,2,4-triazol-1-yl)methyl][1,1'-biphenyl]-2-carboxylic acid;
4'-[(5-isopentyl-3-butyl-1H-1,2,4-triazol-1-yl)methyl][1,1'-biphenyl]-2-carboxylic acid;
4'-[(5-isopentyl-3-secbutyl-1H-1,2,4-triazol-1-yl)methyl][1,1'-biphenyl]-2-carboxylic acid;
4'-[(5-isopentyl-3-isobutyl-1H-1,2,4-triazol-1-yl)methyl][1,1'-biphenyl]-2-carboxylic acid;
4'-[(5-isopentyl-3-tertbutyl-1H-1,2,4-triazol-1-yl)methyl][1,1'-biphenyl]-2-carboxylic acid;
4'-[(5-isopentyl-3-pentyl-1H-1,2,4-triazol-1-yl)methyl][1,1'-biphenyl]-2-carboxylic acid;
4'-[(3,5-diisopentyl-1H-1,2,4-triazol-1-yl)methyl][1,1'-biphenyl]-2-carboxylic acid;
4'-[(5-isopentyl-3-mercapto-1H-1,2,4-triazol-1-yl)methyl][1,1'-biphenyl]-2-carboxylic acid;
4'-[(5-isopentyl-3-thiomethyl-1H-1,2,4-triazol-1-yl)methyl][1,1'-biphenyl]-2-carboxylic acid;
4'-[(5-isopentyl-3-thioethyl-1H-1,2,4-triazol-1-yl)methyl][1,1'-biphenyl]-2-carboxylic acid;
4'-[(5-isopentyl-3-thiopropyl-1H-1,2,4-triazol-1-yl)methyl][1,1'-biphenyl]-2-carboxylic acid;
4'-[(5-isopentyl-3-hydroxy-1H-1,2,4-triazol-1-yl)methyl][1,1'-biphenyl]-2-carboxylic acid;
4'-[(5-isopentyl-3-methoxy-1H-1,2,4-triazol-1-yl)methyl][1,1'-biphenyl]-2-carboxylic acid;
4'-[(5-isopentyl-3-ethoxy-1H-1,2,4-triazol-1-yl)methyl][1,1'-biphenyl]-2-carboxylic acid;
4'-[(5-isopentyl-3-propoxy-1H-1,2,4-triazol-1-yl)methyl][1,1'-biphenyl]-2-carboxylic acid;
4'-[(5-isopentyl-3-cyclohexyl-1H-1,2,4-triazol-1-yl)methyl][1,1'-biphenyl]-2-carboxylic acid;
4'-[(5-isopentyl-3-cyclohexylmethyl-1H-1,2,4-triazol-1-yl)methyl][1,1'-biphenyl]-2-carboxylic acid;
4'-[[5-pentyl-3-(2-cyclohexylethyl)-1H-1,2,4-triazol-1-yl]methyl][1,1'-biphenyl]-2-carboxylic acid;
4'-[(5-isopentyl-3-cyclohexanoyl-1H-1,2,4-triazol-1-yl)methyl][1,1'-biphenyl]-2-carboxylic acid;
4'-[[5-isopentyl-3-(1-oxo-2-cyclohexylethyl)-1H-1,2,4-triazol-1-yl]methyl][1,1'-biphenyl]-2-carboxylic acid;
4'-[(5-isopentyl-3-phenyl-1H-1,2,4-triazol-1-yl)methyl][1,1'-biphenyl]-2-carboxylic acid;
4'-[(5-isopentyl-3-phenylmethyl-1H-1,2,4-triazol-1-yl)methyl][1,1'-biphenyl]-2-carboxylic acid;
4'-[[5-isopentyl-3-(2-phenylethyl)-1H-1,2,4-triazol-1-yl]methyl][1,1'-biphenyl]-2-carboxylic acid;
4'-[(5-isopentyl-3-benzoyl-1H-1,2,4-triazol-1-yl)methyl][1,1'-biphenyl]-2-carboxylic acid;
4'-[[5-isopentyl-3-(1-oxo-2-phenylethyl)-1H-1,2,4-triazol-1-yl]methyl][1,1'-biphenyl]-2-carboxylic acid;
4'-[[5-isopentyl-3-(1,1-dimethoxypropyl)-1H-1,2,4-triazol-1yl]methyl][1,1'-biphenyl]-2-carboxylic acid;
4'-[5-isopentyl-3-(1,1-dimethoxybutyl)-1H-1,2,4-triazol-1-yl]methyl][1,1'-biphenyl]-2-carboxylic acid;
4'-[[5-isopentyl-3-(1,1-dimethoxypentyl)-1H-1,2,4-triazol-1-yl]methyl][1,1'-biphenyl]-2-carboxylic acid;
4'-[[5-isopentyl-3-(1-oxopropyl)-1H-1,2,4-triazol-1-yl]methyl][1,1'-biphenyl]-2-carboxylic acid;
4'-[[5-isopentyl-3-(1-oxobutyl)-1H-1,2,4-triazol-1-yl]methyl][1,1'-biphenyl]-2-carboxylic acid;
4'-[[5-isopentyl-3-(1-oxopentyl)-1H-1,2,4-triazol-1-yl]methyl][1,1'-biphenyl]-2-carboxylic acid;
4'-[[5-isopentyl-3-(1,1-difluoroethyl)-1H-1,2,4-triazol-1-yl]methyl][1,1'-biphenyl]-2-carboxylic acid;
4'-[[5-isopentyl-3-(1,1-difluoropropyl)-1H-1,2,4-triazol-1-yl]methyl][1,1'-biphenyl]-2-carboxylic acid;
4'-[[5-isopentyl-3-(1,1-difluorobutyl)-1H-1,2,4-triazol-1-yl]methyl][1,1'-biphenyl]-2-carboxylic acid;
4'-[[5-isopentyl-3-(1,1-difluoropentyl)-1H-1,2,4-triazol-1-yl]methyl][1,1'-biphenyl]-2-carboxylic acid;
4'-[[5-(1-butenyl)-3-ethyl-1H-1,2,4-triazol-1-yl]methyl][1,1'-biphenyl]-2-carboxylic acid;
4'-[[5-(1-butenyl)-3-propyl-1H-1,2,4-triazol-1-yl]methyl][1,1'-biphenyl]-2-carboxylic acid;
4'-[[5-(1-butenyl)-3-isopropyl-1H-1,2,4-triazol-1-yl]methyl][1,1'-biphenyl]-2-carboxylic acid;
4'-[[5-(1-butenyl))-3-butyl-1H-1,2,4-triazol-1-yl]methyl][1,1'-biphenyl]-2-carboxylic acid;
4'-[[5-(1-butenyl))-3-secbutyl-1H-1,2,4-triazol-1-yl]methyl][1,1'-biphenyl]-2-carboxylic acid;
4'-[[5-(1-butenyl))-3-isobutyl-1H-1,2,4-triazol-1-yl]methyl][1,1'-biphenyl]-2-carboxylic acid;
4'-[[5-(1-butenyl))-3-tertbutyl-1H-1,2,4-triazol-1-yl]methyl][1,1'-biphenyl]-2-carboxylic acid;
4'-[[5-(1-butenyl))-3-pentyl-1H-1,2,4-triazol-1-yl]methyl][1,1'-biphenyl]-2-carboxylic acid;
4'-[[5-(1-butenyl))-3-isopentyl-1H-1,2,4-triazol-1-yl]methyl][1,1'-biphenyl]-2-carboxylic acid;
4'-[[5-(1-butenyl))-3-mercapto-1H-1,2,4-triazol-1-yl]methyl][1,1'-biphenyl]-2-carboxylic acid;
4'-[[5-(1-butenyl))-3-thiomethyl-1H-1,2,4-triazol-1-yl]methyl][1,1'-biphenyl]-2-carboxylic acid;
4'-[[5-(1-butenyl))-3-thioethyl-1H-1,2,4-triazol-1-yl]methyl][1,1'-biphenyl]-2-carboxylic acid;
4'-[[5-(1-butenyl))-3-thiopropyl-1H-1,2,4-triazol-1-yl]methyl][1,1'-biphenyl]-2-carboxylic acid;
4'-[[5-(1-butenyl))-3-hydroxy-1H-1,2,4-triazol-1-yl]methyl][1,1'-biphenyl]-2-carboxylic acid;
4'-[[5-(1-butenyl))-3-methoxy-1H-1,2,4-triazol-1-yl]methyl][1,1'-biphenyl]-2-carboxylic acid;
4'-[[5-(1-butenyl))-3-ethoxy-1H-1,2,4-triazol-1-yl]methyl][1,1'-biphenyl]-2-carboxylic acid;
4'-[[5-(1-butenyl))-3-propoxy-1H-1,2,4-triazol-1-yl]methyl][1,1'-biphenyl]-2-carboxylic acid;
4'-[[5-(1-butenyl))-3-cyclohexyl-1H-1,2,4-triazol-1-yl]methyl][1,1'-biphenyl]-2-carboxylic acid;
4'-[[5-(1-butenyl))-3-cyclohexylmethyl-1H-1,2,4-triazol-1-yl]methyl][1,1'-biphenyl]-2-carboxylic acid;
4'-[[5-(1-butenyl))-3-(2-cyclohexylethyl)-1H-1,2,4-triazol-1-yl]methyl][1,1'-biphenyl]-2-carboxylic acid;
4'-[[5-(1-butenyl))-3-cyclohexanoyl-1H-1,2,4-triazol-1-yl]methyl][1,1'-biphenyl]-2-carboxylic acid;
4'-[[5-(1-butenyl))-3-(1-oxo-2-cyclohexylethyl)-1H-1,2,4-triazol-1-yl]methyl][1,1'-biphenyl]-2-carboxylic acid;
4'-[[5-(1-butenyl))-3-phenyl-1H-1,2,4-triazol-1-yl]methyl][1,1'-biphenyl]-2-carboxylic acid;
4'-[[5-(1-butenyl))-3-phenylmethyl-1H-1,2,4-triazol-1-yl]methyl][1,1'-biphenyl]-2-carboxylic acid;
4'-[[5-(1-butenyl))-3-(2-phenylethyl)-1H-1,2,4-triazol-1-yl]methyl][1,1'-biphenyl]-2-carboxylic acid;
4'-[[5-(1-butenyl))-3-benzoyl-1H-1,2,4-triazol-1-yl]methyl][1,1'-biphenyl]-2-carboxylic acid;
4'-[[5-(1-butenyl))-3-(1-oxo-2-phenylethyl)-1H-1,2,4-triazol-1-yl]methyl][1,1'-biphenyl]-2-carboxylic acid;
4'-[[5-(1-butenyl))-3-(1,1-dimethoxypropyl)-1H-1,2,4-triazol-1-yl]methyl][1,1'-biphenyl]-2-carboxylic acid;
4'-[[5-(1-butenyl))-3-(1,1-dimethoxybutyl)-1H-1,2,4-triazol-1-yl]methyl][1,1'-biphenyl]-2-carboxylic acid;
4'-[[5-(1-butenyl))-3-(1,1-dimethoxypentyl)-1H-1,2,4-triazol-1-yl]methyl][1,1'-biphenyl]-2-carboxylic acid;
4'-[[5-(1-butenyl))-3-(1-oxopropyl)-1H-1,2,4-triazol-1-yl]methyl][1,1'-biphenyl]-2-carboxylic acid;

4'-[[5-(1-butenyl)-3-(1-oxobutyl)-1H-1,2,4-triazol-1-yl]methyl][1,1'-biphenyl]-2-carboxylic acid;
4'-[[5-(1-butenyl)-3-(1-oxopentyl)-1H-1,2,4-triazol-1-yl]methyl][1,1'-biphenyl]-2-carboxylic acid;
4'-[[5-(1-butenyl)-3-(1,1-difluoroethyl)-1H-1,2,4-triazol-1-yl]methyl][1,1'-biphenyl]-2-carboxylic acid;
4'-[[5-(1-butenyl)-3-(1,1-difluoropropyl)-1H-1,2,4-triazol-1-yl]methyl][1,1'-biphenyl]-2-carboxylic acid;
4'-[[5-(1-butenyl)-3-(1,1-difluorobutyl)-1H-1,2,4-triazol-1-yl]methyl][1,1'-biphenyl]-2-carboxylic acid;
4'-[[5-(1-butenyl)-3-(1,1-difluoropentyl)-1H-1,2,4-triazol-1-yl]methyl][1,1'-biphenyl]-2-carboxylic acid;
4'-[[5-(2-butenyl)-3-ethyl-1H-1,2,4-triazol-1-yl]methyl][1,1'-biphenyl]-2-carboxylic acid;
4'-[[5-(2-butenyl)-3-propyl-1H-1,2,4-triazol-1-yl]methyl][1,1'-biphenyl]-2-carboxylic acid;
4'-[[5-(2-butenyl)-3-isopropyl-1H-1,2,4-triazol-1-yl]methyl][1,1'-biphenyl]-2-carboxylic acid;
4'-[[5-(2-butenyl)-3-butyl-1H-1,2,4-triazol-1-yl]methyl][1,1'-biphenyl]-2-carboxylic acid;
4'-[[5-(2-butenyl)-3-secbutyl-1H-1,2,4-triazol-1-yl]methyl][1,1'-biphenyl]-2-carboxylic acid;
4'-[[5-(2-butenyl)-3-isobutyl-1H-1,2,4-triazol-1-yl]methyl][1,1'-biphenyl]-2-carboxylic acid;
4'-[[5-(2-butenyl)-3-tertbutyl-1H-1,2,4-triazol-1-yl]methyl][1,1'-biphenyl]-2-carboxylic acid;
4'-[[5-(2-butenyl)-3-pentyl-1H-1,2,4-triazol-1-yl]methyl][1,1'-biphenyl]-2-carboxylic acid;
4'-[[5-(2-butenyl)-3-isopentyl-1H-1,2,4-triazol-1-yl]methyl][1,1'-biphenyl]-2-carboxylic acid;
4'-[[5-(2-butenyl)-3-mercapto-1H-1,2,4-triazol-1-yl]methyl][1,1'-biphenyl]-2-carboxylic acid;
4'-[[5-(2-butenyl)-3-thiomethyl-1H-1,2,4-triazol-1-yl]methyl][1,1'-biphenyl]-2-carboxylic acid;
4'-[[5-(2-butenyl)-3-thioethyl-1H-1,2,4-triazol-1-yl]methyl][1,1'-biphenyl]-2-carboxylic acid;
4'-[[5-(2-butenyl)-3-thiopropyl-1H-1,2,4-triazol-1-yl]methyl][1,1'-biphenyl]-2-carboxylic acid;
4'-[[5-(2-butenyl)-3-hydroxy-1H-1,2,4-triazol-1-yl]methyl][1,1'-biphenyl]-2-carboxylic acid;
4'-[[5-(2-butenyl)-3-methoxy-1H-1,2,4-triazol-1-yl]methyl][1,1'-biphenyl]-2-carboxylic acid;
4'-[[5-(2-butenyl)-3-ethoxy-1H-1,2,4-triazol-1-yl]methyl][1,1'-biphenyl]-2-carboxylic acid;
4'-[[5-(2-butenyl)-3-propoxy-1H-1,2,4-triazol-1-yl]methyl][1,1'-biphenyl]-2-carboxylic acid;
4'-[[5-(2-butenyl)-3-cyclohexyl-1H-1,2,4-triazol-1-yl]methyl][1,1'-biphenyl]-2-carboxylic acid;
4'-[[5-(2-butenyl)-3-cyclohexylmethyl-1H-1,2,4-triazol-1-yl]methyl][1,1'-biphenyl]-2-carboxylic acid;
4'-[[5-(2-butenyl)-3-(2-cyclohexylethyl)-1H-1,2,4-triazol-1-yl]methyl][1,1'-biphenyl]-2-carboxylic acid;
4'-[[5-(2-butenyl)-3-cyclohexanoyl-1H-1,2,4-triazol-1-yl]methyl][1,1'-biphenyl]-2-carboxylic acid;
4'-[[5-(2-butenyl)-3-(1-oxo-2-cyclohexylethyl)-1H-1,2,4-triazol-1-yl]methyl][1,1'-biphenyl]-2-carboxylic acid;
4'-[[5-(2-butenyl)-3-phenyl-1H-1,2,4-triazol-1-yl]methyl][1,1'-biphenyl]-2-carboxylic acid;
4'-[[5-(2-butenyl)-3-phenylmethyl-1H-1,2,4-triazol-1-yl]methyl][1,1'-biphenyl]-2-carboxylic acid;
4'-[[5-(2-butenyl)-3-(2-phenylethyl)-1H-1,2,4-triazol-1-yl]methyl][1,1'-biphenyl]-2-carboxylic acid;
4'-[[5-(2-butenyl)-3-(1,1-dimethoxypropyl)-1H-1,2,4-triazol-1-yl]methyl][1,1'-biphenyl]-2-carboxylic acid;
4'-[[5-(2-butenyl)-3-(1,1-dimethoxybutyl)-1H-1,2,4-triazol-1-yl]methyl][1,1'-biphenyl]-2-carboxylic acid;
4'-[[5-(2-butenyl)-3-(1,1-dimethoxypentyl)-1H-1,2,4-triazol-1-yl]methyl][1,1'-biphenyl]-2-carboxylic acid;
4'-[[5-(2-butenyl)-3-(1-oxopropyl)-1H-1,2,4-triazol-1-yl]methyl][1,1'-biphenyl]-2-carboxylic acid;
4'-[[5-(2-butenyl)-3-(1-oxobutyl)-1H-1,2,4-triazol-1-yl]methyl][1,1'-biphenyl]-2-carboxylic acid;
4'-[[5-(2-butenyl)-3-(1-oxopentyl)-1H-1,2,4-triazol-1-yl]methyl][1,1'-biphenyl]-2-carboxylic acid;
4'-[[5-(2-butenyl)-3-(1,1-difluoroethyl)-1H-1,2,4-triazol-1-yl]methyl][1,1'-biphenyl]-2-carboxylic acid;
4'-[[5-(2-butenyl)-3-(1,1-difluoropropyl)-1H-1,2,4-triazol-1-yl]methyl][1,1'-biphenyl]-2-carboxylic acid;
4'-[[5-(2-butenyl)-3-(1,1-difluorobutyl)-1H-1,2,4-triazol-1-yl]methyl][1,1'-biphenyl]-2-carboxylic acid;
4'-[[5-(2-butenyl)-3-(1,1-difluoropentyl)-1H-1,2,4-triazol-1-yl]methyl][1,1'-biphenyl]-2-carboxylic acid;
4'-[[5-(3-butenyl)-3-ethyl-1H-1,2,4-triazol-1-yl]methyl][1,1'-biphenyl]-2-carboxylic acid;
4'-[[5-(3-butenyl)-3-propyl-1H-1,2,4-triazol-1-yl]methyl][1,1'-biphenyl]-2-carboxylic acid;
4'-[[5-(3-butenyl)-3-isopropyl-1H-1,2,4-triazol-1-yl]methyl][1,1'-biphenyl]-2-carboxylic acid;
4'-[[5-(3-butenyl)-3-butyl-1H-1,2,4-triazol-1-yl]methyl][1,1'-biphenyl]-2-carboxylic acid;
4'-[[5-(3-butenyl)-3-secbutyl-1H-1,2,4-triazol-1-yl]methyl][1,1'-biphenyl]-2-carboxylic acid;
4'-[[5-(3-butenyl)-3-isobutyl-1H-1,2,4-triazol-1-yl]methyl][1,1'-biphenyl]-2-carboxylic acid;
4'-[[5-(3-butenyl)-3-tertbutyl-1H-1,2,4-triazol-1-yl]methyl][1,1'-biphenyl]-2-carboxylic acid;
4'-[[5-(3-butenyl)-3-pentyl-1H-1,2,4-triazol-1-yl]methyl][1,1'-biphenyl]-2-carboxylic acid;
4'-[[5-(3-butenyl)-3-isopentyl-1H-1,2,4-triazol-1-yl]methyl][1,1'-biphenyl]-2-carboxylic acid;
4'-[[5-(3-butenyl)-3-mercapto-1H-1,2,4-triazol-1-yl]methyl][1,1'-biphenyl]-2-carboxylic acid;
4'-[[5-(3-butenyl)-3-thiomethyl-1H-1,2,4-triazol-1-yl]methyl][1,1'-biphenyl]-2-carboxylic acid;
4'-[[5-(3-butenyl)-3-thioethyl-1H-1,2,4-triazol-1-yl]methyl][1,1'-biphenyl]-2-carboxylic acid;
4'-[[5-(3-butenyl)-3-thiopropyl-1H-1,2,4-triazol-1-yl]methyl][1,1'-biphenyl]-2-carboxylic acid;
4'-[[5-(3-butenyl)-3-hydroxy-1H-1,2,4-triazol-1-yl]methyl][1,1'-biphenyl]-2-carboxylic acid;
4'-[[5-(3-butenyl)-3-methoxy-1H-1,2,4-triazol-1-yl]methyl][1,1'-biphenyl]-2-carboxylic acid;
4'-[[5-(3-butenyl)-3-ethoxy-1H-1,2,4-triazol-1-yl]methyl][1,1'-biphenyl]-2-carboxylic acid;
4'-[[5-(3-butenyl)-3-propoxy-1H-1,2,4-triazol-1-yl]methyl][1,1'-biphenyl]-2-carboxylic acid;
4'-[[5-(3-butenyl)-3-cyclohexyl-1H-1,2,4-triazol-1-yl]methyl][1,1'-biphenyl]-2-carboxylic acid;
4'-[[5-(3-butenyl)-3-cyclohexylmethyl-1H-1,2,4-triazol-1-yl]methyl][1,1'-biphenyl]-2-carboxylic acid;
4'-[[5-(3-butenyl)-3-(2-cyclohexylethyl)-1H-1,2,4-triazol-1-yl]methyl][1,1'-biphenyl]-2-carboxylic acid;
4'-[[5-(3-butenyl)-3-cyclohexanoyl-1H-1,2,4-triazol-1-yl]methyl][1,1'-biphenyl]-2-carboxylic acid;
4'-[[5-(3-butenyl)-3-(1-oxo-2-cyclohexylethyl)-1H-1,2,4-triazol-1-yl]methyl][1,1'-biphenyl]-2-carboxylic acid;
4'-[[5-(3-butenyl)-3-phenyl-1H-1,2,4-triazol-1-yl]methyl][1,1'-biphenyl]-2-carboxylic acid;
4'-[[5-(3-butenyl)-3-phenylmethyl-1H-1,2,4-triazol-1-yl]methyl][1,1'-biphenyl]-2-carboxylic acid;
4'-[[5-(3-butenyl)-3-(2-phenylethyl)-1H-1,2,4-triazol-1-yl]methyl][1,1'-biphenyl]-2-carboxylic acid;
4'-[[5-(3-butenyl)-3-benzoyl-1H-1,2,4-triazol-1-yl]methyl][1,1'-biphenyl]-2-carboxylic acid;
4'-[[5-(3-butenyl)-3-(1-oxo-2-phenylethyl)-1H-1,2,4-triazol-1-yl]methyl][1,1'-biphenyl]-2-carboxylic acid;

4'-[[5-(3-butenyl)-3-(1,1-dimethoxypropyl)-1H-1,2,4-triazol-1-yl]methyl][1,1'-biphenyl]-2-carboxylic acid;
4'-[[5-(3-butenyl)-3-(1,1-dimethoxybutyl)-1H-1,2,4-triazol-1-yl]methyl][1,1'-biphenyl]-2-carboxylic acid;
4'-[[5-(3-butenyl)-3-(1,1-dimethoxypentyl)-1H-1,2,4-triazol-1-yl]methyl][1,1'-biphenyl]-2-carboxylic acid;
4'-[[5-(3-butenyl)-3-(1-oxopropyl)-1H-1,2,4-triazol-1-yl]methyl][1,1'-biphenyl]-2-carboxylic acid;
4'-[[5-(3-butenyl)-3-(1-oxobutyl)-1H-1,2,4-triazol-1-yl]methyl][1,1'-biphenyl]-2-carboxylic acid;
4'-[[5-(3-butenyl)-3-(1-oxopentyl)-1H-1,2,4-triazol-1-yl]methyl][1,1'-biphenyl]-2-carboxylic acid;
4'-[[5-(3-butenyl)-3-(1,1-difluoroethyl)-1H-1,2,4-triazol-1-yl]methyl][1,1'-biphenyl]-2-carboxylic acid;
4'-[[5-(3-butenyl)-3-(1,1-difluoropropyl)-1H-1,2,4-triazol-1-yl]methyl][1,1'-biphenyl]-2-carboxylic acid;
4'-[[5-(3-butenyl)-3-(1-difluorobutyl)-1H-1,2,4-triazol-1-yl]methyl][1,1'-biphenyl]-2-carboxylic acid;
4'-[[5-(3-butenyl)-3-(1-difluoropentyl)-1H-1,2,4-triazol-1-yl]methyl][1,1'-biphenyl]-2-carboxylic acid;
4'-[[5-(1-butynyl)-3-ethyl-1H-1,2,4-triazol-1-yl]methyl][1,1'-biphenyl]-2-carboxylic acid;
4'-[[5-(1-butynyl)-3-propyl-1H-1,2,4-triazol-1-yl]methyl][1,1'-biphenyl]-2-carboxylic acid;
4'-[[5-(1-butynyl)-3-butyl-1H-1,2,4-triazol-1-yl]methyl][1,1'-biphenyl]-2-carboxylic acid;
4'-[[5-(1-butynyl)-3-secbutyl-1H-1,2,4-triazol-1-yl]methyl][1,1'-biphenyl]-2-carboxylic acid;
4'-[[5-(1-butynyl)-3-isobutyl-1H-1,2,4-triazol-1-yl]methyl][1,1'-biphenyl]-2-carboxylic acid;
4'-[[5-(1-butynyl)-3-tertbutyl-1H-1,2,4-triazol-1-yl]methyl][1,1'-biphenyl]-2-carboxylic acid;
4'-[[5-(1-butynyl)-3-pentyl-1H-1,2,4-triazol-1-yl]methyl][1,1'-biphenyl]-2-carboxylic acid;
4'-[[5-(1-butynyl)-3-isopentyl-1H-1,2,4-triazol-1-yl]methyl][1,1'-biphenyl]-2-carboxylic acid;
4'-[[5-(1-butynyl)-3-mercapto-1H-1,2,4-triazol-1-yl]methyl][1,1'-biphenyl]-2-carboxylic acid;
4'-[[5-(1-butynyl)-3-thiomethyl-1H-1,2,4-triazol-1-yl]methyl][1,1'-biphenyl]-2-carboxylic acid;
4'-[[5-(1-butynyl)-3-thioethyl-1H-1,2,4-triazol-1-yl]methyl][1,1'-biphenyl]-2-carboxylic acid;
4'-[[5-(1-butynyl)-3-thiopropyl-1H-1,2,4-triazol-1-yl]methyl][1,1'-biphenyl]-2-carboxylic acid;
4'-[[5-(1-butynyl)-3-hydroxy-1H-1,2,4-triazol-1-yl]methyl][1,1'-biphenyl]-2-carboxylic acid;
4'-[[5-(1-butynyl)-3-methoxy-1H-1,2,4-triazol-1-yl]methyl][1,1'-biphenyl]-2-carboxylic acid;
4'-[[5-(1-butynyl)-3-ethoxy-1H-1,2,4-triazol-1-yl]methyl][1,1'-biphenyl]-2-carboxylic acid;
4'-[[5-(1-butynyl)-3-propoxy-1H-1,2,4-triazol-1-yl]methyl][1,1'-biphenyl]-2-carboxylic acid;
4'-[[5-(1-butynyl)-3-cyclohexyl-1H-1,2,4-triazol-1-yl]methyl][1,1'-biphenyl]-2-carboxylic acid;
4'-[[5-(1-butynyl)-3-cyclohexylmethyl-1H-1,2,4-triazol-1-yl]methyl][1,1'-biphenyl]-2-carboxylic acid;
4'-[[5-(1-butynyl)-3-(2-cyclohexylethyl)-1H-1,2,4-triazol-1-yl]methyl][1,1'-biphenyl]-2-carboxylic acid;
4'-[[5-(1-butynyl)-3-cyclohexanoyl-1H-1,2,4-triazol-1-yl]methyl][1,1'-biphenyl]-2-carboxylic acid;
4'-[[5-(1-butynyl)3-(1-oxo-2-cyclohexylethyl)-1H-1,2,4-1-yl]methyl][1,1'-biphenyl]-2-carboxylic acid;
4'-[[5-(1-butynyl)-3-phenyl-1H-1,2,4-triazol-1-yl]methyl][1,1'-biphenyl]-2-carboxylic acid;
4'-[[5-(1-butynyl)-3-phenylmethyl-1H-1,2,4-triazol-1-yl]methyl][1,1'-biphenyl]-2-carboxylic acid;
4'-[[5-(1-butynyl)-3-(2-phenylethyl)-1H-1,2,4-triazol-1-yl]methyl][1,1'-biphenyl]-2-carboxylic acid;

4'-[[5-(1-butynyl)-3-benzoyl-1H-1,2,4-triazol-1-yl]methyl][1,1'-biphenyl]-2-carboxylic acid;
4'-[[5-(1-butynyl)-3-(1-oxo-2-phenylethyl)-1H-1,2,4-triazol-1-yl]methyl][1,1'-biphenyl]-2-carboxylic acid;
4'-[[5-(1-butynyl)-3-(1,1-dimethoxypropyl)-1H-1,2,4-triazol-1-yl]methyl][1,1'-biphenyl]-2-carboxylic acid;
4'-[[5-(1-butynyl)-3-(1,1-dimethoxybutyl)-1H-1,2,4-triazol-1-yl]methyl][1,1'-biphenyl]-2-carboxylic acid;
4'-[[5-(1-butynyl)-3-(1,1-dimethoxypentyl)-1H-1,2,4-triazol-1-yl]methyl][1,1'-biphenyl]-2-carboxylic acid;
4'-[[5-(1-butynyl)-3-(1-oxopropyl)-1H-1,2,4-triazol-1-yl]methyl][1,1'-biphenyl]-2-carboxylic acid;
4'-[[5-(1-butynyl)-3-(1-oxobutyl)-1H-1,2,4-triazol-1-yl]methyl][1,1'-biphenyl]-2-carboxylic acid;
4'-[[5-(1-butynyl)-3-(1-oxopentyl)-1H-1,2,4-triazol-1-yl]methyl][1,1'-biphenyl]-2-carboxylic acid;
4'-[[5-(1-butynyl)-3-(1,1-difluoroethyl)-1H-1,2,4-triazol-1-yl]methyl][1,1'-biphenyl]-2-carboxylic acid;
4'-[[5-(1-butynyl)-3-(1,1-difluoropropyl)-1H-1,2,4-triazol-1-yl]methyl][1,1'-biphenyl]-2-carboxylic acid;
4'-[[5-(1-butynyl)-3-(1,1-difluorobutyl)-1H-1,2,4-triazol-1-yl]methyl][1,1'-biphenyl]-2-carboxylic acid;
4'-[[5-(1-butynyl)-3-(1,1-difluoropentyl)-1H-1,2,4-triazol-1-yl]methyl][1,1'-biphenyl]-2-carboxylic acid;
4'-[[5-(2-butynyl)-3-ethyl-1H-1,2,4-triazol-1-yl]methyl][1,1'-biphenyl]-2-carboxylic acid;
4'-[[5-(2-butynyl)-3-propyl-1H-1,2,4-triazol-1-yl]methyl][1,1'-biphenyl]-2-carboxylic acid;
4'-[[5-(2-butynyl)-3-butyl-1H-1,2,4-triazol-1-yl]methyl][1,1'-biphenyl]-2-carboxylic acid;
4'-[[5-(2-butynyl)-3-secbutyl-1H-1,2,4-triazol-1-yl]methyl][1,1'-biphenyl]-2-carboxylic acid;
4'-[[5-(2-butynyl)-3-isobutyl-1H-1,2,4-triazol-1-yl]methyl][1,1'-biphenyl]-2-carboxylic acid;
4'-[[5-(2-butynyl)-3-tertbutyl-1H-1,2,4-triazol-1-yl]methyl][1,1'-biphenyl]-2-carboxylic acid;
4'-[[5-(2-butynyl)-3-pentyl-1H-1,2,4-triazol-1-yl]methyl][1,1'-biphenyl]-2-carboxylic acid;
4'-[[5-(2-butynyl)-3-isopentyl-1H-1,2,4-triazol-1-yl]methyl][1,1'-biphenyl]-2-carboxylic acid;
4'-[[5-(2-butynyl)-3-mercapto-1H-1,2,4-triazol-1-yl]methyl][1,1'-biphenyl]-2-carboxylic acid;
4'-[[5-(2-butynyl)-3-thiomethyl-1H-1,2,4-triazol-1-yl]methyl][1,1'-biphenyl]-2-carboxylic acid;
4'-[[5-(2-butynyl)-3-thioethyl-1H-1,2,4-triazol-1-yl]methyl][1,1'-biphenyl]-2-carboxylic acid;
4'-[[5-(2-butynyl)-3-thiopropyl-1H-1,2,4-triazol-1-yl]methyl][1,1'-biphenyl]-2-carboxylic acid;
4'-[[5-(2-butynyl)-3-hydroxy-1H-1,2,4-triazol-1-yl]methyl][1,1'-biphenyl]-2-carboxylic acid;
4'-[[5-(2-butynyl)-3-methoxy-1H-1,2,4-triazol-1-yl]methyl][1,1'-biphenyl]-2-carboxylic acid;
4'-[[5-(2-butynyl)-3-ethoxy-1H-1,2,4-triazol-1-yl]methyl][1,1'-biphenyl]-2-carboxylic acid;
4'-[[5-(2-butynyl)-3-propoxy-1H-1,2,4-triazol-1-yl]methyl][1,1'-biphenyl]-2-carboxylic acid;
4'-[[5-(2-butynyl)-3-cyclohexyl-1H-1,2,4-triazol-1-yl]methyl][1,1'-biphenyl]-2-carboxylic acid;
4'-[[5-(2-butynyl)-3-cyclohexylmethyl-1H-1,2,4-triazol-1-yl]methyl][1,1'-biphenyl]-2-carboxylic acid;
4'-[[5-(2-butynyl)-3-(2-cyclohexylethyl)-1H-1,2,4-triazol-1-yl]methyl][1,1'-biphenyl]-2-carboxylic acid;
4'-[[5-(2-butynyl)-3-cyclohexanoyl-1H-1,2,4-triazol-1-yl]methyl][1,1'-biphenyl]-2-carboxylic acid;
4'-[[5-(2-butynyl)-3-(1-oxo-2-cyclohexylethyl)-1H-1,2,4-triazol-1-yl]methyl][1,1'-biphenyl]-2-carboxylic acid;

4'-[[5-(2-butynyl)-3-phenyl-1H-1,2,4-triazol-1-yl]methyl][1,1'-biphenyl]-2-carboxylic acid;
4'-[[5-(2-butynyl)-3-phenylmethyl-1H-1,2,4-triazol-1-yl]methyl][1,1'-biphenyl]-2-carboxylic acid;
4'-[[5-(2-butynyl)-3-(2-phenylethyl)-1H-1,2,4-triazol-1-yl]methyl][1,1'-biphenyl]-2-carboxylic acid;
4'-[[5-(2-butynyl)-3-benzoyl-1H-1,2,4-triazol-1-yl]methyl][1,1'-biphenyl]-2-carboxylic acid;
4'-[[5-(2-butynyl)-3-(1-oxo-2-phenylethyl)-1H-1,2,4-triazol-1-yl]methyl][1,1'-biphenyl]-2-carboxylic acid;
4'-[[5-(2-butynyl)-3-(1,1-dimethoxypropyl)-1H-1,2,4-triazol-1-yl]methyl][1,1'-biphenyl]-2-carboxylic acid;
4'-[[5-(2-butynyl)-3-(1,1-dimethoxybutyl)-1H-1,2,4-triazol-1-yl]methyl][1,1'-biphenyl]-2-carboxylic acid;
4'-[[5-(2-butynyl)-3-(1,1-dimethoxypentyl)-1H-1,2,4-triazol-1-yl]methyl][1,1'-biphenyl]-2-carboxylic acid;
4'-[[5-(2-butynyl)-3-(1-oxopropyl)-1H-1,2,4-triazol-1-yl]methyl][1,1'-biphenyl]-2-carboxylic acid;
4'-[[5-(2-butynyl)-3-(1-oxobutyl)-1H-1,2,4-triazol-1-yl]methyl][1,1'-biphenyl]-2-carboxylic acid;
4'-[[5-(2-butynyl)-3-(1-oxopentyl)-1H-1,2,4-triazol-1-yl]methyl][1,1'-biphenyl]-2-carboxylic acid;
4'-[[5-(2-butynyl)-3-(1,1-difluoroethyl)-1H-1,2,4-triazol-1-yl]methyl][1,1'-biphenyl]-2-carboxylic acid;
4'-[[5-(2-butynyl)-3-(1,1-difluoropropyl)-1H-1,2,4-triazol-1-yl]methyl][1,1'-biphenyl]-2-carboxylic acid;
4'-[[5-(2-butynyl)-3-(1,1-difluorobutyl)-1H-1,2,4-triazol-1-yl]methyl][1,1'-biphenyl]-2-carboxylic acid;
4'-[[5-(2-butynyl)-3-(1,1-difluoropentyl)-1H-1,2,4-triazol-1-yl]methyl][1,1'-biphenyl]-2-carboxylic acid;
4'-[[5-(3-butynyl)-3-ethyl-1H-1,2,4-triazol-1-yl]methyl][1,1'-biphenyl]-2-carboxylic acid;
4'-[[5-(3-butynyl)-3-propyl-1H-1,2,4-triazol-1-yl]methyl][1,1'-biphenyl]-2-carboxylic acid;
4'-[[5-(3-butynyl)-3-isopropyl-1H-1,2,4-triazol-1-yl]methyl][1,1'-biphenyl]-2-carboxylic acid;
4'-[[5-(3-butynyl)-3-butyl-1H-1,2,4-triazol-1-yl]methyl][1,1'-biphenyl]-2-carboxylic acid;
4'-[[5-(3-butynyl)-3-secbutyl-1H-1,2,4-triazol-1-yl]methyl][1,1'-biphenyl]-2-carboxylic acid;
4'-[[5-(3-butynyl)-3-isobutyl-1H-1,2,4-triazol-1-yl]methyl][1,1'-biphenyl]-2-carboxylic acid;
4'-[[5-(3-butynyl)-3-tertbutyl-1H-1,2,4-triazol-1-yl]methyl][1,1'-biphenyl]-2-carboxylic acid;
4'-[[5-(3-butynyl)-3-isopentyl-1H-1,2,4-triazol-1-yl]methyl][1,1'-biphenyl]-2-carboxylic acid;
4'-[[5-(3-butynyl)-3-pentyl-1H-1,2,4-triazol-1-yl]methyl][1,1'-biphenyl]-2-carboxylic acid;
4'-[[5-(3-butynyl)-3-mercapto-1H-1,2,4-triazol-1-yl]methyl][1,1'-biphenyl]-2-carboxylic acid;
4'-[[5-(3-butynyl)-3-thiomethyl-1H-1,2,4-triazol-1-yl]methyl][1,1'-biphenyl]-2-carboxylic acid;
4'-[[5-(3-butynyl)-3-thioethyl-1H-1,2,4-triazol-1-yl]methyl][1,1'-biphenyl]-2-carboxylic acid;
4'-[[5-(3-butynyl)-3-thiopropyl-1H-1,2,4-triazol-1-yl]methyl][1,1'-biphenyl]-2-carboxylic acid;
4'-[[5-(3-butynyl)-3-hydroxy-1H-1,2,4-triazol-1-yl]methyl][1,1'-biphenyl]-2-carboxylic acid;
4'-[[5-(3-butynyl)-3-methoxy-1H-1,2,4-triazol-1-yl]methyl][1,1'-biphenyl]-2-carboxylic acid;
4'-[[5-(3-butynyl)-3-ethoxy-1H-1,2,4-triazol-1-yl]methyl][1,1'-biphenyl]-2-carboxylic acid;
4'-[[5-(3-butynyl)-3-propoxy-1H-1,2,4-triazol-1-yl]methyl][1,1'-biphenyl]-2-carboxylic acid;
4'-[[5-(3-butynyl)-3-cyclohexyl-1H-1,2,4-triazol-1-yl]methyl][1,1'-biphenyl]-2-carboxylic acid;
4'-[[5-(3-butynyl)-3-cyclohexylmethyl-1H-1,2,4-triazol-1-yl]methyl][1,1'-biphenyl]-2-carboxylic acid;
4'-[[5-(3-butynyl)-3-(2-cyclohexylethyl)-1H-1,2,4-triazol-1-yl]methyl][1,1'-biphenyl]-2-carboxylic acid;
4'-[[5-(3-butynyl)-3-cyclohexanoyl-1H-1,2,4-triazol-1-yl]methyl][1,1'-biphenyl]-2-carboxylic acid;
4'-[[5-(3-butynyl)-3-(1-oxo-2-cyclohexylethyl)-1H-1,2,4-triazol-1-yl]methyl][1,1'-biphenyl]-2-carboxylic acid;
4'-[[5-(3-butynyl)-3-phenyl-1H-1,2,4-triazol-1-yl]methyl][1,1'-biphenyl]-2-carboxylic acid;
4'-[[5-(3-butynyl)-3-phenylmethyl-1H-1,2,4-triazol-1-yl]methyl][1,1'-biphenyl]-2-carboxylic acid;
4'-[[5-(3-butynyl)-3-(2-phenylethyl)-1H-1,2,4-triazol-1-yl]methyl][1,1'-biphenyl]-2-carboxylic acid;
4'-[[5-(3-butynyl)-3-benzoyl-1H-1,2,4-triazol-1-yl]methyl][1,1'-biphenyl]-2-carboxylic acid;
4'-[[5-(3-butynyl)-3-(1-oxo-2-phenylethyl)-1H-1,2,4-triazol-1-yl]methyl][1,1'-biphenyl]-2-carboxylic acid;
4'-[[5-(3-butynyl)-3-(1,1-dimethoxypropyl)-1H-1,2,4-triazol-1-yl]methyl][1,1'-biphenyl]-2-carboxylic acid;
4'-[[5-(3-butynyl)-3-(1,1-dimethoxybutyl)-1H-1,2,4-triazol-1-yl]methyl][1,1'-biphenyl]-2-carboxylic acid;
4'-[[5-(3-butynyl)-3-(1,1-dimethoxypentyl)-1H-1,2,4-triazol-1-yl]methyl][1,1'-biphenyl]-2-carboxylic acid;
4'-[[5-(3-butynyl)-3-(1-oxopropyl)-1H-1,2,4-triazol-1-yl]methyl][1,1'-biphenyl]-2-carboxylic acid;
4'-[[5-(3-butynyl)-3-(1-oxobutyl)-1H-1,2,4-triazol-1-yl]methyl][1,1'-biphenyl]-2-carboxylic acid;
4'-[[5-(3-butynyl)-3-(1-oxopentyl)-1H-1,2,4-triazol-1-yl]methyl][1,1'-biphenyl]-2-carboxylic acid;
4'-[[5-(3-butynyl)-3-(1,1-difluoroethyl)-1H-1,2,4-triazol-1-yl]methyl][1,1'-biphenyl]-2-carboxylic acid;
4'-[[5-(3-butynyl)-3-(1,1-difluoropropyl)-1H-1,2,4-triazol-1-yl]methyl][1,1'-biphenyl]-2-carboxylic acid;
4'-[[5-(3-butynyl)-3-(1,1-difluorobutyl)-1H-1,2,4-triazol-1-yl]methyl][1,1'-biphenyl]-2-carboxylic acid;
4'-[[5-(3-butynyl)-3-(1,1-difluoropentyl)-1H-1,2,4-triazol-1-yl]methyl][1,1'-biphenyl]-2-carboxylic acid;
4'-[(3,5-diethoxy-1H-1,2,4-triazol-1-yl)methyl][1,1'-biphenyl]-2-carboxylic acid;
4'-[(3,5-dipropoxy-1H-1,2,4-triazol-1-yl)methyl][1,1'-biphenyl]-2-carboxylic acid;
4'-[(3,5-diisopropoxy-1H-1,2,4-triazol-1-yl)methyl][1,1'-biphenyl]-2-carboxylic acid;
4'-[(3,5-dibutoxy-1H-1,2,4-triazol-1-yl)methyl][1,1'-biphenyl]-2-carboxylic acid;
4'-[(3,5-dithiomethyl-1H-1,2,4-triazol-1-yl)methyl][1,1'-biphenyl]-2-carboxylic acid;
4'-[(3,5-dithioethyl-1H-1,2,4-triazol-1-yl)methyl][1,1'-biphenyl]-2-carboxylic acid;
4'-[(3,5-dithiopropyl-1H-1,2,4-triazol-1-yl)methyl][1,1'-biphenyl]-2-carboxylic acid;
4'-[(3,5-dithioisopropyl-1H-1,2,4-triazol-1-yl)methyl][1,1'-biphenyl]-2-carboxylic acid;
4'-[[3,5-di(1-butenyl)-1H-1,2,4-triazol-1-yl]methyl][1,1'-biphenyl]-2-carboxylic acid;
4'-[[3,5-di(2-butenyl)-1H-1,2,4-triazol-1-yl]methyl][1,1'-biphenyl]-2-carboxylic acid;
4'-[[3,5-di(3-butenyl)-1H-1,2,4-triazol-1-yl]methyl][1,1'-biphenyl]-2-carboxylic acid;
4'-[[3,5-di(1-butynyl)-1H-1,2,4-triazol-1-yl]methyl][1,1'-biphenyl]-2-carboxylic acid;
4'-[[3,5-di(2-butynyl)-1H-1,2,4-triazol-1-yl]methyl][1,1'-biphenyl]-2-carboxylic acid;
4'-[[3,5-di(3-butynyl)-1H-1,2,4-triazol-1-yl]methyl][1,1'-biphenyl]-2-carboxylic acid;
5-[4'-[(5-butyl-3-chloro-1H-1,2,4-triazol-1-yl)methyl][1,1'-biphenyl]-2-yl]-1H-tetrazole;

5-[4'-[(3-butyl-5-chloro-1H-1,2,4-triazol-1-yl)methyl][1,1'-biphenyl]-2-yl]-1H-tetrazole;
5-[4'-[(5-butyl-3-ethyl-1H-1,2,4-triazol-1-yl)methyl][1,1'-biphenyl]-2-yl]-1H-tetrazole;
5-[4'-[(5-butyl-3-propyl-1H-1,2,4-triazol-1-yl)methyl][1,1'-biphenyl]-2-yl]-1H-tetrazole;
5-[4'-[(5-butyl-3-isopropyl-1H-1,2,4-triazol-1-yl)methyl][1,1'-biphenyl]-2-yl]-1H-tetrazole;
5-[4'-[(3,5-dibutyl-1H-1,2,4-triazol-1-yl)methyl][1,1'-biphenyl]-2-yl]-1H-tetrazole;
5-[4'-[(5-butyl-3-secbutyl-1H-1,2,4-triazol-1-yl)methyl][1,1'-biphenyl]-2-yl]-1H-tetrazole;
5-[4'-[(5-butyl-3-isobutyl-1H-1,2,4-triazol-1-yl)methyl][1,1'-biphenyl]-2-yl]-1H-tetrazole;
5-[4'-[(5-butyl-3-tertbutyl-1H-1,2,4-triazol-1-yl)methyl][1,1'-biphenyl]-2-yl]-1H-tetrazole;
5-[4'-[(5-butyl-3-pentyl-1H-1,2,4-triazol-1-yl)methyl][1,1'-biphenyl]-2-yl]-1H-tetrazole;
5-[4'-[(5-butyl-1H-1,2,4-triazol-1-yl)methyl][1,1'-biphenyl]-2-yl]-1H-tetrazole;
5-[4'-[(3-butyl-1H-1,2,4-triazol-1-yl)methyl][1,1'-biphenyl]-2-yl]-1H-tetrazole;
5-[4'-[(5-butyl-3-isopentyl-1H-1,2,4-triazol-1-yl)methyl][1,1'-biphenyl]-2-yl]-1H-tetrazole;
5-[4'-[(5-butyl-3-mercapto-1H-1,2,4-triazol-1-yl)methyl][1,1'-biphenyl]-2-yl]-1H-tetrazole;
5-[4'-[(5-butyl-3-thiomethyl-1-1,2,4-triazol-1-yl)methyl][1,1'-biphenyl]-2-yl]-1H-tetrazole;
5-[4'-[(5-butyl-3-thioethyl-1H-1,2,4-triazol-1-yl)methyl][1,1'-biphenyl]-2-yl]-1H-tetrazole;
5-[4'-[(5-butyl-3-thiopropyl-1H-1,2,4-triazol-1-yl)methyl][1,1'-biphenyl]-2-yl]-1H-tetrazole;
5-[4'-[(5-butyl-3-hydroxy-1H-1,2,4-triazol-1-yl)methyl][1,1'-biphenyl]-2-yl]-1H-tetrazole;
5-[4'-[(5-butyl-3-methoxy-1H-1,2,4-triazol-1-yl)methyl][1,1'-biphenyl]-2-yl]-1H-tetrazole;
5-[4'-[(5-butyl-3-ethoxy-1H-1,2,4-triazol-1-yl)methyl][1,1'-biphenyl]-2-yl]-1H-tetrazole;
5-[4'-[(5-butyl-3-propoxy-1H-1,2,4-triazol-1-yl)methyl][1,1'-biphenyl]-2-yl]-1H-tetrazole;
5-[4'-[(5-butyl-3-butoxy-1H-1,2,4-triazol-1-yl)methyl][1,1'-biphenyl]-2-yl]-1H-tetrazole;
5-[4'-[(5-butyl-3-cyclohexyl-1H-1,2,4-triazol-1-yl)methyl][1,1'-biphenyl]-2-yl]-1H-tetrazole;
5-[4'-[(5-butyl-3-cyclohexylmethyl-1H-1,2,4-triazol-1-yl)methyl][1,1'-biphenyl]-2-yl]-1H-tetrazole;
5-[4'-[[5-butyl-3-(2-cyclohexylethyl)-1H-1,2,4-triazol-1-yl)methyl][1,1'-biphenyl]-2-yl]-1H-tetrazole;
5-[4'-[(5-butyl-3-cyclohexanoyl-1,2,4-triazol-1-yl)methyl][1,1'-biphenyl]-2-yl]-1H-tetrazole;
5-[4'-[[5-butyl-3-(1-oxo-2-cyclohexylethyl)-1H-1,2,4-triazol-1-yl)methyl][1,1'-biphenyl]-2-yl]-1H-tetrazole;
5-[4'-[(5-butyl-3-phenyl-1,2,4-triazol-1-yl)methyl][1,1'-biphenyl]-2-yl]-1H-tetrazole;
5-[4'-[(5-butyl-3-phenylmethyl-1,2,4-triazol-1-yl)methyl][1,1'-biphenyl]-2-yl]-1H-tetrazole;
5-[4'-[[5-butyl-3-(2-phenylethyl)-1H-1,2,4-triazol-1-yl)methyl][1,1'-biphenyl]-2-yl]-1H-tetrazole;
5-[4'-[(5-butyl-3-benzoyl-1,2,4-triazol-1-yl)methyl][1,1'-biphenyl]-2-yl]-1H-tetrazole;
5-[4'-[[5-butyl-3-(1-oxo-2-phenylethyl)-1H-1,2,4-triazol-1-yl)methyl][1,1'-biphenyl]-2-yl]-1H-tetrazole;
5-[4'-[[5-butyl-3-(1,1-dimethoxypropyl)-1H-1,2,4-triazol-1-yl)methyl][1,1'-biphenyl]-2-yl]-1H-tetrazole;
5-[4'-[[5-butyl-3-(1,1 dimethoxybutyl)-1H-1,2,4-triazol-1-yl)methyl][1,1'-biphenyl]-2-yl]-1H-tetrazole;
5-[4'-[[5-butyl-3-(1,1 dimethoxypentyl)-1H-1,2,4-triazol-1-yl)methyl][1,1'-biphenyl]-2-yl]-1H-tetrazole;
5-[4'-[[5-butyl-3-(1-oxopropyl)-1H-1,2,4-triazol-1-yl)methyl][1,1'-biphenyl]-2-yl]-1H-tetrazole;
5-[4'-[[5-butyl-3-(1-oxobutyl)-1H-1,2,4-triazol-1-yl)methyl][1,1'-biphenyl]-2-yl]-1H-tetrazole;
5-[4'-[[5-butyl-3-(1-oxopentyl)-1H-1,2,4-triazol-1-yl)methyl][1,1'-biphenyl]-2-yl]-1H-tetrazole;
5-[4'-[[5-butyl-3-(1,1-difluoroethyl)-1H-1,2,4-triazol-1-yl)methyl][1,1'-biphenyl]-2-yl]-1H-tetrazole;
5-[4'-[[5-butyl-3-(1,1-difluoropropyl)-1H-1,2,4 triazol-1-yl)methyl][1,1'-biphenyl]-2-yl]-1H-tetrazole;
5-[4'-[[5-butyl-3-(1,1-difluorobutyl)-1H-1,2,4-triazol-1-yl)methyl][1,1'-biphenyl]-2-yl]-1H-tetrazole;
5-[4'-[[3-butyl-5-(1,1-difluorobutyl)-1H-1,2,4-triazol-1-yl)methyl][1,1'-biphenyl]-2-yl]-1H-tetrazole;
5-[4'-[[5-butyl-3-(1,1-difluoropentyl)-1H-1,2,4-triazol-1-yl)methyl][1,1'-biphenyl]-2-yl]-1H-tetrazole;
5-[4'-[(5-propyl-3-ethyl-1H-1,2,4-triazol-1-yl)methyl][1,1'-biphenyl]-2-yl]-1H-tetrazole;
5-[4'-[(3,5-dipropyl-1H-1,2,4-triazol-1-yl)methyl][1,1'-biphenyl]-2-yl]-1H-tetrazole;
5-[4'-[(3,5-isopropyl-1H-1,2,4-triazol-1-yl)methyl][1,1'-biphenyl]-2-yl]-1H-tetrazole;
5-[4'-[(5-propyl-3-isopropyl-1H-1,2,4-triazol-1-yl)methyl][1,1'-biphenyl]-2-yl]-1H-tetrazole;
5-[4'-[(5-propyl-3-butyl-1H-1,2,4-triazol-1-yl)methyl][1,1'-biphenyl]-2-yl]-1H-tetrazole;
5-[4'-[(5-propyl-3-secbutyl-1H-1,2,4-triazol-1-yl)methyl][1,1'-biphenyl]-2-yl]-1H-tetrazole;
5-[4'-[(5-propyl-3-isobutyl-1H-1,2,4-triazol-1-yl)methyl][1,1'-biphenyl]-2-yl]-1H-tetrazole;
5-[4'-[(5-propyl-3-tertbutyl-1H-1,2,4-triazol-1-yl)methyl][1,1'-biphenyl]-2-yl]-1H-tetrazole;
5-[4'-[(5-propyl-3-pentyl-1H-1,2,4-triazol-1-yl)methyl][1,1'-biphenyl]-2-yl]-1H-tetrazole;
5-[4'-[(5-propyl-3-isopentyl-1H-1,2,4-triazol-1-yl)methyl][1,1'-biphenyl]-2-yl]-1H-tetrazole;
5-[4'-[(5-propyl-3-mercapto-1H-1,2,4-triazol-1-yl)methyl][1,1'-biphenyl]-2-yl]-1H-tetrazole;
5-[4'-[(5-propyl-3-thiomethyl-1H-1,2,4-triazol-1-yl)methyl][1,1'-biphenyl]-2-yl]-1H-tetrazole;
5-[4'-[(5-propyl-3-thioethyl-1H-1,2,4-triazol-1-yl)methyl][1,1'-biphenyl]-2-yl]-1H-tetrazole;
5-[(5-propyl-3-thiopropyl-1H-1,2,4-triazol-1-yl)methyl][1,1'-biphenyl]-2-yl]-1H-tetrazole;
5-[4'-[(5-propyl-3-hydroxy-1H-1,2,4-triazol-1-yl)methyl][1,1'-biphenyl]-2-yl]-1H-tetrazole;
5-[4'-[(5-propyl-3-methoxy-1H-1,2,4-triazol-1-yl)methyl][1,1'-biphenyl]-2-yl]-1H-tetrazole;
5-[4'-[(5-propyl-3-ethoxy-1H-1,2,4-triazol-1-yl)methyl][1,1'-biphenyl]-2-yl]-1H-tetrazole;
5-[4'-[(5-propyl-3-propoxy-1H-1,2,4-triazol-1-yl)methyl][1,1'-biphenyl]-2-yl]-1H-tetrazole;
5-[4'-[(5-propyl-3-cyclohexyl-1H-1,2,4-triazol-1-yl)methyl][1,1'-biphenyl]-2-yl]-1H-tetrazole;
5-[4'-[(5-propyl-3-cyclohexylmethyl-1H-1,2,4-triazol-1-yl)methyl][1,1'-biphenyl]-2-yl]-1H-tetrazole;
5-[5-[4'-[[5-propyl-3-(2-cyclohexylethyl)-1H-1,2,4-triazol-1-yl]methyl][1,1'-biphenyl]-2-yl]-1H-tetrazole;
5-[4'-[(5-propyl-3-cyclohexanoyl-1H-1,2,4-triazol-1-yl)methyl][1,1'-biphenyl]-2-yl]-1H-tetrazole;
5-[5-[4'-[[5-propyl-3-(1-oxo-2-cyclohexylethyl)-1H-1,2,4-triazol-1-yl]methyl][1,1'-biphenyl]-2-yl]-1H-tetrazole;
5-[4'-[(5-propyl-3-phenyl-1H-1,2,4-triazol-1-yl)methyl][1,1'-biphenyl]-2-yl]-1H-tetrazole;
5-[4'-[(5-propyl-3-phenylmethyl-1H-1,2,4-triazol-1-yl)methyl][1,1'-biphenyl]-2-yl]-1H-tetrazole;

5-[4'-[[5-propyl-3-(2-phenylethyl)-1H-1,2,4-triazol-1-yl]methyl][1,1'-biphenyl]-2-yl]-1H-tetrazole;
5-[4'-[(5-propyl-3-benzoyl-1H-1,2,4-triazol-1-yl)methyl][1,1'-biphenyl]-2-yl]-1H-tetrazole;
5-[4'-[[5-propyl-3-(1-oxo-2-phenylethyl)-1H-1,2,4-triazol-1-yl]methyl][1,1'-biphenyl]-2-yl]-1H-tetrazole;
5-[4'-[[5-propyl-3-(1,1-dimethoxypropyl)-1H-1,2,4-triazol-1-yl]methyl][1,1'-biphenyl]-2-yl]-1H-tetrazole;
5-[4'-[[5-propyl-3-(1,1-dimethoxybutyl)-1H-1,2,4-triazol-1-yl]methyl][1,1'-biphenyl]-2-yl]-1H-tetrazole;
5-[4'-[[5-propyl-3-(1,1-dimethoxypentyl)-1H-1,2,4-triazol-1-yl]methyl][1,1'-biphenyl]-2-yl]-1H-tetrazole;
5-[4'-[[5-propyl-3-(1-oxopropyl)-1H-1,2,4-triazol-1-yl]methyl][1,1'-biphenyl]-2-yl]-1H-tetrazole;
5-[4'-[[5-propyl-3-(1-oxobutyl)-1H-1,2,4-triazol-1-yl]methyl][1,1'-biphenyl]-2-yl]-1H-tetrazole;
5-[4'-[[5-propyl-3-(1-oxopentyl)-1H-1,2,4-triazol-1-yl]methyl][1,1'-biphenyl]-2-yl]-1H-tetrazole;
5-[4'-[[5-propyl-3-(1,1-difluoroethyl)-1H-1,2,4-triazol-1-yl]methyl][1,1'-biphenyl]-2-yl]-1H-tetrazole;
5-[4'-[[3,5-bis(heptafluoropropyl)-1H-1,2,4-triazol-1-yl]methyl][1,1'-biphenyl]-2-yl]-1H-tetrazole;
5-[4'-[[5-propyl-3-(1,1-difluoropropyl)-1H-1,2,4-triazol-1-yl]methyl][1,1'-biphenyl]-2-yl]-1H-tetrazole;
5-[4'-[[5-propyl-3-(1,1-difluorobutyl)-1H-1,2,4-triazol-1-yl]methyl][1,1'-biphenyl]-2-yl]-1H-tetrazole;
5-[4'-[[5-propyl-3-(1,1-difluoropentyl)-1H-1,2,4-triazol-1-yl]methyl][1,1'-biphenyl]-2-yl]-1H-tetrazole;
5-[4'-[(3,5-diethyl-1H-1,2,4-triazol-1-yl)methyl][1,1'-biphenyl]-2-yl]-1H-tetrazole;
5-[4'-[(5-ethyl-3-propyl-1H-1,2,4-triazol-1-yl)methyl][1,1'-biphenyl]-2-yl]-1H-tetrazole;
5-[4'-[(5-ethyl-3-isopropyl-1H-1,2,4-triazol-1-yl)methyl][1,1'-biphenyl]-2-yl]-1H-tetrazole;
5-[4'-[(5-ethyl-3-butyl-1H-1,2,4-triazol-1-yl)methyl][1,1'-biphenyl]-2-yl]-1H-tetrazole;
5-[4'-[(5-ethyl-3-secbutyl-1H-1,2,4-triazol-1-yl)methyl][1,1'-biphenyl]-2-yl]-1H-tetrazole;
5-[4'-[(5-ethyl-3-isobutyl-1H-1,2,4-triazol-1-yl)methyl][1,1'-biphenyl]-2-yl]-1H-tetrazole;
5-[4'-[(5-ethyl-3-tertbutyl-1H-1,2,4-triazol-1-yl)methyl][1,1'-biphenyl]-2-yl]-1H-tetrazole;
5-[4'-[(5-ethyl-3-pentyl-1H-1,2,4-triazol-1-yl)methyl][1,1'-biphenyl]-2-yl]-1H-tetrazole;
5-[4'-[(5-ethyl-3-isopentyl-1H-1,2,4-triazol-1-yl)methyl][1,1'-biphenyl]-2-yl]-1H-tetrazole;
5-[4'-[(5-ethyl-3-mercapto-1H-1,2,4-triazol-1-yl)methyl][1,1'-biphenyl]-2-yl]-1H-tetrazole;
5-[4'-[(5-ethyl-3-thiomethyl-1H-1,2,4-triazol-1-yl)methyl)][1,1'-biphenyl]-2-yl]-1H-tetrazole;
5-[4'-[(5-ethyl-3-thioethyl-1H-1,2,4-triazol-1-yl)methyl][1,1'-biphenyl]-2-yl]-1H-tetrazole;
5-[4'-[(5-ethyl-3-thiopropyl-1H-1,2,4-triazol-1-yl)methyl][1,1'-biphenyl]-2-yl]-1H-tetrazole;
5-[4'-[(5-ethyl-3-hydroxy-1H-1,2,4-triazol-1-yl)methyl][1,1'-biphenyl]-2-yl]-1H-tetrazole;
5-[4'-[(5-ethyl-3-methoxy-1H-1,2,4-triazol-1-yl)methyl][1,1'-biphenyl]-2-yl]-1H-tetrazole;
5-[4'-[(5-ethyl-3-ethoxy-1H-1,2,4-triazol-1-yl)methyl][1,1'-biphenyl]-2-yl]-1H-tetrazole;
5-[4'-[(5-ethyl-3-propoxy-1H-1,2,4-triazol-1-yl)methyl][1,1'-biphenyl]-2-yl]-1H-tetrazole;
5-[4'-[(5-ethyl-3-cyclohexyl-1H-1,2,4-triazol-1-yl)methyl][1,1'-biphenyl]-2-yl]-1H-tetrazole;
5-[4'-[(5-ethyl-3-cyclohexylmethyl-1H-1,2,4-triazol-1-yl)methyl][1,1'-biphenyl]-2-yl]-1H-tetrazole;
5-[4'-[[5-ethyl-3-(2-cyclohexylethyl)-1H-1,2,4-triazol-1-yl]methyl][1,1'-biphenyl]-2-yl]-1H-tetrazole;
5-[4'-[(5-ethyl-3-cyclohexanoyl-1H-1,2,4-triazol-1-yl)methyl][1,1'-biphenyl]-2-yl]-1H-tetrazole;
5-[4'-[[5-ethyl-3-(1-oxo-2-cyclohexylethyl)-1H-1,2,4-triazol-1-yl]methyl][1,1'-biphenyl]-2-yl]-1H-tetrazole;
5-[4'-[(5-ethyl-3-phenyl-1H-1,2,4-triazol-1-yl)methyl][1,1'-biphenyl]-2-yl]-1H-tetrazole;
5-[4'-[(5-ethyl-3-phenylmethyl-1H-1,2,4-triazol-1-yl)methyl][1,1'-biphenyl]-2-yl]-1H-tetrazole;
5-[4'-[[5-ethyl-3-(2-phenylethyl)-1H-1,2,4-triazol-1-yl]methyl][1,1'-biphenyl]-2-yl]-1H-tetrazole;
5-[4'-[(5-ethyl-3-benzoyl-1H-1,2,4-triazol-1-yl)methyl][1,1'-biphenyl]-2-yl]-1H-tetrazole;
5-[4'-[[5-ethyl-3-(1-oxo-2-phenylethyl)-1H-1,2,4-triazol-1-yl]methyl][1,1'-biphenyl]-2-yl]-1H-tetrazole;
5-[4'-[[5-ethyl-3-(1,1-dimethoxypropyl)-1H-1,2,4-triazol-1-yl]methyl][1,1'-biphenyl]-2-yl]-1H-tetrazole;
5-[4'-[[5-ethyl-3-(1,1-dimethoxybutyl)-1H-1,2,4-triazol-1-yl]methyl][1,1'-biphenyl]-2-yl]-1H-tetrazole;
5-[4'-[[5-ethyl-3-(1,1-dimethoxypentyl)-1H-1,2,4-triazol-1-yl]methyl][1,1'-biphenyl]-2-yl]-1H-tetrazole;
5-[4'-[[5-ethyl-3-(1-oxopropyl)-1H-1,2,4-triazol-1-yl]methyl][1,1'-biphenyl]-2-yl]-1H-tetrazole;
5-[4'-[[5-ethyl-3-(1-oxobutyl)-1H-1,2,4-triazol-1-yl]methyl][1,1'-biphenyl]-2-yl]-1H-tetrazole;
5-[4'-[[5-ethyl-3-(1-oxopentyl)-1H-1,2,4-triazol-1-yl]methyl][1,1'-biphenyl]-2-yl]-1H-tetrazole;
5-[4'-[[5-ethpyl-3-(1,1-difluoroethyl)-1H-1,2,4-triazol-1-yl]methyl][1,1'-biphenyl]-2-yl]-1H-tetrazole;
5-[4'-[[5-ethyl-3-(1,1-difluoropropyl)-1H-1,2,4-triazol-1-yl]methyl][1,1'-biphenyl]-2-yl]-1H-tetrazole;
5-[4'-[[5-ethyl-3-(1,1-difluorobutyl)-1H-1,2,4-triazol-1-yl]methyl][1,1'-biphenyl]-2-yl]-1H-tetrazole;
5-[4'-[[5-ethyl-3-(1,1-difluoropentyl)-1H-1,2,4-triazol-1-yl]methyl][1,1'-biphenyl]-2-yl]-1H-tetrazole;
5-[4'-[(5-secbutyl-3-ethyl-1H-1,2,4-triazol-1-yl)methyl][1,1'-biphenyl]-2-yl]-1H-tetrazole;
5-[4'-[(5-secbutyl-3-propyl-1H-1,2,4-triazol-1-yl)methyl][1,1'-biphenyl]-2-yl]-1H-tetrazole;
5-[4'-[(5-secbutyl-3-isopropyl-1H-1,2,4-triazol-1-yl)methyl][1,1'-biphenyl]-2-yl]-1H-tetrazole;
5-[4'-[(5-secbutyl-3-butyl-1H-1,2,4-triazol-1-yl)methyl][1,1'-biphenyl]-2-yl]-1H-tetrazole;
5-[4'-[(3,5-disecbutyl-1H-1,2,4-triazol-1-yl)methyl][1,1'-biphenyl]-2-yl]-1H-tetrazole;
5-[4'-[(5-secbutyl-3-isobutyl-1H-1,2,4-triazol-1-yl)methyl][1,1'-biphenyl]-2-yl]-1H-tetrazole;
5-[4'-[(5-secbutyl-3-tertbutyl-1H-1,2,4-triazol-1-yl)methyl][1,1'-biphenyl]-2-yl]-1H-tetrazole;
5-[4'-[(5-secbutyl-3-pentyl-1H-1,2,4-triazol-1-yl)methyl][1,1'-biphenyl]-2-yl]-1H-tetrazole;
5-[4'-[(5-secbutyl-3-isopentyl-1H-1,2,4-triazol-1-yl)methyl][1,1'-biphenyl]-2-yl]-1H-tetrazole;
5-[4'-[(5-secbutyl-3-mercapto-1H-1,2,4-triazol-1-yl)methyl][1,1'-biphenyl]-2-yl]-1H-tetrazole;
5-[4'-[(5-secbutyl-3-thiomethyl-1H-1,2,4-triazol-1-yl)methyl][1,1'-biphenyl]-2-yl]-1H-tetrazole;
5-[4'-[(5-secbutyl-3-thioethyl-1H-1,2,4-triazole-1-methyl][1,1'-biphenyl]-2-yl]-1H-tetrazole;
5-[4'-[(5-secbutyl-3-thiopropyl-1H-1,2,4-triazol-1-yl)methyl][1,1'-biphenyl]-2-yl]-1H-tetrazole;
5-[4'-[(5-secbutyl-3-hydroxy-1H-1,2,4-triazol-1-yl)methyl][1,1'-biphenyl]-2-yl]-1H-tetrazole;
5-[4'-[(5-secbutyl-3-methoxy-1H-1,2,4-triazol-1-yl)methyl][1,1'-biphenyl]-2-yl]-1H-tetrazole;
5-[4'-[(5-secbutyl-3-ethoxy-1H-1,2,4-triazol-1-yl)methyl][1,1'-biphenyl]-2-yl]-1H-tetrazole;
5-[4'-[(5-secbutyl-3-propoxy-1H-1,2,4-triazol-1-yl)methyl][1,1'-biphenyl]-2-yl]-1H-tetrazole;

5-[4'-[(5-secbutyl-3-cyclohexyl-1H-1,2,4-triazol-1-yl)methyl][1,1'-biphenyl]-2-yl]-1H-tetrazole;
5-[4'-[(5-secbutyl-3-cyclohexylmethyl-1H-1,2,4-triazol-1-yl)methyl][1,1'-biphenyl]-2-yl]-1H-tetrazole;
5-[4'-[[5-secbutyl-3-(2-cyclohexylethyl)-1H-1,2,4-triazol-1-yl]methyl][1,1'-biphenyl]-2-yl]-1H-tetrazole;
5-[4'-[(5-secbutyl-3-cyclohexanoyl-1H-1,2,4-triazol-1-yl)methyl][1,1'-biphenyl]-2-yl]-1H-tetrazole;
5-[4'-[[5-secbutyl-3-(1-oxo-2-cyclohexylethyl)-1H-1,2,4-triazol-1-yl]methyl][1,1'-biphenyl]-2-yl]-1H-tetrazole;
5-[4'-[(5-secbutyl-3-phenyl-1H-1,2,4-triazol-1-methyl][1,1'-biphenyl]-2-yl]-1H-tetrazole;
5-[4'-[(5-secbutyl-3-phenylmethyl-1H-1,2,4-triazol-1-yl)methyl][1,1'-biphenyl]-2-yl]-1H-tetrazole;
5-[4'-[[5-secbutyl-3-(2-phenylethyl)-1H-1,2,4-triazol-1-yl]methyl][1,1'-biphenyl]-2-yl]-1H-tetrazole;
5-[4'-[(5-secbutyl-3-benzoyl-1H-1,2,4-triazol-1-yl)methyl][1,1'-biphenyl]-2-yl]-1H-tetrazole;
5-[4'-[[5-secbutyl-3-(1-oxo-2-phenylethyl)-1H-1,2,4-triazol-1-yl]methyl][1,1'-biphenyl]-2-yl]-1H-tetrazole;
5-[4'-[[5-secbutyl-3-(1,1-dimethoxypropyl)-1H-1,2,4-triazol-1-yl]methyl][1,1'-biphenyl]-2-yl]-1H-tetrazole;
5-[4'-[[5-secbutyl-3-(1,1-dimethoxybutyl)-1H-1,2,4-triazol-1-yl]methyl][1,1'-biphenyl]-2-yl]-1H-tetrazole;
5-[4'-[[5-secbutyl-3-(1,1-dimethoxypentyl)-1H-1,2,4-triazol-1-yl]methyl][1,1'-biphenyl]-2-yl]-1H-tetrazole;
5-[4'-[[5-secbutyl-3-(1-oxopropyl)-1H-1,2,4-triazol-1-yl]methyl][1,1'-biphenyl]-2-yl]-1H-tetrazole;
5-[4'-[[5-secbutyl-3-(1-oxobutyl)-1H-1,2,4-triazol-1-yl]methyl][1,1'-biphenyl]-2-yl]-1H-tetrazole;
5-[4'-[[5-secbutyl-3-(1-oxopentyl)-1H-1,2,4-triazol-1-yl]methyl][1,1'-biphenyl]-2-yl]-1H-tetrazole;
5-[4'-[[5-secbutyl-3-(1,1-difluoroethyl)-1H-1,2,4-triazol-1-yl]methyl][1,1'-biphenyl]-2-yl]-1H-tetrazole;
5-[4'-[[5-secbutyl-3-(1,1-difluoropropyl)-1H-1,2,4-triazol-1-yl]methyl][1,1'-biphenyl]-2-yl]-1H-tetrazole;
5-[4'-[[5-secbutyl-3-(1,1-difluorobutyl)-1H-1,2,4-triazol-1-yl]methyl][1,1'-biphenyl]-2-yl]-1H-tetrazole;
5-[4'-[[5-secbutyl-3-(1,1-difluoropentyl)-1H-1,2,4-triazol-1-yl]methyl][1,1'-biphenyl]-2-yl]-1H-tetrazole;
5-[4'-[(5-isobutyl-3-ethyl-1H-1,2,4-triazol-1-yl)methyl][1,1'-biphenyl]-2-yl]-1H-tetrazole;
5-[4'-[(5-isobutyl-3-propyl-1H-1,2,4-triazol-1-yl)methyl][1,1'-biphenyl]-2-yl]-1H-tetrazole;
5-[4'-[(5-isobutyl-3-isopropyl-1H-1,2,4-triazol-1-yl)methyl][1,1'-biphenyl]-2-yl]-1H-tetrazole;
5-[4'-[(5-isobutyl-3-butyl-1H-1,2,4-triazol-1-yl)methyl][1,1'-biphenyl]-2-yl]-1H-tetrazole;
5-[4'-[(5-isobutyl-3-secbutyl-1H-1,2,4-triazol-1-yl)methyl][1,1'-biphenyl]-2-yl]-1H-tetrazole;
5-[4'-[(3,5-diisobutyl-1H-1,2,4-triazol-1-yl)methyl][1,1'-biphenyl]-2-yl]-1H-tetrazole;
5-[4'-[(5-isobutyl-3-tertbutyl-1H-1,2,4-triazol-1-yl)methyl][1,1'-biphenyl]-2-yl]-1H-tetrazole;
5-[4'-[(5-isobutyl-3-pentyl-1H-1,2,4-triazol-1-yl)methyl][1,1'-biphenyl]-2-yl]-1H-tetrazole;
5-[4'-[(5-isobutyl-3-isopentyl-1H-1,2,4-triazol-1-yl)methyl][1,1'-biphenyl]-2-yl]-1H-tetrazole;
5-[4'-[(5-isobutyl-3-mercapto-1H-1,2,4-triazol-1-yl)methyl][1,1'-biphenyl]-2-yl]-1H-tetrazole;
5-[4'-[(5-isobutyl-3-thiomethyl-1H-1,2,4-triazol-1-yl)methyl][1,1'-biphenyl]-2-yl]-1H-tetrazole;
5-[4'-[(5-isobutyl-3-thioethyl-1H-1,2,4-triazol-1-yl)methyl][1,1'-biphenyl]-2-yl]-1H-tetrazole;
5-[4'-[(5-isobutyl-3-thiopropyl-1H-1,2,4-triazol-1-yl)methyl][1,1'-biphenyl]-2-yl]-1H-tetrazole;
5-[4'-[(5-isobutyl-3-hydroxy-1H-1,2,4-triazol-1-yl)methyl][1,1'-biphenyl]-2-yl]-1H-tetrazole;
5-[4'-[(5-isobutyl-3-methoxy-1H-1,2,4-triazol-1-yl)methyl][1,1'-biphenyl]-2-yl]-1H-tetrazole;
5-[4'-[(5-isobutyl-3-ethoxy-1H-1,2,4-triazol-1-yl)methyl][1,1'-biphenyl]-2-yl]-1H-tetrazole;
5-[4'-[(5-isobutyl-3-propoxy-1H-1,2,4-triazol-1-yl)methyl][1,1'-biphenyl]-2-yl]-1H-tetrazole;
5-[4'-[(5-isobutyl-3-cyclohexyl-1H-1,2,4-triazol-1-yl)methyl][1,1'-biphenyl]-2-yl]-1H-tetrazole;
5-[4'-[(5-isobutyl-3-cyclohexylmethyl-1H-1,2,4-triazol-1-yl)methyl][1,1'-biphenyl]-2-yl]-1H-tetrazole;
5-[4'-[[5-isobutyl-3-(2-cyclohexylethyl)-1H-1,2,4-triazol-1-yl]methyl][1,1'-biphenyl]-2-yl]-1H-tetrazole;
5-[4'-[(5-isobutyl-3-cyclohexanoyl-1H-1,2,4-triazol-1-yl)methyl][1,1'-biphenyl]-2-yl]-1H-tetrazole;
5-[4'-[[5-isobutyl-3-(1-oxo-2-cyclohexylethyl)-1H-1,2,4-triazol-1-yl]methyl][1,1'-biphenyl]-2-yl]-1H-tetrazole;
5-[4'-[(5-isobutyl-3-phenyl-1H-1,2,4-triazol-1-yl)methyl][1,1'-biphenyl]-2-yl]-1H-tetrazole;
5-[4'-[(5-isobutyl-3-phenylmethyl-1H-1,2,4-triazol-1-yl)methyl][1,1'-biphenyl]-2-yl]-1H-tetrazole;
5-[4'-[[5-isobutyl-3-(2-phenylethyl)-1H-1,2,4-triazol-1-yl]methyl][1,1'-biphenyl]-2-yl]-1H-tetrazole;
5-[4'-[(5-isobutyl-3-benzoyl-1H-1,2,4-triazol-1-yl)methyl][1,1'-biphenyl]-2-yl]-1H-tetrazole;
5-[4'-[[5-isobutyl-3-(1-oxo-2-phenylethyl)-1H-1,2,4-triazol-1-yl]methyl][1,1'-biphenyl]-2-yl]-1H-tetrazole;
5-[4'-[[5-isobutyl-3-(1,1-dimethoxypropyl)-1H-1,2,4-triazol-1-yl]methyl][1,1'-biphenyl]-2-yl]-1H-tetrazole;
5-[4'-[[5-isobutyl-3-(1,1-dimethoxybutyl)-1H-1,2,4-triazol-1-yl]methyl][1,1'-biphenyl]-2-yl]-1H-tetrazole;
5-[4'-[[5-isobutyl-3-(1,1-dimethoxypentyl)-1H-1,2,4-triazol-1-yl]methyl][1,1'-biphenyl]-2-yl]-1H-tetrazole;
5-[4'-[[5-isobutyl-3-(1-oxopropyl)-1H-1,2,4-triazol-1-yl]methyl][1,1'-biphenyl]-2-yl]-1H-tetrazole;
5-[4'-[[5-isobutyl-3-(1-oxobutyl)-1H-1,2,4-triazol-1-yl]methyl][1,1'-biphenyl]-2-yl]-1H-tetrazole;
5-[4'-[[5-isobutyl-3-(1-oxopentyl)-1H-1,2,4-triazol-1-yl]methyl][1,1'-biphenyl]-2-yl]-1H-tetrazole;
5-[4'-[[5-isobutyl-3-(1,1-difluoroethyl)-1H-1,2,4-triazol-1-yl]methyl][1,1'-biphenyl]-2-yl]-1H-tetrazole;
5-[4'-[[5-isobutyl-3-(1,1-difluoropropyl)-1H-1,2,4-triazol--yl]methyl][1,1'-biphenyl]-2-yl]-1H-tetrazole;
5-[4'-[[5-isobutyl-3-(1,1-difluorobutyl)-1H-1,2,4-triazol-1-yl]methyl][1,1'-biphenyl]-2-yl]-1H-tetrazole;
5-[4'-[[5-isobutyl-3-(1,1-difluoropentyl)-1H-1,2,4-triazol-1-yl]methyl][1,1'-biphenyl]-2-yl]-1H-tetrazole;
5-[4'-[(5-tertbutyl-3-ethyl-1H-1,2,4-triazol-1-yl)methyl][1,1'-biphenyl]-2-yl]-1H-tetrazole;
5-[4'-[(5-tertbutyl-3-propyl-1H-1,2,4-triazol-1-yl)methyl][1,1'-biphenyl]-2-yl]-1H-tetrazole;
5-[4'-[(5-tertbutyl-3-isopropyl-1H-1,2,4-triazol-1-yl)methyl][1,1'-biphenyl]-2-yl]-1H-tetrazole;
5-[4'-[(5-tertbutyl-3-butyl-1H-1,2,4-triazol-1-yl)methyl][1,1'-biphenyl]-2-yl]-1H-tetrazole;
5-[4'-[(5-tertbutyl-3-secbutyl-1H-1,2,4-triazol-1-yl)methyl][1,1'-biphenyl]-2-yl]-1H-tetrazole;
5-[4'-[(5-tertbutyl-3-isobutyl-1H-1,2,4-triazol-1-yl)methyl][1,1'-biphenyl]-2-yl]-1H-tetrazole;
5-[4'-[(3,5-ditertbutyl-1H-1,2,4-triazol-1-yl)methyl][1,1'-biphenyl]-2-yl]-1H-tetrazole;
5-[4'-[(5-tertbutyl-3-pentyl-1H-1,2,4-triazol-1-yl)methyl][1,1'-biphenyl]-2-yl]-1H-tetrazole;
5-[4'-[(5-tertbutyl-3-isopentyl-1H-1,2,4-triazol-1-yl)methyl][1,1'-biphenyl]-2-yl]-1H-tetrazole;
5-[4'-[(5-tertbutyl-3-mercapto-1H-1,2,4-triazol-1-yl)methyl][1,1'-biphenyl]-2-yl]-1H-tetrazole;
5-[4'-[(5-tertbutyl-3-thiomethyl-1H-1,2,4-triazol-1-yl)methyl][1,1'-biphenyl]-2-yl]-1H-tetrazole;

5-[4,-[(5-tertbutyl-3-thioethyl-1H-1,2,4-triazol-1-yl)methyl][1,1'-biphenyl]-2-yl]-1H-tetrazole;
5-[4'-[(5-tertbutyl-3-thiopropyl-1H-1,2,4-triazol-1-yl)methyl][1,1'-biphenyl]-2-yl]-1H-tetrazole;
5-[4'-[(5-tertbutyl-3-hydroxy-1H-1,2,4-triazol-1-yl)methyl][1,1'-biphenyl]-2-yl]-1H-tetrazole;
5-[4'-[(5-tertbutyl-3-methoxy-1H-1,2,4-triazol-1-yl)methyl][1,1'-biphenyl]-2-yl]-1H-tetrazole;
5-[4'-[(5-tertbutyl-3-ethoxy-1H-1,2,4-triazol-1-yl)methyl][1,1'-biphenyl]-2-yl]-1H-tetrazole;
5-[4'-[(5-tertbutyl-3-propoxy-1H-1,2,4-triazol-1-yl)methyl][1,1'-biphenyl]-2-yl]-1H-tetrazole;
5-[4'-[(5-tertbutyl-3-cyclohexyl-1H-1,2,4-triazol-1-yl)methyl][1,1'-biphenyl]-2-yl]-1H-tetrazole;
5-[4'-[(5-tertbutyl-3-cyclohexylmethyl-1H-1,2,4-triazol-1-yl)methyl][1,1'-biphenyl]-2-yl]-1H-tetrazole;
5-[4'-[[5-tertbutyl-3-(2-cyclohexylethyl)-1H-1,2,4-triazol-1-yl]methyl][1,1'-biphenyl]-2-yl]-1H-tetrazole;
5-[4'-[(5-tertbutyl-3-cyclohexanoyl-1H-1,2,4-triazol-1-yl)methyl][1,1'-biphenyl]-2-yl]-1H-tetrazole;
5-[4'-[[5-tertbutyl-3-(1-oxo-2-cyclohexylethyl)-1H-1,2,4-triazol-1-yl]methyl][1,1'-biphenyl]-2-yl]-1H-tetrazole;
5-[4'-[(5-tertbutyl-3-phenyl-1H-1,2,4-triazol-1-yl)methyl][1,1'-biphenyl]-2-yl]-1H-tetrazole;
5-[4'-[(5-tertbutyl-3-phenylmethyl-1H-1,2,4-triazol-1-yl)methyl][1,1'-biphenyl]-2-yl]-1H-tetrazole;
5-[4'-[[5-tertbutyl-3-(2-phenylethyl)-1H-1,2,4-triazol-1-yl]methyl][1,1'-biphenyl]-2-yl]-1H-tetrazole;
5-[4'-[(5-tertbutyl-3-benzoyl-1H-1,2,4-triazol-1-yl)methyl][1,1'-biphenyl]-2-yl]-1H-tetrazole;
5-[4'-[[5-tertbutyl-3-(1-oxo-2-phenylethyl)-1H-1,2,4-triazol-1-yl]methyl][1,1'-biphenyl]-2-yl]-1H-tetrazole;
5-[4'-[[5-tertbutyl-3-(1,1-dimethoxypropyl)-1H-1,2,4-triazol-1-yl]methyl][1,1'-biphenyl]-2-yl]-1H-tetrazole;
5-[4'-[[5-tertbutyl-3-(1,1-dimethoxybutyl)-1H-1,2,4-triazol-1-yl]methyl][1,1'-biphenyl]-2-yl]-1H-tetrazole;
5-[4'-[[5-tertbutyl-3-(1,1-dimethoxypentyl)-1H-1,2,4-triazol-1-yl]methyl][1,1'-biphenyl]-2-yl]-1H-tetrazole;
5-[4'-[[5-tertbutyl-3-(1-oxopropyl)-1H-1,2,4-triazol-1-yl]methyl][1,1'-biphenyl]-2-yl]-1H-tetrazole;
5-[4'-[[5-tertbutyl-3-(1-oxobutyl)-1H-1,2,4-triazol-1-yl]methyl][1,1'-biphenyl]-2-yl]-1H-tetrazole;
5-[4'-[[5-tertbutyl-3-(1-oxopentyl)-1H-1,2,4-triazol-1-yl]methyl][1,1'-biphenyl]-2-yl]-1H-tetrazole;
5-[4'-[[5-tertbutyl-3-(1,1-difluoroethyl)-1H-1,2,4-triazol-1-yl]methyl][1,1'-biphenyl]-2-yl]-1H-tetrazole;
5-[4'-[[5-tertbutyl-3-(1,1-difluoropropyl)-1H-1,2,4-triazol-1-yl]methyl][1,1'-biphenyl]-2-yl]-1H-tetrazole;
5-[4'-[[5-tertbutyl-3-(1,1-difluorobutyl)-1H-1,2,4-triazol-1-yl]methyl][1,1'-biphenyl]-2-yl]-1H-tetrazole;
5-[4'-[[5-tertbutyl-3-(1,1-difluoropentyl)-1H-1,2,4-triazol-1-yl]methyl][1,1'-biphenyl]-2-yl]-1H-tetrazole;
5-[4'-[(5-pentyl-3-ethyl-1H-1,2,4-triazol-1-yl)methyl][1,1'-biphenyl]-2-yl]-1H-tetrazole;
5-[4'-[(5-pentyl-3-propyl-1H-1,2,4-triazol-1-yl)methyl][1,1'-biphenyl]-2-yl]-1H-tetrazole;
5-[4'-[(5-pentyl-3-isopropyl-1H-1,2,4-triazol-1-yl)methyl][1,1'-biphenyl]-2-yl]-1H-tetrazole;
5-[4'-[(5-pentyl-3-butyl-1H-1,2,4-triazol-1-yl)methyl][1,1'-biphenyl]-2-yl]-1H-tetrazole;
5-[4'-[(5-pentyl-3-secbutyl-1H-1,2,4-triazol-1-yl)methyl][1,1'-biphenyl]-2-yl]-1H-tetrazole;
5-[4'-[(5-pentyl-3-isobutyl-1H-1,2,4-triazol-1-yl)methyl][1,1'-biphenyl]-2-yl]-1H-tetrazole;
5-[4'-[(5-pentyl-3-tertbutyl-1H-1,2,4-triazol-1-yl)methyl][1,1'-biphenyl]-2-yl]-1H-tetrazole;
5-[4'-[(3,5-dipentyl-1H-1,2,4-triazol-1-yl)methyl][1,1'-biphenyl]-2-yl]-1H-tetrazole;
5-[4'-[(5-pentyl-3-isopentyl-1H-1,2,4-triazol-1-yl)methyl][1,1'-biphenyl]-2-yl]-1H-tetrazole;
5-[4'-[(5-pentyl-3-mercapto-1H-1,2,4-triazol-1-yl)methyl][1,1'-biphenyl]-2-yl]-1H-tetrazole;
5-[4'-[(5-pentyl-3-thiomethyl-1H-1,2,4-triazol-1-yl)methyl][1,1'-biphenyl]-2-yl]-1H-tetrazole;
5-[4'-[(5-pentyl-3-thioethyl-1H-1,2,4-triazol-1-yl)methyl][1,1'-biphenyl]-2-yl]-1H-tetrazole;
5-[4'-[(5-pentyl-3-thiopropyl-1H-1,2,4-triazol-1-yl)methyl][1,1'-biphenyl]-2-yl]-1H-tetrazole;
5-[4'-[(5-pentyl-3-hydroxy-1H-1,2,4-triazol-1-yl)methyl][1,1'-biphenyl]-2-yl]-1H-tetrazole;
5-[4'-[(5-pentyl-3-methoxy-1H-1,2,4-triazol-1-yl)methyl][1,1'-biphenyl]-2-yl]-1H-tetrazole;
5-[4'-[(5-pentyl-3-ethoxy-1H-1,2,4-triazol-1-yl)methyl][1,1'-biphenyl]-2-yl]-1H-tetrazole;
5-[4'-[(5-pentyl-3-propoxy-1H-1,2,4-triazol-1-yl)methyl][1,1'-biphenyl]-2-yl]-1H-tetrazole;
5-[4'-[(5-pentyl-3-cyclohexyl-1H-1,2,4-triazol-1-yl)methyl][1,1'-biphenyl]-2-yl]-1H-tetrazole;
5-[4'-[(5-pentyl-3-cyclohexylmethyl-1H-1,2,4-triazol-1-yl)methyl][1,1'-biphenyl]-2-yl]-1H-tetrazole;
5-[4'-[[5-pentyl-3-(2-cyclohexylethyl)-1H-1,2,4-triazol-1-yl]methyl][1,1'-biphenyl]-2-yl]-1H-tetrazole;
5-[4'-[(5-pentyl-3-cyclohexanoyl-1H-1,2,4-triazol-1-yl)methyl][1,1'-biphenyl]-2-yl]-1H-tetrazole;
5-[4'-[[5-pentyl-3-(1-oxo-2-cyclohexylethyl)-1H-1,2,4-triazol-1-yl]methyl][1,1'-biphenyl]-2-yl]-1H-tetrazole;
5-[4'-[(5-pentyl-3-phenyl-1H-1,2,4-triazol-1-yl)methyl][1,1'-biphenyl]-2-yl]-1H-tetrazole;
5-[4'-[(5-pentyl-3-phenylmethyl-1H-1,2,4-triazol-1-yl)methyl][1,1'-biphenyl]-2-yl]-1H-tetrazole;
5-[4'-[[5-pentyl-3-(2-phenylethyl)-1H-1,2,4-triazol-1-yl]methyl][1,1'-biphenyl]-2-yl]-1H-tetrazole;
5-[4'-[(5-pentyl-3-benzoyl-1H-1,2,4-triazol-1-yl)methyl][1,1'-biphenyl]-2-yl]-1H-tetrazole;
5-[4'-[[5-pentyl-3-(1-oxo-2-phenylethyl)-1H-1,2,4-triazol-1-yl]methyl][1,1'-biphenyl]-2-yl]-1H-tetrazole;
5-[4'-[[5-pentyl-3-(1,1-dimethoxypropyl)-1H-1,2,4-triazol-1-yl]methyl][1,1'-biphenyl]-2-yl]-1H-tetrazole;
5-[4'-[[5-pentyl-3-(1,1-dimethoxybutyl)-1H-1,2,4-triazol-1-yl]methyl][1,1'-biphenyl]-2-yl]-1H-tetrazole;
5-[4'-[[5-pentyl-3-(1,1-dimethoxypentyl)-1H-1,2,4-triazol-1-yl]methyl][1,1'-biphenyl]-2-yl]-1H-tetrazole;
5-[4'-[[5-pentyl-3-(1-oxopropyl)-1H-1,2,4-triazol-1-yl]methyl][1,1'-biphenyl]-2-yl]-1H-tetrazole;
5-[4'-[[5-pentyl-3-(1-oxobutyl)-1H-1,2,4-triazol-1-yl]methyl][1,1'-biphenyl]-2-yl]-1H-tetrazole;
5-[4'-[[5-pentyl-3-(1-oxopentyl)-1H-1,2,4-triazol-1-yl]methyl][1,1'-biphenyl]-2-yl]-1H-tetrazole;
5-[4'-[[5-pentyl-3-(1,1-difluoroethyl)-1H-1,2,4-triazol-1-yl]methyl][1,1'-biphenyl]-2-yl]-1H-tetrazole;
5-[4'-[[5-pentyl-3-(1,1-difluoropropyl)-1H-1,2,4-triazol-1-yl]methyl][1,1'-biphenyl]-2-yl]-1H-tetrazole;
5-[4'-[[5-pentyl-3-(1,1-difluorobutyl)-1H-1,2,4-triazol-1-yl]methyl][1,1'-biphenyl]-2-yl]-1H-tetrazole;
5-[4'-[[5-pentyl-3-(1,1-difluoropentyl)-1H-1,2,4-triazol-1-yl]methyl][1,1'-biphenyl]-2-yl]-1H-tetrazole;
5-[4'-[(5-isopentyl-3-ethyl-1H-1,2,4-triazol-1-yl)methyl][1,1'-biphenyl]-2-yl]-1H-tetrazole;
5-[4'-[(5-isopentyl-3-propyl-1H-1,2,4-triazol-1-yl)methyl][1,1'-biphenyl]-2-yl]-1H-tetrazole;
5-[4'-[(5-isopentyl-3-isopropyl-1H-1,2,4-triazol-1-yl)methyl][1,1'-biphenyl]-2-yl]-1H-tetrazole;
5-[4'-[(5-isopentyl-3-butyl-1H-1,2,4-triazol-1-yl)methyl][1,1'-biphenyl]-2-yl]-1H-tetrazole;

5-[4'-[(5-isopentyl-3-secbutyl-1H-1,2,4-triazol-1-yl)methyl][1,1'-biphenyl]-2-yl]-1H-tetrazole;
5-[4'-[(5-isopentyl-3-isobutyl-1H-1,2,4-triazol-1-yl)methyl][1,1'-biphenyl]-2-yl]-1H-tetrazole;
5-[4'-[(5-isopentyl-3-tertbutyl-1H-1,2,4-triazol-1-yl)methyl][1,1'-biphenyl]-2-yl]-1H-tetrazole;
5-[4'-[(5-isopentyl-3-pentyl-1H-1,2,4-triazol-1-yl)methyl][1,1'-biphenyl]-2-yl]-1H-tetrazole;
5-[4'-[(3,5-diisopentyl-1H-1,2,4-triazol-1-yl)methyl][1,1'-biphenyl]-2-yl]-1H-tetrazole;
5-[4'-[(5-isopentyl-3-mercapto-1H-1,2,4-triazol-1-yl)methyl][1,1'-biphenyl]-2-yl]-1H-tetrazole;
5-[4'-[(5-isopentyl-3-thiomethyl-1H-1,2,4-triazol-1-yl)methyl][1,1'-biphenyl]-2-yl]-1H-tetrazole;
5-[4'-[(5-isopentyl-3-thioethyl-1H-1,2,4-triazol-1-yl)methyl][1,1'-biphenyl]-2-yl]-1H-tetrazole;
5-[4'-[(5-isopentyl-3-thiopropyl-1H-1,2,4-triazol-1-yl)methyl][1,1'-biphenyl]-2-yl]-1H-tetrazole;
5-[4'-(5-isopentyl-3-hydroxy-1H-1,2,4-triazol-1-yl)methyl][1,1'-biphenyl]-2-yl]-1H-tetrazole;
5-[4'-[(5-isopentyl-3-methoxy-1H-1,2,4-triazol-1-yl)methyl][1,1'-biphenyl]-2-yl]-1H-tetrazole;
5-[4'-[(5-isopentyl-3-ethoxy-1H-1,2,4-triazol-1-yl)methyl][1,1'-biphenyl]-2-yl]-1H-tetrazole;
5-[4'-[(5-isopentyl-3-propoxy-1H-1,2,4-triazol-1-yl)methyl][1,1'-biphenyl]-2-yl]-1H-tetrazole;
5-[4'-[(5-isopentyl-3-cyclohexyl-1H-1,2,4-triazol-1-yl)methyl][1,1'-biphenyl]-2-yl]-1H-tetrazole;
5-[4'-[(5-isopentyl-3-cyclohexylmethyl-1H-1,2,4-triazol-1-yl)methyl][1,1'-biphenyl]-2-yl]-1H-tetrazole;
5-[4'-[[5-pentyl-3-(2-cyclohexylethyl)-1H-1,2,4-triazol-1-yl]methyl][1,1'-biphenyl]-2-yl]-1H-tetrazole;
5-[4'-[(5-isopentyl-3-cyclohexanoyl-1H-1,2,4-triazol-1-yl)methyl][1,1'-biphenyl]-2-yl]-1H-tetrazole;
5-[4'-[[5-pentyl-3-(1-oxo-2-cyclohexylethyl)-1H-1,2,4-triazol-1-yl]methyl][1,1'-biphenyl]-2-yl]-1H-tetrazole;
5-[4'-[(5-isopentyl-3-phenyl-1H-1,2,4-triazol-1-yl)methyl][1,1'-biphenyl]-2-yl]-1H-tetrazole;
5-[4'-[(5-isopentyl-3-phenylmethyl-1H-1,2,4-triazol-1-yl)methyl][1,1'-biphenyl]-2-yl]-1H-tetrazole;
5-[4'-[[5-pentyl-3-(2-phenylethyl)-1H-1,2,4-triazol-1-yl]methyl][1,1'-biphenyl]-2-yl]-1H-tetrazole;
5-[4'-[(5-isopentyl-3-benzoyl-1H-1,2,4-triazol-1-yl)methyl][1,1'-biphenyl]-2-yl]-1H-tetrazole;
5-[4'-[[5-isopentyl-3-(1-oxo-2-phenylethyl)-1H-1,2,4-triazol-1-yl]methyl][1,1'-biphenyl]-2-yl]-1H-tetrazole;
5-[4'-[[5-isopentyl-3-(1,1-dimethoxypropyl)-1H-1,2,4-triazol-1-yl]methyl][1,1'-biphenyl]-2-yl]-1H-tetrazole;
5-[4'-[[5-isopentyl-3-(1,1-dimethoxybutyl)-1H-1,2,4-triazol-1-yl]methyl][1,1'-biphenyl]-2-yl]-1H-tetrazole;
5-[4'-[[5-isopentyl-3-(1,1-dimethoxypentyl)-1H-1,2,4-triazol-1-yl]methyl][1,1'-biphenyl]-2-yl]-1H-tetrazole;
5-[4'-[[5-isopentyl-3-(1-oxopropyl)-1H-1,2,4-triazol-1-yl]methyl][1,1'-biphenyl]-2-yl]-1H-tetrazole;
5-[4'-[[5-isopentyl-3-(1-oxobutyl)-1H-1,2,4-triazol-1-yl]methyl][1,1'-biphenyl]-2-yl]-1H-tetrazole;
5-[4'-[[5-isopentyl-3-(1-oxopentyl)-1H-1,2,4-triazol-1-yl]methyl][1,1'-biphenyl]-2-yl]-1H-tetrazole;
5-[4'-[[5-isopentyl-3-(1,1-difluoroethyl)-1H-1,2,4-triazol-1-yl]methyl][1,1'-biphenyl]-2-yl]-1H-tetrazole;
5-[4'-[[5-isopentyl-3-(1,1-difluoropropyl)-1H-1,2,4-triazol-1-yl]methyl][1,1'-biphenyl]-2-yl]-1H-tetrazole;
5-[4'-[[5-isopentyl-3-(1,1-difluorobutyl)-1H-1,2,4-triazol-1-yl]methyl][1,1'-biphenyl]-2-yl]-1H-tetrazole;
5-[4'-[[5-isopentyl-3-(1,1-difluoropentyl)-1H-1,2,4-triazol-1-yl]methyl][1,1'-biphenyl]-2-yl]-1H-tetrazole;
5-[4'-[[5-(1-butenyl)-3-ethyl-1H-1,2,4-triazol-1-yl]methyl][1,1'-biphenyl]-2-yl]-1H-tetrazole;
5-[4'-[[5-(1-butenyl)-3-propyl-1H-1,2,4-triazol-1-yl]methyl][1,1'-biphenyl]-2-yl]-1H-tetrazole;
5-[4'-[[5-(1-butenyl)-3-isopropyl-1H-1,2,4-triazol-1-yl]methyl][1,1'-biphenyl]-2-yl]-1H-tetrazole;
5-[4'-[[5-(1-butenyl)-3-butyl-1H-1,2,4-triazol-1-yl]methyl][1,1'-biphenyl]-2-yl]-1H-tetrazole;
5-[4'-[[5-(1-butenyl)-3-secbutyl-1H-1,2,4-triazol-1-yl]methyl][1,1'-biphenyl]-2-yl]-1H-tetrazole;
5-[4'-[[5-(1-butenyl)-3-isobutyl-1H-1,2,4-triazol-1-yl]methyl][1,1'-biphenyl]-2-yl]-1H-tetrazole;
5-[4'-[[5-(1-butenyl)-3-tertbutyl-1H-1,2,4-triazol-1-yl]methyl][1,1'-biphenyl]-2-yl]-1H-tetrazole;
5-[4'-[[5-(1-butenyl)-3-pentyl-1H-1,2,4-triazol-1-yl]methyl][1,1'-biphenyl]-2-yl]-1H-tetrazole;
5-[4'-[[5-(1-butenyl)-3-isopentyl-1H-1,2,4-triazol-1-yl]methyl][1,1'-biphenyl]-2-yl]-1H-tetrazole;
5-[4'-[[5-(1-butenyl)-3-mercapto-1H-1,2,4-triazol-1-yl]methyl][1,1'-biphenyl]-2-yl]-1H-tetrazole;
5-[4'-[[5-(1-butenyl)-3-thiomethyl-1H-1,2,4-triazol-1-yl]methyl][1,1'-biphenyl]-2-yl]-1H-tetrazole;
5-[4'-[[5-(1-butenyl)-3-thioethyl-1H-1,2,4-triazol-1-yl]methyl][1,1'-biphenyl]-2-yl]-1H-tetrazole;
5-[4'-[[5-(1-butenyl)-3-thiopropyl-1H-1,2,4-triazol-1-yl]methyl][1,1'-biphenyl]-2-yl]-1H-tetrazole;
5-[4'-[[5-(1-butenyl)-3-hydroxy-1H-1,2,4-triazol-1-yl]methyl][1,1'-biphenyl]-2-yl]-1H-tetrazole;
5-[4'-[[5-(1-butenyl)-3-methoxy-1H-1,2,4-triazol-1-yl]methyl][1,1'-biphenyl]-2-yl]-1H-tetrazole;
5-[4'-[[5-(1-butenyl)-3-ethoxy-1H-1,2,4-triazol-1-yl]methyl][1,1'-biphenyl]-2-yl]-1H-tetrazole;
5-[4'-[[5-(1-butenyl)-3-propoxy-1H-1,2,4-triazol-1-yl]methyl][1,1'-biphenyl]-2-yl]-1H-tetrazole;
5-[4'-[[5-(1-butenyl)-3-cyclohexyl-1H-1,2,4-triazol-1-yl]methyl][1,1'-biphenyl]-2-yl]-1H-tetrazole;
5-[4'-[[5-(1-butenyl)-3-cyclohexylmethyl-1H-1,2,4-triazol-1-yl]methyl][1,1'-biphenyl]-2-yl]-1H-tetrazole;
5-[4'-[[5-(1-butenyl)-3-(2-cyclohexylethyl)-1H-1,2,4-triazol-1-yl]methyl][1,1'-biphenyl]-2-yl]-1H-tetrazole;
5-[4'-[[5-(1-butenyl)-3-cyclohexanoyl-1H-1,2,4-triazol-1-yl]methyl][1,1'-biphenyl]-2-yl]-1H-tetrazole;
5-[4'-[[5-(1-butenyl)-3-(1-oxo-2-cyclohexylethyl)-1H-1,2,4-triazol-1-yl]methyl][1,1'-biphenyl]-2-yl]-1H-tetrazole;
5-[4'-[[5-(1-butenyl)-3-phenyl-1H-1,2,4-triazol-1-yl]methyl][1,1'-biphenyl]-2-yl]-1H-tetrazole;
5-[4'-[[5-(1-butenyl)-3-phenylmethyl-1H-1,2,4-triazol-1-yl]methyl][1,1'-biphenyl]-2-yl]-1H-tetrazole;
5-[4'-[[5-(1-butenyl)-3-(2-phenylethyl)-1H-1,2,4-triazol-1-yl]methyl][1,1'-biphenyl]-2-yl]-1H-tetrazole;
5-[4'-[[5-(1-butenyl)-3-benzoyl-1H-1,2,4-triazol-1-yl]methyl][1,1'-biphenyl]-2-yl]-1H-tetrazole;
5-[4'-[[5-(1-butenyl)-3-(1-oxo-2-phenylethyl)-1H-1,2,4-triazol-1-yl]methyl][1,1'-biphenyl]-2-yl]-1H-tetrazole;
5-[4'-[[5-(1-butenyl)-3-(1,1-dimethoxypropyl)-1H-1,2,4-triazol-1-yl]methyl][1,1'-biphenyl]-2-yl]-1H-tetrazole;
5-[4'-[[5-(1-butenyl)-3-(1,1-dimethoxybutyl)-1H-1,2,4-triazol-1-yl]methyl][1,1'-biphenyl]-2-yl]-1H-tetrazole;
5-[4'-[[5-(1-butenyl)-3-(1,1-dimethoxypentyl)-1H-1,2,4-triazol-1-yl]methyl][1,1'-biphenyl]-2-yl]-1H-tetrazole;
5-[4'-[[5-(1-butenyl)-3-(1-oxopropyl)-1H-1,2,4-triazol-1-yl]methyl][1,1'-biphenyl]-2-yl]-1H-tetrazole;
5-[4'-[[5-(1-butenyl)-3-(1-oxobutyl)-1H-1,2,4-triazol-1-yl]methyl][1,1'-biphenyl]-2-yl]-1H-tetrazole;
5-[4'-[[5-(1-butenyl)-3-(1-oxopentyl)-1H-1,2,4-triazol-1-yl]methyl][1,1'-biphenyl]-2-yl]-1H-tetrazole;
5-[4'-[[5-(1-butenyl)-3-(1,1-difluoroethyl)-1H-1,2,4-triazol-1-yl]methyl][1,1'-biphenyl]-2-yl]-1H-tetrazole;

5-[4'-[[5-(1-butenyl)-3-(1,1-difluoropropyl)-1H-1,2,4-triazol-1-yl]methyl][1,1'-biphenyl]-2-yl]-1H-tetrazole;
5-[4'-[[5-(1-butenyl)-3-(1,1-difluorobutyl)-1H-1,2,4-triazol-1-yl]methyl][1,1'-biphenyl]-2-yl]-1H-tetrazole;
5-[4'-[[5-(1-butenyl)-3-(1,1-difluoropentyl)-1H-1,2,4-triazol-1-yl]methyl][1,1'-biphenyl]-2-yl]-1H-tetrazole;
5-[4'-[[5-(2-butenyl)-3-ethyl-1H-1,2,4-triazol-1-yl]methyl][1,1'-biphenyl]-2-yl]-1H-tetrazole;
5-[4'-[[5-(2-butenyl)-3-propyl-1H-1,2,4-triazol-1-yl]methyl][1,1'-biphenyl]-2-yl]-1H-tetrazole;
5-[4'-[[5-(2-butenyl)-3-isopropyl-1H-1,2,4-triazol-1-yl]methyl][1,1'-biphenyl]-2-yl]-1H-tetrazole;
5-[4'-[[5-(2-butenyl)-3-butyl-1H-1,2,4-triazol-1-yl]methyl][1,1'-biphenyl]-2-yl]-1H-tetrazole;
5-[4'-[[5-(2-butenyl)-3-secbutyl-1H-1,2,4-triazol-1-yl]methyl][1,1'-biphenyl]-2-yl]-1H-tetrazole;
5-[4'-[[5-(2-butenyl)-3-isobutyl-1H-1,2,4-triazol-1-yl]methyl][1,1'-biphenyl]-2-yl]-1H-tetrazole;
5-[4'-[[5-(2-butenyl)-3-tertbutyl-1H-1,2,4-triazol-1-yl]methyl][1,1'-biphenyl]-2-yl]-1H-tetrazole;
5-[4'-[[5-(2-butenyl)-3-pentyl-1H-1,2,4-triazol-1-yl]methyl][1,1'-biphenyl]-2-yl]-1H-tetrazole;
5-[4'-[[5-(2-butenyl)-3-isopentyl-1H-1,2,4-triazol-1-yl]methyl][1,1'-biphenyl]-2-yl]-1H-tetrazole;
5-[4'-[[5-(2-butenyl)-3-mercapto-1H-1,2,4-triazol-1-yl]methyl][1,1'-biphenyl]-2-yl]-1H-tetrazole;
5-[4'-[[5-(2-butenyl)-3-thiomethyl-1H-1,2,4-triazol-1-yl]methyl][1,1'-biphenyl]-2-yl]-1H-tetrazole;
5-[4'-[[5-(2-butenyl)-3-thioethyl-1H-1,2,4-triazol-1-yl]methyl][1,1'-biphenyl]-2-yl]-1H-tetrazole;
5-[4'-[[5-(2-butenyl)-3-thiopropyl-1H-1,2,4-triazol-1-yl]methyl][1,1'-biphenyl]-2-yl]-1H-tetrazole;
5-[4'-[[5-(2-butenyl)-3-hydroxy-1H-1,2,4-triazol-1-yl]methyl][1,1'-biphenyl]-2-yl]-1H-tetrazole;
5-[4'-[[5-(2-butenyl)-3-methoxy-1H-1,2,4-triazol-1-yl]methyl][1,1'-biphenyl]-2-yl]-1H-tetrazole;
5-[4'-[[5-(2-butenyl)-3-ethoxy-1H-1,2,4-triazol-1-yl]methyl][1,1'-biphenyl]-2-yl]-1H-tetrazole;
5-[4'-[[5-(2-butenyl)-3-propoxy-1H-1,2,4-triazol-1-yl]methyl][1,1'-biphenyl]-2-yl]-1H-tetrazole;
5-[4'-[[5-(2-butenyl)-3-cyclohexyl-1H-1,2,4-triazol-1-yl]methyl][1,1'-biphenyl]-2-yl]-1H-tetrazole;
5-[4'-[[5-(2-butenyl)-3-cyclohexylmethyl-1H-1,2,4-triazol-1-yl]methyl][1,1'-biphenyl]-2-yl]-1H-tetrazole;
5-[4'-[[5-(2-butenyl)-3-(2-cyclohexylethyl)-1H-1,2,4-triazol-1-yl]methyl][1,1'-biphenyl]-2-yl]-1H-tetrazole;
5-[4'-[[5-(2-butenyl)-3-cyclohexanoyl-1H-1,2,4-triazol-1-yl]methyl][1,1'-biphenyl]-2-yl]-1H-tetrazole;
5-[[5-(2-butenyl)-3-(1-oxo-2-cyclohexylethyl)-1H-1,2,4-triazol-1-yl]methyl][1,1'-biphenyl]-2-yl]-1H-tetrazole;
5-[4'-[[5-(2-butenyl)-3-phenyl-1H-1,2,4-triazol-1-yl]methyl][1,1'-biphenyl]-2-yl]-1H-tetrazole;
5-[4'-[[5-(2-butenyl)-3-phenylmethyl-1H-1,2,4-triazol-1-yl]methyl][1,1'-biphenyl]-2-yl]-1H-tetrazole;
5-[4'-[[5-(2-butenyl)-3-(2-phenylethyl)-1H-1,2,4-triazol-1-yl]methyl][1,1'-biphenyl]-2-yl]-1H-tetrazole;
5-[4'-[[5-(2-butenyl)-3-(1,1-dimethoxypropyl)-1H-1,2,4-triazol-1-yl]methyl][1,1'-biphenyl]-2-yl]-1H-tetrazole;
5-[4'-[[5-(2-butenyl)-3-(1,1-dimethoxybutyl)-1H-1,2,4-triazol-1-yl]methyl][1,1'-biphenyl]-2-yl]-1H-tetrazole;
5-[4'-[[5-(2-butenyl)-3-(1,1-dimethoxypentyl)-1H-1,2,4-triazol-1-yl]methyl][1,1'-biphenyl]-2-yl]-1H-tetrazole;
5-[4'-[[5-(2-butenyl)-3-(1-oxopropyl)-1H-1,2,4-triazol-1-yl]methyl][1,1'-biphenyl]-2-yl]-1H-tetrazole;
5-[[5-(2-butenyl)-3-(1-oxobutyl)-1H-1,2,4-triazol-1-yl]methyl][1,1'-biphenyl]-2-yl]-1H-tetrazole;
5-[4'-[[5-(2-butenyl)-3-(1-oxopentyl)-1H-1,2,4-triazol-1-yl]methyl][1,1'-biphenyl]-2-yl]-1H-tetrazole;

5-[4'-[[5-(2-butenyl)-3-(1,1-difluoroethyl)-1H-1,2,4-triazol-1-yl]methyl][1,1'-biphenyl]-2-yl]-1H-tetrazole;
5-[4'-[[5-(2-butenyl)-3-(1,1-difluoropropyl)-1H-1,2,4-triazol-1-yl]methyl][1,1'-biphenyl]-2-yl]-1H-tetrazole;
5-[4'-[[5-(2-butenyl)-3-(1,1-difluorobutyl)-1H-1,2,4-triazol-1-yl]methyl][1,1'-biphenyl]-2-yl]-1H-tetrazole;
5-[4'-[[5-(2-butenyl)-3-(1,1-difluoropentyl)-1H-1,2,4-triazol-1-yl]methyl][1,1'-biphenyl]-2-yl]-1H-tetrazole;
5-[4'-[[5-(3-butenyl)-3-ethyl-1H-1,2,4-triazol-1-yl]methyl][1,1'-biphenyl]-2-yl]-1H-tetrazole;
5-[4'-[[5-(3-butenyl)-3-propyl-1H-1,2,4-triazol-1-yl]methyl][1,1'-biphenyl]-2-yl]-1H-tetrazole;
5-[4'-[[5-(3-butenyl)-3-isopropyl-1H-1,2,4-triazol-1-yl]methyl][1,1'-biphenyl]-2-yl]-1H-tetrazole;
5-[4'-[[5-(3-butenyl)-3-butyl-1H-1,2,4-triazol-1-yl]methyl][1,1'-biphenyl]-2-yl]-1H-tetrazole;
5-[4'-[[5-(3-butenyl)-3-secbutyl-1H-1,2,4-triazol-1-yl]methyl][1,1'-biphenyl]-2-yl]-1H-tetrazole;
5-[4'-[[5-(3-butenyl)-3-isobutyl-1H-1,2,4-triazol-1-yl]methyl][1,1'-biphenyl]-2-yl]-1H-tetrazole;
5-[4'-[[5-(3-butenyl)-3-tertbutyl-1H-1,2,4-triazol-1-yl]methyl][1,1'-biphenyl]-2-yl]-1H-tetrazole;
5-[4'-[[5-(3-butenyl)-3-pentyl-1H-1,2,4-triazol-1-yl]methyl][1,1'-biphenyl]-2-yl]-1H-tetrazole;
5-[4'-[[5-(3-butenyl)-3-isopentyl-1H-1,2,4-triazol-1-yl]methyl][1,1'-biphenyl]-2-yl]-1H-tetrazole;
5-[4'-[[5-(3-butenyl)-3-mercapto-1H-1,2,4-triazol-1-yl]methyl][1,1'-biphenyl]-2-yl]-1H-tetrazole;
5-[4-[[3-butenyl)-3-thiomethyl-1H-1,2,4-triazol-1-yl]methyl][1,1'-biphenyl]-2-yl]-1H-tetrazole;
5-[4'-[[5-(3-butenyl)-3-thioethyl-1H-1,2,4-triazol-1-yl]methyl][1,1'-biphenyl]-2-yl]-1H-tetrazole;
5-[4'-[[5-(3-butenyl)-3-thiopropyl-1H-1,2,4-triazol-1-yl]methyl][1,1'-biphenyl]-2-yl]-1H-tetrazole;
5-[4'-[[5-(3-butenyl)-3-hydroxy-1H-1,2,4-triazol-1-yl]methyl][1,1'-biphenyl]-2-yl]-1H-tetrazole;
5-[4'-[[5-(3-butenyl)-3-methoxy-1H-1,2,4-triazol-1-yl]methyl][1,1'-biphenyl]-2-yl]-1H-tetrazole;
5-[4'-[[5-(3-butenyl)-3-ethoxy-1H-1,2,4-triazol-1-yl]methyl][1,1'-biphenyl]-2-yl]-1H-tetrazole;
5-[4'-[[5-(3-butenyl)-3-propoxy-1H-1,2,4-triazol-1-yl]methyl][1,1'-biphenyl]-2-yl]-1H-tetrazole;
5-[4'-[[5-(3-butenyl)-3-cyclohexyl-1H-1,2,4-triazol-1-yl]methyl][1,1'-biphenyl]-2-yl]-1H-tetrazole;
5-[4'-[[5-(3-butenyl)-3-cyclohexylmethyl-1H-1,2,4-triazol-1-yl]methyl][1,1'-biphenyl]-2-yl]-1H-tetrazole;
5-[4'-[[5-(3-butenyl)-3-(2-cyclohexylethyl)-1H-1,2,4-triazol-1-yl]methyl][1,1'-biphenyl]-2-yl]-1H-tetrazole;
5-[4'-[[5-(3-butenyl)-3-cyclohexanoyl-1H-1,2,4-triazol-1-yl]methyl][1,1'-biphenyl]-2-yl]-1H-tetrazole;
5-[4'-[[5-(3-butenyl)-3-(1-oxo-cyclohexylethyl)-1H-1,2,4-triazol-1-yl]methyl][1,1'-biphenyl]-2-yl]-1H-tetrazole;
5-[4'-[[5-(3-butenyl)-3-phenyl-1H-1,2,4-triazol-1-yl]methyl][1,1'-biphenyl]-2-yl]-1H-tetrazole;
5-[4'-[[5-(3-butenyl)-3-phenylmethyl-1H-1,2,4-triazol-1-yl]methyl][1,1'-biphenyl]-2-yl]-1H-tetrazole;
5-[4'-[[5-(3-butenyl)-3-(2-phenylethyl)-1H-1,2,4-triazol-1-yl]methyl][1,1'-biphenyl]-2-yl]-1H-tetrazole;
5-[4'-[[5-(3-butenyl)-3-benzoyl-1H-1,2,4-triazol-1-yl]methyl][1,1'-biphenyl]-2-yl]-1H-tetrazole;
5-[4'-[[5-(3-butenyl)-3-(1-oxo-2-phenylethyl)-1H-1,2,4-triazol-1-yl]methyl][1,1'-biphenyl]-2-yl]-1H-tetrazole;
5-[4'-[[5-(3-butenyl)-3-(1,1-dimethoxypropyl)-1H-1,2,4-triazol-1-yl]methyl][1,1'-biphenyl]-2-yl]-1H-tetrazole;
5-[4'-[[5-(3-butenyl)-3-(1,1-dimethoxybutyl)-1H-1,2,4-triazol-1-yl]methyl][1,1'-biphenyl]-2-yl]-1H-tetrazole;

5-[4'-[[5-(3-butenyl)-3-(1,1-dimethoxypentyl)-1H-1,2,4-triazol-1-yl]methyl][1,1'-biphenyl]-2-yl]-1H-tetrazole;
5-[4'-[[5-(3-butenyl)-3-(1-oxopropyl)-1H-1,2,4-triazol-1-yl]methyl][1,1'-biphenyl]-2-yl]-1H-tetrazole;
5-[4'-[[5-(3-butenyl)-3-(1-oxobutyl)-1H-1,2,4-triazol-1-yl]methyl][1,1'-biphenyl]-2-yl]-1H-tetrazole;
5-[4'-[[5-(3-butenyl)-3-(1-oxopentyl)-1H-1,2,4-triazol-1-yl]methyl][1,1'-biphenyl]-2-yl]-1H-tetrazole;
5-[4'-[[5-(3-butenyl)-3-(1,1-difluoroethyl)-1H-1,2,4-triazol-1-yl]methyl][1,1'-biphenyl]-2-yl]-1H-tetrazole;
5-[4'-[[5-(3-butenyl)-3-(1,1-difluoropropyl)-1H-1,2,4-triazol-1-yl]methyl][1,1'-biphenyl]-2-yl]-1H-tetrazole;
5-[4'-[[5-(3-butenyl)-3-(1,1-difluorobutyl)-1H-1,2,4-triazol-1-yl]methyl][1,1'-biphenyl]-2-yl]-1H-tetrazole;
5-[4'-[[5-(3-butenyl)-3-(1,1-difluoropentyl)-1H-1,2,4-triazol-1-yl]methyl][1,1'-biphenyl]-2-yl]-1H-tetrazole;
5-[4'-[[5-(1-butynyl)-3-ethyl-1H-1,2,4-triazol-1-yl]methyl][1,1'-biphenyl]-2-yl]-1H-tetrazole;
5-[4'-[[5-(1-butynyl)-3-propyl-1H-1,2,4-triazol-1-yl]methyl][1,1'-biphenyl]-2-yl]-1H-tetrazole;
5-[4'-[[5-(1-butynyl)-3-butyl-1H-1,2,4-triazol-1-yl]methyl][1,1'-biphenyl]-2-yl]-1H-tetrazole;
5-[4'-[[5-(1-butynyl)-3-secbutyl-1H-1,2,4-triazol-1-yl]methyl][1,1'-biphenyl]-2-yl]-1H-tetrazole;
5-[4'-[[5-(1-butynyl)-3-isobutyl-1H-1,2,4-triazol-1-yl]methyl][1,1'-biphenyl]-2-yl]-1H-tetrazole;
5-[4'-[[5-(1-butynyl)-3-tertbutyl-1H-1,2,4-triazol-1-yl]methyl][1,1'-biphenyl]-2-yl]-1H-tetrazole;
5-[4'-[[5-(1-butynyl)-3-pentyl-1H-1,2,4-triazol-1-yl]methyl][1,1'-biphenyl]-2-yl]-1H-tetrazole;
5-[4'-[[5-(1-butynyl)-3-isopentyl-1H-1,2,4-triazol-1-yl]methyl][1,1'-biphenyl]-2-yl]-1H-tetrazole;
5-[4'-[[5-(1-butynyl)-3-mercapto-1H-1,2,4-triazol-1-yl]methyl][1,1'-biphenyl]-2-yl]-1H-tetrazole;
5-[4'-[[5-(1-butynyl)-3-thiomethyl-1H-1,2,4-triazol-1-yl]methyl][1,1'-biphenyl]-2-yl]-1H-tetrazole;
5-[4'-[[5-(1-butynyl)-3-thioethyl-1H-1,2,4-triazol-1-yl]methyl][1,1'-biphenyl]-2-yl]-1H-tetrazole;
5-[4'-[[5-(1-butynyl)-3-thiopropyl-1H-1,2,4-triazol-1-yl]methyl][1,1'-biphenyl]-2-yl]-1H-tetrazole;
5-[4'-[[5-(1-butynyl)-3-hydroxy-1H-1,2,4-triazol-1-yl]methyl][1,1'-biphenyl]-2-yl]-1H-tetrazole;
5-[4'-[[5-(1-butynyl)-3-methoxy-1H-1,2,4-triazol-1-yl]methyl][1,1'-biphenyl]-2-yl]-1H-tetrazole;
5-[4'-[[5-(1-butynyl)-3-ethoxy-1H-1,2,4-triazol-1-yl]methyl][1,1'-biphenyl]-2-yl]-1H-tetrazole;
5-[4'-[[5-(1-butynyl)-3-propoxy-1H-1,2,4-triazol-1-yl]methyl][1,1,-biphenyl]-2-yl]-1H-tetrazole;
5-[4'-[[5-(1-butynyl)-3-cyclohexyl-1H-1,2,4-triazol-1-yl]methyl][1,1'-biphenyl]-2-yl]-1H-tetrazole;
5-[4'-[[5-(1-butynyl)-3-cyclohexylmethyl-1H-1,2,4-triazol-1-yl]methyl][1,1'-biphenyl]-2-yl]-1H-tetrazole;
5-[4'-[[5-(1-butynyl)-3-(2-cyclohexylethyl)-1H-1,2,4-triazol-1-yl]methyl][1,1'-biphenyl]-2-yl]-1H-tetrazole;
5-[4'-[[5-(1-butynyl)-3-cyclohexanoyl-1H-1,2,4-triazol-1-yl]methyl][1,1'-biphenyl]-2-yl]-1H-tetrazole;
5-[4'-[[5-(1-butynyl)-3-(1-oxo-2-cyclohexylethyl)-1H-1,2,4-triazol-1-yl]methyl][1,1'-biphenyl]-2-yl]-1H-tetrazole;
5-[4'-[[5-(1-butynyl)-3-phenyl-1H-1,2,4-triazol-1-yl]methyl][1,1'-biphenyl]-2-yl]-1H-tetrazole;
5-[4'-[[5-(1-butynyl)-3-phenylmethyl-1H-1,2,4-triazol-1-yl]methyl][1,1'-biphenyl]-2-yl]-1H-tetrazole;
5-[4'-[[5-(1 butynyl)-3-(2-phenylethyl)-1H-1,2 4-triazol-1-yl]methyl][1,1'-biphenyl]-2-yl]-1H-tetrazole;
5-[4'-[[5-(1 butynyl)-3-benzoyl-1H-1,2,4-triazol-1-yl]methyl][1,1'-biphenyl]-2-yl]-1H-tetrazole;
5-[4'-[[5-(1-butynyl)-3-(1-oxo-2 phenylethyl)-1H-1,2,4-triazol-1-yl]methyl][1,1'-biphenyl]-2-yl]-1H-tetrazole;
5-[4'-[[5-(1-butynyl)-3-(1,1-dimethoxypropyl)-1H-1,2,4-triazol-1-yl]methyl][1,1'-biphenyl]-2-yl]-1H-tetrazole;
5-[4'-[[5-(1 butynyl)-3-(1,1-dimethoxybutyl)-1H-1,2,4-triazol-1-yl]methyl][1,1'-biphenyl]-2-yl]-1H-tetrazole;
5-[4'-[[5-(1-butynyl)-3-(1,1-dimethoxypentyl)-1H-1,2,4-triazol-1-yl]methyl][1,1'-biphenyl]-2-yl]-1H-tetrazole;
5-[4'-[[5-(1 butynyl)-3-(1-oxopropyl)-1H-1,2,4-triazol-1-yl]methyl][1,1'-biphenyl]-2-yl]-1H-tetrazole;
5-[4'-[[5-(1 butynyl)-3-(1-oxobutyl)-1H-1,2,4-triazol-1-yl]methyl][1,1'-biphenyl]-2-yl]-1H-tetrazole;
5-[4'-[[5-(1 butynyl)-3-(1-oxopentyl)-1H-1,2,4-triazol-1-yl]methyl][1,1'-biphenyl]-2-yl]-1H-tetrazole;
5-[4'-[[5-(1 butynyl)-3-(1,1-difluoroethyl)-1H-1,2,4-triazol-1-yl]methyl][1,1'-biphenyl]-2-yl]-1H-tetrazole;
5-[4'-[[5-(1 butynyl)-3-(1,1-difluoropropyl)-1H-1,2,4-triazol-1-yl]methyl][1,1'-biphenyl]-2-yl]-1H-tetrazole;
5-[4'-[[5-(1 butynyl)-3-(1,1-difluorobutyl)-1H-1,2,4-triazol-1-yl]methyl][1,1'-biphenyl]-2-yl]-1H-tetrazole;
5-[4'-[[5-(1 butynyl)-3-(1,1-difluoropentyl)-1H-1,2,4-triazol-1-yl]methyl][1,1'-biphenyl]-2-yl]-1H-tetrazole;
5-[4'-[[5-(2-butynyl)-3-ethyl-1H-1,2,4-triazol-1-yl]methyl][1,1'-biphenyl]-2-yl]-1H-tetrazole;
5-[4'-[[5-(2 butynyl)-3-propyl-1H-1,2,4-triazol-1-yl]methyl][1,1'-biphenyl]-2-yl]-1H-tetrazole;
5-[4'-[[5-(2 butynyl)-3-butyl-1H-1,2,4-triazol-1-yl]methyl][1,1'-biphenyl]-2-yl]-1H-tetrazole;
5-[4'-[[5-(2 butynyl)-3-secbutyl-1H-1,2,4-triazol-1-yl]methyl][1,1'-biphenyl]-2-yl]-1H-tetrazole;
5-[4'-[[5-(2-butynyl)-3-isobutyl-1H-1,2,4-triazol-1-yl]methyl][1,1'-biphenyl]-2-yl]-1H-tetrazole;
5-[4'-[[5-(2 butynyl)-3-tertbutyl-1H-1,2,4-triazol-1-yl]methyl][1,1'-biphenyl]-2-yl]-1H-tetrazole;
5-[4'-[[5-(2 butynyl)-3-pentyl-1H-1,2,4-triazol-1-yl]methyl][1,1'-biphenyl]-2-yl]-1H-tetrazole;
5-[4'-[[5-(2 butynyl)-3-isopentyl-1H-1,2,4-triazol-1-yl]methyl][1,1'-biphenyl]-2-yl]-1H-tetrazole;
5-[4'-[[5-(2 butynyl)-3-mercapto-1H-1,2,4-triazol-1-yl]methyl][1,1'-biphenyl]-2-yl]-1H-tetrazole;
5-[4'-[[5-(2 butynyl)-3-thiomethyl-1H-1,2,4-triazol-1-yl]methyl][1,1'-biphenyl]-2-yl]-1H-tetrazole;
5-[4'-[[5-(2-butynyl)-3-thioethyl-1H-1,2,4-triazol-1-yl]methyl][1,1'-biphenyl]-2-yl]-1H-tetrazole;
5-[4'-[[5-(2butynyl)-3-thiopropyl-1H-1,2,4-triazol-1-yl]methyl][1,1'-biphenyl]-2-yl]-1H-tetrazole;
5-[4'-[[5-(2 butynyl)-3-hydroxy-1H-1,2,4-triazol-1-yl]methyl][1,1'-biphenyl]-2-yl]-1H-tetrazole;
5-[4'-[[5-(2-butynyl)-3-methoxy-1H-1,2,4-triazol-1-yl]methyl][1,1'-biphenyl]-2-yl]-1H-tetrazole;
5-[4'-[[5-(2-butynyl)-3-ethoxy-1H-1,2,4-triazol-1-yl]methyl][1,1'-biphenyl]-2-yl]-1H-tetrazole;
5-[4'-[[5-(2 butynyl)-3-propoxy-1H-1,2,4-triazol-1-yl]methyl][1,1'-biphenyl]-2-yl]-1H-tetrazole;
5-[4'-[[5-(2-butynyl)-3-cyclohexyl-1H-1,2,4-triazol-1-yl]methyl][1,1'-biphenyl]-2-yl]-1H-tetrazole;
5-[4'-[[5-(2-butynyl)-3-cyclohexylmethyl-1H-1,2,4-triazol-1-yl]methyl][1,1'-biphenyl]-2-yl]-1H-tetrazole;
5-[4'-[[5-(2 butynyl)-3-(2-cyclohexylethyl)-1H-1,2,4-triazol-1-yl]methyl][1,1'-biphenyl]-2-yl]-1H-tetrazole;
5-[4'-[[5-(2 butynyl)-3-cyclohexanoyl-1H-1,2,4-triazol-1-yl]methyl][1,1'-biphenyl]-2-yl]-1H-tetrazole;
5-[4'-[[5-(2 butynyl)-3-(1-oxo-2-cyclohexylethyl)-1H-1,2,4-triazol-1-yl]methyl][1,1'-biphenyl]-2-yl]-1H-tetrazole;
5-[4'-[[5-(2 butynyl)-3-phenyl-1H-1,2,4-triazol-1-yl]methyl][1,1'-biphenyl]-2-yl]-1H-tetrazole;

5-[4'-[[5-(2 butynyl)-3 phenylmethyl-1H-1,2,4-triazol-1-yl]methyl][1,1'-biphenyl]-2-yl]-1H-tetrazole;
5-[4'-[[5-(2 butynyl)-3-(2-phenylethyl)-1H-1,2,4-triazol-1-yl]methyl][1,1'-biphenyl]-2-yl]-1H-tetrazole;
5-[4'-[[5-(2 butynyl)-3-benzoyl-1H-1,2,4-triazol-1-yl]methyl][1,1'-biphenyl]-2-yl]-1H-tetrazole;
5-[4'-[[5-(2-butynyl)-3-(1-oxo-2 phenylethyl)-1H-1,2,4-triazol-1-yl]methyl][1,1'-biphenyl]-2-yl]-1H-tetrazole;
5-[4'-[[5-(2 butynyl)-3-(1,1-dimethoxypropyl)-1H-1,2,4-triazol-1-yl]methyl][1,1'-biphenyl]-2-yl]-1H-tetrazole;
5-[4'-[[5-(2 butynyl)-3-(1,1-dimethoxybutyl)-1H-1,2,4-triazol-1-yl]methyl][1,1'-biphenyl]-2-yl]-1H-tetrazole;
5-[4'-[[5-(2-butynyl)-3-(1,1-dimethoxypentyl)-1H-1,2,4-triazol-1-yl]methyl][1,1'-biphenyl]-2-yl]-1H-tetrazole;
5-[4'-[[5-(2 butynyl)-3-(1-oxopropyl)-1H-1,2,4-triazol-1-yl]methyl][1,1'-biphenyl]-2-yl]-1H-tetrazole;
5-[4'-[[5-(2 butynyl)-3-(1-oxobutyl)-1H-1,2,4-triazol-1-yl]methyl][1,1'-biphenyl]-2-yl]-1H-tetrazole;
5-[4'-[[5-(2-butynyl)-3-(1-oxopentyl)-1H-1,2,4-triazol-1-yl]methyl][1,1'-biphenyl]-2-yl]-1H-tetrazole;
5-[4'-[[5-(2 butynyl)-3-(1,1-difluoroethyl)-1H-1,2,4-triazol-1-yl]methyl][1,1'-biphenyl]-2-yl]-1H-tetrazole;
5-[4'-[[5-(2 butynyl)-3-(1,1-difluoropropyl)-1H-1,2,4-triazol-1-yl]methyl][1,1'-biphenyl]-2-yl]-1H-tetrazole;
5-[4'-[[5-(2 butynyl)-3-(1,1-difluorobutyl)-1H-1,2,4-triazol-1-yl]methyl][1,1'-biphenyl]-2-yl]-1H-tetrazole;
5-[4'-[[5-(2 butynyl)-3-(1,1-difluoropentyl)-1H-1,2,4-triazol-1-yl]methyl][1,1'-biphenyl]-2-yl]-1H-tetrazole;
5-[4'-[[5-(3 butynyl)-3-ethyl-1H-1,2,4-triazol-1-yl]methyl][1,1'-biphenyl]-2-yl]-1H-tetrazole;
5-[4'-[[5-(3 butynyl)-3-propyl-1H-1,2,4-triazol-1-yl]methyl][1,1'-biphenyl]-2-yl]-1H-tetrazole;
5-[4'-[[5-(3 butynyl)-3-isopropyl-1H-1,2,4-triazol-1-yl]methyl][1,1'-biphenyl]-2-yl]-1H-tetrazole;
5-[4'-[[5-(3-butynyl)-3-butyl-1H-1,2,4-triazol-1-yl]methyl][1,1'-biphenyl]-2-yl]-1H-tetrazole;
5-[4'-[[5-(3-butynyl)-3-secbutyl-1H-1,2,4-triazol-1-yl]methyl][1,1'-biphenyl]-2-yl]-1H-tetrazole;
5-[4'-[[5-(3-butynyl)-3-isobutyl-1H-1,2,4-triazol-1-yl]methyl][1,1'-biphenyl]-2-yl]-1H-tetrazole;
5-[4'-[[5-(3 butynyl)-3-tertbutyl-1H-1,2,4-triazol-1-yl]methyl][1,1'-biphenyl]-2-yl]-1H-tetrazole;
5-[4'-[[5-(3 butynyl)-3-isopentyl-1H-1,2,4-triazol-1-yl]methyl][1,1'-biphenyl]-2-yl]-1H-tetrazole;
5-[4'-[[5-(3-butynyl)-3-pentyl-1H-1,2,4-triazol-1-yl]methyl][1,1'-biphenyl]-2-yl]-1H-tetrazole;
5-[4'-[[5-(3-butynyl)-3-mercapto-1H-1,2,4-triazol-1-yl]methyl][1,1'-biphenyl]-2-yl]-1H-tetrazole;
5-[4'-[[5-(3-butynyl)-3-thiomethyl-1H-1,2,4-triazol-1-yl]methyl][1,1'-biphenyl]-2-yl]-1H-tetrazole;
5-[4'-[[5-(3 butynyl)-3-thioethyl-1H-1,2,4-triazol-1-yl]methyl][1,1'-biphenyl]-2-yl]-1H-tetrazole;
5-[4'-[[5-(3 butynyl)-3-thiopropyl-1H-1,2,4-triazol-1-yl]methyl][1,1'-biphenyl]-2-yl]-1H-tetrazole;
5-[4'-[[5-(3-butynyl)-3-hydroxy-1H-1,2,4-triazol-1-yl]methyl][1,1'-biphenyl]-2-yl]-1H-tetrazole;
5-[4'-[[5-(3-butynyl)-3-methoxy-1H-1,2,4-triazol-1-yl]methyl][1,1'-biphenyl]-2-yl]-1H-tetrazole;
5-[4'-[[5-(3-butynyl)-3-ethoxy-1H-1,2,4-triazol-1-yl]methyl][1,1'-biphenyl]-2-yl]-1H-tetrazole;
5-[4'-[[5-(3-butynyl)-3 propoxy-1H-1,2,4-triazol-1-yl]methyl][1,1'-biphenyl]-2-yl]-1H-tetrazole;
5-[4'-[[5-(3 butynyl)-3-cyclohexyl-1H-1,2,4-triazol-1-yl]methyl][1,1'-biphenyl]-2-yl]-1H-tetrazole;
5-[4'-[[5-(3-butynyl)-3-cyclohexylmethyl-1H-1,2,4-triazol-1-yl]methyl][1,1'-biphenyl]-2-yl]-1H-tetrazole;
5-[4'-[[5-(3 butynyl)-3-(2-cyclohexylethyl)-1H-1,2,4-triazol-1-yl]methyl][1,1'-biphenyl]-2-yl]-1H-tetrazole;
5-[4'-[[5-(3 butynyl)-3-cyclohexanoyl-1H-1,2,4-triazol-1-yl]methyl][1,1'-biphenyl]-2-yl]-1H-tetrazole;
5-[4'-[[5-(3 butynyl)-3-(1-oxo-2-cyclohexylethyl)-1H-1,2,4-triazol-1-yl]methyl][1,1'-biphenyl]-2-yl]-1H-tetrazole;
5-[4'-[(3,5-dithiomethyl-1H-1,2,4-triazol-1-yl)methyl][1,1'-biphenyl]-2-yl]-1H-tetrazole;
5-[4'-[(3,5-dithioethyl-1H-1,2,4-triazol-1-yl)methyl][1,1'-biphenyl]-2-yl]-1H-tetrazole;
5-[4'-[(3,5-dithiopropyl-1H-1,2,4-triazol-1-yl)methyl][1,1'-biphenyl]-2-yl]-1H-tetrazole;
5-[4'-[(3,5-dithioisopropyl-1H-1,2,4-triazol-1-yl)methyl][1,1'-biphenyl]-2-yl]-1H-tetrazole;
5-[4'-[[3,5-di(1-butenyl)-1H-1,2,4-triazol-1-yl]methyl][1,1'-biphenyl]-2-yl]-1H-tetrazole;
5-[4'-[[3,5-di(2-butenyl)-1H-1,2,4-triazol-1-yl]methyl][1,1'-biphenyl]-2-yl]-1H-tetrazole;
5-[4'-[[3,5-di(3-butenyl)-1H-1,2,4-triazol-1-yl]methyl][1,1'-biphenyl]-2-yl]-1H-tetrazole;
5-[4'-[[3,5-di(1-butynyl)-1H-1,2,4-triazol-1-yl]methyl][1,1'-biphenyl]-2-yl]-1H-tetrazole;
5-[4'-[[3,5-di(2-butynyl)-1H-1,2,4-triazol-1-yl]methyl][1,1'-biphenyl]-2-yl]-1H-tetrazole; and
5-[4'-[[3,5-di(3-butynyl)-1H-1,2,4-triazol-1-yl]methyl][1,1,-biphenyl]-2-yl]-1H-tetrazole.

A family of specific compounds of more particular interest within Formula I consists of compounds having an acidic group attached at the $R^5$ or $R^9$ "ortho" position as follows:

2-[[4-[(5-butyl-3-chloro-1H-1,2,4-triazol-1-yl)methyl]phenyl]methyl]benzoic acid;
2-[[4-[(3-butyl-5-chloro-1H-1,2,4-triazol-1-yl)methyl]phenyl]methyl]benzoic acid;
2-[[4-[(5-butyl-3-propyl-1H-1,2,4-triazol-1-yl)methyl]phenyl]methyl]benzoic acid;
2-[[4-[(3,5-dibutyl-1H-1,2,4-triazol-1-yl)methyl]phenyl]methyl]benzoic acid;
2-[[4-[(3,5-dibutyl-1H-1,2,4-triazol-1-yl)methyl]phenyl]methyl]benzoic acid;
2-[[4-[(5 butyl-3-isopentyl-1H-1,2,4-triazol-1-yl)methyl]phenyl]methyl]benzoic acid;
2-[[4-[[5-butyl-3-(1,1-dimethoxybutyl)-1H-1,2,4-triazol-1-yl]methyl]phenyl]methyl]benzoic acid;
2-[[4-[[5 butyl-3-(1-oxobutyl)-1H-1,2,4-triazol-1-yl]methyl]phenyl]methyl]benzoic acid;
2-[[4-[[5 butyl-3-(1-oxopentyl)-1H-1,2,4-triazol-1-yl]methyl]phenyl]methyl]benzoic acid;
2-[[4-[[5 butyl-3-(1,1-difluoroethyl)-1H-1,2,4-triazol-1-yl]methyl]phenyl]methyl]benzoic acid;
2-[[4-[[5-butyl-3-(1,1-difluoropropyl)-1H-1,2,4-triazol-1-yl]methyl]phenyl]methyl]benzoic acid;
2-[[4-[[5 butyl-3-(1,1-difluorobutyl)-1H-1,2,4-triazol-1-yl]methyl]phenyl]methyl]benzoic acid;
2-[[4-[[3 butyl-5-(1,1-difluorobutyl)-1H-1,2,4-triazol-1-yl]methyl]phenyl]methyl]benzoic acid;
2-[[4-[[5-butyl-3-(1,1-difluoropentyl)-1H-1,2,4-triazol-1-yl]methyl]phenyl]methyl]benzoic acid;
2-[[4-[(3,5-dipropyl-1H-1,2,4-triazol-1-yl)methyl]phenyl]methyl]benzoic acid;
2-[[4-[(3,5-isopropyl-1H-1,2,4-triazol-1-yl)methyl]phenyl]methyl]benzoic acid;
2-[[4-[(5-propyl-3 butyl-1H-1,2,4-triazol-1-yl)methyl]phenyl]methyl]benzoic acid;
2-[[4-[[5 propyl-3-(1,1-difluoroethyl)-1H-1,2,4-triazol-1-yl]methyl]phenyl]methyl]benzoic acid;
2-[[4-[[5 propyl-3-(1,1-difluoropropyl)-1H-1,2,4-triazol-1-yl]methyl]phenyl]methyl]benzoic acid;

2-[[4-[[5-propyl-3-(1,1-difluorobutyl)-1H-1,2,4-triazol-1-yl]methyl]phenyl]methyl]benzoic acid;
2-[[4-[[5-propyl-3-(1,1-difluoropentyl)-1H-1,2,4-triazol-1-yl]methyl][1,1'-biphenyl]-2-carboxylic acid;
2-[[4-[[5-ethyl-3-(1,1-difluorobutyl)-1H-1,2,4-triazol-1-yl]methyl]phenyl]methyl]benzoic acid;
2-[[4-[(3,5-disecbutyl-1H-1,2,4-triazol-1-yl)methyl]phenyl]methyl]benzoic acid;
2-[[4-[[5-secbutyl-3-(1,1-difluorobutyl)-1H-1,2,4-triazol-1-yl]methyl]phenyl]methyl]benzoic acid;
2-[[4-[(3,5-diisobutyl-1H-1,2,4-triazol-1-yl)methyl]phenyl]methyl]benzoic acid;
2-[[4-[[5-isobutyl-3-(1,1-difluorobutyl)-1H-1,2,4-triazol-1-yl]methyl]phenyl]methyl]benzoic acid;
2-[[4-[(3,5-ditertbutyl-1H-1,2,4-triazol-1-yl)methyl]phenyl]methyl]benzoic acid;
2-[[4-[[5-tertbutyl-3-(1,1-difluorobutyl)-1H-1,2,4-triazol-1-yl]methyl]phenyl]methyl]benzoic acid;
2-[[4-[(3,5-dipentyl-1H-1,2,4-triazol-1-yl)methyl]phenyl]methyl]benzoic acid;
2-[[4-[[5-pentyl-3-(1,1-difluorobutyl)-1H-1,2,4-triazol-1-yl]methyl]phenyl]methyl]benzoic acid;
2-[[4-[(3,5-diisopentyl-1H-1,2,4-triazol-1-yl)methyl]phenyl]methyl]benzoic acid;
2-[[4-[[5-isopentyl-3-(1,1-difluorobutyl)-1H-1,2,4-triazol-1-yl]methyl]phenyl]methyl]benzoic acid;
2-[4-[[5-(1 butenyl)-3-(1,1-difluorobutyl)-1H-1,2,4-triazol-1-yl]methyl]phenyl]methyl]benzoic acid;
2-[[4-[[5-(2-butenyl)-3-(1,1-difluorobutyl)-1H-1,2,4-triazol-1-yl]methyl]phenyl]methyl]benzoic acid;
2-[[4-[[5-(3 butenyl)-3-(1,1 difluorobutyl)-1H-1,2,4-triazol-1-yl]methyl]phenyl]methyl]benzoic acid;
2-[[4-[[5-(1 butynyl)-3-(1,1-difluorobutyl)-1H-1,2,4-triazol-1-yl]methyl]phenyl]methyl]benzoic acid;
2-[[4-[[5-(2 butynyl)-3-(1,1-difluorobutyl)-1H-1,2,4-triazol-1-yl]methyl]phenyl]methyl]benzoic acid;
2-[[4-[[5-(3 butynyl)-3-(1,1-difluorobutyl)-1H-1,2,4-triazol-1-yl]methyl]phenyl]methyl]benzoic acid;
2-[[4-[(3,5-diethoxy-1H-1,2,4-triazol-1-yl)methyl]phenyl]methyl]benzoic acid;
2-[[4-[(3,5-dipropoxy-1H-1,2,4-triazol-1-yl)methyl]phenyl]methyl]benzoic acid;
2-[[4-[(3,5-diisopropoxy-1H-1,2,4-triazol-1-yl)methyl]phenyl]methyl]benzoic acid;
2-[[4-[(3,5-dibutoxy-1H-1,2,4-triazol-1-yl)methyl]phenyl]methyl]benzoic acid;
2-[[4-[(3,5-dithioethyl-1H-1,2,4-triazol-1-yl)methyl]phenyl]methyl]benzoic acid;
2-[[4-[(3,5-dithiopropyl-1H-1,2,4-triazol-1-yl)methyl]phenyl]methyl]benzoic acid;
2-[[4-[(3,5-dithioisopropyl-1H-1,2,4-triazol-1-yl)methyl]phenyl]methyl]benzoic acid;
2-[[4-[3,5-di(1-butenyl)-1H-1,2,4-triazol-1-yl]methyl]phenyl]methyl]benzoic acid;
2-[[4-[[3,5-di(2-butenyl)-1H-1,2,4-triazol-1-yl]methyl]phenyl]methyl]benzoic acid;
2-[[4-[[3,5-di(3-butenyl)-1H-1,2,4-triazol-1-yl]methyl]phenyl]methyl]benzoic acid;
2-[[4-[[3,5-di(1-butynyl)-1H-1,2,4-triazol-1-yl]methyl]phenyl]methyl]benzoic acid;
2-[[4-[[3,5-di(2-butynyl)-1H-1,2,4-triazol-1-yl]methyl]phenyl]methyl]benzoic acid;
2-[[4-[[3,5-di(3-butynyl)-1H-1,2,4-triazol-1-yl]methyl]phenyl]methyl]benzoic acid;
5-[2-[[4-[(5-butyl-3-chloro-1H-1,2,4-triazol-1-yl)methyl]phenyl]methyl]phenyl]-1H-tetrazole;
5-[2-[[4-[(3-butyl-5-chloro-1H-1,2,4-triazol-1-yl)methyl]phenyl]methyl]phenyl-1H-tetrazole;
5-[2-[[4-[(5-butyl-3-propyl-1H-1,2,4-triazol-1-yl)methyl]phenyl]methyl]phenyl]-1H-tetrazole;
5-[2-[[4-[(3,5-dibutyl-1H-1,2,4-triazol-1-yl)methyl]phenyl]methyl]phenyl]-1H-tetrazole;
5-[2-[[4-[(5-butyl-3-isopentyl-1H-1,2,4-triazol-1-yl)methyl]phenyl]methyl]phenyl]-1H-tetrazole;
5-[2-[[4-[[5-butyl-3-(1,1 dimethoxybutyl)-1H-1,2,4-triazol-1-yl]methyl]phenyl]methyl]phenyl]-1H-tetrazole;
5-[2-[[4-[[5-butyl-3-(1-oxobutyl)-1H-1,2,4-triazol-1-yl]methyl]phenyl]methyl]phenyl]-1H-tetrazole;
5-[2-[[4-[[5-butyl-3-(1,1-difluoroethyl)-1H-1,2,4-triazol-1-yl]methyl]phenyl]methyl]phenyl]-1H-tetrazole;
5-[2-[[4-[[5-butyl-3-(1,1-difluoropropyl)-1H-1,2,4-triazol-1-yl]methyl]phenyl]methyl]phenyl]-1H-tetrazole;
5-[2-[[4-[[5-butyl-3-(1,1-difluorobutyl)-1H-1,2,4-triazol-1-yl]methyl]phenyl]methyl]phenyl]-1H-tetrazole;
5-[2-[[4-[[3-butyl-5-(1,1-difluorobutyl)-1H-1,2,4-triazol-1-yl]methyl]phenyl]methyl]phenyl]-1H-tetrazole;
5-[2-[[4-[[5-butyl-3-(1,1-difluoropentyl)-1H-1,2,4-triazol-1-yl]methyl]phenyl]methyl]phenyl][-1H-tetrazole;
5-[2-[[4-[(3,5-dipropyl-1H-1,2,4-triazol-1-yl)methyl]phenyl]methyl]phenyl]-1H-tetrazole;
5-[2-[[4-[(3,5-isopropyl-1H-1,2,4-triazol-1-yl)methyl]phenyl]methyl]phenyl]-1H-tetrazole;
5-[2-[[4-[(5-propyl-3-isopentyl-1H-1,2,4-triazol-1-yl)methyl]phenyl]methyl]phenyl]-1H-tetrazole;
5-[2-[[4-[[5-propyl-3-(1,1-dimethoxybutyl -1H-1,2,4-triazol-1-yl]methyl]phenyl]methyl]phenyl]-1H-tetrazole;
5-[2-[[4-[[5-propyl-3-(1-oxobutyl)-1H-1,2,4-triazol-1-yl]methyl]phenyl]methyl]phenyl]-1H-tetrazole;
5-[2-[[4-[[5-propyl-3-(1,1-difluoroethyl)-1H-1,2,4-triazol-1-yl]methyl]phenyl]methyl]phenyl]-1H-tetrazole;
5-[2-[[4-[[5-propyl-3-(1,1-difluoropropyl)-1H-1,2,4-triazol-1-yl]methyl]phenyl]methyl]phenyl][1,1'-biphenyl]-2-yl]-1H-tetrazole;
5-[2-[[4-[[5-propyl-3-(1,1-difluorobutyl)-1H-1,2,4-triazol-1-yl]methyl]phenyl]methyl]phenyl]-1H-tetrazole;
5-[2-[[4-[[5-propyl-3-(1,1-difluoropentyl)-1H-1,2,4-triazol-1-yl]methyl]phenyl]methyl]phenyl]-2-yl]-1H-tetrazole;
5-[2-[[4-[[5-ethyl-3-(1,1-difluorobutyl)-1H-1,2,4-triazol-1-yl]methyl]phenyl]methyl]phenyl]-1H-tetrazole;
5-[2-[[4-[(5-secbutyl-3-propyl-1H-1,2,4-triazol-1-yl)methyl]phenyl]methyl]phenyl]-1H-tetrazole;
5-[2-[[4-[(5-secbutyl-3-butyl-1H-1,2,4-triazol-1-yl)methyl]phenyl]methyl]phenyl]-1H-tetrazole;
5-[2-[[4-[(3,5-disecbutyl-1H-1,2,4-triazol-1-yl)methyl]phenyl]methyl]phenyl]-1H-tetrazole;
5-[2-[[4-[(5-secbutyl-3-isopentyl-1H-1,2,4-triazol-1-yl)methyl]phenyl]methyl]phenyl]-1H-tetrazole;
5-[2-[[4-[[5-secbutyl-3-(1,1-difluoroethyl)-1H-1,2,4-triazol-1-yl]methyl]phenyl]methyl]phenyl]-1H-tetrazole;
5-[2-[[4-[[5-secbutyl-3-(1,1-difluoropropyl)-1H-1,2,4-triazol-1-yl]methyl]phenyl]methyl]phenyl]-1H-tetrazole;
5-[2-[[4-[[5-secbutyl-3-(1,1-difluorobutyl)-1H-1,2,4-triazol-1-yl]methyl]phenyl]methyl]phenyl]1H-tetrazole;
5-[2-[[4-[[5-secbutyl-3-(1,1-difluoropentyl)-1H-1,2,4-triazol-1-yl]methyl]phenyl]methyl]phenyl]-1H-tetrazole;

5-[2-[[4-[(5-isobutyl-3-propyl-1H-1,2,4-triazol-1-yl)methyl]phenyl]methyl]phenyl]-1H-tetrazole;
5-[2-[[4-[(5-isobutyl-3-butyl-1H-1,2,4-triazol-1-yl)methyl]phenyl]methyl]phenyl]-1H-tetrazole;
5-[2-[[4-[(3,5-diisobutyl-1H-1,2,4-triazol-1-yl)methyl]-phenyl]methyl]phenyl]-1H-tetrazole;
5-[2-[[4-[(5-isobutyl-3-isopentyl-1H-1,2,4-triazol-1-yl)methyl]phenyl]methyl]phenyl]-1H-tetrazole;
5-[2-[[4-[[5-isobutyl-3-(1,1-difluoroethyl)-1H-1,2,4-triazol-1-yl]methyl phenyl]methyl]phenyl]-1H-tetrazole;
5-[2-[[4-[5-isobutyl-3-(1,1-difluoropropyl)-1H-1,2,4-triazol-1-yl]methyl]phenyl]methyl]phenyl]-1H-tetrazole;
5-[2-[[4-[[5-isobutyl-3-(1,1-difluorobutyl)-1H-1,2,4-triazol-1-yl]methyl]phenyl]methyl]phenyl]-1H-tetrazole;
5-[2-[[4-[[5-isobutyl-3-(1,1-difluoropentyl)-1H-1,2,4-triazol-1-yl]methyl]phenyl]methyl]phenyl]-1H-tetrazole;
5-[2-[[4-[(5-tertbutyl-3-propyl-1H-1,2,4-triazol-1-yl)methyl]phenyl]methyl]phenyl]-1H-tetrazole;
5-[2-[[4-[(5-tertbutyl-3-butyl-1H-1,2,4-triazol-1-yl)methyl]phenyl]methyl]phenyl]-1H-tetrazole;
5-[2-[[4-[(3,5-ditertbutyl-1H-1,2,4-triazol-1-yl)methyl]-phenyl]methyl]phenyl]-1H-tetrazole;
5-[2-[[4-[(5-tertbutyl-3-isopentyl-1H-1,2,4-triazol-1-yl)methyl]phenyl]methyl]phenyl]-1H-tetrazole;
5-[2-[[4-[[5-tertbutyl-3-(1,1-difluoroethyl)-1H-1,2,4-triazol-1-yl]methyl]phenyl]methyl]phenyl]-1H-tetrazole;
5-[2-[[4-[[5-tertbutyl-3-(1,1-difluoropropyl)-1H-1,2,4-triazol-1-yl]methyl]phenyl]methyl]phenyl]-1H-tetrazole;
5-[2-[[4-[[5-tertbutyl-3-(1,1-difluorobutyl)-1H-1,2,4-triazol-1-yl]methyl]phenyl]methyl]phenyl]-1H-tetrazole; -.
5-[2-[[4-[[5-tertbutyl-3-(1,1-difluoropentyl)-1H-1,2,4-triazol-1-yl]methyl]phenyl]methyl]phenyl]-1H-tetrazole;
5-[2-[[4-[(5-pentyl-3-propyl-1H-1,2,4-triazol-1-yl)methyl]phenyl]methyl]phenyl]-1H-tetrazole;
5-[2-[[4-[(5-pentyl-3-butyl-1H-1,2,4-triazol-1-yl)methyl]phenyl]methyl]phenyl]-1H-tetrazole;
5-[2-[[4-[(3,5-dipentyl-1H-1,2,4-triazol-1-yl)methyl]-phenyl]methyl]phenyl]-1H-tetrazole;
5-[2-[[4-[(5-pentyl-3-isopentyl-1H-1,2,4-triazol-1-yl)methyl]phenyl]methyl]phenyl]-1H-tetrazole;
5-[2-[[4-[[5-pentyl-3-(1,1-difluoroethyl)-1H-1,2,4-triazol-1-yl]methyl]phenyl]methyl]phenyl]-1H-tetrazole;
5-[2-[[4-[[5-pentyl-3-(1,1-difluoropropyl)-1H-1,2,4-triazol-1-yl]methyl]phenyl]methyl]phenyl]-1H-tetrazole;
5-[2-[[4-[[5-pentyl-3-(1,1-difluorobutyl)-1H-1,2,4-triazol-1-yl]methyl]phenyl]methyl]phenyl]-1H-tetrazole;
5-[2-[[4-[[5-pentyl-3-(1,1-difluoropentyl)-1H-1,2,4-triazol-1-yl]methyl]phenyl]methyl]phenyl]-1H-tetrazole;
5-[2-[[4-[(5-isopentyl-3-ethyl-1H-1,2,4-triazol-1-yl)methyl]phenyl]methyl]phenyl]-1H-tetrazole;
5-[2-[[4-[(5-isopentyl-3-propyl-1H-1,2,4-triazol-1-yl)methyl]phenyl]methyl]phenyl]-1H-tetrazole;
5-[2-[[4-[(5-isopentyl-3-butyl-1H-1,2,4-triazol-1-yl)methyl]phenyl]methyl]phenyl]-1H-tetrazole;
5-[2-[[4-[(3,5-diisopentyl-1H-1,2,4-triazol-1-yl)methyl]-phenyl]methyl]phenyl]-1H-tetrazole;

5-[2-[[4-[[5-isopentyl-3-(1,1-difluoroethyl)-1H-1,2,4-triazol-1-yl]methyl]phenyl]methyl]phenyl]-1H-tetrazole:
5-[2-[[4-[[5-isopentyl-3-(1,1-difluoropropyl)-1H-1,2,4-triazol-1-yl]methyl]phenyl]methyl]phenyl]-1H-tetrazole;
5-[2-[[4-[[5-isopentyl-3-(1,1-difluorobutyl)-1H-1,2,4-triazol-1-yl]methyl]phenyl]methyl]phenyl]-1H-tetrazole;
5-[2-[[4-[[5-isopentyl-3-(1,1-difluoropentyl)-1H-1,2,4-triazol-1-yl]methyl]phenyl]methyl]phenyl]-1H-tetrazole;
5-[2-[[4-[[5-(1-butenyl)-3-propyl-1H-1,2,4-triazol-1-yl]methyl]phenyl]methyl]phenyl]-1H-tetrazole;
5-[2-[[4-[[5-(1-butenyl)-3-butyl-1H-1,2,4-triazol-1-yl]methyl]phenyl]methyl]phenyl]-1H-tetrazole;
5-[2-[[4-[[5-(1-butenyl)-3-isopentyl-1H-1,2,4-triazol-1-yl]methyl]phenyl]methyl]phenyl]-1H-tetrazole;
5-[2-[[4-[[5-(1-butenyl)-3-(1,1-dimethoxybutyl)-1H-1,2,4-triazol-1-yl]methyl]phenyl]methyl]phenyl]-1H-tetrazole;
5-[2-[[4-[[5-(1-butenyl)-3-(1,1-difluorobutyl)-1H-1,2,4-triazol-1-yl]methyl]phenyl]methyl]phenyl]-1H-tetrazole;
5-[2-[[4-[[5-(2-butenyl)-3-(1,1-difluorobutyl)-1H-1,2,4-triazol-1-yl]methyl]phenyl]methyl]phenyl]-1H-tetrazole;
5-[2-[[4-[[5-(3-butenyl)-3-(1,1-difluorobutyl)-1H-1,2,4-triazol-1-yl]methyl]phenyl]methyl]phenyl]-1H-tetrazole;
5-[2-[[4-[[5-(1-butynyl)-3-(1,1-difluorobutyl)-1H-1,2,4-triazol-1-yl]methyl]phenyl]methyl]phenyl]-1H-tetrazole;
5-[2-[[4-[[5-(2-butynyl)-3-(1,1-difluorobutyl)-1H-1,2,4-triazol-1-yl]methyl]phenyl]methyl]phenyl]-1H-tetrazole;
5-[2-[[4-[[5-(3-butynyl)-3-(1,1-difluorobutyl)-1H-1,2,4-triazol-1-yl]methyl]phenyl]methyl]phenyl]-1H-tetrazole;
5-[2-[[4-[(3,5-dipropoxy-1H-1,2,4-triazol-1-yl)methyl]-phenyl]methyl]phenyl]-1H-tetrazole;
5-[2-[[4-[(3,5-diisopropoxy-1H-1,2,4-triazol-1-yl)methyl]phenyl]methyl]phenyl]-1H-tetrazole;
5-[2-[[4-[(3,5-dibutoxy-1H-1,2,4-triazol-1-yl)methyl]-phenyl]methyl]phenyl]-1H-tetrazole;
5-[2-[[4-[(3,5-dithioethyl-1H-1,2,4-triazol-1-yl)methyl]-phenyl]methyl]phenyl]-1H-tetrazole;
5-[2-[[4-[(3,5-dithiopropyl-1H-1,2,4-triazol-1-yl)methyl]phenyl]methyl]phenyl]-1H-tetrazole;
5-[2-[4-[(3,5-dithioisopropyl-1H-1,2,4-triazol-1-yl)methyl]phenyl]methyl]phenyl]-1H-tetrazole;
5-[2-[[4-[[3,5-di(1-butenyl)-1H-1,2,4-triazol-1-yl]methyl]phenyl]methyl]phenyl]-1H-tetrazole;
5-[2-[[4-[(3,5-di(2-butenyl)-1H-1,2,4-triazol-1-yl]methyl]phenyl]methyl]phenyl]-1H-tetrazole;
5-[2-[[4-[(3,5-di(3-butenyl)-1H-1,2,4-triazol-1-yl]methyl]phenyl]methyl]phenyl]-1H-tetrazole;
5-[2-[[4-[[3,5-di(1-butynyl)-1H-1,2,4-triazol-1-yl]methyl]phenyl]methyl]phenyl][-1H-tetrazole;
5-[2-[[4-[[3,5-di(2-butynyl)-1H-1,2,4-triazol-1-yl]methyl]phenyl]methyl]phenyl]-1H-tetrazole; and
5-[2-[[4-[[3,5-di(3-butynyl)-1H-1,2,4-triazol-1-yl]methyl]phenyl]methyl]phenyl]-1H-tetrazole.

Another family of specific compounds of more particular interest within Formula I consists of compounds having an acidic group attached at the $R^6$ or $R^8$ "meta" position as follows:

3-[[4-[(5-butyl-3-chloro-1H-1,2,4-triazol-1-yl)methyl]-
phenyl]methyl]benzoic acid;
3-[[4-[(3-butyl-5-chloro-1H-1,2,4-triazol-1-yl)methyl]-
phenyl]methyl]benzoic acid;
3-[[4-[(5-butyl-3-propyl-1H-1,2,4-triazol-1-yl)methyl]-
phenyl]methyl]benzoic acid;
3-[[4-[(3,5-dibutyl-1H-1,2,4-triazol-1-yl)methyl]phenyl]-
methyl]benzoic acid;
3-[[4-[(3,5-dibutyl-1H-1,2,4-triazol-1-yl)methyl]phenyl]-
methyl]benzoic acid;
3-[[4-[(5-butyl-3-isopentyl-1H-1,2,4-triazol-1-yl)me-
thyl]phenyl]methyl]benzoic acid;
3-[[4-[[5-butyl-3-(1,1-dimethoxybutyl)-1H-1,2,4-triazol-
1-yl]methyl]phenyl]methyl]benzoic acid;
3-[[4-[[5-butyl-3-(1-oxobutyl)-1H-1,2,4-triazol-1-yl]me-
thyl]phenyl]methyl]benzoic acid;
3-[[4-[[5-butyl-3-(1-oxopentyl)-1H-1,2,4-triazol-1-yl]me-
thyl]phenyl]methyl]benzoic acid;
3-[[4-[[5-butyl-3-(1,1-difluoroethyl)-1H-1,2,4-triazol-1-
yl]methyl]phenyl]methyl]benzoic acid;
3-[[4-[[5-butyl-3-(1,1-difluoropropyl)-1H-1,2,4-triazol-1-
yl]methyl]phenyl]methyl]benzoic acid;
3-[[4-[[5-butyl-3-(1,1-difluorobutyl)-1H-1,2,4-triazol-1-
yl]methyl]phenyl]methyl]benzoic acid;
3-[[4-[[3-butyl-5-(1,1-difluorobutyl)-1H-1,2,4-triazol-1-
yl]methyl]phenyl]methyl]benzoic acid;
3-[[4-[[5-butyl-3-(1,1-difluoropentyl)-1H-1,2,4-triazol-1-
yl]methyl]phenyl]methyl]benzoic acid;
3-[[4-[(3,5-dipropyl-1H-1,2,4-triazol-1-yl)methyl]-
phenyl]methyl]benzoic acid;
3-[[4-[(3,5-isopropyl-1H-1,2,4-triazol-1-yl)methyl]-
phenyl]methyl]benzoic acid;
3-[[4-[(5-propyl-3-butyl-1H-1,2,4-triazol-1-yl)methyl]-
phenyl]methyl]benzoic acid;
3-[[4-[[5-propyl-3-(1,1-difluoroethyl)-1H-1,2,4-triazol-1-
yl]methyl]phenyl]methyl]benzoic acid;
3-[[4-[[5-propyl-3-(1,1-difluoropropyl)-1H-1,2,4-triazol-
1-yl]methyl]phenyl]methyl]benzoic acid;
3-[[4-[[5-propyl-3-(1,1-difluorobutyl)-1H-1,2,4-triazol-1-
yl]methyl]phenyl]methyl]benzoic acid;
3-[[4-[[5-propyl-3-(1,1-difluoropentyl)-1H-1,2,4-triazol-
1-yl]methyl][1,1'-biphenyl]-2-carboxylic acid;
3-[[4-[[5-ethyl-3-(1,1-difluorobutyl)-1H-1,2,4-triazol-1-
yl]methyl]phenyl]methyl]benzoic acid;
3-[[4-[(3,5-disecbutyl-1H-1,2,4-triazol-1-yl)methyl]-
phenyl]methyl]benzoic acid;
3-[[4-[[5-secbutyl-3-(1,1-difluorobutyl)-1H-1,2,4-triazol-
1-yl]methyl]phenyl]methyl benzoic acid;
3-[[4-[(3,5-diisobutyl-1H-1,2,4-triazol-1-yl)methyl]-
phenyl]methyl]benzoic acid;
3-[[4-[[5-isobutyl-3-(1,1-difluorobutyl)-1H-1,2,4-triazol-
1-yl]methyl]phenyl]methyl]benzoic acid;
3-[[4-[(3,5-ditertbutyl-1H-1,2,4-triazol-1-yl)methyl]-
phenyl]methyl]benzoic acid;
3-[[4-[[5-tertbutyl-3-(1,1-difluorobutyl)-1H-1,2,4-
triazol-1-yl]methyl]phenyl]methyl]benzoic acid;
3-[[4-[(3,5-dipentyl-1H-1,2,4-triazol-1-yl)methyl]-
phenyl]methyl]benzoic acid;
3-[[4-[[5-pentyl-3-(1,1-difluorobutyl)-1H-1,2,4-triazol-1-
yl]methyl]phenyl]methyl]benzoic acid;
3-[[4-[(3,5-diisopentyl-1H-1,2,4-triazol-1-yl)methyl]-
phenyl]methyl]benzoic acid;
3-[[4-[[5-isopentyl-3-(1,1-difluorobutyl)-1H-1,2,4-
triazol-1-yl]methyl]phenyl]methyl]benzoic acid;
3-[[4-[[5-(1-butenyl)-3-(1,1-difluorobutyl)-1H-1,2,4-
triazol-1-yl]methyl]phenyl]methyl]benzoic acid;
3-[[4-[[5-(2-butenyl)-3-(1,1-difluorobutyl)-1H-1,2,4-
triazol-1-yl]methyl]phenyl]methyl]benzoic acid;

3-[[4-[[5-(3-butenyl)-3-(1,1-difluorobutyl)-1H-1,2,4-
triazol-1-yl]methyl]phenyl]methyl]benzoic acid;
3-[[4-[[5-(1-butynyl)-3-(1,1-difluorobutyl)-1H-1,2,4-
triazol-1-yl]methyl]phenyl]methyl]benzoic acid;
3-[[4-[[5-(2-butynyl)-3-(1,1-difluorobutyl)-1H-1,2,4-
triazol-1-yl]methyl]phenyl]methyl]benzoic acid;
3-[[4-[[5-(3-butynyl)-3-(1,1-difluorobutyl)-1H-1,2,4-
triazol-1-yl]methyl]phenyl]methyl]benzoic acid;
3-[[4-[(3,5-diethoxy-1H-1,2,4-triazol-1-yl)methyl]-
phenyl]methyl]benzoic acid;
3-[[4-[(3,5-dipropoxy-1H-1,2,4-triazol-1-yl)methyl]-
phenyl]methyl]benzoic acid;
3-[[4-[(3,5-diisopropoxy-1H-1,2,4-triazol-1-yl)methyl]-
phenyl]methyl]benzoic acid;
3-[[4-[(3,5-dibutoxy-1H-1,2,4-triazol-1-yl)methyl]-
phenyl]methyl]benzoic acid;
3-[[4-[(3,5-dithioethyl-1H-1,2,4-triazol-1-yl)methyl]-
phenyl]methyl]benzoic acid;
3-[[4-[(3,5-dithiopropyl-1H-1,2,4-triazol-1-yl)methyl]-
phenyl]methyl]benzoic acid;
3-[[4-[(3,5-dithioisopropyl-1H-1,2,4-triazol-1-yl)me-
thyl]phenyl]methyl]benzoic acid;
3-[[4-[[3,5-di(1-butenyl)-1H-1,2,4-triazol-1-yl]methyl]-
phenyl]methyl]benzoic acid;
3-[[4-[[3,5-di(2-butenyl)-1H-1,2,4-triazol-1-yl]methyl]-
phenyl]methyl]benzoic acid;
3-[[4-[[3,5-di(3-butenyl)-1H-1,2,4-triazol-1-yl]methyl]-
phenyl]methyl]benzoic acid;
3-[[4-[[3,5-di(1-butynyl)-1H-1,2,4-triazol-1-yl]methyl]-
phenyl]methyl]benzoic acid;
3-[[4-[[3,5-di(2-butynyl)-1H-1,2,4-triazol-1-yl]methyl]-
phenyl]methyl]benzoic acid;
3-[[4-[[3,5-di(3-butynyl)-1H-1,2,4-triazol-1-yl]methyl]-
phenyl]methyl]benzoic acid;
5-[3-[[4-[(5-butyl-3-chloro-1H-1,2,4-triazol-1-yl)me-
thyl]phenyl]methyl]phenyl]-1H-tetrazole;
5-[3-[[4-[(3-butyl-5-chloro-1H-1,2,4-triazol-1-yl)me-
thyl]phenyl]methyl]phenyl-1H-tetrazole;
5-[3-[[4-[(5-butyl-3-propyl-1H-1,2,4-triazol-1-yl)me-
thyl]phenyl]methyl]phenyl]-1H-tetrazole;
5-[3-[[4-[(3,5-dibutyl-1H-1,2,4-triazol-1-yl)methyl]-
phenyl]methyl]phenyl]-1H-tetrazole;
5-[3-[[4-[(5-butyl-3-isopentyl-1H-1,2,4-triazol-1-yl)me-
thyl]phenyl]methyl]phenyl]-1H-tetrazole;
5-[3-[[4-[[5-butyl-3-(1,1 dimethoxybutyl)-1H-1,2,4-
triazol-1-yl]methyl]phenyl]methyl]phenyl]-1H-tet-
razole;
5-[3-[[4-[[5-butyl-3-(1-oxobutyl)-1H-1,2,4-triazol-1-
yl]methyl1phenyl]methyl]phenyl]-1H-tetrazole;
5-[3-[[4-[[5-butyl-3-(1,1-difluoroethyl)-1H-1,2,4-triazol-
1-yl]methyl]phenyl]methyl]phenyl]-1H-tetrazole;
5-[3-[[4-[[5-butyl-3-(1,1-difluoropropyl)-1H-1,2,4-
triazol-1-yl]methyl]phenyl]methyl]phenyl]-1H-tet-
razole;
5-[3-[[4-[[5-butyl-3-(1,1-difluorobutyl)-1H-1,2,4-triazol-
1-yl]methyl]phenyl]methyl]phenyl]-1H-tetrazole;
5-[3-[[4-[[3-butyl-5-(1,1-difluorobutyl)-1H-1,2,4-triazol-
1-yl]methyl]phenyl]methyl]phenyl]-1H-tetrazole;
5-[3-[[4-[[5-butyl-3-(1,1-difluoropentyl)-1H-1,2,4-
triazol-1-yl]methyl]phenyl]methyl]phenyl][-1H-tet-
razole;
5-[3-[[4-[(3,5-dipropyl-1H-1,2,4-triazol-1-yl)methyl]-
phenyl]methyl]phenyl]-1H-tetrazole;
5-[3-[[4-[(3,5-isopropyl-1H-1,2,4-triazol-1-yl)methyl]-
phenyl]methyl]phenyl]-1H-tetrazole;
5-[3-[[4-[(5-propyl-3-isopentyl-1H-1,2,4-triazol-1-yl)me-
thyl]phenyl]methyl]phenyl]-1H-tetrazole;

5-[3-[[4-[[5-propyl-3-(1,1-dimethoxybutyl)-1H-1,2,4-triazol-1-yl]methyl]phenyl]methyl]phenyl]-1H-tetrazole;

5-[3-[[4-[[5-propyl-3-(1-oxobutyl)-1H-1,2,4-triazol-1-yl]methyl]phenyl]methyl]phenyl]-1H-tetrazole;

5-[3-[[4-[[5-propyl-3-(1,1-difluoroethyl)-1H-1,2,4-triazol-1-yl]methyl]phenyl]methyl]phenyl]-1H-tetrazole;

5-[3-[[4-[[5-propyl-3-(1,1-difluoropropyl)-1H-1,2,4-triazol-1-yl]methyl]phenyl]methyl]phenyl][1,1'-biphenyl]-2-yl]-1H-tetrazole;

5-[3-[[4-[[5-propyl-3-(1,1-difluorobutyl)-1H-1,2,4-triazol-1-yl]methyl]phenyl]methyl]phenyl]-1H-tetrazole;

5-[3-[[4-[[5-propyl-3-(1,1-difluoropentyl)-1H-1,2,4-triazol-1-yl]methyl]phenyl]methyl]phenyl]-2-yl]-1H-tetrazole;

5-[3-[[4-[[5-ethyl-3-(1,1-difluorobutyl)-1H-1,2,4-triazol-1-yl]methyl]phenyl]methyl]phenyl]-1H-tetrazole;

5-[3-[[4-[(5-secbutyl-3-propyl-1H-1,2,4-triazol-1-yl)methyl]phenyl]methyl]phenyl]-1H-tetrazole;

5-[3-[[4-[(5-secbutyl-3-butyl-1H-1,2,4-triazol-1-yl)methyl]phenyl]methyl]phenyl]-1H-tetrazole;

5-[3-[[4-[(3,5-disecbutyl-1H-1,2,4-triazol-1-yl)methyl]phenyl]methyl]phenyl]-1H-tetrazole;

5-[3-[[4-[(5-secbutyl-3-isopentyl-1H-1,2,4-triazol-1-yl)methyl]phenyl]methyl]phenyl]-1H-tetrazole;

5-[3-[[4-[[5-secbutyl-3-(1,1-difluoroethyl)-1H-1,2,4-triazol-1-yl]methyl]phenyl]methyl]phenyl]-1H-tetrazole;

5-[3-[[4-[[5-secbutyl-3-(1,1-difluoropropyl)-1H-1,2,4-triazol-1-yl]methyl]phenyl]methyl]phenyl]-1H-tetrazole;

5-[3-[[4-[[5-secbutyl-3-(1,1-difluorobutyl)-1H-1,2,4-triazol-1-yl]methyl]phenyl]methyl]phenyl]1H-tetrazole;

5-[3-[[4-[[5-secbutyl-3-(1,1-difluoropentyl)-1H-1,2,4-triazol-1-yl]methyl]phenyl]methyl]phenyl]-1H-tetrazole;

5-[3-[[4-[(5-isobutyl-3-propyl-1H-1,2,4-triazol-1-yl)methyl]phenyl]methyl]phenyl]-1H-tetrazole;

5-[3-[[4-[(5-isobutyl-3-butyl-1H-1,2,4-triazol-1-yl)methyl]phenyl]methyl]phenyl]-1H-tetrazole;

5-[3-[[4-[(3,5-diisobutyl-1H-1,2,4-triazol-1-yl)methyl]phenyl]methyl]phenyl]-1H-tetrazole;

5-[3-[[4-[(5-isobutyl-3-isopentyl-1H-1,2,4-triazol-1-yl)methyl]phenyl]methyl]phenyl]-1H-tetrazole;

5-[3-[[4-[[5-isobutyl-3-(1,1-difluoroethyl)-1H-1,2,4-triazol-1-yl]methyl]phenyl]methyl]phenyl]-1H-tetrazole;

5-[3-[[4-[[5-isobutyl-3-(1,1-difluoropropyl)-1H-1,2,4-triazol-1-yl]methyl]phenyl]methyl]phenyl]-1H-tetrazole;

5-[3-[[4-[[5-isobutyl-3-(1,1-difluorobutyl)-1H-1,2,4-triazol-1-yl]methyl]phenyl]methyl]phenyl]-1H-tetrazole;

5-[3-[[4-[[5-isobutyl-3-(1,1-difluoropentyl)-1H-1,2,4-triazol-1-yl]methyl]phenyl]methyl]phenyl]-1H-tetrazole;

5-[3-[[4-[(5-tertbutyl-3-propyl-1H-1,2,4-triazol-1-yl)methyl]phenyl]methyl]phenyl]-1H-tetrazole;

5-[3-[[4-[(5-tertbutyl-3-butyl-1H-1,2,4-triazol-1-yl)methyl]phenyl]methyl]phenyl]-1H-tetrazole;

5-[3-[[4-[(3,5-ditertbutyl-1H-1,2,4-triazol-1-yl)methyl]phenyl]methyl]phenyl]-1H-tetrazole;

5-[3-[[4-[(5-tertbutyl-3-isopentyl-1H-1,2,4-triazol-1-yl)methyl]phenyl]methyl]phenyl]-1H-tetrazole;

5-[3-[[4-[[5-tertbutyl-3-(1,1-difluoroethyl)-1H-1,2,4-triazol-1-yl]methyl]phenyl]methyl]phenyl]-1H-tetrazole;

5-[3-[[4-[[5-tertbutyl-3-(1,1-difluoropropyl)-1H-1,2,4-triazol-1-yl]methyl]phenyl]methyl]phenyl]-1H-tetrazole;

5-[3-[[4-[[5-tertbutyl-3-(1,1-difluorobutyl)-1H-1,2,4-triazol-1-yl]methyl]phenyl]methyl]phenyl]-1H-tetrazole;

5-[3-[[4-[[5-tertbutyl-3-(1,1-difluoropentyl)-1H-1,2,4-triazol-1-yl]methyl]phenyl]methyl]phenyl]-1H-tetrazole;

5-[3-[[4-[(5-pentyl-3-propyl-1H-1,2,4-triazol-1-yl)methyl]phenyl]methyl]phenyl]-1H-tetrazole;

5-[3-[[4-[(5-pentyl-3-butyl-1H-1,2,4-triazol-1-yl)methyl]phenyl]methyl]phenyl]-1H-tetrazole;

5-[3-[[4-[(3,5-dipentyl-1H-1,2,4-triazol-1-yl)methyl]phenyl]methyl]phenyl]-1H-tetrazole;

5-[3-[[4-[(5-pentyl-3-isopentyl-1H-1,2,4-triazol-1-yl)methyl]phenyl]methyl]phenyl]-1H-tetrazole;

5-[3-[[4-[[5-pentyl-3-(1,1-difluoroethyl) 1H-1,2,4-triazol-1-yl]methyl]phenyl]methyl]phenyl]-1H-tetrazole;

5-[3-[[4-[[5-pentyl-3-(1,1-difluoropropyl)-1H-1,2,4-triazol-1-yl]methyl]phenyl]methyl]phenyl]-1H-tetrazole;

5-[3-[[4-[[5-pentyl-3-(1,1-difluorobutyl)-1H-1,2,4-triazol-1-yl]methyl]phenyl]methyl]phenyl]-1H-tetrazole;

5-[3-[[4-[[5-pentyl-3-(1,1-difluoropentyl)-1H-1,2,4-triazol-1-yl]methyl]phenyl]methyl]phenyl]-1H-tetrazole;

5-[3-[[4-[(5-isopentyl-3-ethyl-1H-1,2,4-triazol-1-yl)methyl]phenyl]methyl]phenyl]-1H-tetrazole;

5-[3-[[4-[(5-isopentyl-3-propyl-1H-1,2,4-triazol-1-yl)methyl]phenyl]methyl]phenyl]-1H-tetrazole;

5-[3-[[4-[(5-isopentyl-3-butyl-1H-1,2,4-triazol-1-yl)methyl]phenyl]methyl]phenyl]-1H-tetrazole;

5-[3-[[4-[(3,5-diisopentyl-1H-1,2,4-triazol-1-yl)methyl]phenyl]methyl]phenyl]-1H-tetrazole;

5-[3-[[4-[[5-isopentyl-3-(1,1-difluoroethyl)-1H-1,2,4-triazol-1-yl]methyl]phenyl]methyl]phenyl]-1H-tetrazole;

5-[3-[[4-[[5-isopentyl-3-(1,1-difluoropropyl)-1H-1,2,4-triazol-1-yl]methyl]phenyl]methyl]phenyl]-1H-tetrazole;

5-[3-[[4-[[5-isopentyl-3-(1,1-difluorobutyl)-1H-1,2,4-triazol-1-yl]methyl]phenyl]methyl]phenyl]-1H-tetrazole;

5-[3-[[4-[[5-isopentyl-3-(1,1-difluoropentyl)-1H-1,2,4-triazol-1-yl]methyl]phenyl]methyl]phenyl]-1H-tetrazole;

5-[3-[[4-[[5-(1-butenyl)-3-propyl-1H-1,2,4-triazol-1-yl]methyl]phenyl]methyl]phenyl]-1H-tetrazole;

5-[3-[[4-[[5-(1-butenyl)-3-butyl-1H-1,2,4-triazol-1-yl]methyl]phenyl]methyl]phenyl]-1H-tetrazole;

5-[3-[[4-[[5-(1-butenyl)-3-isopentyl-1H-1,2,4-triazol-1-yl]methyl]phenyl]methyl]phenyl]-1H-tetrazole;

5-[3-[[4-[[5-(1-butenyl)-3-(1,1-dimethoxybutyl)-1H-1,2,4-triazol-1-yl]methyl]phenyl]methyl]phenyl]-1H-tetrazole;

5-[3-[[4-[[5-(1-butenyl)-3-(1,1-difluorobutyl)-1H-1,2,4-triazol-1-yl]methyl]phenyl]methyl]phenyl]-1H-tetrazole;

5-[3-[[4-[[5-(2-butenyl)-3-(1,1-difluorobutyl)-1H-1,2,4-triazol-1-yl]methyl]phenyl]methyl]phenyl]-1H-tetrazole;

5-[3-[[4-[[5-(3-butenyl)-3-(1,1-difluorobutyl)-1H-1,2,4-triazol-1-yl]methyl]phenyl]methyl]phenyl]-1H-tetrazole;
5-[3-[[4-[[5-(1-butynyl)-3-(1,1-difluorobutyl)-1H-1,2,4-triazol-1-yl]methyl]phenyl]methyl]phenyl]-1H-tetrazole;
5-[3-[[4-[[5-(2-butynyl)-3-(1,1-difluorobutyl)-1H-1,2,4-triazol-1-yl]methyl]phenyl]methyl]phenyl]-1H-tetrazole;
5-[3-[[4-[[5-(3-butynyl)-3-(1,1-difluorobutyl)-1H-1,2,4-triazol-1-yl]methyl]phenyl]methyl]phenyl]-1H-tetrazole;
5-[3-[[4-[(3,5-dipropoxy-1H-1,2,4-triazol-1-yl)methyl]phenyl]methyl]phenyl]-1H-tetrazole;
5-[3-[[.4-[(3,5-diisopropoxy-1H-1,2,4-triazol-1-yl)methyl]phenyl]methyl]phenyl]-1H-tetrazole;
5-[3-[[4-[(3,5-dibutoxy-1H-1,2,4-triazol-1-yl)methyl]phenyl]methyl]phenyl]-1H-tetrazole;
5-[3-[[4-[(3,5-dithioethyl-1H-1,2,4-triazol-1-yl)methyl]phenyl]methyl]phenyl]-1H-tetrazole;
5-[3-[[4-[(3,5-dithiopropyl-1H-1,2,4-triazol-1-yl)methyl]phenyl]methyl]phenyl]-1H-tetrazole;
5-[3-[[4-[(3,5-dithioisopropyl-1H-1,2,4-triazol-1-yl)methyl]phenyl]methyl]phenyl]-1H-tetrazole;
5-[3-[[4-[[3,5-di(1-butenyl)-1H-1,2,4-triazol-1-yl]methyl]phenyl]methyl]phenyl]-1H-tetrazole;
5-[3-[[4-[[3,5-di(2-butenyl)-1H-1,2,4-triazol-1-yl]methyl]phenyl]methyl]phenyl]-1H-tetrazole;
5-[3-[[4-[[3,5-di(3-butenyl)-1H-1,2,4-triazol-1-yl]methyl]phenyl]methyl]phenyl]-1H-tetrazole;
5-[3-[[4-[[3,5-di(1-butynyl)-1H-1,2,4-triazol-1-yl]methyl]phenyl]methyl]phenyl][-1H-tetrazole;
5-[3-[[4-[[3,5-di(2-butynyl)-1H-1,2,4-triazol-1-yl]methyl]phenyl]methyl]phenyl]-1H-tetrazole; and
5-[3-[[4-[[3,5-di(3-butynyl)-1H-1,2,4-triazol-1-yl]methyl]phenyl]methyl]phenyl]-1H-tetrazole.

Another family of specific compounds of more particular interest within Formula I, and more specifically within Formula II, consists of compounds having an acidic group attached at the $R^5$ or $R^9$ "ortho" position of the biphenyl moiety as follows:

4'-[(3,5-dibutyl-1H-1,2,4-triazol-1-yl)methyl][1,1'-biphenyl]-2-carboxylic acid, hydrazide;
4'-[(3,5-dibutyl-1H-1,2,4-triazol-1-yl)methyl][1,1'-biphenyl]-2-carboxylic acid, 2-[(trifluoromethyl)sulfonyl]hydrazide;
4'-[(5-butyl-3-chloro-1H-1,2,4-triazol-1-yl)methyl][1,1'-biphenyl]-2-carboxylic acid;
4'-[(3-butyl-5-chloro-1H-1,2,4-triazol-1-yl)methyl][1,1'-biphenyl]-2-carboxylic acid;
4'-[(5-butyl-3-propyl-1H-1,2,4-triazol-1-yl)methyl][1,1'-biphenyl]-2-carboxylic acid;
methyl 4'-[(3,5-dibutyl-1H-1,2,4-triazol-1-yl)methyl][1,1'-biphenyl]-2-carboxylate;
4'-[(3,5-dibutyl-1H-1,2,4-triazol-1-yl)methyl][1,1'-biphenyl]-2-carboxylic acid;
4'-[(5-butyl-3-isopentyl-1H-1,2,4-triazol-1-yl)methyl][1,1'-biphenyl]-2-carboxylic acid;
4'-[[5butyl-3-(1,1-dimethoxybutyl)-1H-1,2,4-triazol-1-yl]methyl][1,1'-biphenyl]-2-carboxylic acid;
4'-[[5-butyl-3-(1-oxobutyl)-1H-1,2,4-triazol-1-yl]methyl][1,1'-biphenyl]-2-carboxylic acid;
4'-[[5-butyl-3-(1-oxopentyl)-1H-1,2,4-triazol-1-yl]methyl][1,1'-biphenyl]-2-carboxylic acid;
4'-[[5butyl-3-(1,1-difluoroethyl)-1H-1,2,4-triazol-1-yl]methyl][1,1'-biphenyl]-2-carboxylic acid;
4'-[[5-butyl-3-(1,1-difluoropropyl)-1H-1,2,4-triazol-1-yl]methyl][1,1'-biphenyl]-2-carboxylic acid;
4'-[[5-butyl-3-(1,1-difluorobutyl)-1H-1,2,4-triazol-1-yl]methyl][1,1'-biphenyl]-2-carboxylic acid;
4'-[[3butyl-5-(1,1-difluorobutyl)-1H-1,2,4-triazol-1-yl]methyl][1,1'-biphenyl]-2-carboxylic acid;
4'-[[5-butyl-3-(1,1-difluoropentyl)-1H-1,2,4-triazol-1-yl]methyl][1,1'-biphenyl]-2-carboxylic acid;
4'-[(3,5-dipropyl-1H-1,2,4-triazol-1-yl)methyl][1,1'-biphenyl]-2-carboxylic acid;
4'-[(3,5-isopropyl-1H-1,2,4-triazol-1-yl)methyl][1,1'-biphenyl]-2-carboxylic acid;
4'-[(5-propyl-3-butyl-1H-1,2,4-triazol-1-yl)methyl][1,1'-biphenyl]-2-carboxylic acid;
4'-[[5-propyl-3-(1,1-difluoroethyl)-1H-1,2,4-triazol-1-yl]methyl][1,1'-biphenyl]-2-carboxylic acid;
4'-[[5-propyl-3-(1,1-difluoropropyl)-1H-1,2,4-triazol-1-yl]methyl][1,1'-biphenyl]-2-carboxylic acid;
4'-[[5-propyl-3-(1,1-difluorobutyl)-1H-1,2,4-triazol-1-yl]methyl][1,1'-biphenyl]-2-carboxylic acid;
4'-[[5-propyl-3-(1,1-difluoropentyl)-1H-1,2,4-triazol-1-yl]methyl][1,1'-biphenyl]-2-carboxylic acid;
4'-[[5-ethyl-3-(1,1-difluorobutyl)-1H-1,2,4-triazol-1-yl]methyl][1,1'-biphenyl]-2-carboxylic acid;
4'-[(3,5-disecbutyl-1H-1,2,4-triazol-1-yl)methyl][1,1'-biphenyl]-2-carboxylic acid;
4'-[[5-secbutyl-3-(1,1-difluorobutyl)-1H-1,2,4-triazol-1-yl]methyl][1,1'-biphenyl]-2-carboxylic acid;
4'-[(3,5-diisobutyl-1H-1,2,4-triazol-1-yl)methyl][1,1'-biphenyl]-2-carboxylic acid;
4'-[[5-isobutyl-3-(1,1-difluorobutyl)-1H-1,2,4-triazol-1-yl]methyl][1,1'-biphenyl]-2-carboxylic acid;
4'-[(3,5-ditertbutyl-1H-1,2,4-triazol-1-yl)methyl][1,1'-biphenyl]-2-carboxylic acid;
4'-[[5-tertbutyl-3-(1,1-difluorobutyl)-1H-1,2,4-triazol-1-yl]methyl][1,1'-biphenyl]-2-carboxylic acid;
4'-[(3,5-dipentyl-1H-1,2,4-triazol-1-yl)methyl][1,1'-biphenyl]-2-carboxylic acid;
4'-[[5-pentyl-3-(1,1-difluorobutyl)-1H-1,2,4-triazol-1-yl]methyl][1,1'-biphenyl]-2-carboxylic acid;
4'-[(3,5-diisopentyl-1H-1,2,4-triazol-1-yl)methyl][1,1'-biphenyl]-2-carboxylic acid;
4'-[[5-isopentyl-3-(1,1-difluorobutyl)-1H-1,2,4-triazol-1-yl]methyl][1,1'-biphenyl]-2-carboxylic acid;
4'-[[5-(1 butenyl)-3-(1,1-difluorobutyl)-1H-1,2,4-triazol-1-yl]methyl][1,1'-biphenyl]-2-carboxylic acid;
4'-[[5-(2-butenyl)-3-(1,1-difluorobutyl)-1H-1,2,4-triazol-1-yl]methyl][1,1'-biphenyl]-2-carboxylic acid;
4'-[[5-(3-butenyl)-3-(1,1-difluorobutyl)-1H-1,2,4-triazol-1-yl]methyl][1,1'-biphenyl]-2-carboxylic acid;
4'-[[5-(1-butynyl)-3-(1,1-difluorobutyl)-1H-1,2,4-triazol-1-yl]methyl][1,1'-biphenyl]-2-carboxylic acid;
4'-[[5-(2-butynyl)-3-(1,1-difluorobutyl)-1H-1,2,4-triazol-1-yl]methyl][1,1'-biphenyl]-2-carboxylic acid;
4'-[[5-(3-butynyl)-3-(1,1-difluorobutyl)-1H-1,2,4-triazol-1-yl]methyl][1,1'-biphenyl]-2-carboxylic acid;
4'-[(3,5-diethoxy-1H-1,2,4-triazol-1-yl)methyl][1,1'-biphenyl]-2-carboxylic acid;
4'-[(3,5-dipropoxy-1H-1,2,4-triazol-1-yl)methyl][1,1'-biphenyl]-2-carboxylic acid;
4'-[(3,5-diisopropoxy-1H-1,2,4-triazol-1-yl)methyl][1,1'-biphenyl]-2-carboxylic acid;
4'-[(3,5-dibutoxy-1H-1,2,4-triazol-1-yl)methyl][1,1'-biphenyl]-2-carboxylic acid;
4'-[(3,5-dithioethyl-1H-1,2,4-triazol-1-yl)methyl][1,1'-biphenyl]-2-carboxylic acid;
4'-[(3,5-dithiopropyl-1H-1,2,4-triazol-1-yl)methyl][1,1'-biphenyl]-2-carboxylic acid;
4'-[(3,5-dithioisopropyl-1H-1,2,4-triazol-1-yl)methyl][1,1'-biphenyl]-2-carboxylic acid;

4'-[[3,5-di(1-butenyl)-1H-1,2,4-triazol-1-yl]methyl][1,1'-biphenyl]-2-carboxylic acid;
4'-[[3,5-di(2-butenyl)-1H-1,2,4-triazol-1-yl]methyl][1,1'-biphenyl]-2-carboxylic acid;
4'-[[3,5-di(3-butenyl)-1H-1,2,4-triazol-1-yl]methyl][1,1'-biphenyl]-2-carboxylic acid;
4'-[[3,5-di(1-butynyl)-1H-1,2,4-triazol-1-yl]methyl][1,1'-biphenyl]-2-carboxylic acid;
4'-[[3,5-di(2-butynyl)-1H-1,2,4-triazol-1-yl]methyl][1,1'-biphenyl]-2-carboxylic acid;
4'-[[3,5-di(3 butynyl)-1H-1,2,4-triazol-1-yl]methyl][1,1'-biphenyl]-2-carboxylic acid;
5-[4'-[(5-butyl-3-chloro-1H-1,2,4-triazol-1-yl)methyl][1,1'-biphenyl]-2-yl]-1H-tetrazole;
5-[4'-[(3-butyl-5-chloro-1H-1,2,4-triazol-1-yl)methyl][1,1'-biphenyl]-2-yl]-1H-tetrazole;
5-[4'-[(5-butyl-3-propyl-1H-1,2,4-triazol-1-yl)methyl][1,1'-biphenyl]-2-yl]-1H-tetrazole;
5-[4'-[(3,5-dibutyl-1H-1,2,4-triazol-1-yl)methyl][1,1'-biphenyl]-2-yl]-1H-tetrazole;
5-[4'-[(5 butyl-3-isopentyl-1H-1,2,4-triazol-1-yl)methyl][1,1'-biphenyl]-2-yl]-1H-tetrazole;
5-[4'-[[5-butyl-3-(1,1 dimethoxybutyl)-1H-1,2,4-triazol-1-yl]methyl][1,1'-phenyl]-2-yl]-1H-tetrazole;
5-[4'-[[5 butyl-3-(1-oxobutyl)-1H-1,2,4-triazol-1-yl]methyl][1,1'-biphenyl]-2-yl]-1H-tetrazole;
5-[4'-[[5-butyl-3-(1,1-difluoroethyl)-1H-1,2,4-triazol-1-yl]methyl][1,1'-biphenyl]-2-yl]-1H-tetrazole;
5-[4'-[[5 butyl-3-(1,1-difluoropropyl)-1H-1,2,4-triazol-1-yl]methyl][1,1'-biphenyl]-2-yl]-1H-tetrazole;
5-[4'-[[5 butyl-3-(1,1-difluorobutyl)-1H-1,2,4-triazol-1-yl]methyl][1,1 -biphenyl]-2-yl]-1H-tetrazole;
5-[4'-[[3-butyl-5-(1,1-difluorobutyl)-1H-1,2,4-triazol-1-yl]methyl][1,1 -biphenyl]-2-yl]-1H-tetrazole;
5-[4'-[[5-butyl-3-(1,1-difluoropentyl)-1H-1,2,4-triazol-1-yl]methyl][1,1'-biphenyl]-2-yl]-1H-tetrazole;
5-[4'-[(3,5-dipropyl-1H-1,2,4-triazol-1-yl)methyl][1,1'-biphenyl]-2-yl]-1H-tetrazole;
5-[4'-[(3,5-isopropyl-1H-1,2,4-triazol-1-yl)methyl][1,1'-biphenyl]-2-yl]-1H-tetrazole;
5-[4'-[(5 propyl-3-isopentyl-1H-1,2,4-triazol-1-yl)methyl][1,1'-biphenyl]-2-yl]-1H-tetrazole;
5-[4'-[[5-propyl-3-(1,1-dimethoxybutyl)-1H-1,2,4-triazol-1-yl]methyl][1,1'-biphenyl]-2-yl]-1H-tetrazole;
5-[4'-[[5 propyl-3-(1-oxobutyl)-1H-1,2,4-triazol-1-yl]methyl][1,1'-biphenyl]-2-yl]-1H-tetrazole;
5-[4'-[[5 propyl-3-(1,1-difluoroethyl)-1H-1,2,4-triazol-1-yl]methyl][1,1'-biphenyl]-2-yl]-1H-tetrazole;
5-[4'-[[5 propyl-3-(1,1-difluoropropyl)-1H-1,2,4-triazol-1-yl]methyl][1,1'-biphenyl]-2-yl]-1H-tetrazole;
5-[4'-[[5 propyl-3-(1,1-difluorobutyl)-1H-1,2,4-triazol-1-yl]methyl][1,1'-biphenyl]-2-yl]-1H-tetrazole;
5-[4'-[[5 propyl-3-(1,1-difluoropentyl)-1H-1,2,4-triazol-1-yl]methyl][1,1'-biphenyl]-2-yl]-1H-tetrazole;
5-[4'-[[5-ethyl-3-(1,1-difluorobutyl)-1H-1,2,4-triazol-1-yl]methyl][1,1'-biphenyl]-2-yl]-1H-tetrazole;
5-[4'-[(5-secbutyl-3 propyl-1H-1,2,4-triazol-1-yl)methyl][1,1'-biphenyl]-2-yl]-1H-tetrazole;
5-[4'-[(5-secbutyl-3 butyl-1H-1,2,4-triazol-1-yl)methyl][1,1'-biphenyl]-2-yl]-1H-tetrazole;
5-[4'-[(3,5-disecbutyl-1H-1,2,4-triazol-1-yl)methyl][1,1'-biphenyl]-2-yl]-1H-tetrazole;
5-[4'-[(5-secbutyl-3-isopentyl-1H-1,2,4-triazol-1-yl)methyl][1,1'-biphenyl]-2-yl]-1H-tetrazole;
5-[4'-[[5-secbutyl-3-(1,1-difluoroethyl)-1H-1,2,4-triazol-1-yl]methyl][1,1'-biphenyl]-2-yl]-1H-tetrazole;
5-[4'-[[5-secbutyl-3-(1,1-difluoropropyl)-1H-1,2,4-triazol-1-yl]methyl][1,1'-biphenyl]-2-yl]-1H-tetrazole;
5-[4'-[[5-secbutyl-3-(1,1-difluorobutyl)-1H-1,2,4-triazol-1-yl]methyl][1,1'-biphenyl]-2-yl]-1H-tetrazole;
5-[4'-[[5-secbutyl-3-(1,1-difluoropentyl)-1H-1,2,4-triazol-1-yl]methyl][1,1'-biphenyl]-2-yl]-1H-tetrazole;
5-[4'-[(5-isobutyl-3 propyl-1H-1,2,4-triazol-1-yl)methyl][1,1'-biphenyl]-2-yl]-1H-tetrazole;
5-[4'-[(5-isobutyl-3-butyl-1H-1,2,4-triazol-1-yl)methyl][1,1'-biphenyl]-2-yl]-1H-tetrazole;
5-[4'-[(3,5 diisobutyl-1H-1,2,4-triazol-1-yl)methyl][1,1'-biphenyl]-2-yl]-1H-tetrazole;
5-[4'-[(5-isobutyl-3-isopentyl-1H-1,2,4-triazol-1-yl)methyl][1,1'-biphenyl]-2-yl]-1H-tetrazole;
5-[4'-[[5-isobutyl-3-(1,1-difluoroethyl)-1H-1,2,4-triazol-1-yl]methyl][1,1'-biphenyl]-2-yl]-1H-tetrazole;
5-[4'-[[5-isobutyl-3-(1,1-difluoropropyl)-1H-1,2,4-triazol-1 yl]methyl][1,1'-biphenyl]-2-yl]-1H-tetrazole;
5-[4'-[[5-isobutyl-3-(1,1-difluorobutyl)-1H-1,2,4-triazol-1-yl]methyl][1,1'-biphenyl]-2-yl]-1H-tetrazole;
5-[4'-[[5-isobutyl-3-(1,1-difluoropentyl)-1H-1,2,4-triazol-1-yl]methyl][1,1'-biphenyl]-2-yl]-1H-tetrazole;
5-[4'-[(5-tertbutyl-3 propyl-1H-1,2,4-triazol-1-yl)methyl][1,1'-biphenyl]-2-yl]-1H-tetrazole;
5-[4'-[(5-tertbutyl-3-butyl-1H-1,2,4-triazol-1-yl)methyl][1,1'-biphenyl]-2-yl]-1H-tetrazole;
5-[4'-[(3,5-ditertbutyl-1H-1,2,4-triazol-1-yl)methyl][1,1'-biphenyl]-2-yl]-1H-tetrazole;
5-[4'-[(5-tertbutyl-3-isopentyl-1H-1,2,4-triazol-1-yl)methyl][1,1'-biphenyl]-2-yl]-1H-tetrazole;
5-[4'-[[5-tertbutyl-3-(1,1-difluoroethyl)-1H-1,2,4-triazol-1-yl]methyl][1,1'-biphenyl]-2-yl]-1H-tetrazole;
5-[4'-[[5-tertbutyl-3-(1,1-difluoropropyl)-1H-1,2,4-triazol-1-yl]methyl][1,1'-biphenyl]-2-yl]-1H-tetrazole;
5-[4'-[[5-tertbutyl-3-(1,1-difluorobutyl)-1H-1,2,4-triazol-1 yl]methyl][1,1'-biphenyl]-2-yl]-1H-tetrazole;
5-[4'-[[5-tertbutyl-3-(1,1-difluoropentyl)-1H-1,2,4-triazol-1-yl]methyl][1,1'-biphenyl]-2-yl]-1H-tetrazole;
5-[4'-[(5-pentyl-3 propyl-1H-1,2,4-triazol-1-yl)methyl][1,1'-biphenyl]-2-yl]-1H-tetrazole;
5-[4'-[(5-pentyl-3 butyl-1H-1,2,4-triazol-1-yl)methyl][1,1'-biphenyl]-2-yl]-1H-tetrazole;
5-[4'-[(3,5-dipentyl-1H-1,2,4-triazol-1-yl)methyl][1,1'-biphenyl]-2-yl]-1H-tetrazole;
5-[4'-[(5-pentyl-3-isopentyl-1H-1,2,4-triazol-1-yl)methyl][1,1'-biphenyl]-2-yl]-1H-tetrazole;
5-[4'-[[5 pentyl-3-(1,1-difluoroethyl)-1H-1,2,4-triazol-1-yl]methyl][1,1'-biphenyl]-2-yl]-1H-tetrazole;
5-[4'-[[5-pentyl-3-(1,1-difluoropropyl)-1H-1,2,4-triazol-1-yl]methyl][1,1'-biphenyl]-2-yl]-1H-tetrazole;
5-[4'-[[5-pentyl-3-(1,1-difluorobutyl)-1H-1,2,4-triazol-1-yl]methyl][1,1'-biphenyl]-2-yl]-1H-tetrazole;
5-[4'-[[5 pentyl-3-(1,1-difluoropentyl)-1H-1,2,4-triazol-1-yl]methyl][1,1'-biphenyl]-2-yl]-1H-tetrazole;
5-[4'-[(5-isopentyl-3-ethyl-1H-1,2,4-triazol-1-yl)methyl][1,1'-biphenyl]-2-yl]-1H-tetrazole;
5-[4'-[(5-isopentyl-3-propyl-1H-1,2,4-triazol-1-yl)methyl][1,1'-biphenyl]-2-yl]-1H-tetrazole;
5-[4'-[(5-isopentyl-3 butyl-1H-1,2,4-triazol-1-yl)methyl][1,1'-biphenyl]-2-yl]-1H-tetrazole;
5-[4'-[(3,5-diisopentyl-1H-1,2,4-triazol-1-yl)methyl][1,1'-biphenyl]-2-yl]-1H-tetrazole;
5-[4'-[[5-isopentyl-3-(1,1-difluoroethyl)-1H-1,2,4-triazol-1-yl]methyl][1,1'-biphenyl]-2-yl]-1H-tetrazole;
5-[4'-[[5-isopentyl-3-(1,1-difluoropropyl)-1H-1,2,4-triazol-1-yl]methyl][1,1'-biphenyl]-2-yl]-1H-tetrazole;
5-[4'-[[5-isopentyl-3-(1,1-difluorobutyl)-1H-1,2,4-triazol-1-yl]methyl][1,1'-biphenyl]-2-yl]-1H-tetrazole;
5-[4'-[[5-isopentyl-3-(1,1-difluoropentyl)-1H-1,2,4-triazol-1-yl]methyl][1,1'-biphenyl]-2-yl]-1H-tetrazole;

5-[4'-[[5-(1-butenyl)-3-propyl-1H-1,2,4-triazol-1-yl]methyl][1,1'-biphenyl]-2-yl]-1H-tetrazole;
5-[4'-[[5-(1 butenyl)-3 butyl-1H-1,2,4-triazol-1-yl]methyl][1,1'-biphenyl]-2-yl]-1H-tetrazole;
5-[4'-[[5-(1 butenyl)-3-isopentyl-1H-1,2,4-triazol-1-yl]methyl][1,1'-biphenyl]-2-yl]-1H-tetrazole;
5-[4'-[[5-(1-butenyl)-3-(1,1-dimethoxybutyl)-1H-1,2,4-triazol-1-yl]methyl][1,1'-biphenyl]-2-yl]-1H-tetrazole;
5-[4'-[[5-(1-butenyl)-3-(1,1-difluorobutyl)-1H-1,2,4-triazol-1-yl]methyl][1,1'-biphenyl]-2-yl]-1H-tetrazole;
5-[4'-[[5-(2 butenyl)-3-(1,1-difluorobutyl)-1H-1,2,4-triazol-1-yl]methyl][1,1'-biphenyl]-2-yl]-1H-tetrazole;
5-[4'-[[5-(3 butenyl)-3-(1,1-difluorobutyl)-1H-1,2,4-triazol-1-yl]methyl][1,1'-biphenyl]-2-yl]-1H-tetrazole;
5-[4'-[[5-(1-butynyl)-3-(1,1-difluorobutyl)-1H-1,2,4-triazol-1-yl]methyl][1,1'-biphenyl]-2-yl]-1H-tetrazole;
5-[4'-[[5-(2 butynyl)-3-(1,1-difluorobutyl)-1H-1,2,4-triazol-1-yl]methyl][1,1'-biphenyl]-2-yl]-1H-tetrazole;
5-[4'-[[5-(3 butynyl)-3-(1,1-difluorobutyl)-1H-1,2,4-triazol-1-yl]methyl][1,1'-biphenyl]-2-yl]-1H-tetrazole;
5-[4'-[(3,5-dipropoxy-1H-1,2,4-triazol-1-yl)methyl][1,1'-biphenyl]-2-yl]-1H-tetrazole;
5-[4'-[(3,5-diisopropoxy-1H-1,2,4-triazol-1-yl)methyl][1,1'-biphenyl]-2-yl]-1H-tetrazole;
5-[4'-[(3,5-dibutoxy-1H-1,2,4-triazol-1-yl)methyl][1,1'-biphenyl]-2-yl]-1H-tetrazole;
5-[4'-[(3,5-dithioethyl-1H-1,2,4-triazol-1-yl)methyl][1,1'-biphenyl]-2-yl]-1H-tetrazole;
5-[(3,5-dithiopropyl-1H-1,2,4-triazol-1-yl)methyl][1,1'-biphenyl]-2-yl]-1H-tetrazole;
5-[4'-[(3,5-dithioisopropyl-1H-1,2,4-triazol-1-yl)methyl][1,1'-biphenyl]-2-yl]-1H-tetrazole;
5-[4'-[[3,5-di(1-butenyl)-1H-1,2,4-triazol-1-yl]methyl][1,1'-biphenyl]-2-yl]-1H-tetrazole;
5-[4'-[[3,5-di(2-butenyl)-1H-1,2,4-triazol-1-yl]methyl][1,1'-biphenyl]-2-yl]-1H-tetrazole;
5-[4'-[[3,5-di(3-butenyl)-1H-1,2,4-triazol-1-yl]methyl][1,1'-biphenyl]-2-yl]-1H-tetrazole;
5-[4'-[[3,5-di(1-butynyl)-1H-1,2,4-triazol-1-yl]methyl][1,1'-biphenyl]-2-yl]-1H-tetrazole;
5-[4'-[[3,5-di(2-butynyl)-1H-1,2,4-triazol-1-yl]methyl][1,1'-biphenyl]-2-yl]-1H-tetrazole; and
5-[4'-[[3,5-di(3-butynyl)-1H-1,2,4-triazol-1-yl]methyl][1,1'-biphenyl]-2-yl]-1H-tetrazole.

Another family of specific compounds of more particular interest within Formula I, and more specifically within Formula II, consists of compounds having an acidic group attached at the $R^6$ or $R^8$ "meta" position of the biphenyl moiety as follows:

4'-[(3,5-dibutyl-1H-1,2,4-triazol-1-yl)methyl][1,1'-biphenyl]-3-carboxylic acid, hydrazide;
4'-[(3,5-dibutyl-1H-1,2,4-triazol-1-yl)methyl][1,1'-biphenyl]-3-carboxylic acid, 2-[(trifluoromethyl)sulfonyl]hydrazide;
4'-[(5-butyl-3-chloro-1H-1,2,4-triazol-1-yl)methyl][1,1'-biphenyl]-3-carboxylic acid;
4'-[(3-butyl-5-chloro-1H-1,2,4-triazol-1-yl)methyl][1,1'-biphenyl]-3-carboxylic acid;
4'-[(5-butyl-3-propyl-1H-1,2,4-triazol-1-yl)methyl][1,1-biphenyl]-3-carboxylic acid;
methyl 4'-[(3,5-dibutyl-1H-1,2,4-triazol-1-yl)methyl][1,1'-biphenyl]-3-carboxylate;
4'-[(3,5-dibutyl-1H-1,2,4-triazol-1-yl)methyl][1,1'-biphenyl]-3-carboxylic acid;
4'-[(5-butyl-3-isopentyl-1H-1,2,4-triazol-1-yl)methyl][1,1'-biphenyl]-3-carboxylic acid;
4'-[[5-butyl-3-(1,1-dimethoxybutyl)-1H-1,2,4-triazol-1-yl]methyl][1,1'-biphenyl]-3-carboxylic acid;
4'-[[5-butyl-3-(1-oxobutyl)-1H-1,2,4-triazol-1-yl]methyl][1,1'-biphenyl]-3-carboxylic acid;
4'-[[5-butyl-3-(1-oxopentyl)-1H-1,2,4-triazol-1-yl]methyl][1,1'-biphenyl]-3-carboxylic acid;
4'-[[5-butyl-3-(1,1-difluoroethyl)-1H-1,2,4-triazol-1-yl]methyl][1,1'-biphenyl]-3-carboxylic acid;
4'-[[5-butyl-3-(1,1-difluoropropyl)-1H-1,2,4-triazol-1-yl]methyl][1,1'-biphenyl]-3-carboxylic acid;
4'-[[5-butyl-3-(1,1-difluorobutyl)-1H-1,2,4-triazol-1-yl]methyl][1,1'-biphenyl]-3-carboxylic acid;
4'-[[3-butyl-5-(1,1-difluorobutyl)-1H-1,2,4-triazol-1-yl]methyl][1,1'-biphenyl]-3-carboxylic acid;
4'-[[5-butyl-3-(1,1-difluoropentyl)-1H-1,2,4-triazol-1-yl]methyl][1,1'-biphenyl]-3-carboxylic acid;
4'-[(3,5-dipropyl-1H-1,2,4-triazol-1-yl)methyl][1,1'-biphenyl]-3-carboxylic acid;
4'-[(3,5-isopropyl-1H-1,2,4-triazol-1-yl)methyl][1,1'-biphenyl]-3-carboxylic acid;
4'-[(5-propyl-3-butyl-1H-1,2,4-triazol-1-yl)methyl][1,1'-biphenyl]-3-carboxylic acid;
4'-[[5-propyl-3-(1,1-difluoroethyl)-1H-1,2,4-triazol-1-yl]methyl][1,1'-biphenyl]-3-carboxylic acid;
4'-[[5-propyl-3-(1,1-difluoropropyl)-1H-1,2,4-triazol-1-yl]methyl][1,1'-biphenyl]-3-carboxylic acid;
4'-[[5-propyl-3-(1,1-difluorobutyl)-1H-1,2,4-triazol-1-yl]methyl][1,1'-biphenyl]-3-carboxylic acid;
4'-[[5-propyl-3-(1,1-difluoropentyl)-1H-1,2,4-triazol-1-yl]methyl][1,1'-biphenyl]-3-carboxylic acid;
4'-[[5-ethyl-3-(1,1-difluorobutyl)-1H-1,2,4-triazol-1-yl]methyl][1,1'-biphenyl]-3-carboxylic acid;
4'-[(3,5-disecbutyl-1H-1,2,4-triazol-1-yl)methyl][1,1'-biphenyl]-3-carboxylic acid;
4'-[[5-secbutyl-3-(1,1-difluorobutyl)-1H-1,2,4-triazol-1-yl]methyl][1,1'-biphenyl]-3-carboxylic acid;
4'-[(3,5-diisobutyl-1H-1,2,4-triazol-1-yl)methyl][1,1'-biphenyl]-3-carboxylic acid;
4'-[[5-isobutyl-3-(1,1-difluorobutyl)-1H-1,2,4-triazol-1-yl]methyl][1,1'-biphenyl]-3-carboxylic acid;
4'-[(3,5-ditertbutyl-1H-1,2,4-triazol-1-yl)methyl][1,1'-biphenyl]-3-carboxylic acid;
4'-[[5-tertbutyl-3-(1,1-difluorobutyl)-1H-1,2,4-triazol-1-yl]methyl][1,1'-biphenyl]-3-carboxylic acid;
4'-[(3,5-dipentyl-1H-1,2,4-triazol-1-yl)methyl][1,1'-biphenyl]-3-carboxylic acid;
4'-[[5-pentyl-3-(1,1-difluorobutyl)-1H-1,2,4-triazol-1-yl]methyl][1,1'-biphenyl]-3-carboxylic acid;
4'-[(3,5-diisopentyl-1H-1,2,4-triazol-1-yl)methyl][1,1'-biphenyl]-3-carboxylic acid;
4'-[[5-isopentyl-3-(1,1-difluorobutyl)-1H-1,2,4-triazol-1-yl]methyl][1,1'-biphenyl]-3-carboxylic acid;
4'-[[5-(1-butenyl)-3-(1,1-difluorobutyl)-1H-1,2,4-triazol-1-yl]methyl][1,1'-biphenyl]-3-carboxylic acid;
4'-[[5-(2-butenyl)-3-(1,1-difluorobutyl)-1H-1,2,4-triazol-1-yl]methyl][1,1'-biphenyl]-3-carboxylic acid;
4'-[[5-(3-butenyl)-3-(1,1-difluorobutyl)-1H-1,2,4-triazol-1-yl]methyl][1,1'-biphenyl]-3-carboxylic acid;
4'-[[5-(1-butynyl)-3-(1,1-difluorobutyl)-1H-1,2,4-triazol-1-yl]methyl][1,1'-biphenyl]-3-carboxylic acid;
4'-[[5-(2-butynyl)-3-(1,1-difluorobutyl)-1H-1,2,4-triazol-1-yl]methyl][1,1'-biphenyl]-3-carboxylic acid;
4'-[[5-(3-butynyl)-3-(1,1-difluorobutyl)-1H-1,2,4-triazol-1-yl]methyl][1,1'-biphenyl]-3-carboxylic acid;
4'-[(3,5-diethoxy-1H-1,2,4-triazol-1-yl)methyl][1,1'-biphenyl]-3-carboxylic acid;
4'-[(3,5-dipropoxy-1H-1,2,4-triazol-1-yl)methyl][1,1'-biphenyl]-3-carboxylic acid;
4'-[(3,5-diisopropoxy-1H-1,2,4-triazol-1-yl)methyl][1,1'-biphenyl]-3-carboxylic acid;

4'-[(3,5-dibutoxy-1H-1,2,4-triazol-1-yl)methyl][1,1'-biphenyl]-3-carboxylic acid;
4'-[(3,5-dithioethyl-1H-1,2,4-triazol-1-yl)methyl][1,1'-biphenyl]-3-carboxylic acid;
4'-[(3,5-dithiopropyl-1H-1,2,4-triazol-1-yl)methyl][1,1'-biphenyl]-3-carboxylic acid;
4'-[(3,5-dithioisopropyl-1H-1,2,4-triazol-1-yl)methyl][1,1'-biphenyl]-3-carboxylic acid;
4'-[[3,5-di(1-butenyl)-1H-1,2,4-triazol-1-yl]methyl][1,1'-biphenyl]-3-carboxylic acid;
4'-[[3,5-di(2-butenyl)-1H-1,2,4-triazol-1-yl]methyl][1,1'-biphenyl]-3-carboxylic acid;
4'-[[3,5-di(3-butenyl)-1H-1,2,4-triazol-1-yl]methyl][1,1'-biphenyl]-3-carboxylic acid;
4'-[[3,5-di(1-butynyl)-1H-1,2,4-triazol-1-yl]methyl][1,1'-biphenyl]-3-carboxylic acid;
4'-[[3,5-di(2-butynyl)-1H-1,2,4-triazol-1-yl]methyl][1,1'-biphenyl]-3-carboxylic acid;
4'-[[3,5-di(3-butynyl)-1H-1,2,4-triazol-1-yl]methyl][1,1'-biphenyl]-3-carboxylic acid;
5-[4'-[(5-butyl-3-chloro-1H-1,2,4-triazol-1-yl)methyl][1,1'-biphenyl]-3-yl]-1H-tetrazole;
5-[4'-[(3-butyl-5-chloro-1H-1,2,4-triazol-1-yl)methyl][1,1'-biphenyl]-3-yl]-1H-tetrazole;
5-[4'-[(5-butyl-3-propyl-1H-1,2,4-triazol-1-yl)methyl][1,1'-biphenyl]-3-yl]-1H-tetrazole;
5-[4'-[(3,5-dibutyl-1H-1,2,4-triazol-1-yl)methyl][1,1'-biphenyl]-3-yl]-1H-tetrazole;
5-[4'-[(5-butyl-3-isopentyl-1H-1,2,4-triazol-1-yl)methyl][1,1'-biphenyl]-3-yl]-1H-tetrazole;
5-[4'-[[5-butyl-3-(1,1 dimethoxybutyl)-1H-1,2,4-triazol-1-yl]methyl][1,1'-biphenyl]-3-yl]-1H-tetrazole;
5-[4'-[[5-butyl-3-(1-oxobutyl)-1H-1,2,4-triazol-1-yl]methyl][1,1'-biphenyl]-3-yl]-1H-tetrazole;
5-[4'-[[5-butyl-3-(1,1-difluoroethyl)-1H-1,2,4-triazol-1-yl]methyl][1,1'-biphenyl]-3-yl]-1H-tetrazole;
5-[4'-[[5-butyl-3-(1,1-difluoropropyl)-1H-1,2,4-triazol-1-yl]methyl][1,1'-biphenyl]-3-yl]-1H-tetrazole;
5-[4'-[[5-butyl-3-(1,1-difluorobutyl)-1H-1,2,4-triazol-1-yl]methyl][1,1'-biphenyl]-3-yl]-1H-tetrazole;
5-[4'-[[3-butyl-5-(1,1-difluorobutyl)-1H-1,2,4-triazol-1-yl]methyl][1,1'-biphenyl]-3-yl]-1H-tetrazole;
5-[4,-[[5-butyl-3-(1,1-difluoropentyl)-1H-1,2,4-triazol-1-yl]methyl][1,1'-biphenyl]-3-yl]-1H-tetrazole;
5-[4'-[(3,5-dipropyl-1H-1,2,4-triazol-1-yl)methyl][1,1'-biphenyl]-3-yl]-1H-tetrazole;
5-[4'-[(3,5-isopropyl-1H-1,2,4-triazol-1-yl)methyl][1,1'-biphenyl]-3-yl]-1H-tetrazole;
5-[4'-[(5-propyl-3-isopentyl-1H-1,2,4-triazol-1-yl)methyl][1,1'-biphenyl]-3-yl]-1H-tetrazole;
5-[4'-[[5-propyl-3-(1,1-dimethoxybutyl)-1H-1,2,4-triazol-1-yl]methyl][1,1'-biphenyl]-3-yl]-1H-tetrazole;
5-[4'-[[5-propyl-3-(1-oxobutyl)-1H-1,2,4-triazol-1-yl]methyl][1,1'-biphenyl]-3-yl]-1H-tetrazole;
5-[4'-[[5-propyl-3-(1,1-difluoroethyl)-1H-1,2,4-triazol-1-yl]methyl][1,1'-biphenyl]-3-yl]-1H-tetrazole;
5-[4'-[[5-propyl-3-(1,1-difluoropropyl)-1H-1,2,4-triazol-1-methyl][1,1'-biphenyl]-3-yl]-1H-tetrazole;
5-[4'-[[5-propyl-3-(1,1-difluorobutyl)-1H-1,2,4-triazol-1-yl]methyl][1,1'-biphenyl]-3-yl]-1H-tetrazole;
5-[4'-[[5-propyl-3-(1,1-difluoropentyl)-1H-1,2,4-triazol-1-yl]methyl][1,1'-biphenyl]-3-yl]-1H-tetrazole;
5-[4'-[[5-ethyl-3-(1,1-difluorobutyl)-1H-1,2,4-triazol-1-yl]methyl][1,1'-biphenyl]-3-yl]-1H-tetrazole;
5-[4'-[(5-secbutyl-3-propyl-1H-1,2,4-triazol-1-yl)methyl][1,1'-biphenyl]-3-yl]-1H-tetrazole;
5-[4'-[(5-secbutyl-3-butyl-1H-1,2,4-triazol-1-yl)methyl][1,1'-biphenyl]-3-yl]-1H-tetrazole;
5-[4'-[(3,5-disecbutyl-1H-1,2,4-triazol-1-yl)methyl][1,1'-biphenyl]-3-yl]-1H-tetrazole;
5-[4'-[(5-secbutyl-3-isopentyl-1H-1,2,4-triazol-1-yl)methyl][1,1'-biphenyl]-3-yl]-1H-tetrazole;
5-[4'-[[5-secbutyl-3-(1,1-difluoroethyl)-1H-1,2,4-triazol-1-yl]methyl][1,1'-biphenyl]-3-yl]-1H-tetrazole;
5-[4'-[[5-secbutyl-3-(1,1-difluoropropyl)-1H-1,2,4-triazol-1-yl]methyl][1,1'-biphenyl]-3-yl]-1H-tetrazole;
5-[4'-[[5-secbutyl-3-(1,1-difluorobutyl)-1H-1,2,4-triazol-1-yl]methyl][1,1'-biphenyl]-3-yl]-1H-tetrazole;
5-[4'-[[5-secbutyl-3-(1,1-difluoropentyl)-1H-1,2,4-triazol-1-yl]methyl][1,1'-biphenyl]-3-yl]-1H-tetrazole;
5-[4'-[(5-isobutyl-3-propyl-1H-1,2,4-triazol-1-yl)methyl][1,1'-biphenyl]-3-yl]-1H-tetrazole;
5-[4'-[(5-isobutyl-3-butyl-1H-1,2,4-triazol-1-yl)methyl][1,1'-biphenyl]-3-yl]-1H-tetrazole;
5-[4'-[(3,5-diisobutyl-1H-1,2,4-triazol-1-yl)methyl][1,1'-biphenyl]-3-yl]-1H-tetrazole;
5-[4'-[(5-isobutyl-3-isopentyl-1H-1,2,4-triazol-1-yl)methyl][1,1'-biphenyl]-3-yl]-1H-tetrazole;
5-[4'-[[5-isobutyl-3-(1,1-difluoroethyl)-1H-1,2,4-triazol-1-yl]methyl][1,1'-biphenyl]-3-yl]-1H-tetrazole;
5-[4'-[[5-isobutyl-3-(1,1-difluoropropyl)-1H-1,2,4-triazol-1-yl]methyl][1,1'-biphenyl]-3-yl]-1H-tetrazole;
5-[4'-[[5-isobutyl-3-(1,1-difluorobutyl)-1H-1,2,4-triazol-1-yl]methyl][1,1'-biphenyl]-3-yl]-1H-tetrazole;
5-[4'-[[5-isobutyl-3-(1,1-difluoropentyl)-1H-1,2,4-triazol-1-yl]methyl][1,1'-biphenyl]-3-yl]-1H-tetrazole;
5-[4'-[(5-tertbutyl-3-propyl-1H-1,2,4-triazol-1-yl)methyl][1,1'-biphenyl]-3-yl]-1H-tetrazole;
5-[4'-[(5-tertbutyl-3-butyl-1H-1,2,4-triazol-1-yl)methyl][1,1'-biphenyl]-3-yl]-1H-tetrazole;
5-[4'-[(3,5-ditertbutyl-1H-1,2,4-triazol-1-yl)methyl][1,1'-biphenyl]-3-yl]-1H-tetrazole;
5-[4'-[(5-tertbutyl-3-isopentyl-1H-1,2,4-triazol-1-yl)methyl][1,1'-biphenyl]-3-yl]-1H-tetrazole;
5-[4'-[[5-tertbutyl-3-(1,1 difluoroethyl)-1H-1,2,4-triazol-1-yl]methyl][1,1'-biphenyl]-3-yl]-1H-tetrazole;
5-[4'-[[5-tertbutyl-3-(1,1-difluoropropyl)-1H-1,2,4-triazol-1-yl]methyl][1,1'-biphenyl]-3-yl]-1H-tetrazole;
5-[4'-[[5-tertbutyl-3-(1,1-difluorobutyl)-1H-1,2,4-triazol-1-yl]methyl][1,1'-biphenyl]-3-yl]-1H-tetrazole;
5-[4'-[[5-tertbutyl-3-(1,1-difluoropentyl)-1H-1,2,4-triazol-1-yl]methyl][1,1'-biphenyl]-3-yl]-1H-tetrazole;
5-[4'-[(5-pentyl-3-propyl-1H-1,2,4-triazol-1-yl)methyl][1,1'-biphenyl]-3-yl]-1H-tetrazole;
5-[4'-[(5-pentyl-3-butyl-1H-1,2,4-triazol-1-yl)methyl][1,1'-biphenyl]-3-yl]-1H-tetrazole;
5-[4'-[(3,5-dipentyl-1H-1,2,4-triazol-1-yl)methyl][1,1'-biphenyl]-3-yl]-1H-tetrazole;
5-[4'-[(5-pentyl-3-isopentyl-1H-1,2,4-triazol-1-yl)methyl][1,1'-biphenyl]-3-yl]-1H-tetrazole;
5-[4'-[[5-pentyl-3-(1,1-difluoroethyl)-1H-1,2,4-triazol-1-yl]methyl][1,1'-biphenyl]-3-yl]-1H-tetrazole;
5-[4'-[[5-pentyl-3-(1,1-difluoropropyl)-1H-1,2,4-triazol-1-yl]methyl][1,1'-biphenyl]-3-yl]-1H-tetrazole;
5-[4'-[[5-pentyl-3-(1,1-difluorobutyl)-1H-1,2,4-triazol-1-yl]methyl][1,1'-biphenyl]-3-yl]-1H-tetrazole;
5-[4'-[[5-pentyl-3-(1,1-difluoropentyl)-1H-1,2,4-triazol-1-yl]methyl][1,1'-biphenyl]-3-yl]-1H-tetrazole;
5-[4'-[(5-isopentyl-3-ethyl-1H-1,2,4-triazol-1-yl)methyl][1,1'-biphenyl]-3-yl]-1H-tetrazole;
5-[4'-[(5-isopentyl-3-propyl-1H-1,2,4-triazol-1-yl)methyl][1,1'-biphenyl]-3-yl]-1H-tetrazole; -.,
5-[4'-[(5-isopentyl-3-butyl-1H-1,2,4-triazol-1-yl)methyl][1,1'-biphenyl]-3-yl]-1H-tetrazole;
5-[4'-[(3,5-diisopentyl-1H-1,2,4-triazol-1-yl)methyl][1,1'-biphenyl]-3-yl]-1H-tetrazole;

5-
5-[4'-[[5-isopentyl-3-(1,1-difluoroethyl)-1H-1,2,4-triazol-1-yl]methyl][1,1'-biphenyl]-3-yl]-1H-tetrazole;
5-[4'-[[5-isopentyl-3-(1,1-difluoropropyl)-1H-1,2,4-triazol-1-yl]methyl][1,1'-biphenyl]-3-yl]-1H-tetrazole;
5-[4'-[[5-isopentyl-3-(1,1-difluorobutyl)-1H-1,2,4-triazol-1-yl]methyl][1,1'-biphenyl]-3-yl]-1H-tetrazole;
5-[4'-[[5-isopentyl-3-(1,1-difluoropentyl)-1H-1,2,4-triazol-1-yl]methyl][1,1'-biphenyl]-3-yl]-1H-tetrazole;
5-[4'-[[5-(1-butenyl)-3-propyl-1H-1,2,4-triazol-1-yl]methyl][1,1'-biphenyl]-3-yl]-1H-tetrazole;
5-[4'-[[5-(1-butenyl)-3-butyl-1H-1,2,4-triazol-1-yl]methyl][1,1'-biphenyl]-3-yl]-1H-tetrazole;
5-[4'-[[5-(1-butenyl)-3-isopentyl-1H-1,2,4-triazol-1-yl]methyl][1,1 biphenyl]-3-yl]-1H-tetrazole;
5-[4'-[[5-(1-butenyl)-3-(1,1-dimethoxybutyl)-1H-1,2,4-triazol-1-yl]methyl][1,1,-biphenyl]-3-yl]-1H-tetrazole;
5-[4'-[[5-(1-butenyl)-3-(1,1-difluorobutyl)-1H-1,2,4-triazol-1-yl]methyl][1,1'-biphenyl]-3-yl]-1H-tetrazole;
5-[4'-[[5-(2-butenyl)-3-(1,1-difluorobutyl)-1H-1,2,4-triazol-1-yl]methyl][1,1'-biphenyl]-3-yl]-1H-tetrazole;
5-[4'-[[5-(3-butenyl)-3-(1,1-difluorobutyl)-1H-1,2,4-triazol-1-yl]methyl][1,1'-biphenyl]-3-yl]-1H-tetrazole;
5-[4'-[[5-(1-butynyl)-3-(1,1-difluorobutyl)-1H-1,2,4-triazol-1-yl]methyl][1,1'-biphenyl]-3-yl]-1H-tetrazole;
5-[4'-[[5-(2-butynyl)-3-(1,1-difluorobutyl)-1H-1,2,4-triazol-1-yl]methyl][1,1'-biphenyl]-3-yl]-1H-tetrazole;
5-[4'-[[5-(3-butynyl)-3-(1,1-difluorobutyl)-1H-1,2,4-triazol-1-yl]methyl][1,1'-biphenyl]-3-yl]-1H-tetrazole;
5-[4'-[(3,5-dipropoxy-1H-1,2,4-triazol-1-yl)methyl][1,1'-biphenyl]-3-yl]-1H-tetrazole;
5-[4'-[(3,5-diisopropoxy-1H-1,2,4-triazol-1-yl)methyl][1,1'-biphenyl]-3-yl]-1H-tetrazole;
5-[4'-[(3,5-dibutoxy-1H-1,2,4-triazol-1-yl)methyl][1,1'-biphenyl]-3-yl]-1H-tetrazole;
5-[4'-[(3,5-dithioethyl-1H-1,2,4-triazol-1-yl)methyl][1,1'-biphenyl]-3-yl]-1H-tetrazole;
5-[4'-[(3,5-dithiopropyl-1H-1,2,4-triazol-1-yl)methyl][1,1'-biphenyl]-3-yl]-1H-tetrazole;
5-[4'-[(3,5-dithioisopropyl-1H-1,2,4-triazol-1-yl)methyl][1,1'-biphenyl]-3-yl]-1H-tetrazole;
5-[4'-[[3,5-di(1-butenyl)-1H-1,2,4-triazol-1-yl]methyl][1,1'-biphenyl]-3-yl]-1H-tetrazole;
5-[4'-[[3,5-di(2-butenyl)-1H-1,2,4-triazol-1-yl]methyl][1,1'-biphenyl]-3-yl]-1H-tetrazole;
5-[4'-[[3,5-di(3-butenyl)-1H-1,2,4-triazol-1-yl]methyl][1,1'-biphenyl]-3-yl]-1H-tetrazole;
5-[4'-[[3,5-di(1-butynyl)-1H-1,2,4-triazol-1-yl]methyl][1,1'-biphenyl]-3-yl]-1H-tetrazole;
5-[4'-[3.5-di,(2-butynyl)-1H-1,2,4-triazol-1-yl]methyl][1,1'-biphenyl]-3-yl]-1H-tetrazole; and
5-[4'-[[3,5-di(3-butynyl)-1H-1,2,4-triazol-1-yl]methyl][1,1'-biphenyl]-3-yl]-1H-tetrazole.

A family of specific compounds of highest interest within Formula I, and more specifically within Formula II, consists of the following compounds:
methyl 4'-[(3,5-dibutyl-1H-1,2,4-triazol-1-yl)methyl][1,1'-biphenyl]-2-carboxylate;
4'-[(3,5-dibutyl-1H-1,2,4-triazol-1-yl)methyl][1,1'-biphenyl]-2-carboxylic acid;
5-[4'-[(3,5-dibutyl-1H-1,2,4-triazol-1-yl)methyl][1,1'-biphenyl]-2-yl]-1H-tetrazole;
4'-[(3,5-dibutyl-1H-1,2,4-triazol-1-yl)methyl][1,1'-biphenyl]-2-carboxylic acid, hydrazide;
4'-[(3,5-dibutyl-1H-1,2,4-triazol-1-yl)methyl][1,1'-biphenyl]-2-carboxylic acid, 2-[(trifluoromethyl)sulfonyl]hydrazide;
4'-[(5 butyl-3-chloro-1H-1,2,4-triazol-1-yl)methyl][1,1'-biphenyl]-2-carboxylic acid;
5'-[(5-butyl-3-chloro-1H-1,2,4-triazol-1-yl)methyl][1,1'-biphenyl]-2-yl]-1H-tetrazole;
4'-[(3 butyl-5-chloro-1H-1,2,4-triazol-1-yl)methyl][1,1'-biphenyl]-2-carboxylic acid;
5'-[(3 butyl-5-chloro-1H-1,2,4-triazol-1-yl)methyl][1,1'-biphenyl]-2-yl]-1H-tetrazole;
5-[4'-[[5 butyl-3-(1,1-difluorobutyl)-1H-1,2,4-triazol-1-yl]methyl][1,1'-biphenyl]-2-yl]-1H-tetrazole;
5-[4'-[[3 butyl-5-(1,1-difluorobutyl)-1H-1,2,4-triazol-1-yl]methyl][1,1'-biphenyl]-2-yl]-1H-tetrazole;
5-[4'-[(3,5-dipropyl-1H-1,2,4-triazol-1-yl)methyl][1,1'-biphenyl]-2-yl]-1H-tetrazole;
5-[4'-[(3,5-dipentyl-1H-1,2,4-triazol-1-yl)methyl][1,1'-biphenyl-2-yl]-1H-tetrazole;
5-[4'-[(5-butyl-3 propyl-1H-1,2,4-triazol-1-yl)methyl][1,1'-biphenyl]-2-yl]-1H-tetrazole;
5-[4'-[(3 butyl-5-propyl-1H-1,2,4-triazol-1-yl)methyl][1,1'-biphenyl]-2-yl]-1H-tetrazole;
5-[4'-[(3-butyl-5-isopentyl-1H-1,2,4-triazol-1-yl)methyl][1,1'-biphenyl]-2-yl]-1H-tetrazole; and
5-[4'-[(5-butyl-3-isopentyl-1H-1,2,4-triazol-1-yl)methyl][1,1'-biphenyl]-2-yl]-1H-tetrazole.

General Synthetic Procedures

The compounds of the invention can be synthesized according to the following procedures of Schemes I-VI.

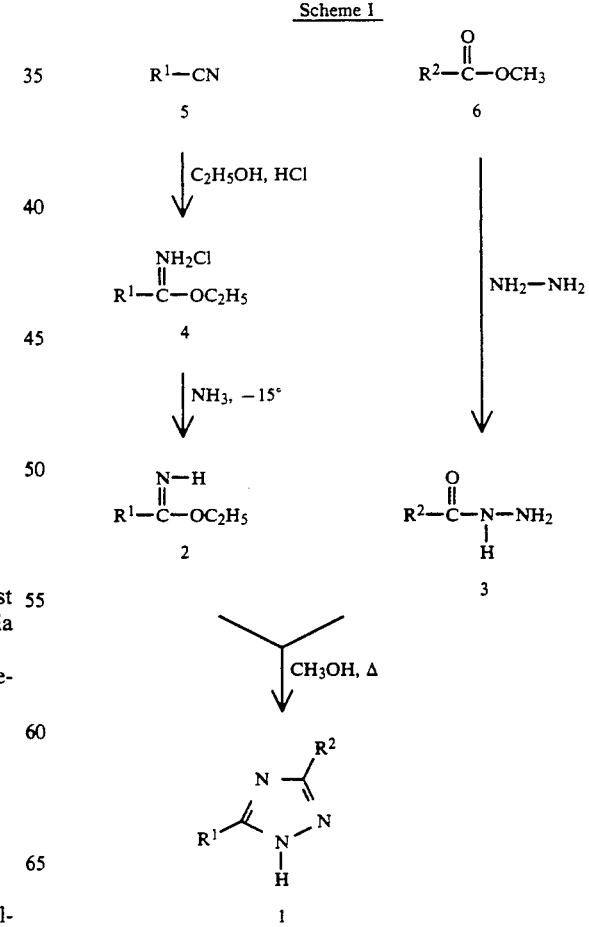

Scheme I

Synthetic Scheme I shows the preparation of 1H-1,2,4-triazoles 1 from ethyl iminoesters 2 and the corresponding hydrizide 3 via the general procedure outlined by H. Paul, G. Hilgetog, and G. Jahnchen, *Chem. Ber.*, 101, 2033 (1968). The free, iminoesters 2 can be prepared from the corresponding iminoester hydrochlorides 4, which in turn can be prepared from the corresponding nitrile 5; the procedures for the preparation of 2 and 4 from 5 are outlined by P. Reynaud and R. D. Moreau, *Bull. Soc. Chim. France*, 2997 (1964). The hydrazides 3 can be either purchased or prepared from the corresponding methyl esters 6 and hydrazine.

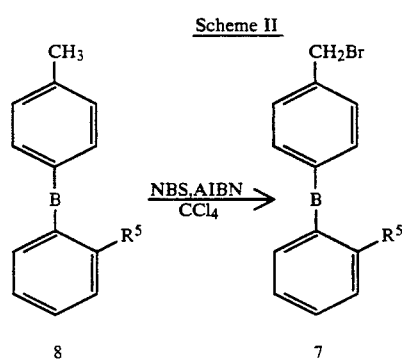

Synthetic Scheme II shows the preparation of the alkylating agent 7 from the corresponding precursor 8. When $R^5$ equals $CO_2CH_3$ and B is a carbon-carbon single bond, 8 was purchased from Chemo Dynamics Inc.

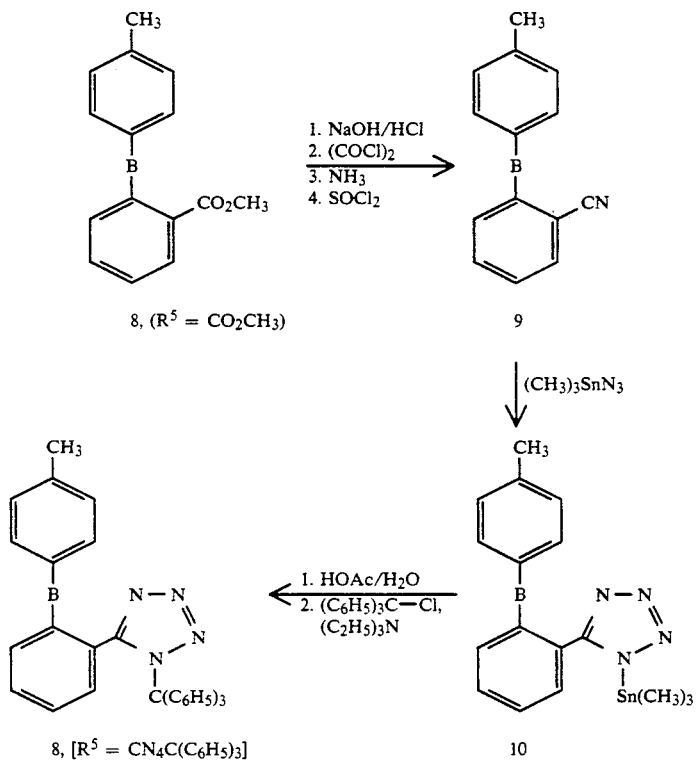

Synthetic Scheme III shows the preparation of the alkylating agent precursor 8 where $R^5$ equal $CN_4(C_6H_5)_3$ from the corresponding methyl ester 8 ($R^5=CO_2CH_3$). In step 1, the methyl ester is converted to the corresponding acid ($R^5=CO_2H$) by the action of sodium hydroxide/hydrochloric acid. In step 2, the acid is converted to the corresponding acid chloride ($R^5=COCl$) by the action of oxalyl chloride. In step 3, the acid chloride is converted to the corresponding primary amide ($R^5=CONH_2$) by the action of ammonium. In step 4, the amide is converted to the corresponding nitrile 9 by the action of thionyl chloride at reflux. The nitrile 9 is reacted with trimethyltinazide in toluene at reflux to give the corresponding trimethytin protected tetrazole 10; deprotection with acetic acid/water and reprotection with triphenylmethyl chloride/triethylamine gives the N-trityl tetrazole 8 ($R^5=CN_4C(C_6H_5)_3$).

Scheme IV

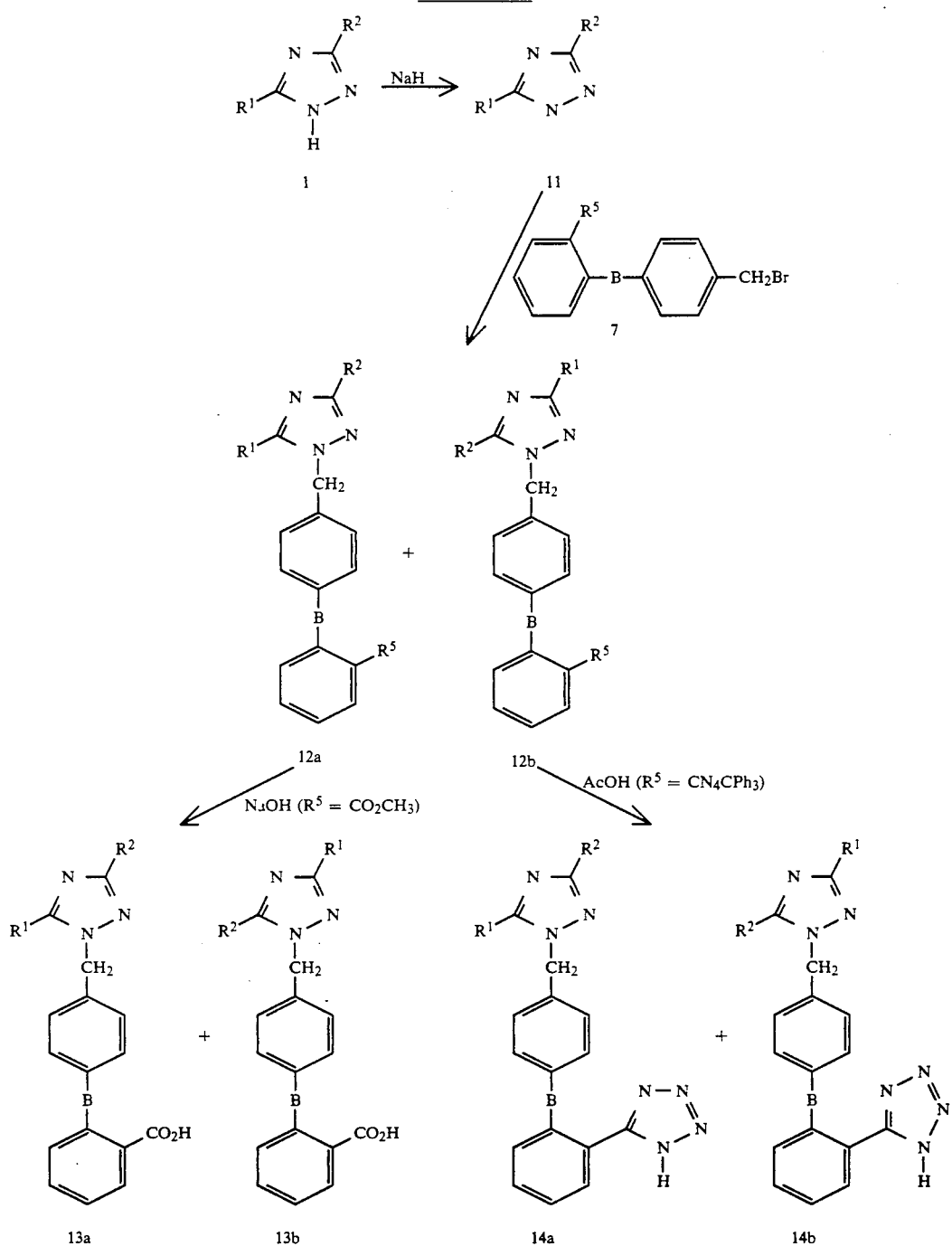

Synthetic Scheme IV shows the coupling reaction of the 1H-1,2,4-triazole 1 with the appropriate alkylating reagent 7. In the first step, 1 is treated with a base, such as sodium hydride, to generate the corresponding anion 11. Anion 11 is reacted with an alkylating agent 7 to give a mixture of regioisomers 12a and 12b. The isomer mixture may be converted to mixtures of the corresponding acids 13a and 13b or tetrazoles 14a and 14b by treatment with the appropriate reagent. Or, the isomers 12a and 12b may be separated by chromatographic methods, and each isomer may be reacted with the appropriate reagent to provide the acid- or tetrazole-substituted end product.

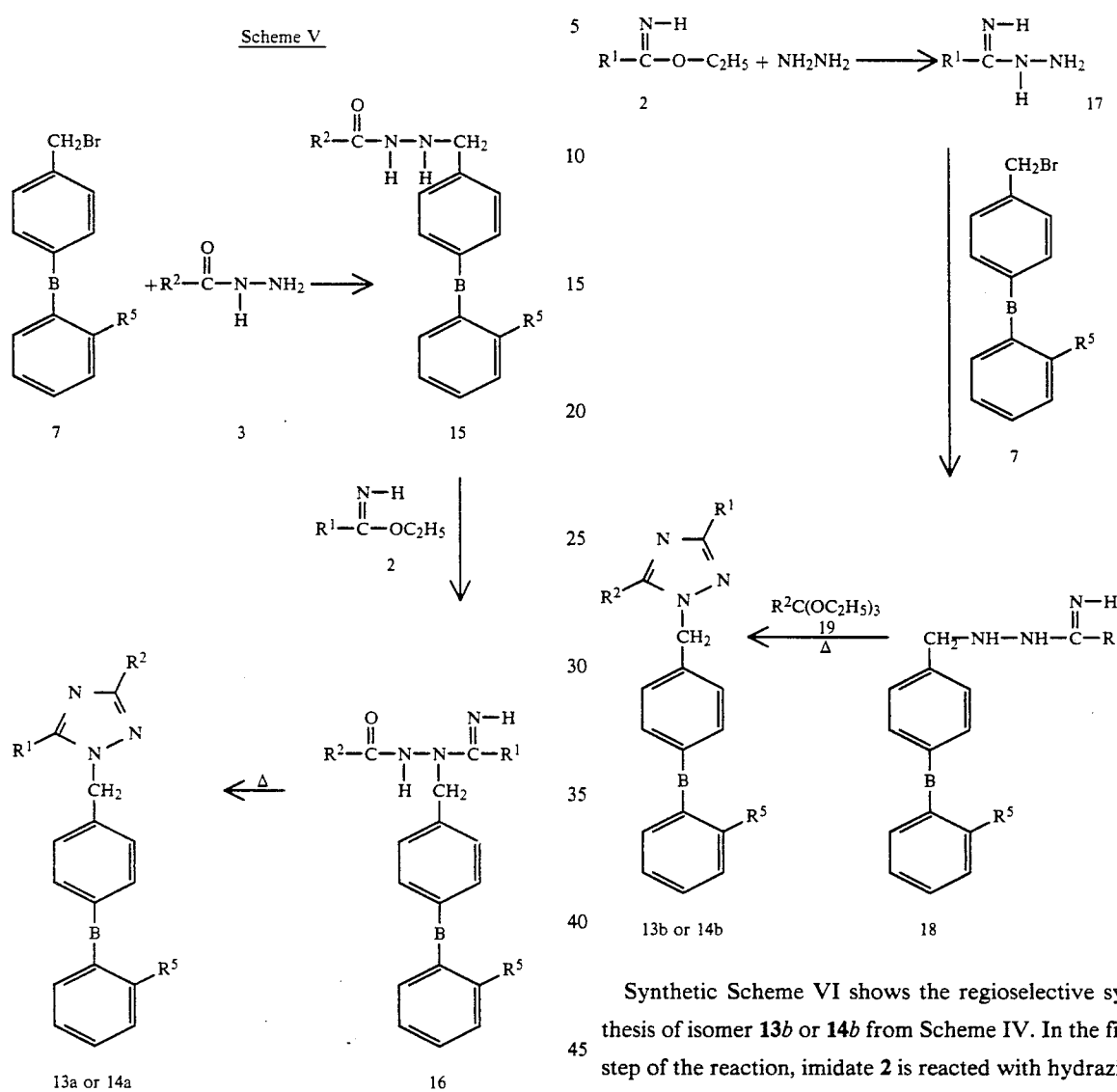

Synthetic Scheme V shows the regioselective synthesis of isomer 13a or 14a from Scheme IV. In the first step of the reaction, an alkylating agent 7 is reacted with an appropriate hydrazide 3 to provide substituted hydrazide 15. An imidate 2 is reacted with hydrazide 15 to provide intermediate 16 which cyclizes upon heating to provide the corresponding product compound 13a or 14a.

Synthetic Scheme VI shows the regioselective synthesis of isomer 13b or 14b from Scheme IV. In the first step of the reaction, imidate 2 is reacted with hydrazine to give amidazone 17. This intermediate is reacted with alkylating agent 7 to give intermediate 18 which is then cyclized in the presence of heat and an appropriate orthoester 19 to yield the corresponding product compound 13b or 14b.

The following Examples 1–17 are detailed descriptions of the methods of preparation of compounds of Formula I and, more specifically, within Formula II. These detailed preparations fall within the scope of, and serve to exemplify, the above described General Synthetic Procedures which form part of the invention. These Examples 1–17 are presented for illustrative purposes only and are not intended as a restriction on the scope of the invention. All parts are by weight unless otherwise indicated.

EXAMPLE 1

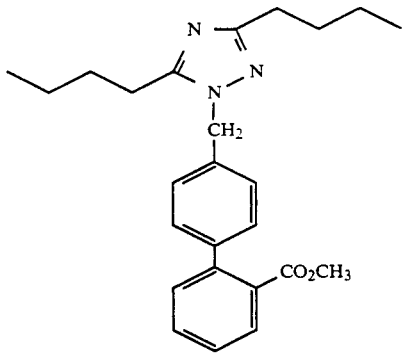

methyl 4'-[(3,5-dibutyl-1H-1,2,4-triazol-1-yl)methyl][1,1'-biphenyl]-2-carboxylate Step 1: Preparation of 4-bromomethyl-2'-methoxycarbonylbiphenyl A 47.46 g (210 mmol) sample of methyl 2-(p-tolyl)-benzoate (Chemo Dynamics Inc.) was dissolved in 3 L of carbon tetrachloride and treated with 37.33 g (209 mmol) of N-bromosuccinimide (NBS) and 1.17 g (7.13 mmol) of azobisisobutyronitrile (AIBN) at reflux under nitrogen for 24 hours. The reaction mixture was treated again with 1.0 g (6.1 mmol) of AIBN and stirred at reflux for an additional 24 hours. The reaction was filtered and the solvent removed in in vacuo. Purification by silica gel chromatography (Waters Prep-500A) using ethyl acetate/hexane (5:95) as eluent provided 50.0 g (78%) of a colorless solid: mp 48°–51° C.; NMR (CDCl$_3$) δ 3.64 (s, 3H), 4.54 (s, 2H), 7.23–7.63 (m, 7H), 7.81–7.89 (m, 1H). NMR indicated that this material was only 91% pure; it contained 9% of the corresponding dibromocompound (δ 6.70); however, no further attempts at purification were made and this mixture was used in all subsequent alkylation reactions.

Step 2: Preparation of 3,5-dibutyl-1H-1,2,4-triazole

A solution of 64.5 g (0.50 mol) of ethyl iminovalerate [P. Reynaud and R. C. Moreau, *Bull. Soc. Chim. France*, 2997 (1964)] in 100 mL of methanol was added slowly to 58.0 g (0.50 mol) of valeric acid hydrazide (Lancaster Synthesis) in 400 mL of methanol at 0° C. under a nitrogen atmosphere. After the addition was complete, the reaction was allowed to warm to ambient temperature and then stir at reflux for 2 days. The solvent was removed in vacuo; purification by silica gel chromatography (Waters Prep-500A) using ethyl acetate/hexane (80:20) gave 78.9 g (93%) of a colorless solid: mp 50.5°–51.5° C.; NMR (CDCl$_3$) δ 0.88 (t, J=7 Hz, 6H), 1.28–1.33 (m, 4H), 1.63–1.77 (m, 4H), 2.72 (t, J=7 Hz, 4H); MS (FAB) m/e (rel intensity) 183 (12%), 182 (100), 181 (3), 180 (6), 152 (8), 139 (4); HRMS. Calcd for M+H: 182.1657. Found: 182.1661.

Step 3: Preparation of methyl 4'-[(3,5-dibutyl-1H-1,2,4-triazol-1-yl)methyl][1,1'-biphenyl]-2-carboxylate Under a static nitrogen atmosphere, 2.01 g (11.0 mmol) of solid 3,5-dibutyl-1H-1,2,4-triazole was added in small portions to 12 mmol of sodium hydride in 50 ml of dimethylformamide (DMF); stirring was continued until hydrogen evolution had ceased. The anion solution was cooled to −10° C. (ice/methanol) and treated with a solution of 3.37 g (11.0 mmol) of 4-bromomethyl-2'-methoxycarbonylbiphenyl in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). Silica gel chromatography (Waters Prep-500A) using 40% ethyl acetate/hexane gave 2.0 g (41%) of compound as an oil: NMR (CDCl$_3$) δ 0.90 (t, J=7 HZ, 3H), 0.94 (t, J=7 Hz, 3H), 1.28–1.47 (m, 4H), 1.62–1.80 (m, 4H), 2.63–2.75 (m, 4H), 3.63 (s, 3H), 5.27 (s, 2H), 7.13–7.18 (m, 2H), 7.25–7.35 (m, 3H), 7.37–7.44 (m, 1H), 7.48–7.55 (m, 1H), 7.80–7.85 (m, 1H).

EXAMPLE 2

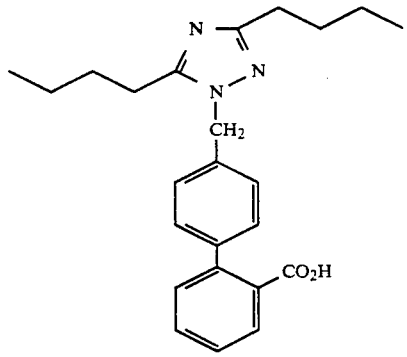

4'-[(3,5-dibutyl-1H-1,2,4-triazol-1-yl)methyl][1,1'-biphenyl]-2-carboxylic acid

A 2.0 g (4.9 mmol) sample of the methyl ester product compound from Example 1 was dissolved in 80 ml of ethanol and treated with 80 ml of 10% NaOH at ambient temperature for 3 days. The ethanol was removed in vacuo and the aqueous phase acidified to pH 1 with hydrochloric acid which caused the product to precipitate; filtration and drying in vacuo gave 1.65 g (86%) of colorless compound mp 134°–135° C.; NMR (DMSO-d$_6$) δ 0.85 (t, J=7 Hz, 3H), 0.90 (t, J=7 Hz, 3H), 1.23–1.39 (m, 4H), 1.53–1.68 (m, 4H), 2.59 (t, J=7 Hz, 2H), 2.78 (t, J=7 Hz, 2H), 5.37 (s, 2H), 5.37 (s, 2H), 7.18–7.26 (m, 2H), 7.28–7.37 (m, 3H), 7.42–7.48 (m, 1H), 7.53–7.60 (m, 1H), 7.70–7.75 (m, 1H).

EXAMPLE 3

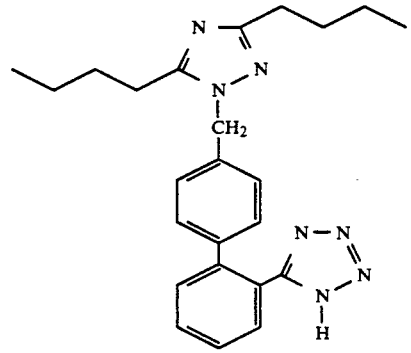

5-[4'-[(3,5-dibutyl-1H-1,2,4-triazol-1-yl)methyl][1,1'-biphenyl]2-yl]-1H-tetrazole

Step 1: Preparation of N-Triphenylmethyl-5-[2-(4'-bromemethylbiphen-2-yl]tetrazole A 542 5 g (2.4 mol) sample of methyl 2-(p-tolyl)benzoate (Chemo Dynamics Inc.) was dissolved in 5.5 L of ethanol and treated with 3 L (7.5 mol) of 2.5 N sodium hydroxide. The reaction was stirred overnight at ambient temperature and treated with an additional 480 ml (6.0 mol) of sodium hydroxide; stirring was continued for an additional 24 h and the ethanol removed in vacuo. The remaining solution was cooled in ice and acidified to pH 1 with hydrochloric acid which caused the product to precipitate; filtration and drying in vacuo gave 510 g (100%) of crude 2-(p-tolyl)benzoic acid: mp 145.0°–147.5° C.; NMR (CDCl$_3$) δ 2.40 (s, 3H), 7.17–7.28 (m, 4H), 7.35–7.45 (m, 2H), 7.51–7.59 (m, 1H), 7.90–7.97 (m, 1H). The crude acid was suspended in 1 L of toluene and slowly treated with 400 g (3.15 mol) of oxalyl chloride under nitrogen. The reaction was allowed to stir at ambient temperature for 4.5 h and concentrated in vacuo to remove excess oxalyl chloride. The residue was redissolved in 2 L of toluene and treated with 92.8 g (5.46 mol) of anhydrous ammonia. The reaction was filtered and the filtrate concentrated in vacuo producing 424 g (84%) of crude 2-(p-tolyl)benzamide: mp 128°–130° C.; NMR (CDCl$_3$) δ 2.40 (s, 3H), 5.28 (br s, 1H), 5.77 (br s, 1H), 7.21–7.53 (m, 7H), 7.76–7.83 (m, 1H). The crude amide was treated with 1420 ml (19.5 mol) of thionyl chloride at reflux for 3.5 h. The reaction was filtered and the thionyl chloride removed in vacuo. The residue was dissolved in 800 ml of toluene and reconcentrated in vacuo. On standing overnight, the residue crystallized. The crystals were collected and washed with hexane to give 296 g (64%) of 2-(p-tolyl)benzonitrile: mp 50.5°–52.0° C.; NMR (CDCl$_3$) δ 2.42 (s, 3H), 7.22–7.34 (m, 2H), 7.37–7.52 (m, 3H), 7.58–7.66 (m, 1H), 7.72–7.78 (m, 1H). A 286 g (1.48 mol) sample of the crude nitrile was dissolved in 1630 mL to toluene and treated with 377 g (1.8 mol) of trimethyltinazide at reflux for 24 h. The reaction was cooled; filtration gave 600 g of crude N-trimethylstannyl-5-[2-(4'-methylbiphen-2-yl]tetrazole: mp 271°–272° C. (dec.); NMR (DMSO-d$_6$) δ 0.36 (br t, J=34 Hz, 9H), 2.24 (s, 3H), 6.89–7.06 (m, 4H), 7.35–7.55 (m, 4H). The crude N-trimethylstannyl tetrazole was suspended in 4270 mL of toluene and 287 mL of anhydrous tetrahydrofuran (THF) and treated with 63.4 g (173 mol) of anhydrous hydrogen chloride at ambient temperature under nitrogen with stirring. The reaction was allowed to stand overnight and filtered; recrystallization from toluene gave 217 g (62%) of 5-[2-(4'methylbiphen-2-yl)]tetrazole as a solid: mp 149°–152° C.; NMR (DMSO-d$_6$) δ 2.28 (s, 3H), 6.94–7.02 (m, 2H), 7.08–7.15 (m, 2H), 7.50–7.59 (m, 2H), 7.62–7.72 (m, 2H). A 200 g (0.85 mol) sample of the tetrazole was suspended in 3.3 L of dichloromethane and treated with 262 g (0.91 mol) of triphenylmethyl chloride and 141 mL (1.0 mol) of anhydrous triethylamine. The reaction was stirred at reflux for 3 h under nitrogen, washed with water, dried (MgSO$_4$), and concentrated in vacuo. Recrystallization gave 338 g (83%) of N-triphenylmethyl-5-[2-(4'-methylbiphen-2-yl)]tetrazole as a colorless solid: mp 170°–173° C.; NMR (CDCl$_3$) δ 2.27 (s, 3H), 6.86–6.96 (m, 8H), 6.98–7.04 (m, 2H), 7.09–7.52 (m, 12H), 7.86–7.94 (m, 1H). The N-triphenylmethyl tetrazole was dissolved in 4260 mL of carbon tetrachloride and treated with 126.4 g (0.71 mol) of N-bromosuccinimide (NBS) and 11.9 g (49 mmol) of benzoyl peroxide at reflux for 3.5 h. The reaction was filtered and the solvent removed in vacuo. Recrystallization from toluene gave 277 g (59%) of N-triphenylmethyl-5-[2-(4'-bromomethylbiphen-2-yl)]tetrazole as a colorless solid: mp 140°–142° C.; NMR (CDCl$_3$) δ 4.39 (s, 2H), 6.85–6.95 (m, 7H), 7.06–7.15 (m, 4H), 7.22–7.43 (m, 9H), 7.45–7.55 (m, 2H), 7.94–8.01 (m, 1H). NMR indicated that this material was only 85% pure; it contained 7% of corresponding dibromo-compound (δ 6.50) and 8% of starting material (δ 2.27); however, no further attempts at purification were made and this mixture was used in all subsequent alkylation reactions.

Step 2: Preparation of 5-[4'-[(3,5-dibutyl-1H-1,2,4-triazol-1-yl)methyl][1,1'-biphenyl]-2-yl]-1H-tetrazole Under a static nitrogen atmosphere, 2.77 g (15.0 mmol) of solid 3,5-dibutyl-1H-1,2,4-triazole (from Step 2 of Example 1) was added in small portions to 15 mmol of sodium hydride in 50 ml of dimethylformamide (DMF); stirring was continued until hydrogen evolution had ceased. The anion solution was cooled to −10° C. (ice/methanol) and treated with a solution of 8.45 g (15.0 mmol) of N-triphenylmethyl-5-[2-(4'-bromomethylbiphen-2-yl)]tetrazole in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). The crude material (8.61 g) was redissolved in 86 ml of toluene and treated with anhydrous HCl to remove the protecting group. Purification by reverse phase chromatography (Waters Delta Prep-3000) using isocratic 40% acetonitrile/water (0.05% TFA) provided 1.72 g (27%) of colorless compound: mp 150.5°–152.0° C.; NMR (DMSO-d$_6$) δ 0.84 (t, J=7 Hz, 3H), 0.88 (t, J=7 Hz, 3H), 1.22–1.38 (m, 4H), 1.49–1.66 (m, 4H), 2.66 (t, J=7 Hz, 2H), 2.73 (t, J=7 Hz, 2H), 5.32 (s, 2H), 7.05–7.15 (m, 4H), 7.50–7.72 (m, 4H); MS (FAB) m/e (rel intensity) 416 (30), 373 (10), 235 (5), 207 (100), 192 (30); HRMS. Calcd for M+H: 416.2563. Found: 416.2600.

EXAMPLE 4

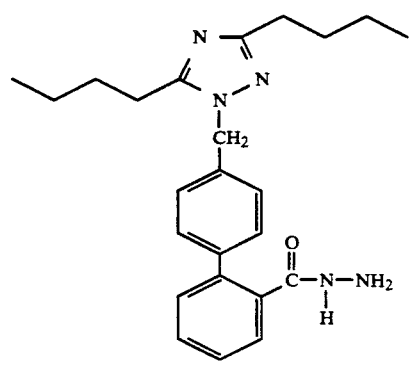

4'-[(3,5-dibutyl-1H-1,2,4-triazol-1-yl)methyl][1,1'-biphenyl]-2-carboxylic acid, hydrazide A 7.10 g (17.5 mmol) sample of the methyl ester product compound of Example 1 was dissolved in 150 ml of methanol and treated with 22 ml (22.2 g 695 mmol) of anhydrous hydrazine under a static nitrogen atmosphere. The reaction was stirred at reflux for 2 days and concentrated in vacuo to give 7.03 g (99%) of compound which was a colorless glass: NMR (CDCl$_3$) δ 0.88 (t, J=7 Hz, 3H), 0.94 (t, J=7 Hz, 3H), 1.28–1.47 (m, 4H), 1.62–1.78 (m, 4H), 2.62–2.73 (m, 4H), 3.5–4.1 (br s, 2H), 5.26 (s, 2H), 6.53 (s, 1H), 7.13–7.63 (m, 8H).

EXAMPLE 5

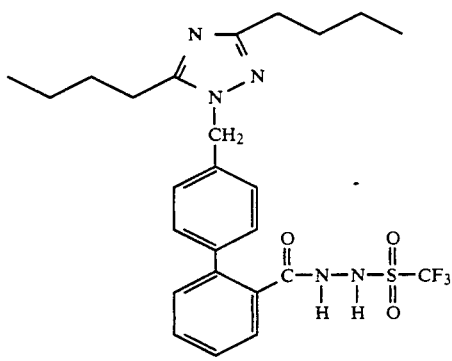

4'-[(3,5-dibutyl-1H-1,2,4-triazol-1-yl)methyl][1,1'-biphenyl]-2-carboxylic acid, 2-[(trifluoromethyl)sulfonyl]hydrazide A 1.0 g (2.48 mmol) sample of the hydrazide product compound of Example 4 was dissolved in 20 ml of toluene and cooled to 0° C. under a static nitrogen atmosphere. The solution was treated with 1.41 g (5.0 mmol) of trifluoromethylsulfonyl anhydride. Concentration in vacuo produced 3.91 g of crude material which was a dark oil. Purification by silica gel chromatography (Waters Prep-500A) using 50% ethyl acetate/hexane gave 1.0 g (75%) of pale yellow compound: mp 345° C. (dec); NMR (DMSO-d$_6$) δ 0.86 (t, J=7 HZ, 3H), 0.88 (t, J=7 Hz, 3H), 1.25–1.38 (m, 4H), 1.55–1.65 (m, 4H), 2.50–2.59 (m, 2H), 2.67–2.73 (m, 2H), 5.32 (s, 2H), 7.15–7.50 (m, 8H); MS (FAB) m/e (rel intensity) 538, (100), 405 (15), 389 (10), 374 (25), 356 (15).

EXAMPLE 6

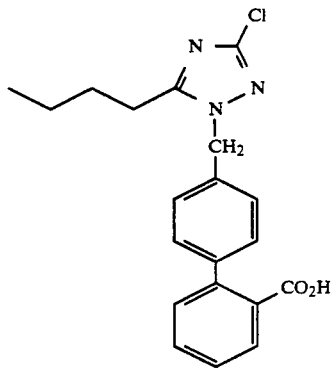

4'-[(5-butyl-3-chloro-1H-1,2,4-triazol-1-yl)methyl][1,1'-biphenyl]-2-carboxylic acid

Step 1: Preparation of 3-butyl-5-chloro-1H-1,2,4-triazole

A 10.0 g (80 mmol) sample of 3-butyl-1H-1,2,4-triazole [H. Paul, G. Hilgetag, and G. Jahnchen, Chem. Ber., 101, 2033(1968)] was dissolved in 320 mL of water containing 7.0 g (177 mmol) of sodium hydroxide. With stirring, the solution was cooled to 0° C. and chlorine was introduced over 3 h. The reaction was purged with nitrogen overnight and the solution extracted with chloroform. The extracts were combined, dried (MgSO$_4$), and concentrated in vacuo to give 16.8 g of a colorless oil which was placed in 200 mL of water and treated twice with 8.0 g (80 mmol) of sodium metabisulfite. The pH of the reaction medium was adjusted to 6 with 1M sodium carbonate prior to extraction with chloroform; the extracts were dried (MgSO$_4$) and concentrated in vacuo to give 14.9 g of crude product. Purification by silica gel chromatograph (Waters Prep-500A) using chloroform/methanol (95:5) gave 9.53 g (75%) of a colorless solid: mp 104°–105° C.; NMR (CDCl$_3$) δ 0.94 (t, J=7 Hz, 3H), 1.33–1.47 (m, 2H), 1.68–1.83 (m, 2H), 2.80 (t, J=7 158 Hz, 2H); MS (FAB) m/e (rel intensity) 162 (28), 160 (100), (10), 130 (5), 126 (10), 117 (5); HRMS. Calcd for M+H: 160.0642. Found: 160.0651.

Step 2: Preparation of 4'-[(5-butyl-3-chloro-1H-1,2,4-triazol-1-yl)methyl][1,1'-biphenyl]-2-carboxylic acid Under a static nitrogen atmosphere, 5.0 g (31.3 mmol) of solid 5-butyl-3-chloro-1H-1,2,4-triazole was added in small portions to 32 mmol of sodium hydride in 50 ml of dimethylformamide (DMF); stirring was continued until hydrogen evolution had ceased. The anion solution was cooled to −10° C. (ice/methanol) and treated with a solution of 9.55 g (31.3 mmol) of 4-bromomethyl-2'-methoxycarbonylbiphenyl in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$) to give 12.2 g of crude material was obtained which was a clear golden oil. A 4.81 g sample of this material was dissolved in 250 ml of methanol and treated with 250 ml of 10% NaOH at ambient temperature for 2 days. A portion of the isomer mixture of acids was separated by reverse phase chromatography (Waters Delta Prep-3000) using isocratic 45% acetronitrile/water (0.05% TFA). The faster moving isomer (250 mg) was identified as the 3-chloro isomer: NMR (DMSO-d$_6$) δ 0.86 (t, J=7 Hz, 3H), 1.23–1.36 (m, J=7 Hz, 2H), 1.54–1.65 (m, J=7 Hz, 1H), 2.80 (t, J=7 Hz, 2H), 5.40 (s, 2H), 7.23–7.58 (m, 7H), 7.72–7.77 9 m, 1H).

EXAMPLE 7

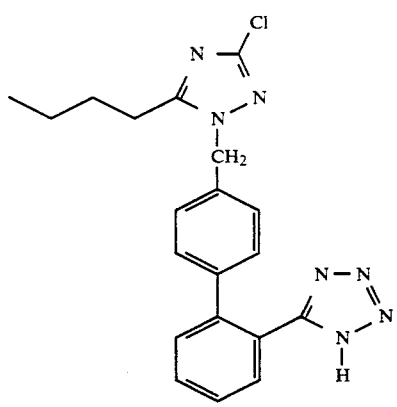

5'-[(5-butyl-3-chloro-1H-1,2,4-triazol-1-yl)methyl][1,1'-biphenyl]-2-yl]-1H-tetrazole Under a static nitrogen atmosphere, 2.00 g (12.4 mmol) of solid 3-butyl-5-chloro-1H-1,2,4-triazole (from Step 1 of Example 6) was added in small portions to 12.5 mmol of sodium hydride in 50 ml of dimethylformamide (DMF); stirring was continued until hydrogen evolution had ceased. The anion solution was cooled to $-10°$ C. (ice/methanol) and treated with a solution of 7.0 g (12.5 mmol) of N-triphenylmethyl-5-[2-(4'-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water; and dried ($MgSO_4$); 8.0 g of crude material was obtained. A 6.0 g sample of this material was dissolved in 70 ml of toluene and 6 ml of THF. Anhydrous hydrogen chloride was introduced into the solution for 45 min. and the reaction was allowed to stir for an additional 30 min. The solvent was decanted off and the remaining oil washed with toluene to give 3.31 g (89%) of a mixture of isomeric tetrazoles. A portion of this mixture was purified by reverse phase chromatography (Waters Delta Prep-3000) using isocratic 55% acetonitrile/water (0.05% TFA). The faster moving isomer (289 mg) was identified as the 3-chloro isomer: NMR ($CDCl_3$) δ 0.92 (t, J=7 Hz, 3H), 1.35-1.45 (m, 2H), 1.69-1.77 (m, 2H), 2.77 (t, J=7 Hz, 2H), 5.27 (s, 2H), 7.20-7.65 (m, 7H), 8.05-8.10 (m, 1H); MS (FAB) m/e (rel intensity) 394 (70), 235 (65), 207 (100), 192 (40), 178 (45).

EXAMPLE 8

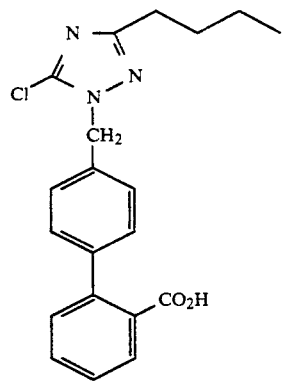

4'-[(3-butyl-5-chloro-1H-1,2,4-triazol-1-yl)methyl][1,1'-biphenyl]-2-carboxylic acid The slower moving isomer (120 mg) isolated in Example 6 was identified as the 5-chloro isomer: NMR (DMSO-$d_6$) δ 0.88 (t, J=7 Hz, 3H), 1.25-1.35 (m, J=7 Hz, 2H), 1.56-1.67 (m, J=7 Hz, 2H), 2,49 (t, J=7 Hz, 2H), 5.37 (s, 2H), 7.23-7.58 (m, 7H), 7.72-7.77 (m, 1H).

EXAMPLE 9

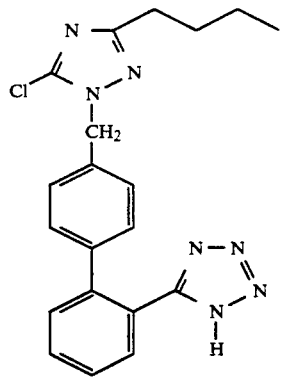

5'-[(3-butyl-5-chloro-1H-1,2,4-triazol-1-yl)methyl][1,1'-biphenyl]-2-yl]-1H-tetrazole The slower moving isomer (250 mg) isolated in Example 7 was identified as the 5-chloro isomer: NMR ($CDCl_3$) δ 0.88 (t, J=7 Hz, 3H), 1.35-1.45 (m, 2H), 1.65-1.79 (m, 2H), 2.54 (t, J=7 Hz, 2H), 5.23 (s, 2H), 7.15-7.65 (m, 7H), 8.00-8.05 (m, 1H).

EXAMPLE 10

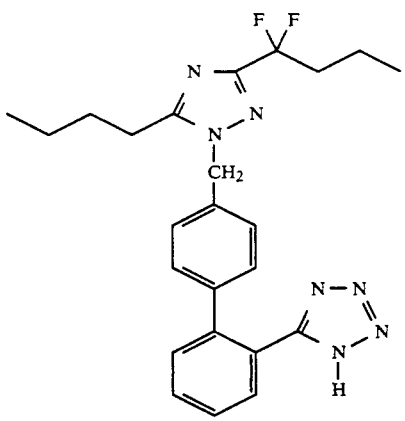

5-[4'-[[5-butyl-3-(1,1-difluorobutyl)-1H-1,2,4-triazol-1-yl]methyl][1,1'-biphenyl]-2-yl]-1H-tetrazole

Step 1: Preparation of 3-butyl5-(1,1-difluoro)butyl-1H-1,2,4-triazole

Under nitrogen, a stirred solution of 56.9 g (0.65 mol) of N-tert-butyl-N-methylamine (Fluka) and 66.1 g (0.65 mol) of triethylamine in 1 L of methylene chloride was cooled to 0° C. and treated with neat difluoroacetic anhydride [E. Sawicki, *J. Org. Chem.*, 21, 376 (1956)] at such a rate as to maintain the reaction temperature below 10° C. The reaction was allowed to warm to ambient temperature and stir overnight. All volitiles were removed in vacuo (bath temperature < 35° C.) and the residue redissolved in methylene chloride; the solution was washed with saturated sodium bicarbonate, dried (MgSO4), and concentrated to give 94 g (89%) of a yellow liquid. Vacuum distillation gave 86 g (81%) of colorless N-tert-butyl-N-methyldifluoroacetamide: bp 87°–88° C. (22 mm); 'H NMR (CDCl3) δ 1.37 (s, 9H), 2.93 (t, J=3 Hz, 3H), 5.97 (t, J=57 Hz, 1H); $^{19}$F NMR (CDCl3) δ -122.20 (d, J=57 Hz, 2F). A 17.0 g (103 mmol) sample of the amide was dissolved in 50 mL of dry THF and added slowly to a solution of 145 mmol of lithium diisopropylamine (LDA) in 450 mL of dry THF at −78° C. The reaction was allowed to stir for 1 h at −78° C. prior to the addition of 17 mL (175 mmol) of 1-iodopropane by syringe. Stirring at −78° C. was continued for 1 hr and then the reaction was allowed to warm to ambient temperature overnight. Methanol (10 mL) was added and the reaction was concentrated in vacuo; the residue was dissolved in methylene chlorick and washed with 1N hydrochloric acid, dried (MgSO4) and reconcentrated to give 17.6 g (83%) of crude product. Purification by vacuum distillation gave 13.3 g (62%) of colorless N-tert-butyl-N-methyl-2,2-difluorovaleramide: bp 125°–130° C. (84 mm); 'H NMR (CDCl3) δ 0.94 (t, J=7 Hz, 3H), 1.37 (s, 9H), 1.40–1.52 (m, 2H), 1.95–2.15 (m, 2H); $^{19}$F NMR (CDCl3) δ -100.29 (t, J=20 Hz, 2F). The difluorovaleramide was dissolved in 30 mL of trifluoroacetic acid (TFA) and stirred at reflux overnight under nitrogen. The solvent was removed in vacuo and the residue dissolved in methylene chloride; the solution was washed with water, dried (MgSO4) and concentrated to give 9.7 g (100%) of crude N-methyl-2,2-difluorovaleramide: 'H NMR (CDCl3) δ 0.92 (t, J=7 Hz, 3H), 1.36–1.51 (m, 2H), 1.90–2.11 (m, 2H), 2.84 (d, J=6 Hz, 3H), 6.60–6.85 (br s, 1H); $^{19}$F NMR (CDCl3) δ -106.98 (t, J=19 Hz, 2F). The crude N-methyl amide was dissolved in 40 mL of 6N hydrochloric acid and stirred at reflux for 24 hr. The reaction was cooled to ambient temperature and extracted with methylene chloride; the extracts were combined, dried (MgSO4), and concentrated to give 8.0 g (56%) of crude 2,2-difluorovaleric acid: 'H NMR (CDCl3) δ 1.00 (t, J=7 Hz, 3H), 1.46–1.63 (m, 2H), 1.97–2.17 (m, 2H); $^{19}$F NMR (CDCl3) δ -107.16 (t, J=18 Hz, 2F). A 4.83 g (35 mmol) sample of the crude acid was dissolved in 25 mL (35.2 g, 174 mmol) of phthaloyl chloride in a flask equipped with a reflux condenser and stirred under nitrogen in a 110° C. oil bath for 6 hrs. The condenser was replaced with a distillation head and 3.22 g (60%) of colorless 2,2-difluorovaleryl chloride was collected: bp 96°; 'H NMR (CDCl3) δ 1.03 (t, J=7 Hz, 3H), 1.48–1.65 (m, 2H), 2.03–2.23 (m, 2H); $^{19}$F NMR (CDCl3) δ -102.41 (t, J=18 Hz, 2F). The 2,2-difluorovaleryl chloride (20.6 mmol) was dissolved in 10 mL of methylene chloride and dropwise to a solution of 135 g (42 mmol) of anhydrous hydrazine in 20 mL of methylene chloride at 0° C. After the addition was complete, the reaction was stirred at ambient temperature for 1 h, washed with water, dried (MgSO4), and concentrated to give 3.12 g (91%) of 2,2-difluorovaleric acid hydrazide: NMR (CDCl3) δ 0.96 (t, J=7 Hz, 3H), 1.40–1.56 (m, 2H), 1.96–2.17 (m, 2H), 3.93 (br s, 2H), 7.67 (br s, 1H). A 2.84 g (18.7 mmol) sample of the crude hydrazide was dissolved in 50 mL of methanol and treated with 2.41 g (18.7 mmol) of ethyl iminovalerate. Under nitrogen, the reaction was stirred at reflux for 3 days and concentrated in vacuo. Purification by silica gel chromatography (Waters Prep-500A) using ethyl acetate/hexane (60:40) gave 3.0 g (74%) of 3-butyl-5-(1,1-difluoro)butyl-1H-1,2,4-triazole as a colorless solid: mp 92°–93° C.; 'H NMR (CDCl3) δ 0.97 (t, J=Hz, 3H), 0.92 (t, J=7 Hz, 3H), 1.30–1.45 (m, 2H), 1.47–1.62 (m, 2H), 1.66–1.81 (m, 2H), 2.18–2.38 (m, 2H), 2.83 (t, J=7 Hz, 2H); $^{19}$F NMR (CDCl3) δ -97.27 (t, J=18 Hz, 2F); MS (FAB) m/e (rel intensity) 218 (100), 198 (8), 188 (5), 178 (8), 170 (5); HRMS. Calcd for M+H: 218.1469. Found: 218.1461.

Step 2: Preparation of 5-[4'-[[5butyl-3-(1,1-difluorobutyl)-1H-1,2,4-triazol-1-yl]methyl][1,1'-biphenyl]-2-yl]-1H-tetrazole Under a static nitrogen atmosphere, 2.0 g (9.2 mmol) of solid 3-butyl-5-(1,1-difluoro)butyl-1H-1,2,4-triazole was added in small portions to 10 mmol of sodium hydride in 50 ml of dimethylformamide (DMF); stirring was continued until hydrogen evolution had ceased. The anion solution was cooled to −10° C. (ice/methanol) and treated with a solution of 5.1 g (9.2 mmol) of N-triphenylmethyl-5-[2-(4'-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO4). Silica gel chromatography using 2.5% ethyl acetate/toluene produced 680 mg (10.7%) of a faster moving isomer and 4.91 g (77.2%) of a slower moving isomer. The slower moving isomer was dissolved in 40 ml 10% water/acetic acid and stirred at ambient temperature overnight. The solvent was removed in vacuo;

the residue was dissolved in water and the pH adjusted to 9. The water layer was washed with benzene, acidified to pH 4 with 3N HCl, and extracted with ethyl acetate. The ethyl acetate was dried (Mg SO4) and remove in vacuo. The product was recrystallized from acetonitrile yielding 1.38 g (44%) of the 3-(1,1-difluoro)butyl isomer as colorless solid: mp 165.0°-167.5° C.; NMR (CDCl3) δ d 0.86 (t, J=7 Hz, 3H), 0.94 (t, J=7 Hz, 3H), 1.24-1.38 (m, 2H), 1.40-1.55 (m, 2H), 1.55-1.68 (m, 2H), 2.10-2.29 (m, 2H), 2.63 (t, J=7 Hz, 2H), 5.27 (s, 2H), 7.00-7.05 (m, 2H), 7.10-7.17 (m, 2H), 7.38-7.43 (m, 1H), 7.48-7.64 (m, 2H), 7.92-7.97 (m, 1H); 19F NMR (CDCl3) δ -97.38 (t, J=18 Hz, 2F); MS (FAB) m/e (rel intensity) 452 (83), 432 (21), 235 (45), 207 (100), 192 (42), 178 (29); HRMS. Calcd for M+H: 452.2374. Found: 452.2398.

EXAMPLE 11

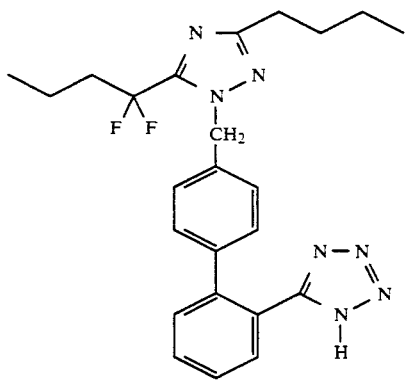

5-[4'-[[3-butyl-5-(1,1-difluorobutyl)-1H-1,2,4-triazol-1-yl]methyl][1,1'-biphenyl]-2-yl]-1H-tetrazole The faster moving isomer isolated in Example 10 was hydrolyzed in an identical manner. Purification by reverse phase chromatography (Waters Delta Prep-3000) using 42% acetonitrile/water (0.05% TFA) for 20 minutes, 45% acetonitrile/water (0.05% TFA) for 20 minutes, 50% acetonitrile/water (0.05% TFA) for 20 minutes and then 60% acetonitrile/water (0.05% TFA). The acetonitrile was removed in vacuo, the pH was adjusted to pH4 with 1N NaOH, and the product extracted with ethyl acetate. The ethyl acetate was dried (MgSO4) and removed in vacuo to give 150 mg (35%) of the 5-(1,1-difluoro)butyl isomer: NMR (CDCl3) δ d 0.91 (t, J=7 Hz, 3H), 1.01 (t, J=7 Hz, 3H), 1.27-1.42 (m, 2H), 1.54-1.72 (m, 4H), 2.27-2.43 (m, 2H), 2.61 (t, J=7 Hz, 2H), 5.46 (s, 2H), 7.17-7.22 (m, 2H), 7.25-7.30 (m, 2H)7.38-7.45 (m, 1H), 7.52-7.65 (m, 2H), 8.15-8.20 (m, 1H); MS (FAB) m/e (rel intensity) 452 (47), 235 (90), 207 (100), 178 (33); HRMS. Calcd for M+H: 452.2374. Found: 452.2418.

EXAMPLE 12

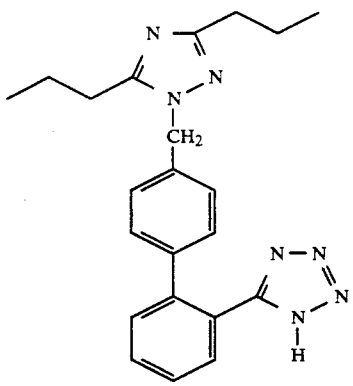

5-[4'-[(3,5-dipropyl-1H-1,2,4-triazol-1-yl)methyl][1,1'-biphenyl]-2-yl]-1H-tetrazole Step 1: Preparationof 3,5-dipropyl-1H-1,2,4-triazole Under nitrogen, a solution of 375 g (11.8 mol) of anhydrous hydrazine in 1600 mL of methanol was cooled to 0° C. and treated with 1.0 kg (9.8 mol) of methyl butyrate. The reaction was allowed to warm to ambient temperature and stir overnight prior to stirring at reflux for 5 h. The reaction was concentrated in vacuo; recrystallization from toluene/ethyl acetate gave 825.5 g (83%) of butyric acid hydrazide as a colorless solid: mp 44.5°-46.0° C.; NMR (CDCl3) δ 0.88 (t, J=7 Hz, 3H), 1.53-1.68 (m, 2H), 2.09 (t, J=7 Hz, 2H), 3.89 (br s, 2H), 7.62 (br s, 1H). A 5.0 g (43 mmol) sample of the hydrazide was dissolved in 40 mL of methanol and treated with 4.4 g (43 mmol) of ethyl iminobutyrate [P. Reynaud and R. C. Moreau, Bull. Soc. Chim. France, 2997 (1964)] under nitrogen. The reaction was stirred at reflux for 3 days and concentrated in vacuo. Purification by silica gel chromatography (Waters Prep-500A) using ethyl acetate/hexane (60:40) gave 5.37 g (81%) of 3,5-dipropyl-1H-1,2,4-triazole as a colorless solid: mp 69°-70° C.; NMR (CDCl3) δ 0.92 (t, J=7 Hz, 6H), 1.64-1.81 (m, 4H), 2.68 (t, J=7 Hz, 4H); MS (FAB) m/e (rel intensity) 154 (100), 138 (5), 125 (5), 112 (3); HRMS. Calcd for M+H: 154.1344. Found: 154.1390.

Step 2: Preparation of 5-[4'-[(3,5-dipropyl-1H-1,2,4-triazole-1-yl)methyl][1,1'-biphenyl]-2-yl]-1H-tetrazole Under a static nitrogen atmosphere, 2.00 g (13.1 mmol) of solid 3,5-dipropyl-1H-1,2,4-triazole was added in small portions to 14 mmol of sodium hydride in 50 ml of dimethylformamide (DMF); stirring was continued until hydrogen evolution had ceased. The anion solution was cooled to −10° C. (ice/methanol) and treated with a solution of 7.3 g (13.1 mmol) of N-triphenylmethyl-5-[2-(4'-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any ur'reacted sodium hydride and the DMF was removed in vacuo. The residue was dissolved in ethyl acetate, washed with water, and dried (MgSO4). Silica gel chromatography using 33% ethyl acetate/toluene produced 6.5 g (78.6%) of the protected tetrazole which was dissolved in 50 ml of 10% water/acetic acid and stirred at ambient temperature overnight. The solvent was removed in vacuo and the crude product dissolved in water which was made basic with 2.5 N NaOH. The water was extracted with benzene, acidified, and extracted with ethyl acetate. The ethyl acetate was dried (MgSO4) and removed in vacuo. Recrystallization from acetonitrile gave 2.67 g (67%) of a colorless solid: mp 164.5°-167.0° C.; NMR (CDCl3) δ d 0.77 (t, J=7 Hz, 3H), 0.83 (t, J=7 Hz, 3H), 1.39-1.59 (m, 4H), 2.21 (t, J=7 Hz, 2H), 2.38 (t, J=7 Hz, 2H), 5.16 (s, 2H), 6.80-6.87 (m, 2H), 7.03-7.08 (m, 2H), 7.41-7.44 (m, 1H), 7 50-7.66 (m, 2H), 7.81-7.87 (m, 1H); MS (FAB) m/e (rel intensity) 388 (29), 207 (100), 192 (38), 178 (28), 165 (20), 154 (37); HRMS. Calcd for M+H: 388.2249. Found: 388.2284.

EXAMPLE 13

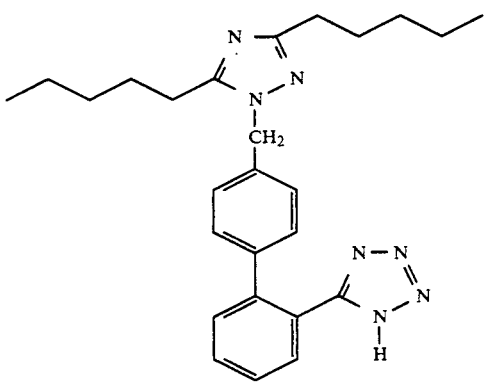

5-[4'-[(3,5-dipentyl-1H-1,2,4-triazol-1-yl)methyl][1,1'-biphenyl]-2-yl]-1H-tetrazole Step 1: Preparation of 3,5-dipentyl-1H-1,2,4-triazole Under nitroqen, a solution of 262 g (8 2 mol) of anhydrous hydrazine in 1300 mL of methanol was cooled to 0° C. and treated with 885 g (6.8 mol) of methyl caproate. The reaction was allowed to warm to ambient temperature and stir overnight prior to stirring at reflux for 7 h. The reaction was concentrated in vacuo; recrystallization from toluene gave 707 g (80%) of caproic acid hydrazide as a colorless solid: mp 72.5°-73.9° C.; NMR (CDCl3) δ 0.82 (t, J=7 Hz, 3H), 1.15-1.33 (m, 4H), 1.51-1.64 (m, 2H), 2.10 (t, J=7 Hz, 2H), 3.91 (br s, 2H), 7.56 (br s, 1H). A 5.0 g (39 mmol) sample of the hydrazide was dissolved in 40 mL of methanol and treated with 11.2 g (78 mmol) of ethyl iminocaproate [P. Reynaud and R. C. Moreau, Bull. Soc., Chim. France, 2997 (1964)-which. was only about 50% pure by NMR] under nitrogen. The reaction was stirred at reflux for 2 days and concentrated in vacuo. Purification by silica gel chromatography (Waters Prep-500A) using ethyl acetate/hexane (48:52) gave 7.56 g (92%) of 3,5-dipentyl-1H-1,2,4-triazole as a colorless solid: mp 66°-68° C.; NMR (CDCl3) δ 0.88 (t, J=7 Hz, 6H), 1.24-1.41 (m, 8H), 1.66- 1.81 (m, 4H), 2.72 (t, J=7 Hz, 4H); MS (FAB) m/e (rel intensity) 210 (100), 166 (14); HRMS. Calcd for M+H: 210.1970. Found: 210.1964.

Step 2: Preparation of 5-[4'[(3,5-dipentyl-1H-1,2,4-triazol-1-yl)methyl][1,1'-biphenyl]-2-yl]-1H-tetrazole Under a static nitrogen atmosphere, 2.0 g (9.6 mmol) of solid 3,5-dipentyl-1H-1,2,4-triazole was added in small portions to 10 mmol of sodium hydride in 50 ml of dimethylformamide (DMF); stirring was continued until hydrogen evolution had ceased. The anion solution was cooled to −10° C. (ice/methanol) and treated with a solution of 5.35 g (9.6 mmol) of N-triphenylmethyl-5-[2-(4'-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO4). Silica gel chromatography using 33% ethyl acetate/hexane produced 5.1 g (78%) of the protected tetrazole which was taken up in 40 ml of 10% water in acetic acid and stirred at ambient temperature for 3 days. The solvent was removed in vacuo, the residue dissolved in water, and the pH adjusted to 9. The aqueous layer was washed in benzene, acidified and extracted with ethyl acetate. The solution was dried (MgSO4) and concentrate in vacuo. Recrystallization from acetonitrile gave 2.1 g (62%) of a colorless solid: mp 116°-120° C.; NMR (CDCl3) δ d 0.82 (t, J=7 Hz, 6H), 1.07-1.31 (m, 8H), 1.40-1.60 (m, 4H), 2.22 (t, J=7 Hz, 2H), 2.41 (t, J=7 Hz, 2H), 5.15 (s, 2H), 6.80-6.87 (m, 2H), 7.03-7.10 (m, 2H), 7.41-7.48 (m, 1H), 7.52-7.66 (m, 2H), 7.87-7.93 (m, 1H); MS (FAB) m/e (rel intensity) 444 (100), 207 (72), 178 (13); HRMS. Calcd for M+H: 444.2876. Found: 444.2910.

EXAMPLE 14

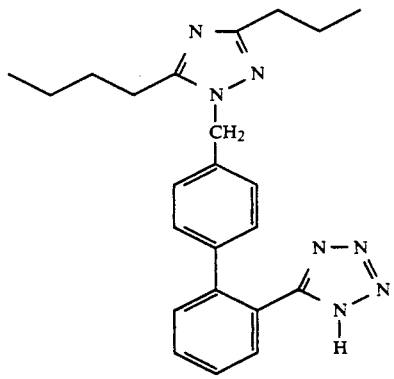

5-[4'-[(5-butyl-3-propyl-1H-1,2,4-triazol-1-yl)methyl]-[1,1'-biphenyl]-2-yl]-1H-tetrazole Step 1: Preparation of 5-butyl-3-propyl-1H-1,2,4-triazole A 3.95 g (38.7 mmol) sample of butyric acid hydrazide (from Step 1 of Example 12) was dissolved in 30 mL of methanol and treated with 5.0 g (38.8 mmol) of ethyl iminovalerate under nitrogen. The reaction was stirred at reflux for 3 days and concentrated in vacuo. Purification by silica gel chromatography (Waters Prep-500A) using ethyl acetate/hexane (80:20) gave 5.51 g (85%) of 5-butyl-3-propyl-1H-1,2,4-triazole as a colorless solid: mp 48.5°-50.0° C.; NMR (CDCl3) δ 0.92 (t, J=7 Hz, 3H), 0.97 (t, J=7 Hz, 3H), 1.31-1.46 (m, 2H), 1.66-1.84 (m, 4H), 2.72 (t, J=7 Hz, 2H), 2.75 (t, J=7 Hz, 2H); MS (FAB) m/e (rel intensity) 168 (100), 166 (4), 152 (3), 138 (3), 125 (3); HRMS. Calcd for M+H: 168.1501. Found: 168.1534.

Step 2: Preparation of
5-[4′-[(5-butyl-3propyl-1H-1,2,4-triazol-1-yl)methyl][1,1′-biphenyl]-2-yl]-1H-tetrazole Under a static nitrogen atmosphere, 2.0 g (12 mmol) of solid 5-butyl-3-propyl-1H-1,2,4-triazole was added in small portions to 12 mmol of sodium hydride in 50 ml of dimethylformamide (DMF); stirring was continued until hydrogen evolution had ceased. The anion solution was cooled to −10° C. (ice/methanol) and treated with a solution of 6.7 g (12 mmol) of N-triphenylmethyl-5-[2-(4′-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). Silica gel chromatography using 15% ethyl acetate/toluene produced 5.96 g (77%) of a mixture of the two isomers which was dissolved in 40 ml of 10% water in acetic acid and stirred at ambient temperture ovenight. The solvent was removed in vacuo and the residue dissolved in 50% acetonitrile/water. Purification of 1 g sample of the isomeric product mixture by rev.erse phase chromatography (Waters Delta Prep-3000) using 25% acetonitrile/water (0.05% TFA) for 50 minutes followed by 28% acetonitrile/water (0.05% TFA) provided two isomers. The faster moving isomer compound was dissolved in the minimal amount of acetonitrile and diluted with water. The pH was adjusted to 8 with 1N NaOH, the acetonitrile removed in vacuo, the pH readjusted to 5 with 1N HCl, and the product extracted with ethyl acetate. The solvent was removed in vacuo and the product lyophilized from acetonitrile/water providing 175 mg (18%) of the 5-butyl-3-propyl isomer as a colorless solid: NMR (CDCl$_3$) δ d 0.78 (t, J=7 Hz, 3H), 0.82 (t. J=7 Hz, 3H), 1.20–1.33 (m, 2H), 1.41–1.57 (m, 4H), 2.21 (t, J=7 Hz, 2H), 2.41 (t, J=7 Hz, 2H), 5.16 (s, 2H), 6.82–6.89 (m, 2H), 7.05–7.11 (m, 2H), 7.42.7.48 (m, 1H), 7.52–7.67 (m, 2H), 7.88–7.94 (m, 1H); MS (FAB) m/e (rel intensity) 402 (50), 207 (100), 192 (25), 168 (39), 152 (8), 125 (5); HRMS. Calcd for M+H: 402.2406. Found: 402.2424.

EXAMPLE 15

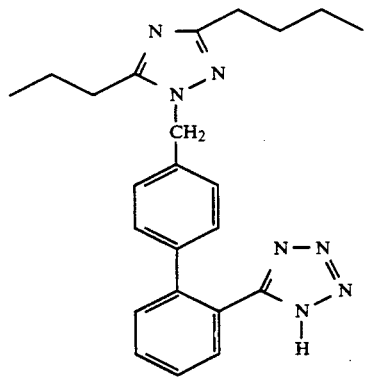

5-[4′-[(3-butyl-5-propyl-1H-1,2,4-triazol-1-yl)methyl]-[1,1′-biphenyl]-2-yl]-1H-tetrazole The slower moving isomer for Example 14 was isolated in an identical manner and provided 108 mg (11%) of the 3-butyl-5-propyl isomer as a colorless solid: NMR (CDCl$_3$) δ d 0.86 (t, J=7 Hz, 3H), 0.89 (t, J=7 Hz, 3H), 1.19–1.32 (m, 2H), 1.48–1.69 (m, 4H), 2.41 (t, J=7 Hz, 2H), 2.52 (t, J=7 Hz, 2H), 5.22 (s, 2H), 6.95–7.02 (m, 2H), 7.11–7.16 (m, 2H), 7.42–7.48 (m, 1H), 7.53–7.68 (m, 2H), 7.97–8.02 (m, 1H); MS (FAB) m/e (rel intensity) 402 (50), 259 (10), 235 (5), 225 (10), 207 (100), 192 (38); HRMS. Calcd for M+H: 402.2406. Found: 402.2435.

EXAMPLE 16

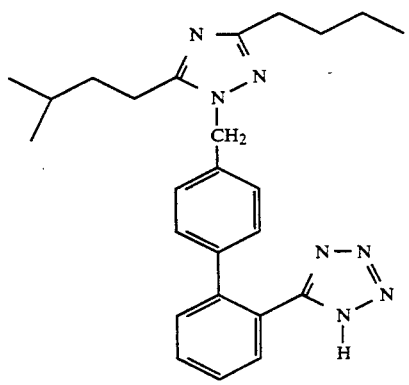

5-[4′-[(3-butyl-5-isopentyl-1H-1,2,4-triazol-1-yl)methyl]-[1,1′-biphenyl]-2-yl]-1H-tetrazole Step 1: Preparation of
3-butyl-5-isopentyl-1H-1,2,4-triazole Under nitrogen, a sclution of 53.8 g (1.68 mol) of anhydrous hydrazine in 300 mL of methanol was cooled to 0° C. and treated with 186 g (1.4 mol) of methyl 4-methylvalerate. The reaction was allowed to warm to ambient temperature and stir overnight prior to stirring at reflux for 4 h. The reaction was concentrated in vacuo giving 166 g (93%) of 4-methylvaleric acid hydrazide as a colorless solid: 49°–51° C.; NMR (CDCl$_3$) δ 0.89 (d, J=7 Hz, 6H), 1.48–1.64 (m, 3H), 2.15 (t, J=7 Hz, 2H), 3.91 (br s, 2H), 6.94 (br s, 1H). A 7.86 g (60 mmol) sample of the hydrazide was dissolved in 50 mL of methanol and treated with 7.8 g (60 mmol) of ethyl iminovalerate under nitrogen. The reaction was stirred at reflux overnight and concentrated in vacuo. Purification by silica gel chromatography (Waters Prep-500A) using ethyl acetate/hexane (40:60) gave 9.6 g (82%) of 3-butyl-5-isopentyl-1H-1,2,4-triazole as a colorless solid which melts close to ambient temperature: NMR (CDCl$_3$) δ 0.81– 0.90 (m, 9H), 1.25–1.40 (m, 2H), 1.47–1.74 (m, 5H), 2.70 (t, J=7 Hz, 4H); MS (FAB) m/e (rel intensity) 196 (100); HRMS. Calcd for M+H: 196.1814. Found: 196.1832.

Step 2: Preparation of
5-[4′-[(3-butyl-5-isopentyl-1H-1,2,4-triazol-1-yl)methyl][1,1′-biphenyl]-2-yl]-1H-tetrazole Under a static nitrogen atmosphere, 2.0 g (10.3 mmol) of solid 3-butyl-5-isopentyl-1H-1,2,4-triazole was added in small portions to 11 mmol of sodium hydride in 50 ml of dimethylformamide (DMF); stirring was continued until hydrogen evolution had ceased. The anion solution was cooled to −10° C. (ice/methanol) and treated with a solution of 5.7 g (10.2 mmol) of N-triphenylmethyl-5-[2-(4′-bromomethylbiphen-2-yl)]tetrazole (from Step 1 of Example 3) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). The crude material (8.0 g) was deprotected in 50 ml of 10% water in acetic acid at ambient temperature overnight. Purification of 1.5 g sample by reverse phase chromatography (Waters Delta Prep-3000) using isocratic 30% acetonitrile/water (0.05% TFA) provided two isomers. The faster moving isomer compound was dissolved in the minimal amount of acetonitrile and diluted with water. The pH was adjusted to 9 with 1N NaOH, the acetonitrile removed in vacuo, the pH readjusted to 5 with 1N HCl, and the product extracted with ethyl acetate. The solvent was removed in vacuo and the product lyophylized from acetonitrile/water providing 33.1 mg (2.2%) of the 3-butyl-5-isopentyl isomer as a colorless solid: NMR (CDCl$_3$) δ d 0.85 (t, J=7 Hz, 9H), 1.18–1.31 (m, 2H), 1.43–1.59 (m, 4H), 2.38 (t, J=7 Hz, 2H), 2.54 (t, J=7 Hz, 2H), 5.19 (s, 2H), 6.93–7.00 (m, 2H), 7.09–7.16 (m, 2H), 7.41–7.47 (m, 1H), 7.52–7.67 (m, 2H), 7.96–8.01 (m, 1H); MS (FAB) m/e (rel intensity) 430 (52), 387 (7), 207 (100), 196 (43), 178 (23), 165 (16), 152 (13); HRMS. Calcd for M+H: 430.2719. Found: 430.2772.

EXAMPLE 17

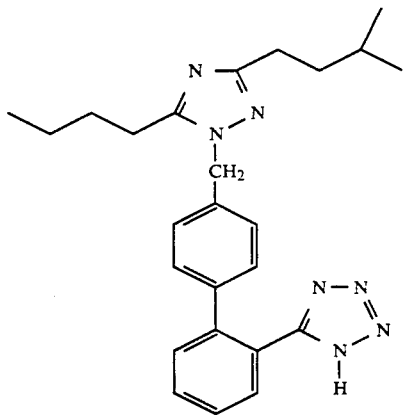

5-[4'-[(5-butyl-3-isopentyl-1H-1,2,4-triazol-1-yl]methyl)[1,1'-biphenyl]-2-yl]-1H-tetrazole The slower moving isomer from Example 16 was isolated in an identical manner and provided 36.5 mg (2.43%) of the 5-butyl-isopentyl isomer as a colorless solid: NMR (CDCl$_3$) δ d 0.79–0.88 (m, 9H), 1.22–1.36 (m, 2H), 1.38–1.61 (m, 5H), 5.18 (s, 2H), 6.88–6.96 (m, 2H), 7.08–7.14 (m, 2H), 7.41–7.47 (m, 1H), 7.53–7.67 (m, 2H), 7.94–7.99 (m, 1H): MS (FAB) m/e (rel intensity) 430 (38), 387 (8), 207 (100), 196 (37), 178 (27), 165 (15), 152 (12); HRMS. Calcd for M+H: 430.2719. Found: 430.2760.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 10$^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were aralyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FTO3 Grass transducer coupled to a Model 7D Grass Polygraph for recording isometric force responses. The bath was filled with 20 ml of oxygenated (95% oxygen/5% carbon dioxide) Krebs solution of the following composition (nM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for, one hour before approximately one gram of passive tension was placed on the rings. Angiotensin II concentration-response curves were then recorded (3×10$^{-10}$ to 1×10$^{-5}$ M). Each concentration of AII was allowed to elicit its maximal contraction, and then AII was washed out repeatedly for 30 minutes before rechallenging with a higher concentration of AII. Aorta rings were exposed to the test antagonist at 10$^{-5}$ M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [Br. J. Pharmacol. Chemother., 2, 189-206 (1947)]. The pA$_2$ value is the concentration of the antagonist which increases the EC$_{50}$ value for AII by a factor of 2. Each test antagonist was evaluated in aorta rings from two rabbits. Results are reported in Table I.

Assay C: In Vivo Intraduodenal Pressor Assay Response for AII Antagonists

Male Sprague-Dawley rats weighing 225-300 grams were anesthetized with Inactin (100 mg/kg, i.p.) and catheters were implanted into the trachea, femoral artery, femoral vein and duodenum. Arterial pressure was recorded from the femoral artery catheter on a Gould chart recorder (Gould, Cleveland, Ohio). The femoral vein catheter was used for injections of angiotensin II, mecamylamine and atropine. The tracheal catheter allows for airway patency, and the duodenal catheter was used for intraduodenal (i.d.) administration of test compounds. After surgery, the rats were allowed to equilibrate for 30 minutes. Mecamylamine (3 mg/kg, 0.3 ml/kg) and atropine (400 ug/kg, 0.3 ml/kg) were then given i.v. to produce ganglion blockade. These compounds were administered every 90 minutes throughout the test procedure. Angiotensin II was given in bolus does i.v. (30 ng/kg in saline with 0.5% bovine serum albumin, 0.1 ml/kg) every 10 minutes three times or until the increase in arterial pressure produced was within 3 mmHg for two consecutive AII injections. The last two AII injections were averaged and were taken as the control AII pressor response. Ten minutes after the final control AII injection, the test compound (dissolved in sodium bicarbonate) was administered i.d. at a dose of 30 or 100 mg/kg in a volume of 0.2 ml. Angiotensin II injections were then given 5, 10, 20, 30, 45, 60, 75, 90, and 120 minutes after administration of the test compound and response of arterial pressure was monitored. The response to AII was calculated as percent of the control response and then the percent inhibition is calculated as 100 minus the percent control response. Duration of action of a test compound was defined as the time from peak percent inhibition to 50% of peak. One compound at one dose was tested in each rat. Each test compound was tested in two rats and the values for the two rats were averaged. Results are reported in Table I.

TABLE I

| Test Compound Example # | [1]Assay A IC$_{50}$ (nM) | [2]Assay B PA$_2$ | [3]Assay C Inhibition (%) | [3]Assay C Duration (min.) |
|---|---|---|---|---|
| 1 | NT | NT | NT | NT |
| 2 | 95 | 7.48 | 98 | 90-120 |
| 3 | 5.4 | 8.70 | 100 | 200+ |
| 4 | NT | NT | NT | NT |
| 5 | 200 | 7.20 | 38 | 20-30 |
| 6 | 1300 | 6.69 | 90 | 120 |
| 7 | 84 | 8.03 | NT | NT |
| 8 | 1700 | NT | NT | NT |
| 9 | 700 | 7.39 | 100 | 230 |
| 10 | 4.9 | 8.19/7.59 | 100 | 240 |
| 11 | 160 | 6.45/6.77 | NT | NT |
| 12 | 6.0 | 8.66/8.59 | NT | NT |
| 13 | 17 | 8.70/8.85 | NT | NT |
| 14 | 7.2 | 8.84/8.71 | NT | NT |
| 15 | 16 | 8.31/8.30 | NT | NT |
| 16 | 6.4 | 8.95/9.24 | NT | NT |
| 17 | 4.0 | 8.64/8.40 | NT | NT |

NT = NOT TESTED
[1]Assay A: Angiotensin II Binding Activity
[2]Assay B: In Vitro Vascular Smooth Muscle Response
[3]Assay C: In Vitro Intraduodenal Pressor Response (activity measured @ 30 mg/kg test compound, except for Compounds #5 and #6 which were measured at 100 mg/kg).

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of frrm about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a circulatory disorder, said method comprising administering to a subject having such disorder a therapeutically-effective amount of a compound, or a pharmaceutically-acceptable salt thereof, of the group consisting of:
   5-[4'-[(3,5-dibutyl-1H-1,2,4-triazol-1-yl)methyl][1,1'-biphenyl]-2-yl]-1H-tetrazole;
   5'-[(5-butyl-3-chloro-1H-1,2,4-triazol-1-yl)methyl][1,1'-biphenyl]-2-yl]-1H-tetrazole;
   5'-[(3-butyl-5-chloro-1H-1,2,4-triazol-1-yl)methyl][1,1'-biphenyl]-2-yl]-1H-tetrazole;
   5-[4'-[[5-butyl-3-(1,1-difluorobutyl)-1H-1,2,4-triazol-1-yl]methyl][1, 1'-biphenyl]-2-yl]-1H-tetrazole;
   5-[4'-[[3-butyl-5 -(1,1-difluorobutyl)-1H-1,2,4-triazol-1-yl]methyl][1, 1'-biphenyl]-2-yl]-1H-tetrazole;
   5-[4'-[(3,5-dipropyl-1H-1,2,4-triazol-1-yl)methyl][1,1'-biphenyl]-2-yl]-1H-tetrazole;
   5-[4'-[(3,5-dipentyl-1H-1,2,4-triazol-1-yl)methyl][1,1'-biphenyl-2-yl]-1H-tetrazole;
   5-[4'-[(5-butyl-3-propyl-1H-1,2,4-triazol-1-yl)methyl][1,1'-biphenyl]-2-yl]-1H-tetrazole;
   5-[4'-[(3-butyl-5-propyl-1H-1,2,4-triazol-1-yl)methyl][1,1'-biphenyl]-2-yl]-1H-tetrazole;
   5-[4'-[(3-butyl-5-isopentyl-1H-1,2,4triazol-1-yl)methyl][1,1'-biphenyl]-2-yl]-1H-tetrazole; and
   5-[4'-[(5-butyl-3-isopentyl-1H-1,2,4-triazol-1-yl)methyl][1,1'-biphenyl]-2-yl]-1H-tetrazole.

2. The method of claim 1 wherien said circulatory disorder is a cardiovascular disorder.

3. The method of claim 2 wherein said cardiovascular disorder is hypertension.

4. The method of claim 3 wherein said cardiovascular disorder is congestive heart failure.

5. The method of claim 1 wherein said compound is 5-[4'-[(3,5-dibutyl-1H-1,2,4-triazol-1-yl)methyl][1,1'-biphenyl]-2-yl]-1H-tetrazole or a pharmaceutically-acceptable salt thereof.

6. A pharmaceutical composition comprising a therapeutically-effective amount of an angiotensin II antagonist compound and a pharmaceutically-acceptable carrier or diluent, said antagonist compound selected from compounds, or a pharmaceutically-acceptable salt thereof, of the group consisting of:
   5-[4'-[(3,5-dibutyl-1H-1,2,4-triazol-1-yl)methyl][1,1'-biphenyl]-2-yl]-1H-tetrazole;
   5'-[(5-butyl-3-chloro-1H-1,2,4-triazol-1-yl)methyl][1,1'-biphenyl]-2-yl]-1H-tetrazole;
   5'-[(3-butyl-5-chloro-1H-1,2,4-triazol-1-yl)methyl][1,1'-biphenyl]-2-yl]-1H-tetrazole;
   5-[4'-[[5-butyl-3-(1,1-difluorbutyl)-1H-1,2,4-triazol-1-yl]methyl][1, 1'-biphenyl]-2-yl]-1H-tetrazole;
   5-[4'-[[3-butyl-5-(1,1-difluorbutyl)-1H-1,2,4-triazol-1-yl]methyl][1, 1'-biphenyl]-2-yl]-1H-tetrazole;
   5-[4'-[(3,5-dipropyl-1H-1,2,4-triazol-1-yl)methyl][1,1'-biphenyl]-2-yl]-1H-tetrazole;
   5-[4'-[(3,5-dipentyl-1H-1,2,4-triazol-1-yl)methyl][1,1'-biphenyl-2-yl]-1H-tetrazole;
   5-[4'-[(5-butyl-3-propyl-1H-1,2,4-triazol-1-yl)methyl][1,1'-biphenyl]-2-yl]-1H-tetrazole;
   5-[4'-[(3-butyl-5-propyl-1H-1,2,4-triazol-1-yl)methyl][1,1'-biphenyl]-2-yl]-1H-tetrazole;
   5-[4'-[(3-butyl-5-isopentyl-1H-1,2,4-triazol-1-yl)methyl][1,1'-biphenyl]-2-yl]-1H-tetrazole; and
   5-[4'-[(5-butyl-3-isopentyl-1H-1,2,4-triazol-1-yl)methyl][1,1'-biphenyl]-2-yl]-1H-tetrazole.

7. The composition of claim 6 wherein said antagonist compound is
   5-[4'-[(3,5-dibutyl-1H-1,2,4-triazol-1-yl)methyl][1,1'-biphenyl]-2-yl]-1H-tetrazole or a pharmaceutically-acceptable salt thereof.

8. A compound which is
   5-[4'-[(3,5-dibutyl-1H-1,2,4-triazol-1-yl)methyl][1,1'-biphenyl]-2-yl]-1H-tetrazole or a pharmaceutically-acceptable salt thereof.

9. A compound which is
   5'-[(5-butyl-3-chloro-1H-1,2,4-triazol-1-yl)methyl][1,1'-biphenyl]-2-yl]-1H-tetrazole or a pharmaceutically-acceptable salt thereof.

10. A compound which is
    5'-[(3-butyl-5-chloro-1H-1,2,4-triazol-1-yl)methyl][1,1'-biphenyl]-2-yl]-1H-tetrazole or a pharmaceutically-acceptable salt thereof.

11. A compound which is
    5-[4'-[[5-butyl-3-(1,1-difluorbutyl)-1H-1,2,4-triazol-1-yl]methyl][1, 1'-biphenyl]-2-yl]-1H-tetrazole or a pharmaceutically-acceptable salt thereof.

12. A compound which is
    5-[4'-[[3-butyl-5-(1,1-difluorbutyl)-1H-1,2,4-triazol-1-yl]methyl][1, 1'-biphenyl]-2-yl]-1H-tetrazole or a pharmaceutically-acceptable salt thereof.

13. A compound which is
    5-[4'-[(3,5-dipropyl-1H-1,2,4-triazol-1-yl)methyl][1,1'-biphenyl]-2-yl]-1H-tetrazole or a pharmaceutically-acceptable salt thereof.

14. A compound which is
    5-[4'-[(3,5-dipentyl-1H-1,2,4-triazol-1-yl)methyl][1,1'-biphenyl-2-yl]-1H-tetrazole or a pharmaceutically-acceptable salt thereof.

15. A compound which is

5-[4'-[(5-butyl-3-propyl-1H-1,2,4-triazol-1-yl)methyl][1,1'-biphenyl]-2-yl]-1H-tetrazole or a pharmaceutically-acceptable salt thereof.

16. A compound which is
5-[4'-[(3-butyl-5-propyl-1H-1,2,4-triazol-1-yl)methyl][1,1'-biphenyl]-2-yl]-1H-tetrazole or a pharmaceutically-acceptable salt thereof.

17. A compound which is
5-[4'-[(3-butyl-5-isopentyl-1H-1,2,4-triazol-1-yl)methyl][1,1'-biphenyl]-2-yl]-1H-tetrazole or a pharmaceutically-acceptable salt thereof.

18. A compound which is
5-[4'-[(5-butyl-3-isopentyl-1H-1,2,4-triazol-1-yl)methyl][1,1'-biphenyl]-2-yl]-1H-tetrazole or a pharmaceutically-acceptable salt thereof.

* * * * *